(12) United States Patent
Chen et al.

(10) Patent No.: US 12,428,378 B2
(45) Date of Patent: Sep. 30, 2025

(54) METHODS AND MATERIALS FOR INCREASING LEVEL OF PHOSPHORYLATED AMPK PROTEIN

(71) Applicant: University of Pittsburgh—Of the Commonwealth System of Higher Education, Pittsburgh, PA (US)

(72) Inventors: Beibei Chen, Sewickley, PA (US); Toren Finkel, Pittsburgh, PA (US); Yuan Liu, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 619 days.

(21) Appl. No.: 17/641,606

(22) PCT Filed: Sep. 9, 2020

(86) PCT No.: PCT/US2020/049929
§ 371 (c)(1),
(2) Date: Mar. 9, 2022

(87) PCT Pub. No.: WO2021/050538
PCT Pub. Date: Mar. 18, 2021

(65) Prior Publication Data
US 2022/0340533 A1    Oct. 27, 2022

Related U.S. Application Data

(60) Provisional application No. 63/024,283, filed on May 13, 2020, provisional application No. 62/898,285, filed on Sep. 10, 2019.

(51) Int. Cl.
| | | |
|---|---|---|
| A61K 31/133 | (2006.01) |
| A61K 31/135 | (2006.01) |
| C07C 215/08 | (2006.01) |
| C07C 217/20 | (2006.01) |
| C07C 217/34 | (2006.01) |
| C07C 225/10 | (2006.01) |
| C07D 209/08 | (2006.01) |
| C07D 211/76 | (2006.01) |
| C07D 213/38 | (2006.01) |
| C07D 213/71 | (2006.01) |
| C07D 213/82 | (2006.01) |
| C07D 215/40 | (2006.01) |
| C07D 223/18 | (2006.01) |
| C07D 231/12 | (2006.01) |
| C07D 233/24 | (2006.01) |
| C07D 239/26 | (2006.01) |
| C07D 277/28 | (2006.01) |
| C07D 413/14 | (2006.01) |
| C07D 417/04 | (2006.01) |

(52) U.S. Cl.
CPC .......... *C07D 223/18* (2013.01); *C07C 217/20* (2013.01); *C07C 225/10* (2013.01); *C07D 209/08* (2013.01); *C07D 211/76* (2013.01); *C07D 213/38* (2013.01); *C07D 213/71* (2013.01); *C07D 213/82* (2013.01); *C07D 215/40* (2013.01); *C07D 231/12* (2013.01); *C07D 233/24* (2013.01); *C07D 239/26* (2013.01); *C07D 277/28* (2013.01); *C07D 413/14* (2013.01); *C07D 417/04* (2013.01); *C07B 2200/05* (2013.01)

(58) Field of Classification Search
CPC .. A61K 31/133; A61K 31/135; C07C 215/08; C07C 217/34; C07D 223/18; C07D 211/76; C07D 213/38; C07D 413/14; C07D 417/04
See application file for complete search history.

(56) References Cited

U.S. PATENT DOCUMENTS

| | | | |
|---|---|---|---|
| 4,110,472 A | 8/1978 | Hiltmann et al. |
| 4,410,472 A | 10/1983 | Grubbs et al. |
| 4,552,960 A | 11/1985 | Krumkalns et al. |

(Continued)

FOREIGN PATENT DOCUMENTS

| | | |
|---|---|---|
| CA | 2043216 A1 | 11/1991 |
| CA | 2078057 A1 | 3/1993 |

(Continued)

OTHER PUBLICATIONS

[No Author], "Type 2 diabetes and metformin. First choice for monotherapy: weak evidence of efficacy but well-known and acceptable adverse effects," Prescrire International, Nov. 2014, 23(154):269-272.

(Continued)

*Primary Examiner* — Bruck Kifle
(74) *Attorney, Agent, or Firm* — Fish & Richardson P.C.

(57) ABSTRACT

This document provides methods and materials for increasing the level of phosphorylated AMPK. For example, compounds (e.g., organic compounds) having the ability to increase the level of phosphorylated AMPK within cells, formulations containing compounds having the ability to increase the level of phosphorylated AMPK within cells, methods for making compounds having the ability to increase the level of phosphorylated AMPK within cells, methods for making formulations containing compounds having the ability to increase the level of phosphorylated AMPK within cells, methods for increasing the level of phosphorylated AMPK within cells, and methods for treating mammals (e.g., humans) having a condition responsive to an increase in the level of phosphorylated AMPK are provided.

20 Claims, 10 Drawing Sheets

(56) References Cited

U.S. PATENT DOCUMENTS

| | | | |
|---|---|---|---|
| 4,559,354 | A | 12/1985 | Fuhrer et al. |
| 5,304,121 | A | 4/1994 | Sahatjian |
| 5,391,552 | A | 2/1995 | Inazu et al. |
| 5,541,204 | A | 7/1996 | Sher et al. |
| 5,886,026 | A | 3/1999 | Hunter et al. |
| 6,099,562 | A | 8/2000 | Ding et al. |
| 6,326,492 | B1 | 12/2001 | Wang et al. |
| 6,803,031 | B2 | 10/2004 | Rabinowitz et al. |
| 7,321,041 | B2 | 1/2008 | Cywin et al. |
| 7,365,085 | B2 | 4/2008 | Bhat et al. |
| 7,678,911 | B2 | 3/2010 | Cywin et al. |
| 7,705,151 | B2 | 4/2010 | Cywin et al. |
| 9,500,640 | B2 | 11/2016 | Wang et al. |
| 11,040,935 | B2 | 6/2021 | Chen et al. |
| 11,673,853 | B2 | 6/2023 | Chen et al. |
| 2009/0227589 | A1 | 9/2009 | Cuberes-Altisent et al. |
| 2010/0029689 | A1 | 2/2010 | Hopper et al. |
| 2010/0279997 | A1 | 11/2010 | Burns Barbier et al. |
| 2014/0018341 | A1 | 1/2014 | Wang et al. |
| 2014/0350064 | A1 | 11/2014 | Chen |
| 2015/0148318 | A1 | 5/2015 | Wang et al. |
| 2020/0062693 | A1 | 2/2020 | Chen et al. |
| 2022/0153685 | A1 | 5/2022 | Chen et al. |

FOREIGN PATENT DOCUMENTS

| | | | |
|---|---|---|---|
| EP | 0039892 | A1 | 11/1981 |
| EP | 1426370 | A1 | 6/2004 |
| JP | S57-026653 | A | 2/1982 |
| JP | 2003-501352 | A | 1/2003 |
| JP | 2004-504305 | A | 2/2004 |
| JP | 2004-535420 | A | 11/2004 |
| RU | 2416409 | C2 | 4/2011 |
| WO | WO 2002/000622 | A2 | 1/2002 |
| WO | WO 2002/006210 | A1 | 1/2002 |
| WO | WO 2002/006248 | A2 | 1/2002 |
| WO | WO 2002/048134 | A2 | 6/2002 |
| WO | WO 2007/118041 | A1 | 10/2007 |
| WO | WO 2008/015558 | A2 | 2/2008 |
| WO | WO 2008/142454 | A1 | 11/2008 |
| WO | WO 2010/051374 | A1 | 5/2010 |
| WO | WO 2014/011917 | A2 | 1/2014 |
| WO | WO 2014/012054 | A1 | 1/2014 |
| WO | WO 2015/054027 | A1 | 4/2015 |
| WO | WO 2018/067685 | | 4/2018 |

OTHER PUBLICATIONS

Bergeron et al., "Effect of AMPK activation on muscle glucose metabolism in conscious rats," Am. J. Physiology, May 1999, 276(5):E938-944.

Carling, "AMPK signalling in health and disease," Curr. Opin. Cell Biology, Apr. 2017, 45:31-37.

Castanares-Zapatero et al., "Connection between cardiac vascular permeability, myocardial edema and inflammation during sepsis: role of the a1AMP-activated protein kinase isoform," Crit. Care Medicine, Dec. 2013, 41(12):e411-e422.

Chang et al., "Does OKT3 monoclonal antibody react with an antigen-recognition structure on human T cells?," Proc. Natl Acad. Sci. USA, Mar. 1981, 78(3):1805-1808.

Chen et al., "A small molecule NRF2 activator BC-1901S ameliorates inflammation through DCAF1/NRF2 axis," Redox Biology, May 2020, 32:101485, 11 pages.

Chen et al., "The ubiquitin E3 ligase SCF-FBXO24 recognizes deacetylated nucleoside diphosphate kinase A to enhance its degradation," Mol. Cell. Biology, Mar. 2015, 35(6):1001-1013.

Cool et al., "Identification and characterization of a small molecule AMPK activator that treats key components of type 2 diabetes and the metabolic syndrome," Cell Metabolism, Jun. 2006, 3(6):403-416.

Corton et al., "5-aminoimidazole-4-carboxamide ribonucleoside. A specific method for activating AMP-activated protein kinase in intact cells?," Eur. J. Biochemistry, Apr. 15, 1995, 229(2):558-565.

Deshaies et al., "Ring domain E3 ubiquitin ligases," Annu. Rev. Biochemistry, Jul. 7, 2009, 78:399-434.

Ducommun et al., "Enhanced activation of cellular AMPK by dual-small molecule treatment: AICAR and A769662," Am. J. Physiol. Endocrinol. Metabolism, Mar. 2014, 306(6):E688-E696.

Durante et al., "Effects of endurance training on activity and expression of AMP-activated protein kinase isoforms in rat muscles," Am. J Physiol. Endocrinol. Metabolism, Jul. 2002, 283(1):E178-E186.

Egan et al., "Phosphorylation of ULK1 (hATG1) by AMP-activated protein kinase connects energy sensing to mitophagy," Science, Jan. 28, 2011, 331(6016):456-461.

Fullerton et al., "Single phosphorylation sites in Acc1 and Acc2 regulate lipid homeostasis and the insulin-sensitizing effects of metformin," Nat. Medicine, Nov. 3, 2013, 19(12):1649-1654.

Groenendijk et al., "Sorafenib synergizes with metformin in NSCLC through AMPK pathway activation," Int. J. Cancer, Mar. 15, 2015, 136(6):1434-1444.

Gwinn et al., "AMPK phosphorylation of raptor mediates a metabolic checkpoint," Mol. Cell, Apr. 25, 2008, 30(2):214-226.

Hardie et al., "AMPK: a nutrient and energy sensor that maintains energy homeostasis," Nat. Rev. Mol. Cell Biology, Mar. 22, 2012, 13(4):251-262.

Hardie, "AMPK: positive and negative regulation, and its role in whole-body energy homeostasis," Curr. Opin. Cell Biology, Apr. 2015, 33:1-7.

Hardie, "Regulation of AMP-activated protein kinase by natural and synthetic activators," Acta Pharm. Sin. B, Jan. 2016, 6(1):1-19.

Hawley et al., "Complexes between the LKB1 tumor suppressor, STRAD$\alpha/\beta$ and MO25$\alpha/\beta$ are upstream kinases in the AMP-activated protein kinase cascade," J. Biology, Sep. 24, 2003, 2(4):28, 16 pages.

Hawley et al., "The ancient drug salicylate directly activates AMP-activated protein kinase," Science, May 18, 2012, 336(6083):918-922.

Herzig et al., "AMPK: guardian of metabolism and mitochondrial homeostasis," Nat. Rev. Mol. Cell Biology, Oct. 4, 2017, 19:121-135.

Hoogendijk et al., "AMP-activated protein kinase activation by 5-aminoimidazole-4-carbox-amide-1-$\beta$-D-ribofuranoside (AICAR) reduces lipoteichoic acid-induced lung inflammation," J. Biol. Chemistry, Mar. 8, 2013, 288(10):7047-7052.

Illum, "Is nose-to-brain transport of drugs in man a reality?," J. Pharm. Pharmacology, Jan. 2004, 56(1):3-17.

Illum, "Transport of drugs from the nasal cavity to the central nervous system," Eur. J. Pharm. Sciences, Jul. 2000, 11(1):1-18.

Jafari et al., "The cellular thermal shift assay for evaluating drug target interactions in cells," Nat. Protocols, Aug. 7, 2014, 9(9):2100-2122.

Kim et al., "AMPK activators: mechanisms of action and physiological activities," Exp. Mol. Medicine, Apr. 1, 2016, 48(4):e224, 12 pages.

Kim et al., "AMPK and mTOR regulate autophagy through direct phosphorylation of Ulk1," Nat. Cell Biology, Jan. 23, 2011, 13(2):132-141.

Krug et al., "A Curated Resource for Phosphosite-specific Signature Analysis," Mol. Cell Proteomics, Dec. 18, 2018, 18(3):576-593.

Liu et al., "A Fbxo48 inhibitor prevents pAMPK$\alpha$ degradation and ameliorates insulin resistance," Nat. Chem. Biology, Jan. 25, 2021, 17(3):298-306.

Mihaylova et al., "The AMPK signalling pathway coordinates cell growth, autophagy and metabolism," Nat. Cell Biology, Sep. 2, 2011, 13(9):1016-1023.

Mizushima et al., "How to interpret LC3 immunoblotting," Autophagy, Nov./Dec. 2007, 3(6):542-545.

Myers et al., "Systemic pan-AMPK activator MK-8722 improves glucose homeostasis but induces cardiac hypertrophy," Science, Aug. 4, 2017, 357(6350):507-511.

Ojuka, "Role of calcium and AMP kinase in the regulation of mitochondrial biogenesis and GLUT4 levels in muscle," Proc. Nutr. Society, May 2004, 63(2):275-278.

(56) References Cited

OTHER PUBLICATIONS

Owen et al., "Evidence that metformin exerts its anti-diabetic effects through inhibition of complex 1 of the mitochondrial respiratory chain," Biochem. Journal, Jun. 15, 2000, 348(Pt 3):607-614.
Park et al., "Activation of AMPK enhances neutrophil chemotaxis and bacterial killing," Mol. Medicine, Nov. 8, 2013, 19(1):387-398.
PCT International Preliminary Report on Patentability in International Appln. No. PCT/US2020/049929, dated Mar. 15, 2022, 7 pages.
PCT International Search Report and Written Opinion in International Appln. No. PCT/US2020/049929, dated Feb. 4, 2021, 10 pages.
Pineda et al., "Degradation of AMPK by a cancer-specific ubiquitin ligase," Cell, Feb. 12, 2015, 160(4):715-728.
PubChem CID 110906234, "1-(Pyridin-2-ylmethylamino)-3-[4-(trifluoromethyl)phenoxyl]propan-2-ol," dated Jan. 20, 2016, 7 pages.
PubChem CID 422253, "N-(3-Phenoxypropyl)dibenzylaminem," dated Mar. 26, 2005, 10 pages.
PubChem CID 66782018, "1-(Propan-2-ylamino )-3-(1H-pyrazol-5-yloxy)propan-2-ol," dated Nov. 30, 2012, 7 pages.
PubChem CID 70043021, "1-(Tert-butylamino)-3-(furan-2-yloxy)propan-2-ol," dated Dec. 1, 2012, 7 pages.
Rohaan et al., "Adoptive cellular therapies: the current landscape," Virchows Archiv, Nov. 23, 2018, 474(4):449-461.
Rohm et al., "An AMP-activated protein kinase-stabilizing peptide ameliorates adipose tissue wasting in cancer cachexia in mice," Nat. Medicine, Aug. 28, 2016, 22(10):1120-1130.
Ruderman et al., "AMPK, insulin resistance and the metabolic syndrome," J. Clin. Investigation, Jul. 2013, 123(7):2764-2772.
Salminen et al., "AMP-activated protein kinase inhibits NF-κB signaling and inflammation: impact on healthspan and lifespan," J. Mol. Medicine, Jul. 2011, 89(7):667-676.
Sanders et al., "Investigating the mechanism for AMP activation of the AMP-activated protein kinase cascade," Biochem. Journal, Apr. 2007, 403(1):139-148.
Sengupta et al., "Discovery of NV-5138, the first selective brain mTORC1 activator," Sci. Reports, Mar. 11, 2019, 9:4107, 10 pages.
Shaw et al., "The tumor suppressor LKB1 kinase directly activates AMP-activated kinase and regulates apoptosis in response to energy stress," Proc. Natl Acad. Sci. USA, Mar. 9, 2004, 101(10):3329-3335.
Skalniak et al., "Small-molecule inhibitors of PD-1/PD-L1 immune checkpoint alleviate the PD-L1-induced exhaustion of T-cells," Oncotarget, Aug. 7, 2017, 8(42):72167-72181.
Smith et al., "Treatment of nonalcoholic fatty liver disease: role of AMPK," Am. J. Physiol. Endocrinol. Metabolism, Oct. 1, 2016, 311(4):E730-E740.
Steneberg et al., "PAN-AMPK activator O304 improves glucose homeostasis and microvascular perfusion in mice and type 2 diabetes patients," JCI Insight, Jun. 21, 2018, 3(12):e99114, 19 pages.
Tamás et al., "Regulation of the energy sensor AMP-activated protein kinase by antigen receptor and Ca2+ in T lymphocytes," J. Exp. Medicine, Jul. 10, 2006, 203(7):1665-1670.
Thomson et al., "Skeletal muscle and heart LKB1 deficiency causes decreased voluntary running and reduced muscle mitochondrial marker enzyme expression in mice," Am. J Physiol. Endocrinol. Metabolism, Feb. 2007, 292(1):E196-E202.
Toyama et al., "AMP-activated protein kinase mediates mitochondrial fission in response to energy stress," Science, Jan. 15, 2016, 351(6270):275-281.
Viollet et al., "Cellular and molecular mechanisms of metformin: an overview," Clin. Science, Mar. 2012, 122(6):253-270.
Vlotides et al., "Anticancer effects of metformin on neuroendocrine tumor cells in vitro," Hormones, Oct.-Dec. 2014, 13(4):498-508.
Winder et al., "AMP-activated protein kinase, a metabolic master switch: possible roles in Type 2 diabetes," Am. J. Physiology, Jul. 1, 1999, 277(1 Pt 1):E1-E10.
Winder et al., "Energy-sensing and signaling by AMP-activated protein kinase in skeletal muscle," J. Appl. Physiology, Sep. 1, 2001, 91(3):1017-1028.

Xiao et al., "Structural basis of AMPK regulation by small molecule activators," Nat. Communications, Dec. 19, 2013, 4:3017, 10 pages.
Xiu et al., "Genetic analysis of the FBXO48 gene in Chinese Han patients with Parkinson disease," Neurosci. Letters, Apr. 29, 2013, 541:224-226.
Zhang et al., "Fructose-1,6-bisphosphate and aldolase mediate glucose sensing by AMPK," Nature, Jul. 19, 2017, 548(7665):112-116.
Zhang et al., "Metformin activates AMPK through the lysosomal pathway," Cell Metabolism, Oct. 11, 2016, 24(4):521-522.
Zhou et al., "Role of AMP-activated protein kinase in mechanism of metformin action," J. Clin. Investigation, Oct. 2001, 108(8):1167-1174.
Zogovic et al., "Coordinated activation of AMP-activated protein kinase, extracellular signal-regulated kinase, and autophagy regulates phorbol myristate acetate-induced differentiation of SH-SY5Y neuroblastoma cells," J. Neurochemistry, Apr. 2015, 133(2):223-232.
Beasley et al., "Analgesics. Part I. Some Aryloxypropanolamines," J. Pharm. Pharmacol., Sep. 1958, 10(1):47-59.
Bergeron et al., "Effect of AMPK activation on muscle glucose metabolism in conscious rats," Am. J. Physiol., May 1999, 276(5):E938-E944.
Cepanec et al., "Calcium trifluoromethanesulfonate-catalysed aminolysis of epoxides, " Tetrahedron, Mar. 2003, 59(14):2435-2439.
Deng et al., "Deubiquitination and Activation of AMPK by USP10," Mol. Cell, Feb. 2016, 61(4):614-624.
Durante et al., "Effects of endurance training on activity and expression of AMP-activated protein kinase isoforms in rat muscles," Am. J. Physiol. Endocrinol. Metab., Jul. 2002, 283(1):E178-E186.
EurekAler.org [online], "Scripps Research Institute scientists help unravel central mystery of Alzheimer's disease," Apr. 2013, retrieved on Sep. 5, 2019, retrieved from URL<https://www.eurekalert.org/pub_releases/2013-04/sri-sri040513.php>, 4 pages.
Extended European Search Report in European Appln. No. 20863077.2, dated Oct. 31, 2023, 8 pages.
Florant, et al., "To eat or not to eat: the effect of AICAR on food intake regulation in yellow-bellied marmots (*Marmota flaviventris*)," J. Exp. Biol., Feb. 2010, 213:2031-2037.
Gârea et al., "Synthesis and characterization of new nanocomposites based on epoxy resins and organophilic clays," Polym. Int., Sep. 2007, 56(9):1106-1114.
Immediata et al., "β-Naphthyl derivatives of ethanolamine and n-substituted ethanolamines," J. Org. Chem., 1940, 5(5):512-27.
Khalil et al., "Synthesis of Certain (Heterocyclic Substituted Aryloxy) Propanolamines as Potential Adrenoceptor Antagonists," Bull. Fac. Pharm. Cario Univ., 2002, 40(1):23-29.
Khalil et al., "Synthesis of Certain Propanolamines as Potential Adrenoceptor Antagonists," Bull. Fac. Pharm. Cario Univ., 2002, 40(2):23-29.
Lizza et al., "Solvent-Directed Epoxide Opening with Primary Amines for the Synthesis of β-Amino Alcohols," Synthesis, Nov. 2016, 49(6):1231-1242.
Musi et al., "Metformin increases AMP-activated protein kinase activity in skeletal muscle of subjects with type 2 diabetes," Diabetes, Jul. 2002, 51(7):2074-2081.
Notari, "Theory and Practice of Prodrug Kinetics," Methods Enzymol., 1985, 112(24):309-323.
Ojuka, "Role of calcium and AMP kinase in the regulation of mitochondrial biogenesis and GLUT4 levels in muscle," Proc. Nutr. Soc., May 2004, 63(2): 275-278.
PCT International Preliminary Report on Patentability in International Appln. No. PCT/US2017/055109 dated Apr. 9, 2019, 7 pages.
PCT International Search Report and Written Opinion in International Appln. Np. PCT/US2017/055109 dated Jan. 18, 2018, 9 pages.
Perrone et al., "Stereospecific synthesis and bio-activity of novel β3-adrenoceptor agonists and inverse agonists," Bioorg. Med. Chem., Mar. 2008, 16(5):2473-2488.
Pineda et al., "Degradation of AMPK by a Cancer-Specific Ubiquitin Ligase," Cell, Feb. 2015, 160(4):715-728.

(56) References Cited

OTHER PUBLICATIONS

PubChem [online], "Substance record for 1-Benzylamino-2-propanol," Dec. 3, 2015, retrieved on Sep. 5, 2019, retrieved from URL<https://pubchem.ncbi.nlm.nih.gov/substance/255445051>, 4 pages.

Reddy et al., "Lewis Acid Mediated Nucleophilic Ring-Opening of 1-Benzhydryl Azetidine-3-ol with Aryl Alcohols: A Formal Synthesis of Carvedilol," Asian J. Chem., Aug. 2012, 24(8):3468-3472.

Ronnett., "AMPK in the brain: its roles in energy balance and neuroprotection," J. Neurochem., May 2009, 109(Suppl. 1):17-23.

STN Registry No. 102761-21-7, "2-Propanol, 1-[bis(phenylmethyl)amino]-3-(2-methylphenoxy)," dated Jan. 21, 1986, 2 pages.

STN Registry No. 1053064-49-5, "2-Propanol, 1-[bis(phenylmethyl)amino]-3-(4-methylphenoxy)-, hydrochloride (1:1)," dated Sep. 26, 2008, 2 pages.

STN Registry No. 1061046-20-5, "2-Propanol, 1-[4-[[(2-methoxyethyl) (1-methylethyl)amino]methyl]phenoxy]-3-[methyl(phenylmethyl)amino]," dated Oct. 14, 2008, 1 page.

STN Registry No. 1065487-01-5, "2-Propanol, 1-[4-[(cyclopropylamino)methyl]phenoxy]-3-[methyl(phenylmethyl)amino]," dated Oct. 24, 2008, 2 pages.

STN Registry No. 1069519-97-6, "2-Propanol, 1-[methyl(phenylmethyl)amino]-3-[4-[[[(2-methylphenyl)methyl]amino]methyl]phenoxy]-," dated Nov. 2, 2008, 1 page.

STN Registry No. 1181769-10-7, "2-Propanol, 1-(4-fluorophenoxy)-3-[(4-fluorophenyl)amino]," dated Sep. 9, 2009, 1 page.

STN Registry No. 1288379-85-0, "2-Propanol, 1-[(diphenylmethyl)amino]-3-(4-fluorophenoxy)," dated May 1, 2011, 2 pages.

STN Registry No. 1392100-59-2, "2-Propanol, 1-[(diphenylmethyl)amino]-3-phenoxy," dated Aug. 22, 2012, 1 page.

STN Registry No. 152533-41-0, "2-Propanol, 1-[bis(phenylmethyl)amino]-3-phenoxy," dated Jan. 27, 1994, 2 pages.

STN Registry No. 311812-45-0, "2-Propanol, 1-[bis(phenylmethyl)amino]-3-(4-methoxyphenoxy)," dated Dec. 28, 2000, 2 pages.

STN Registry No. 332150-46-6, "2-Propanol, 1,1'-[1,4-phenylenebis(oxy)]bis[3-[(phenylmethyl)amino], " dated Apr. 24, 2001, 1 page.

STN Registry No. 424805-21-0, "[1, 1' 1-Biphenyl)-4-carbonitrile, 4' -[3-[bis (phenylmethyl) amino] -2-hydroxypropoxy]," dated Jun. 3, 2002, 1 page.

STN Registry No. 424810-74-2, "2-Propanol, 1-[bis(phenylmethyl)amino]-3-(2-naphthalenyloxy)," dated Jun. 3, 2002, 2 pages.

STN Registry No. 432496-91-8, "2-Propanol, 1-[bis(phenylmethyl)amino]-3-(4-methylphenoxy)," dated Jun. 20, 2002, 2 pages.

STN Registry No. 437765-31-6, "2-Propanol, 1-[bis(phenylmethyl)amino]-3-(4-fluorophenoxy)-, (2S)-," dated Jul. 9, 2002, 3 pages.

STN Registry No. 449783-37-3, "2-Propanol, 1,1'-[1,4-phenylenebis(oxy)]bis[3-[bis(phenylmethyl)amino]," dated Sep. 12, 2002, 2 pages.

STN Registry No. 861092-43-5, "2-Naphthalenemethanol, a-[[bis(phenylmethyl)amino]methyl]," dated Aug. 19, 2005, 2 pages.

STN Registry No. 864234-45-7, "4(3H)-Quinazolinone, 3-[4-[3-[bis(phenylmethyl)am.ino]-2-hydroxypropoxy]phenyl]-2-methyl-," dated Sep. 30, 2005, 3 pages.

STN Registry No. 864350-65-2, "[1]Benzothieno[2,3-d]pyrimidin-4(3H)-one, 3-[4-[3-[bis(phenylmethyl)amino]-2-hydroxypropoxy]phenyl]-5,6,7,8-tetrahydro-2-methyl-," dated Sep. 30, 2005, 3 pages.

Tanaka et al., "Potent Plasmodium falciparum Gametocytocidal Activity of Diaminonaphthoquinones, Lead Antimalarial Chemotypes Identified in an Antimalarial Compound Screen," Antimicrob. Agents Chemother., Mar. 2015, 59(3):1389-1397.

Thomson et al., "Skeletal muscle and heart LKB1 deficiency causes decreased voluntary running and reduced muscle mitochondrial marker enzyme expression in mice," Am. J. Physiol. Endocrinol. Metab., Jan. 2007, 292(1):E196-E202.

Wang et al., "Ghrelin inhibits insulin secretion through the AMPK-UCP2 pathway in β cells," FEBS Lett., Apr. 2010, 584(8):1503-1508.

Winder and Hardie, "AMP-activated protein kinase, a metabolic master switch: possible roles in Type 2 diabetes," Am. J. Physiol., Jul. 1999, 277(1):E1-E10.

Winder, "Energy-sensing and signaling by AMP-activated protein kinase in skeletal muscle," J. Appl. Physiol., Sep. 2001, 91(3):1017-1028.

Yamamoto et al., "Regio-and stereo-selective ring opening of epoxides with amide cuprate reagents," J. Chem. Soc. Chem. Commun., 1993, 1993(15):1201-1203.

Zhang et al., "Discovery of Novel Antimalarial Compounds Enabled by QSAR-Based Virtual Screening," J. Chem. Inf. Modeling, Dec. 2012, 53(2):475-492.

Zhou et al., "Role of AMP-activated protein kinase in mechanism of metformin action," J. Clin. Invest., Oct. 2001, 108(8):1167-1174.

Zindell et al., "Morpholine containing CB2 selective agonists," Bioorg. Med. Chem. Lett., Mar. 2009, 19(6):1604-1609.

U.S. Appl. No. 16/339,534, filed Apr. 4, 2019, Beibei Chen, Issued as U.S. Pat. No. 11,040,935.

U.S. Appl. No. 17/313,577, filed May 6, 2021, Beibei Chen, Issued as U.S. Pat. No. 11,673,853.

These could be monocytes, neutrophils, granulocytes, NKCs, MDSCs etc

METHODS AND MATERIALS FOR INCREASING LEVEL OF PHOSPHORYLATED AMPK PROTEIN

CLAIM OF PRIORITY

This application claims priority to U.S. Provisional Patent Application Ser. No. 62/898,285, filed on Sep. 10, 2019, and U.S. Provisional Patent Application Ser. No. 63/024,283, filed on May 13, 2020, the entire contents of which are hereby incorporated by reference.

FEDERALLY SPONSORED RESEARCH AND DEVELOPMENT

This invention was made with government support under grant numbers HL139860 and DK119627 awarded by the National Institutes of Health (NIH). The government has certain rights in the invention.

TECHNICAL FIELD

This document relates to methods and materials for increasing the level of phosphorylated 5' adenosine monophosphate (AMP)-activated protein kinase (AMPK) polypeptide within cells. For example, this document provides compounds (e.g., organic compounds) having the ability to increase the level of phosphorylated AMPK within cells, formulations containing compounds having the ability to increase the level of phosphorylated AMPK within cells, methods for making compounds having the ability to increase the level of phosphorylated AMPK within cells, methods for increasing the level of phosphorylated AMPK within cells, and methods for treating mammals (e.g., humans) having a condition responsive to an increase in the level of phosphorylated AMPK within cells.

BACKGROUND

AMPK, also known as 5' adenosine monophosphate (AMP)-activated protein kinase, is an enzyme that plays a role in cellular energy homeostasis. AMPK functions as a metabolic fuel gauge and master metabolic regulator that is activated in response to environmental stressors to restore cellular energy balance. Upon metabolic stress, AMPK suppresses anabolic and promotes catabolic processes to regain energy homeostasis. In the heart, AMPK coordinates the activation of glucose and fatty acid metabolic pathways to ensure increased production of myocardial ATP when required, such as during cardiac ischemia/reperfusion and hypertrophy, causing an increase in AMPK activity to be viewed as both protective and maladaptive.

AMPK exists as an obligate heterotrimer, composed of three subunits: a catalytic kinase a subunit and two associated regulatory subunits, β and γ subunits, that together make a functional enzyme. It is expressed in a number of tissues, including the liver, brain, and skeletal muscle. See Winder W. et al., *Am. J. Physiol.*, 277 (1 Pt 1): E1-10 (1999).

AMPK can act as a metabolic master switch regulating several intracellular systems including the cellular uptake of glucose, the β-oxidation of fatty acids, and the biogenesis of glucose transporter 4 (GLUT4) and mitochondria. See Thomson et al., *Am. J. Physiol. Endocrinol. Metab.*, 292(1): E196-202 (2007); Ojuka E. et al., *Proc. Nutr Soc.*, 63(2): 275-8 (2004); Durante et al., *Am. J. Physiol. Endocrinol. Metab.*, 283(1): E178-86 (2002); Bergeron et al., *Am. J. Physiol.*, 276(5 Pt 1): E938-44 (1999); and Winder W. et al, *J. Appl. Physiol.*, 91(3): 1017-28 (2001).

SUMMARY

This document provides methods and materials for increasing the level of phosphorylated AMPK within cells. For example, the document provides compounds (e.g., organic compounds) having the ability to increase the level of phosphorylated AMPK within cells, formulations containing compounds having the ability to increase the level of phosphorylated AMPK within cells, methods for making compounds having the ability to increase the level of phosphorylated AMPK within cells, methods for making formulations containing compounds having the ability to increase the level of phosphorylated AMPK within cells, methods for increasing the level of phosphorylated AMPK within cells, and methods for treating mammals (e.g., humans) having a condition responsive to an increase in the level of phosphorylated AMPK.

As described herein, the compounds provided herein can be used to increase the level of phosphorylated AMPK within cells in vitro or in vivo. In some cases, the compounds provided herein can be used to treat mammals (e.g., humans) having a disease, disorder, or condition associated with a low cellular level of phosphorylated AMPK. In some cases, the compounds provided herein can be used to treat mammals (e.g., humans) having a disease, disorder, or condition that is responsive to an increase in the level of phosphorylated AMPK within cells.

In some embodiments, this document provides a method for increasing the level of phosphorylated AMPK within a cell. The method comprises (or consists essentially of or consists of) administering, to a mammal (e.g., a human) containing the cell, a compound of Formula (I):

$$R^1\text{-}O\text{-}L^1\text{-}X\text{-}L^2\text{-}N(R^2)\text{-}R^3 \quad (I)$$

or a pharmaceutically acceptable salt thereof, wherein $R^1$, $L^1$, X, $L^2$, $R^2$, and $R^3$ are as described herein.

In some embodiments:
$R^1$ is selected from 5-6 membered heteroaryl and a group of formula:

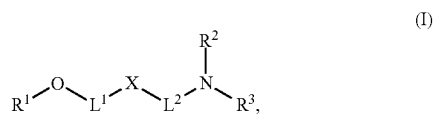

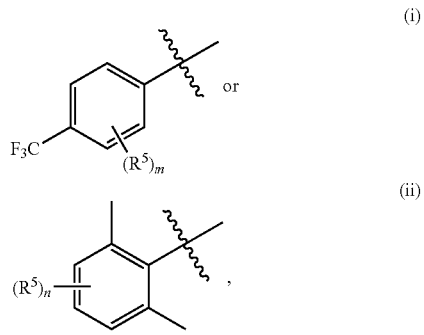

wherein said 5-6 membered heteroaryl of $R^1$ is optionally substituted with 1, 2, 3, 4, or 5 substituents independently selected from $R^5$;

$L^1$ is $C_{1-4}$ alkylene, which is optionally substituted with halo or $OR^4$;

$L^2$ is $C_{1-4}$ alkylene or $L^2$ is absent;

X is selected from $CR^7(OR^4)$, C=O, and $C_{3-6}$ cycloalkylene; or X is absent;

$R^7$ is selected from H, $C_{1-6}$ alkyl, $C_{1-6}$ haloalkyl, $C_{2-6}$ alkenyl, and $C_{2-6}$ alkynyl;

$R^2$ and $R^3$ are each independently selected from H, $C_{1-6}$ alkyl, $Cy^1$, $C_{1-6}$ haloalkyl, $C_{2-6}$ alkenyl, $C_{2-6}$ alkynyl, $C(=O)Cy^1$, and $S(=O)_2Cy^1$, wherein said $C_{1-6}$ alkyl, $C_{2-6}$ alkenyl, $C_{2-6}$ alkynyl, and $C_{1-6}$ haloalkyl are each optionally substituted with 1 or 2 independently selected $Cy^1$;

provided that at least one of $R^2$ and $R^3$ is other than H;

$R^4$ is selected from H, $C(O)R^{b1}$, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;

or $R^4$ and $R^2$ together with the O atom to which $R^4$ is attached and N atom to which $R^2$ is attached form 5-10 membered heterocycloalkyl, which is optionally substituted with 1 or 2 independently selected $Cy^1$;

or $R^2$ and $R^3$, together with the N atom to which they are attached, form 4-16 membered heterocycloalkyl ring, which is optionally substituted with 1 or 2 substituents independently selected from $R^6$;

each $R^6$ is independently selected from $C_{1-6}$ alkyl, $OR^{a1}$, $C(O)NR^{c1}R^{d1}$, $C(O)OR^{a1}$, $C_{1-6}$ haloalkyl, and $Cy^1$, wherein said $C_{1-6}$ alkyl is optionally substituted with a substituent selected from $OR^{a1}$, $C(O)NR^{c1}R^{d1}$, and $C(O)OR^{a1}$;

m is 0, 1, 2, 3, or 4;

n is 0, 1, 2, or 3;

each $R^5$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, thio, $C_{1-6}$ alkylthio, carboxy, amino, $C_{1-6}$ alkylamino, and di($C_{1-6}$ alkyl)amino;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_4$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino, provided that when $R^4$ is H, then at least one of $R^2$ and $R^3$ is selected from $C_{1-6}$ alkyl, $Cy^2$, $C_{1-6}$ haloalkyl, $C_{2-6}$ alkenyl, $C_{2-6}$ alkynyl, $C(=O)Cy^2$, and $S(=O)_2Cy^2$, wherein said $C_{1-6}$ alkyl, $C_{2-6}$ alkenyl, and $C_{2-6}$ alkynyl are each optionally substituted with 1 or 2 independently selected $Cy^2$, and each of said $Cy^2$ is independently selected from $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

In some embodiments:

$R^1$ is selected from 5-6 membered heteroaryl and a group of formula:

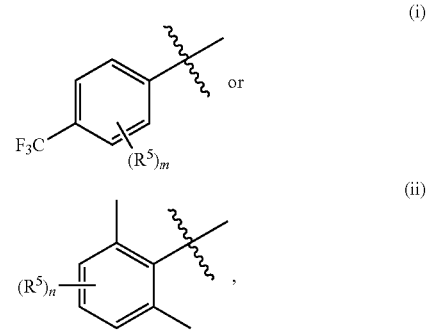

wherein said 5-6 membered heteroaryl of $R^1$ is optionally substituted with 1, 2, 3, 4, or 5 substituents independently selected from $R^5$;

$L^1$ is $C_{1-4}$ alkylene, which is optionally substituted with halo or $OR^4$;

$L^2$ is $C_{1-4}$ alkylene or $L^2$ is absent;

X is selected from $CR^7(OR^4)$, C=O, and $C_{3-6}$ cycloalkylene; or X is absent;

$R^7$ is selected from H, $C_{1-6}$ alkyl, $C_{1-6}$ haloalkyl, $C_{2-6}$ alkenyl, and $C_{2-6}$ alkynyl;

$R^2$ and $R^3$ are each independently selected from H, $C_{1-6}$ alkyl, $Cy^1$, $C_{1-6}$ haloalkyl, $C_{2-6}$ alkenyl, $C_{2-6}$ alkynyl, C(=O)$Cy^1$, and S(=O)$_2Cy^1$, wherein said $C_{1-6}$ alkyl, $C_{2-6}$ alkenyl, $C_{2-6}$ alkynyl, and $C_{1-6}$ haloalkyl are each optionally substituted with 1 or 2 independently selected $Cy^1$;

provided that at least one of $R^2$ and $R^3$ is other than H;

$R^4$ is selected from H, C(O)$R^{b1}$, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;

or $R^4$ and $R^2$ together with the O atom to which $R^4$ is attached and N atom to which $R^2$ is attached form 5-10 membered heterocycloalkyl, which is optionally substituted with 1 or 2 independently selected $Cy^1$;

or $R^2$ and $R^3$, together with the N atom to which they are attached, form 4-16 membered heterocycloalkyl ring, which is optionally substituted with 1 or 2 substituents independently selected from $R^6$;

each $R^6$ is independently selected from $C_{1-6}$ alkyl, $OR^{a1}$, C(O)$NR^{c1}R^{d1}$, C(O)$OR^{a1}$, $C_{1-6}$ haloalkyl, and $Cy^1$, wherein said $C_{1-6}$ alkyl is optionally substituted with a substituent selected from $OR^{a1}$, C(O)$NR^{c1}R^{d1}$, and C(O)$OR^{a1}$;

m is 0, 1, 2, 3, or 4;

n is 0, 1, 2, or 3;

each $R^5$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, thio, $C_{1-6}$ alkylthio, carboxy, amino, $C_{1-6}$ alkylamino, and di($C_{1-6}$ alkyl)amino;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^2$, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}$S(O)$_2R^{b1}$, S(O)$_2R^{b1}$, and S(O)$_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a1}$, C(O)$R^{b1}$, C(O)$NR^{c1}R^{a1}$, C(O)$OR^{a1}$, $NR^{c1}R^{d1}$, $NR^{c1}$C(O)$R^{b1}$, $NR^{c1}$C(O)$OR^{a1}$, $NR^{c1}$S(O)$_2R^{b1}$, S(O)$_2R^{b1}$, and S(O)$_2NR^{c1}R^{a1}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{a1}$, C(O)$OR^{a1}$, $NR^{c1}R^{a1}$, $NR^{c1}$C(O)$R^{b1}$, $NR^{c1}$C(O)$OR^{a1}$, $NR^{c1}$S(O)$_2R^{b1}$, S(O)$_2R^{b1}$, and S(O)$_2NR^{c1}R^{a1}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a1}$, C(O)$R^{b1}$, C(O)$NR^{c1}R^{a1}$, C(O)$OR^{a1}$, $NR^{c1}R^{d1}$, $NR^{c1}$C(O)$R^{b1}$, $NR^{c1}$C(O)$OR^{a1}$, NR'S(O)$_2R^{b1}$, S(O)$_2R^{b1}$, and S(O)$_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, provided that when $R^4$ is H, then $R^2$ and $R^3$ are both independently selected from $C_{1-6}$ alkyl, $C_{1-6}$ haloalkyl, $C_{2-6}$ alkenyl, $C_{2-6}$ alkynyl, $Cy^3$, C(=O)$Cy^3$, and S(=O)$_2Cy^3$, wherein said $C_{1-6}$ alkyl, $C_{1-6}$ haloalkyl, $C_{2-6}$ alkenyl, and $C_{2-6}$ alkynyl are each substituted with 1 or 2 independently selected $Cy^3$, and each of said $Cy^3$ is independently selected from $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

In some embodiments:

X is selected from CH(OR$^4$) and C=O; or X is absent; and $R^4$ is selected from $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$.

In some embodiments, the compound of Formula (I) has formula:

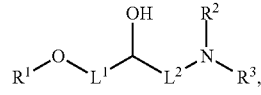

or a pharmaceutically acceptable salt thereof.

In some embodiments, the compound of Formula (I) has formula:

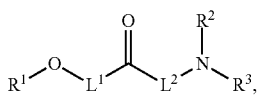

or a pharmaceutically acceptable salt thereof.

In some embodiments, the compound of Formula (I) has formula:

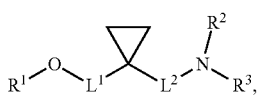

or a pharmaceutically acceptable salt thereof.

In some embodiments, $L^2$ is $C_{1-4}$ alkylene.

In some embodiments, $L^2$ is methylene.

In some embodiments, the compound of Formula (I) has formula:

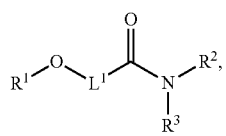

or a pharmaceutically acceptable salt thereof.

In some embodiments, the compound of Formula (I) has formula:

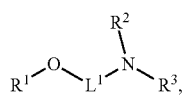

or a pharmaceutically acceptable salt thereof.

In some embodiments, $L^1$ is selected from methylene and ethylene.

In some embodiments, $L^1$ is methylene.

In some embodiments, $R^1$ is 5-6 membered heteroaryl, optionally substituted with 1, 2, or 3 substituents independently selected from $R^5$.

In some embodiments, the 5-6 membered heteroaryl is selected from pyridinyl and pyrimidinyl.

In some embodiments, m is 0, 1, or 2.

In some embodiments, n is 0, 1, or 2.

In some embodiments, $R^5$ is selected from halo, $C_{1-6}$ alkyl, $C_{1-4}$ haloalkyl, $C_{1-6}$ alkoxy, and $C_{1-6}$ haloalkoxy.

In some embodiments, $R^1$ is a group of formula:

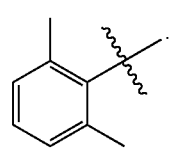 [SMILES: *c1c(C)cccc1C]

In some embodiments, $R^1$ is a group of formula:

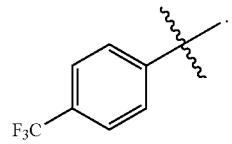

In some embodiments, the compound of Formula (I) is selected from:

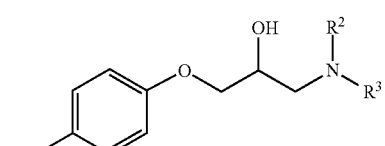

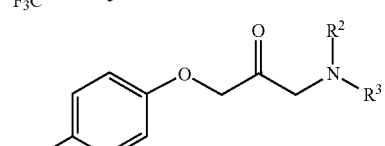

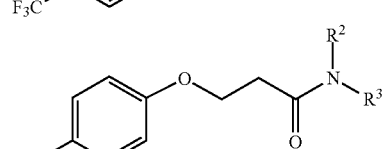

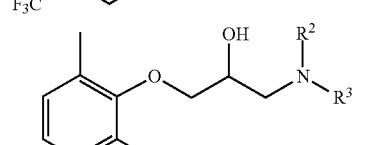

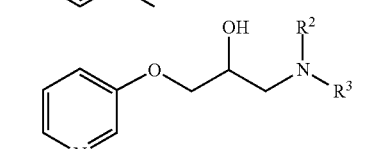

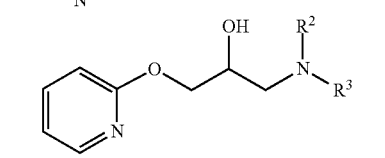

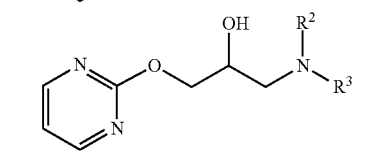

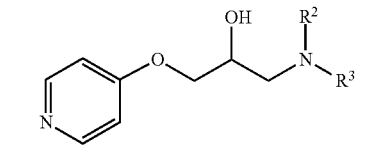

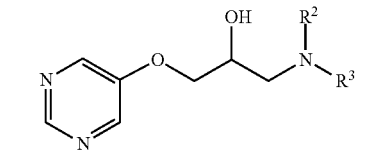

-continued

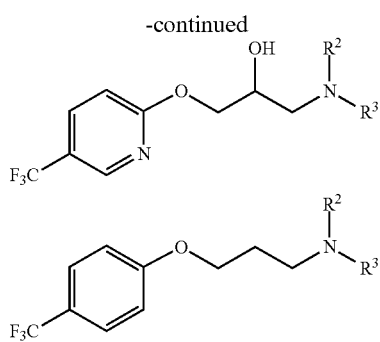

or a pharmaceutically acceptable salt thereof.

In some embodiments, the compound of Formula (I) is selected from:

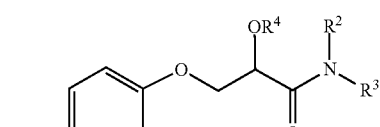

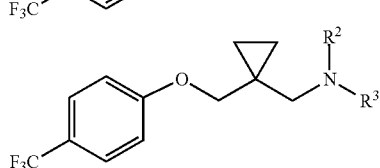

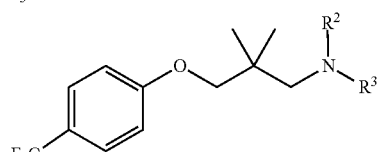

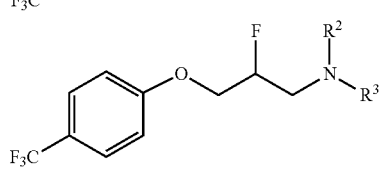

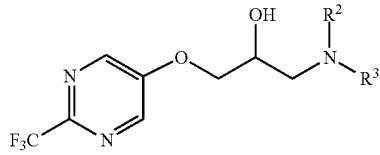

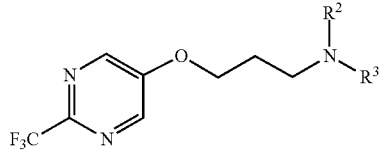

or a pharmaceutically acceptable salt thereof.

In some embodiments, $R^2$ and $R^3$ are each independently selected from H, $C_{1-6}$ alkyl, $Cy^1$, $C(=O)Cy^1$, and $S(=O)_2Cy^1$, wherein said $C_{1-6}$ alkyl, is optionally substituted with 1 or 2 independently selected $Cy^1$.

In some embodiments, $R^2$ and $R^3$ are each independently an $C_{1-6}$ alkyl substituted with 1 or 2 independently selected $Cy^1$.

In some embodiments:

$R^2$ is selected from H and $C_{1-6}$ alkyl; and $R^3$ is $C_{1-6}$ alkyl substituted with 1 or 2 independently selected $Cy^1$.

In some embodiments:

$R^2$ is $C_{1-6}$ alkyl substituted with 1 or 2 independently selected $Cy^1$; and $R^3$ is selected from $Cy^1$, $C(=O)Cy^1$ and $S(=O)_2Cy^1$.

In some embodiments, $R^2$ and $R^3$, together with the N atom to which they are attached, form 4-16 membered heterocycloalkyl ring, which is optionally substituted with $Cy^1$.

In some embodiments, the 4-16 membered heterocycloalkyl ring is selected from tetrahydroisoquinolinyl, isoindolinyl, and dihydrodibenzoazepinyl.

In some embodiments, $R^2$ and $R^3$, together with the N atom to which they are attached, form a ring of formula selected from:

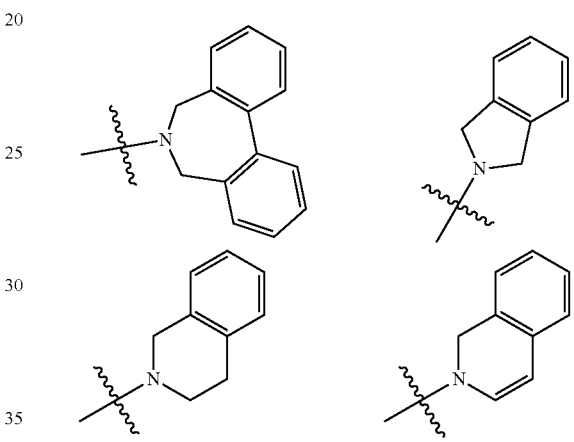

each of which is optionally substituted with a substituent selected from $Cy^1$, $C(O)OR^{a1}$, and an $C_{1-6}$ alkyl optionally substituted with $OR^{a1}$.

In some embodiments, $R^2$ and $R^3$, together with the N atom to which they are attached, form a ring of formula selected from:

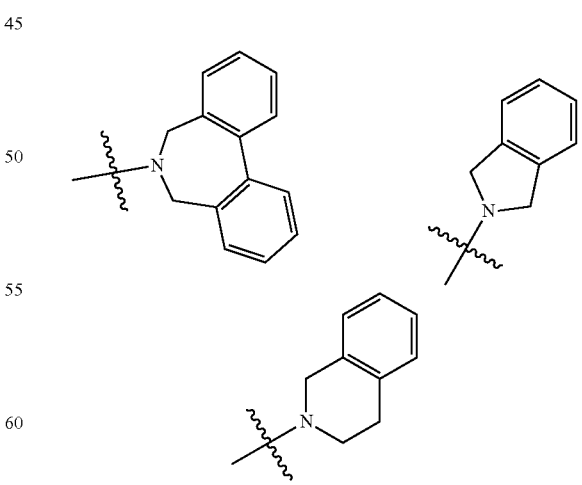

each of which is optionally substituted with $Cy^1$.

In some embodiments, the compound of Formula (I) is selected from:

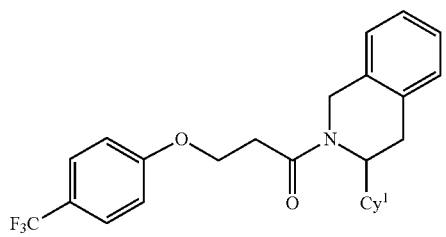

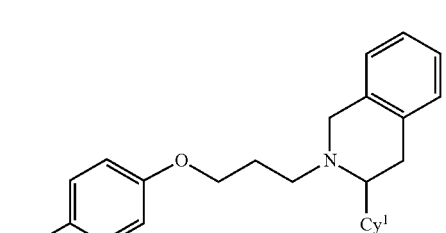

or a pharmaceutically acceptable salt thereof.

In some embodiments, the compound of Formula (I) has formula:

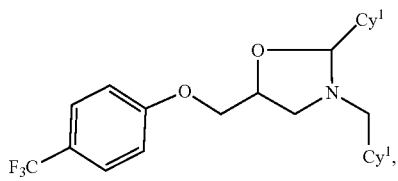

or a pharmaceutically acceptable salt thereof.

In some embodiments, $Cy^1$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy1}$.

In some embodiments, $Cy^1$ is selected from phenyl, cyclopropyl, cyclohexyl, pyridinyl, pyrimidinyl, pyridazinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

In some embodiments, $Cy^1$ is selected from phenyl, cyclopropyl, cyclohexyl, pyridinyl, pyrimidinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

In some embodiments, each $R^{Cy1}$ is independently selected from halo, CN, $C(O)NR^{c1}R^{d1}$, $C_{1-6}$ alkyl, $C_{1-6}$ haloalkyl, and 5-10 membered heteroaryl, wherein said 5-10 membered heteroaryl is optionally substituted with halo, $C_{1-6}$ alkyl, $C_{1-6}$ alkoxy, $C_{1-6}$ haloalkyl, and $C_{1-6}$ haloalkoxy.

In some embodiments, the compound of Formula (I) is selected from any one of the following compounds:

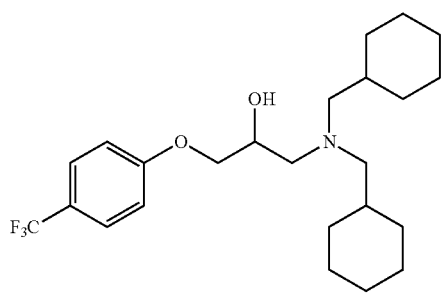

BC19801

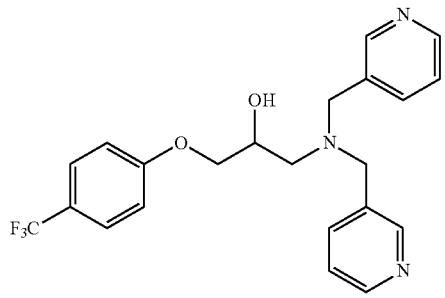

BC19805

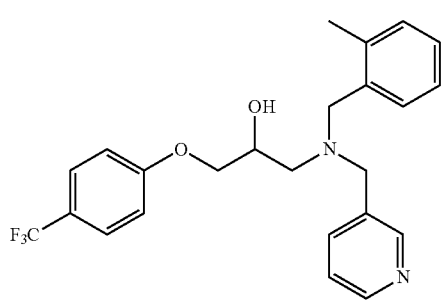

BC19806

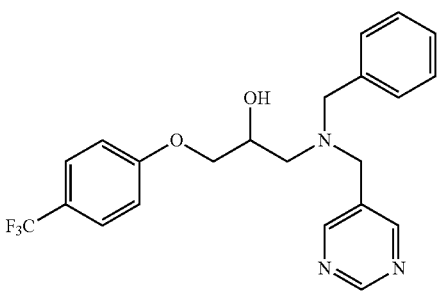

BC19811

23 BC19823

24 BC19824

25 BC19825

26 BC19826

27 BC19827

28 BC19828

29 BC19829

30 BC19830

-continued
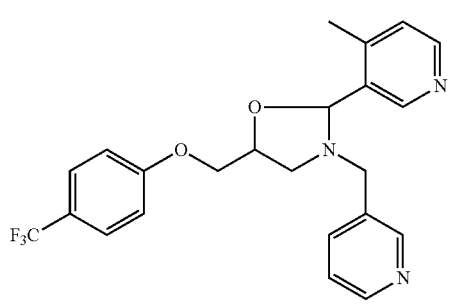
BC19831
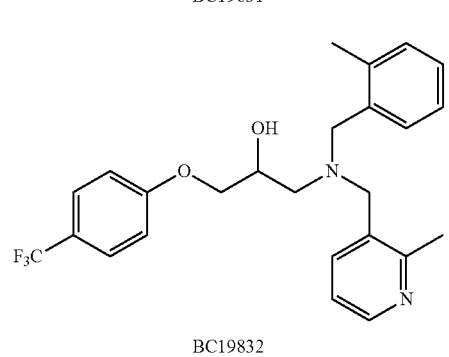
BC19832
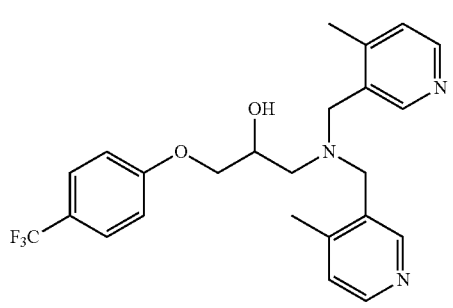
BC19833
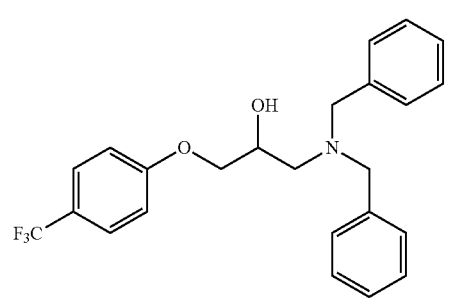
BC19834
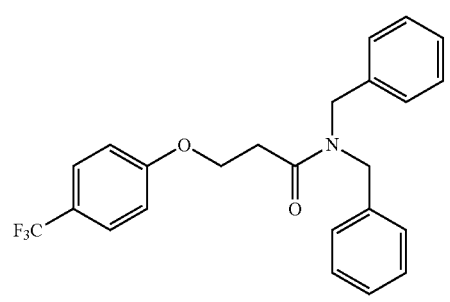
BC19835
-continued
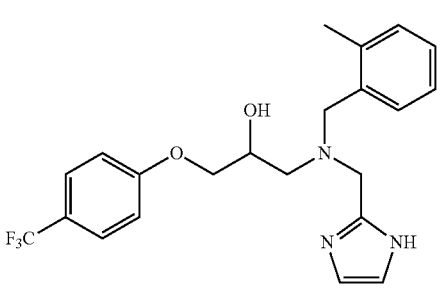
BC19836
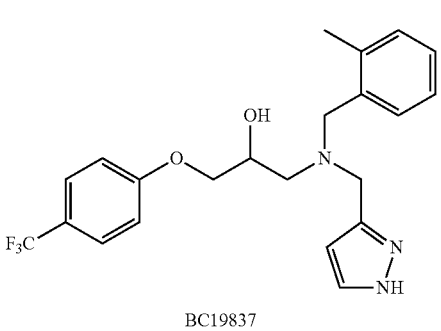
BC19837
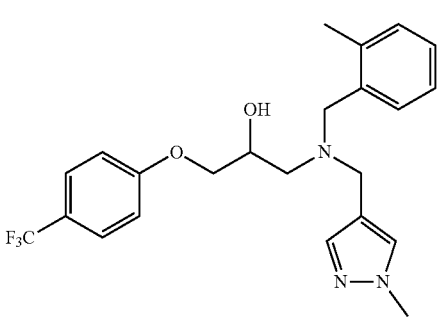
BC19838
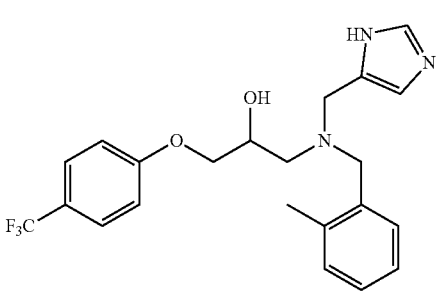
BC19839
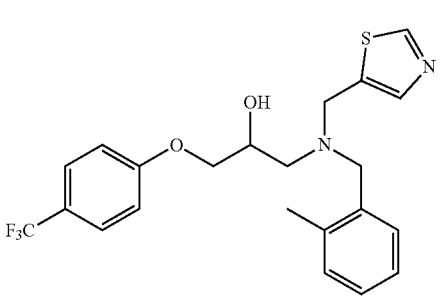
BC19840

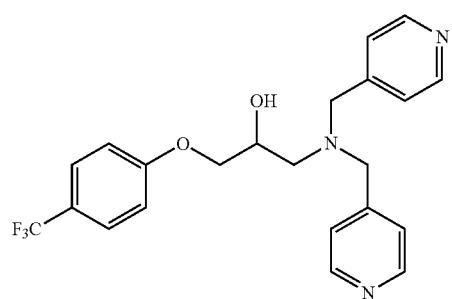
BC19841
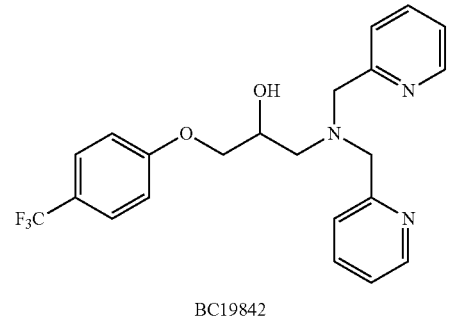
BC19842
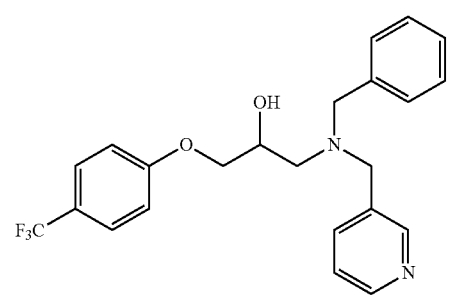
BC19843
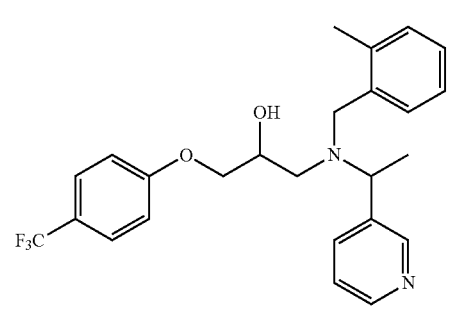
BC19845
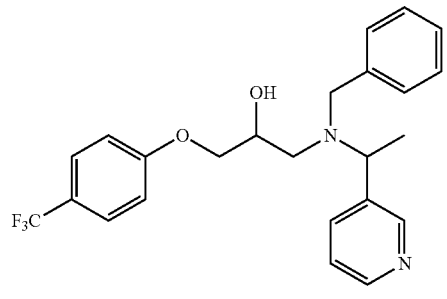
BC19846
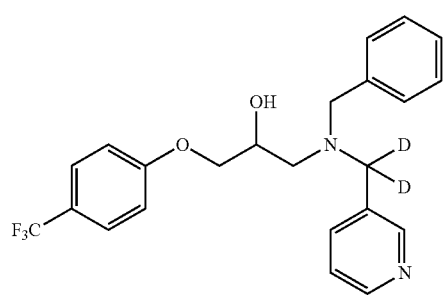
BC19847
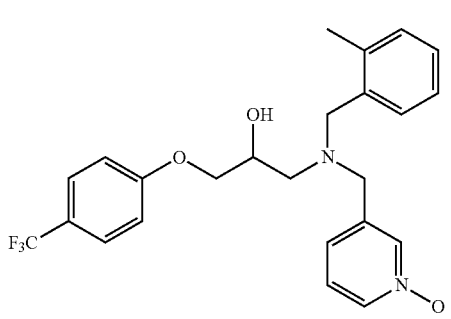
BC19851
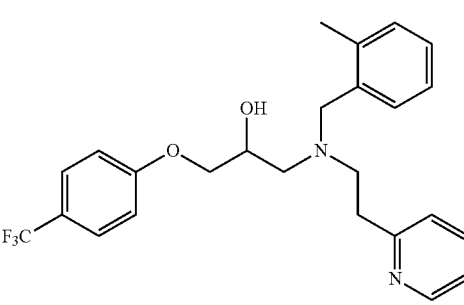
BC19852
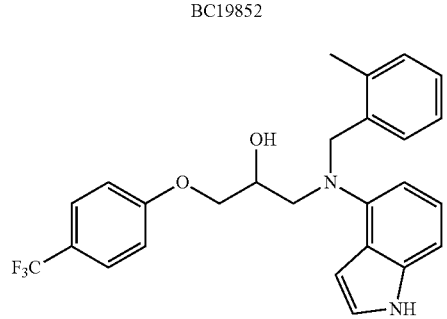
BC19853

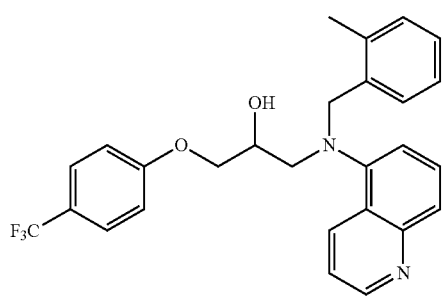
BC19854
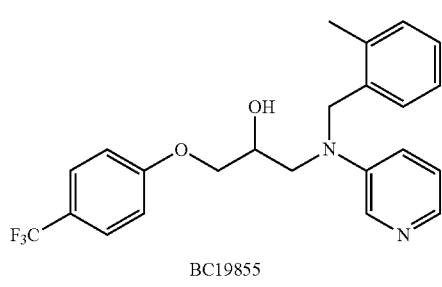
BC19855
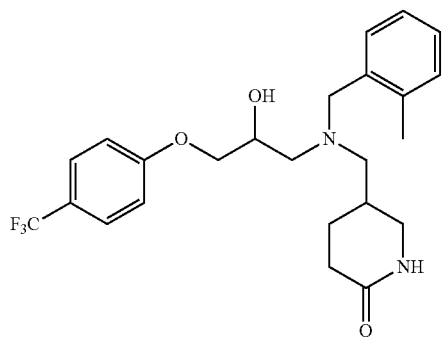
BC19858
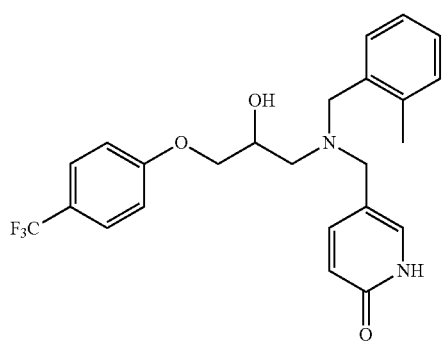
BC19859
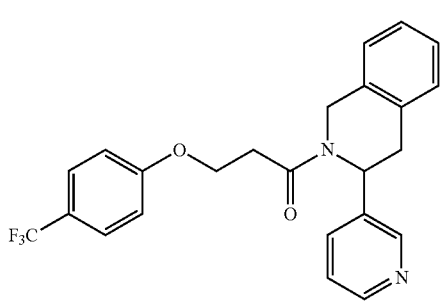
BC19862
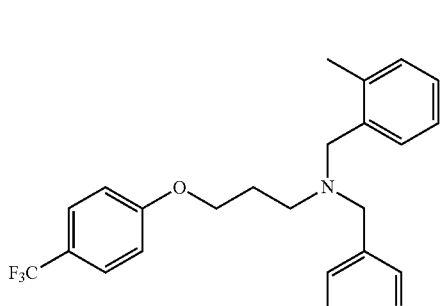
BC19863
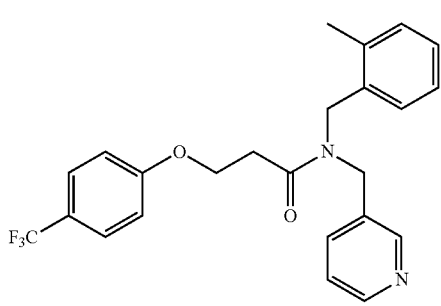
BC19864
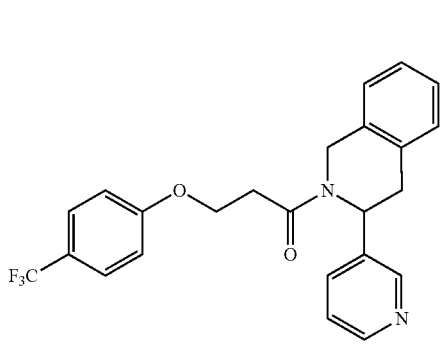
BC19865

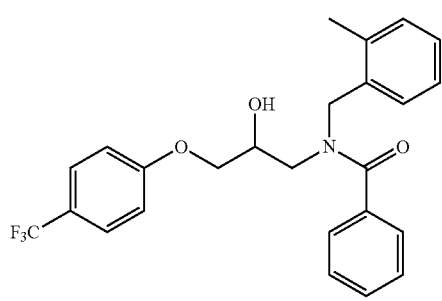
BC19866
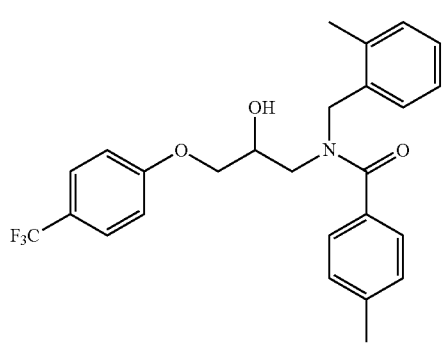
BC19867
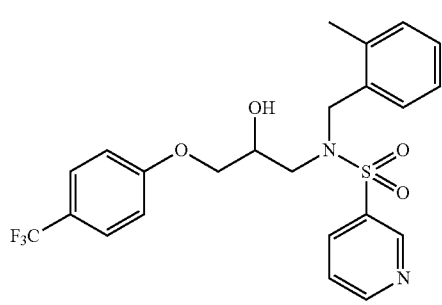
BC19868
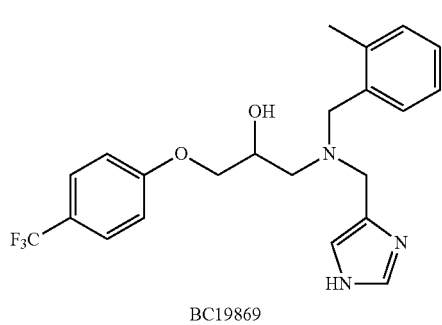
BC19869
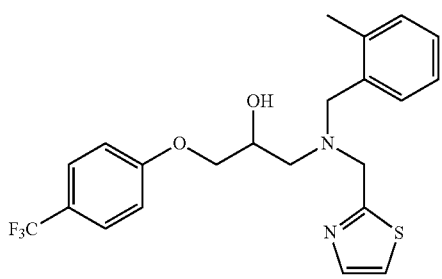
BC19870
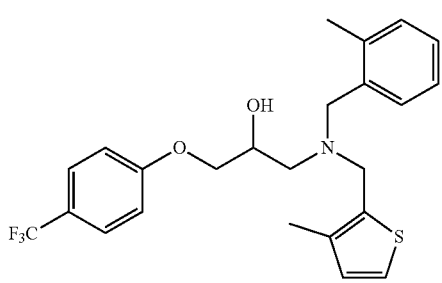
BC19871
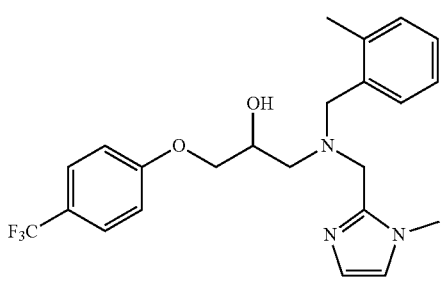
BC19872
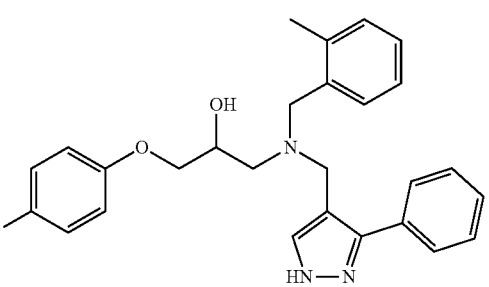
BC19873
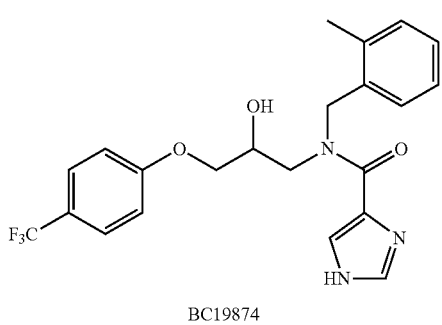
BC19874

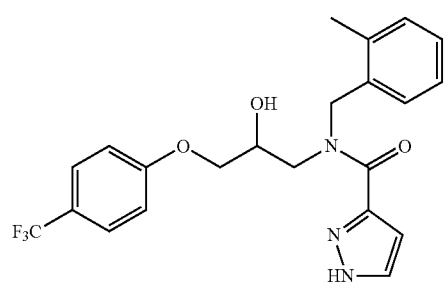
BC19875
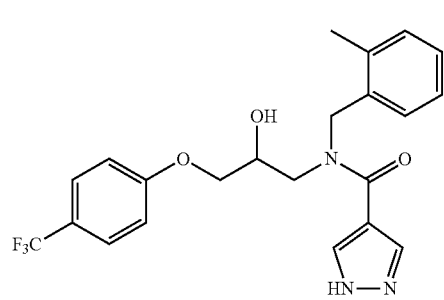
BC19876

BC19877
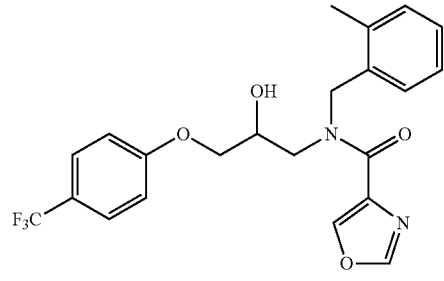
BC19878

BC19879
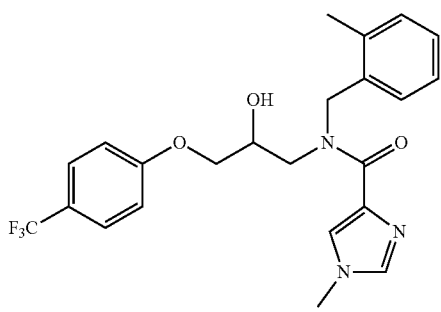
BC19880
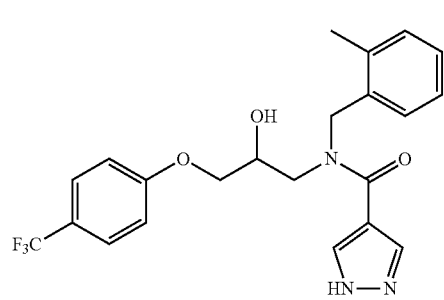
BC19881
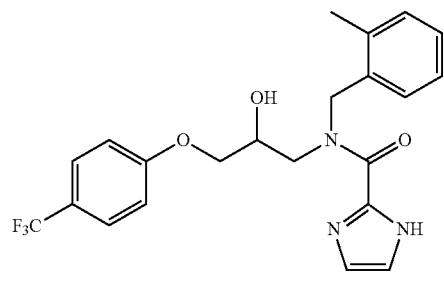
BC19882
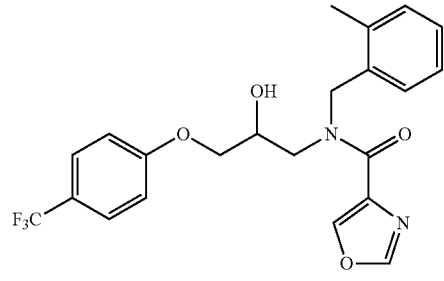
BC19883
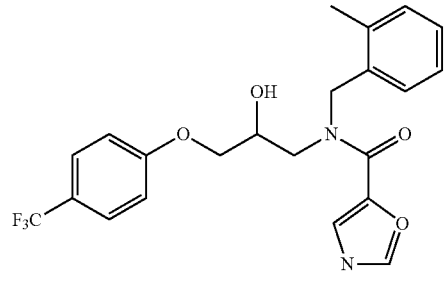
BC19884

85
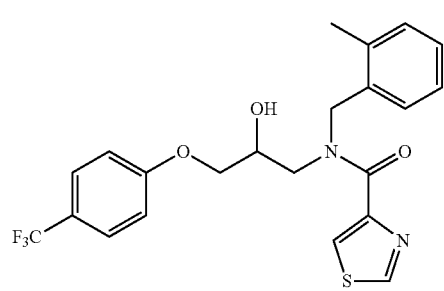
BC19885
86
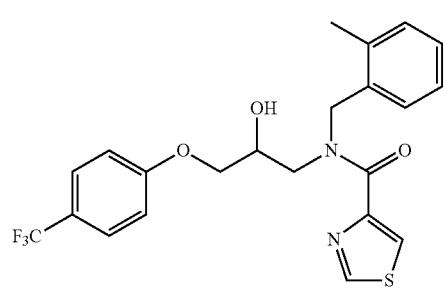
BC19886
or a pharmaceutically acceptable salt thereof.
In some embodiments, the compound of Formula (I) is selected from any one of the following compounds:
89
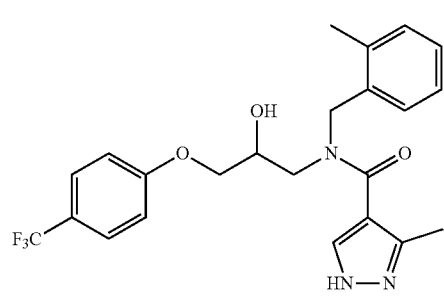
BC19889
90
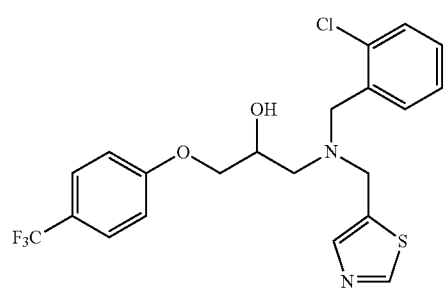
BC19890
91
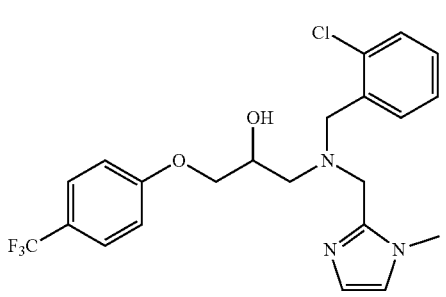
BC19891
97
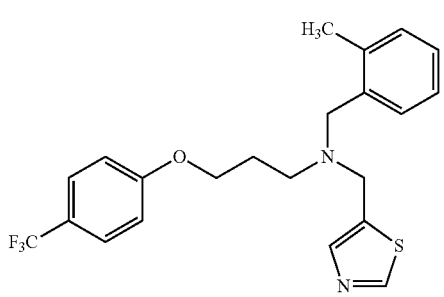
BC19897
99
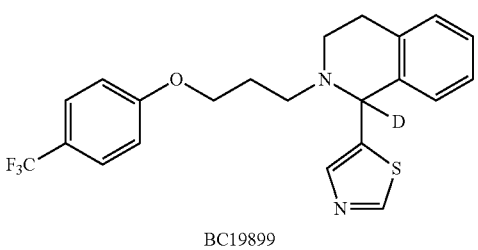
BC19899
100
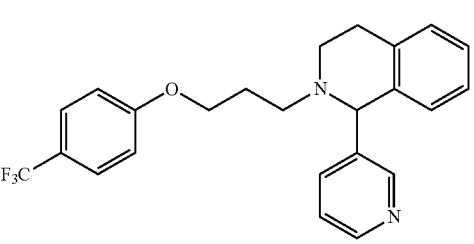
BC191000
101
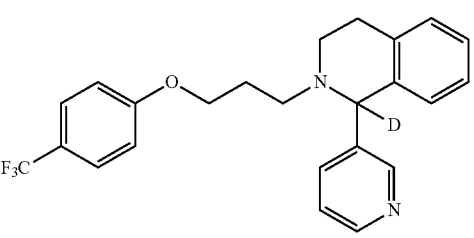
BC191001

-continued
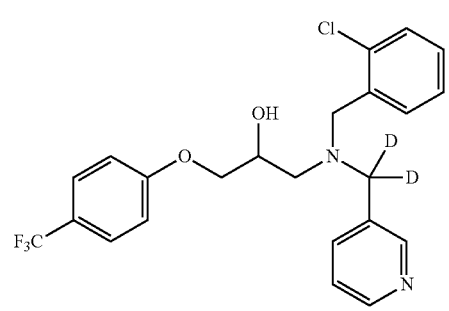
BC191002
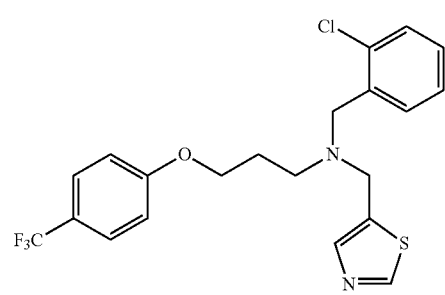
BC191004
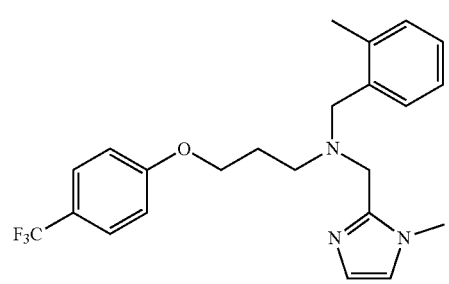
BC191005
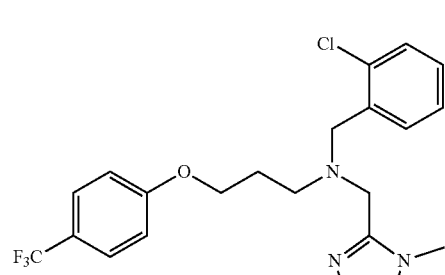
BC191006
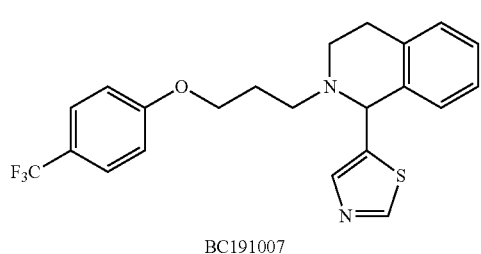
BC191007
-continued
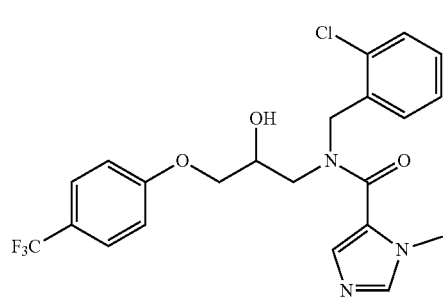
BC191008
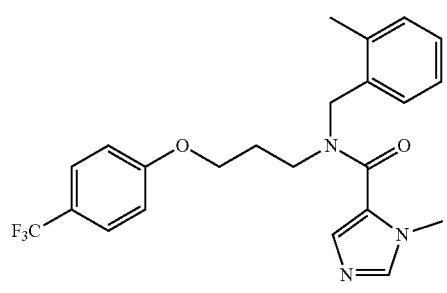
BC191009
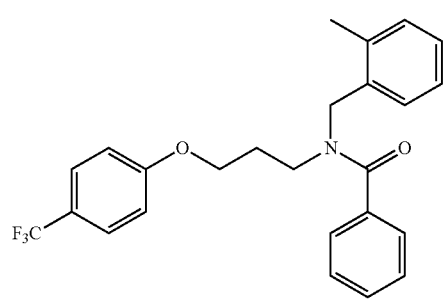
BC191010
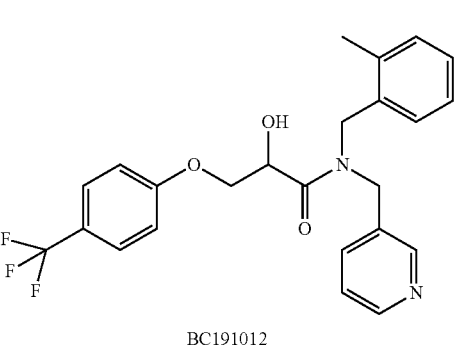
BC191012
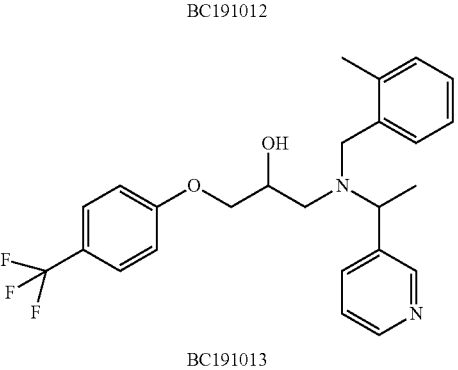
BC191013

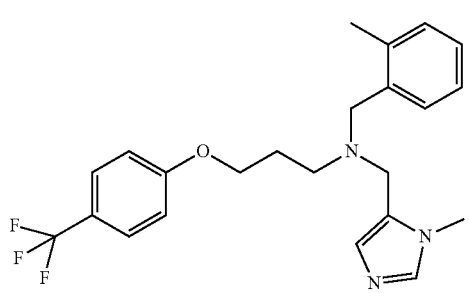
BC191014
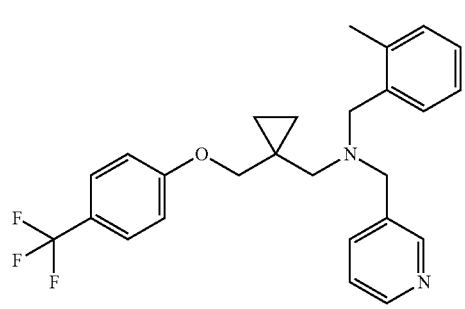
BC191015
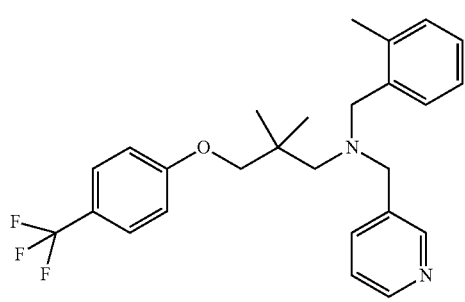
BC191016
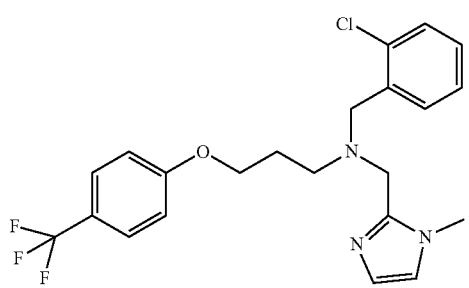
BC191017
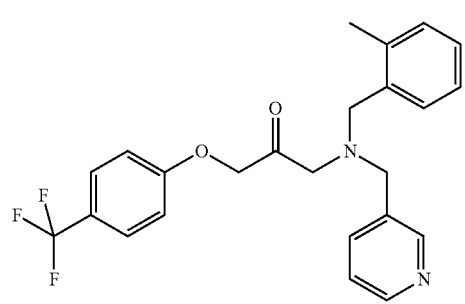
BC191018
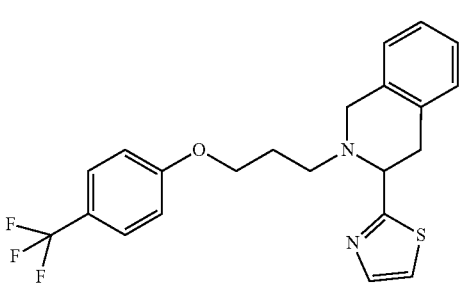
BC191019
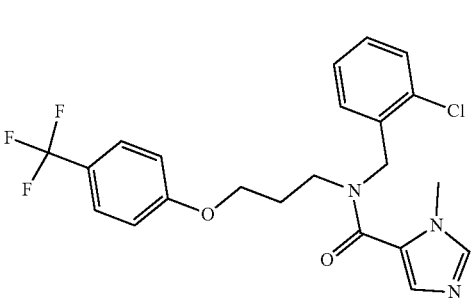
BC191020
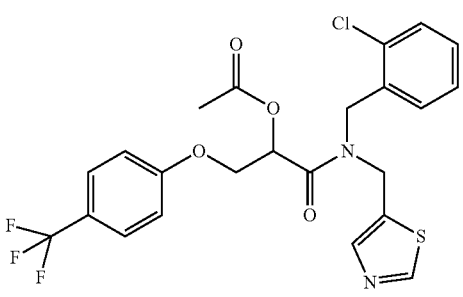
BC191021
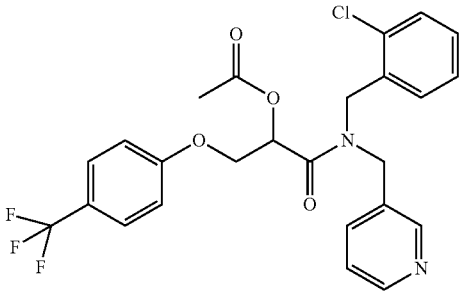
BC191022
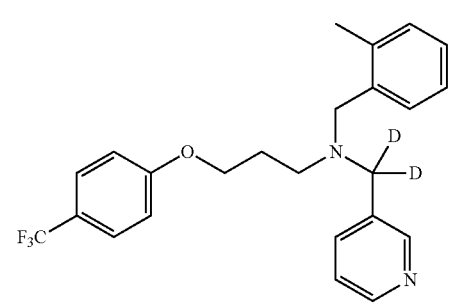
BC191024

136
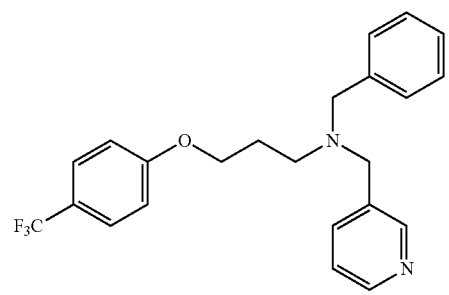
BC191025
137
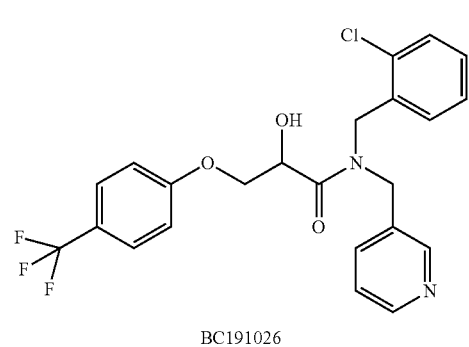
BC191026
138
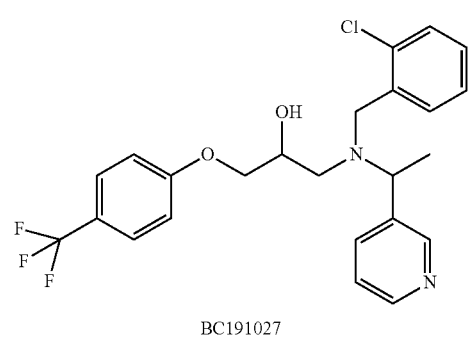
BC191027
141
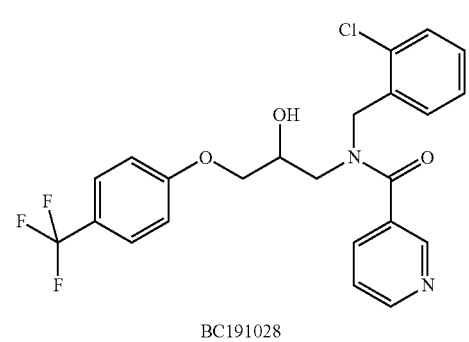
BC191028
142
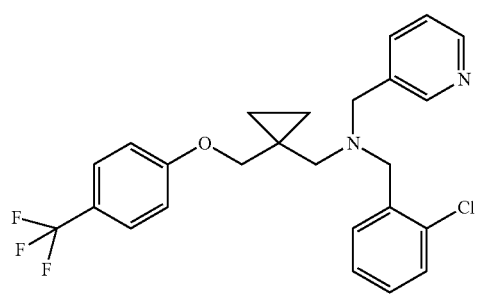
BC191029
143
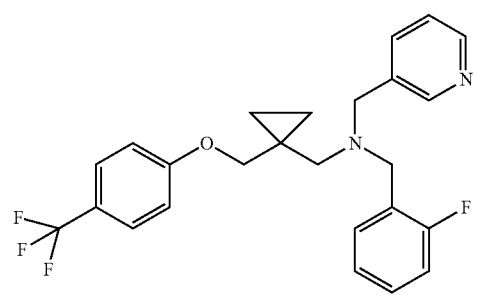
BC191030
144
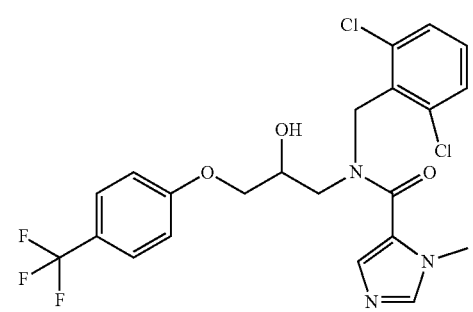
BC191031
145
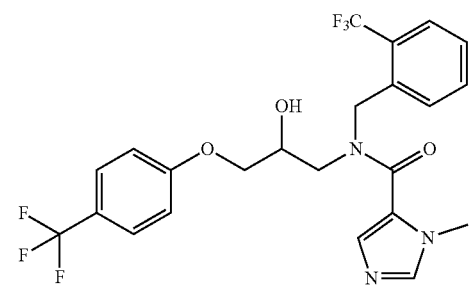
BC191032

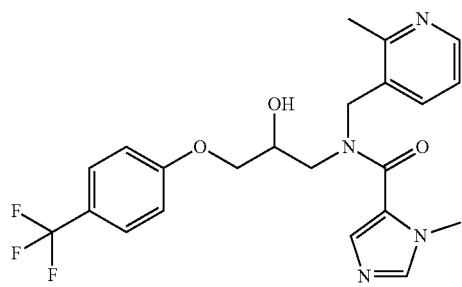
BC191033
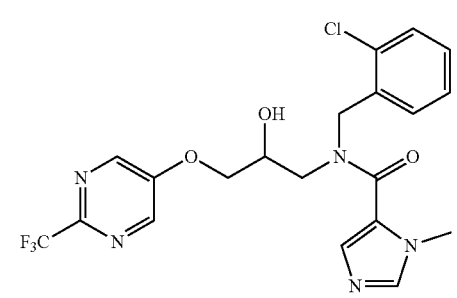
BC191035
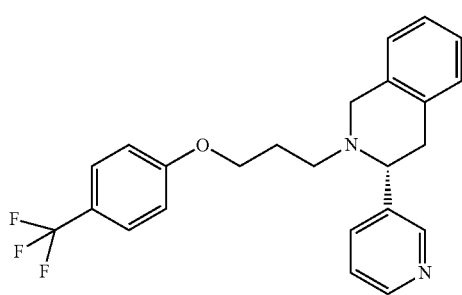
BC19865A
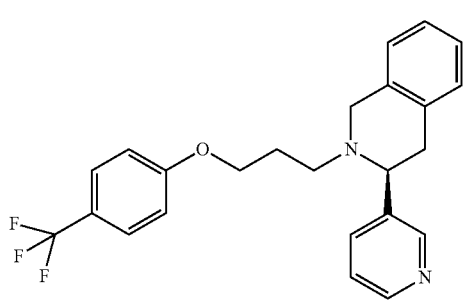
BC19865B
-continued
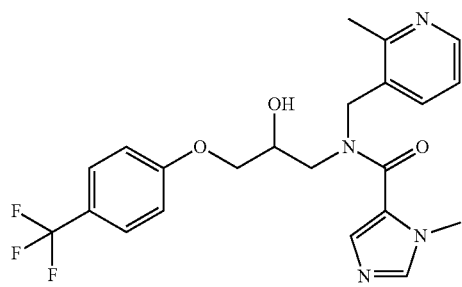
BC191037
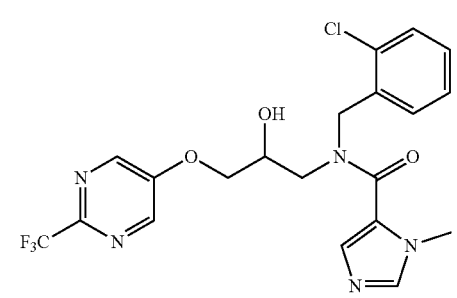
BC191038
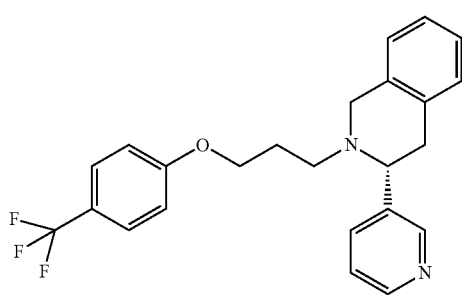
BC191039
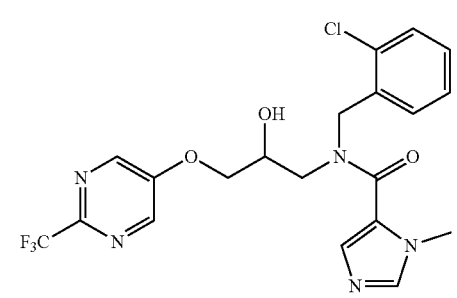
BC191040
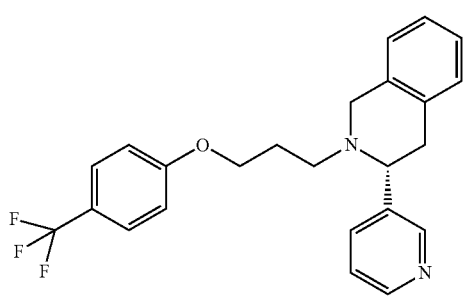
BC191041

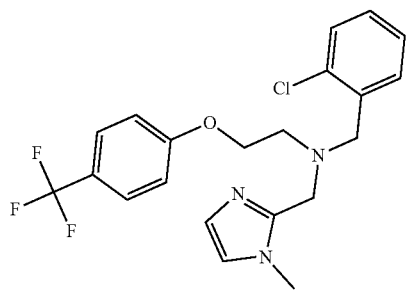
BC191042
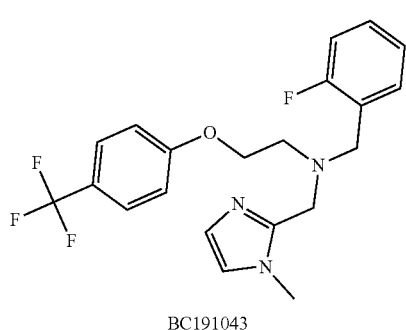
BC191043
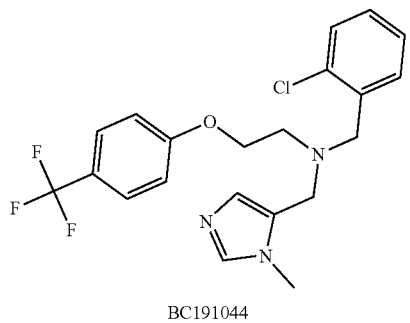
BC191044
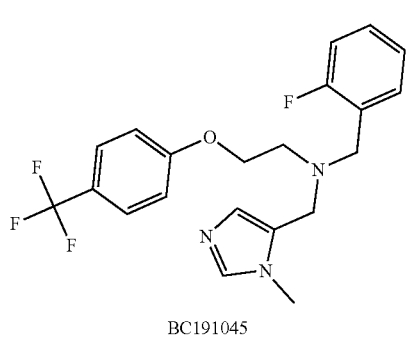
BC191045
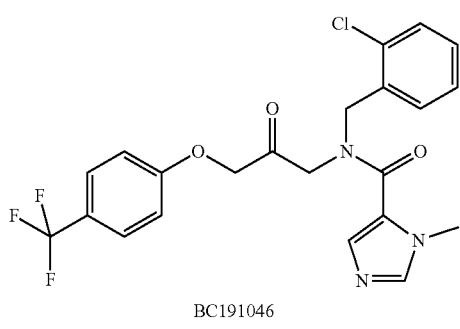
BC191046
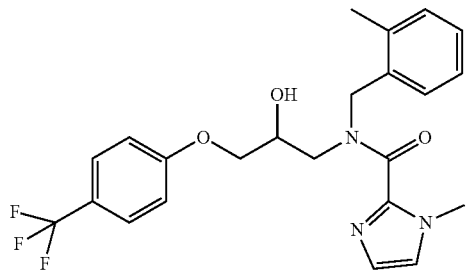
BC191047
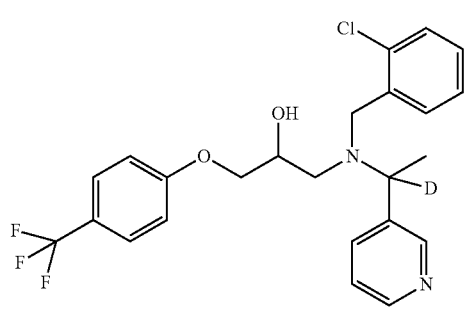
BC191048
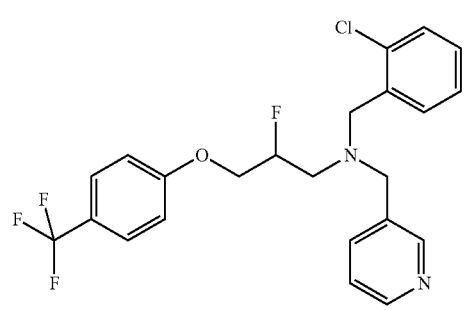
BC191049
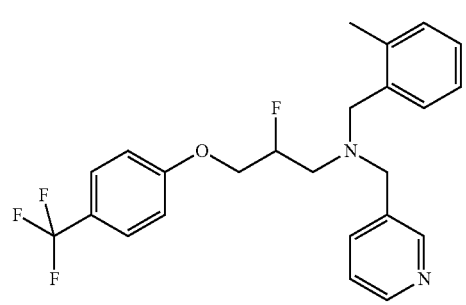
BC191050
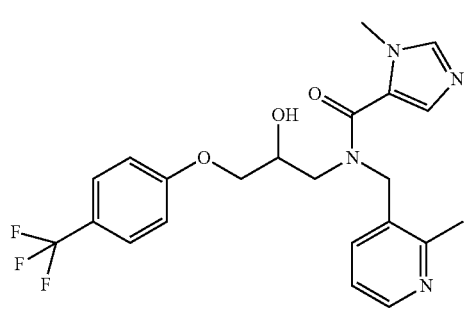
BC191051

-continued
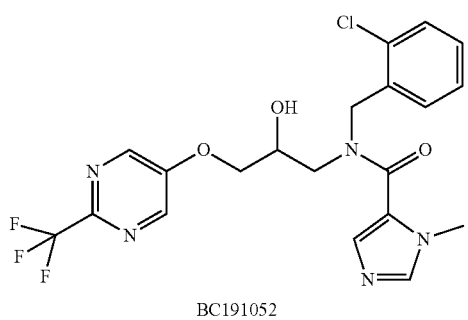
BC191052
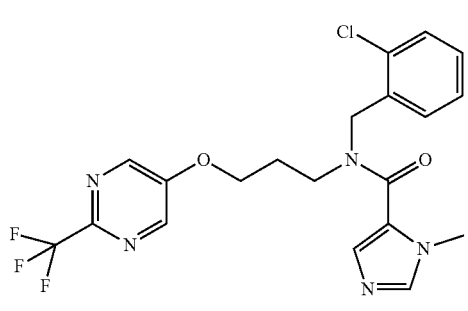
BC191053
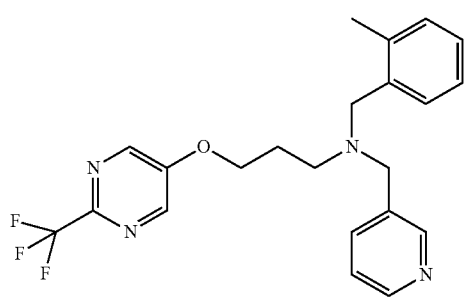
BC191054
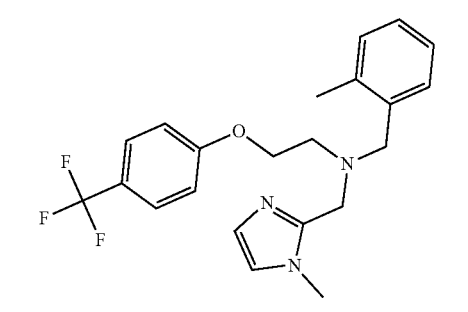
BC191055
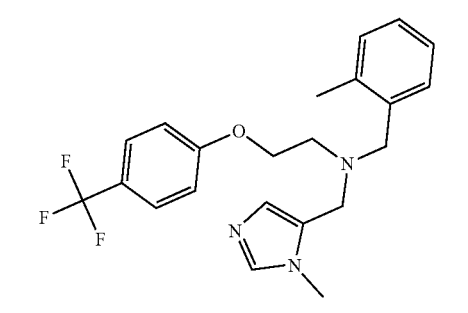
BC191056
-continued
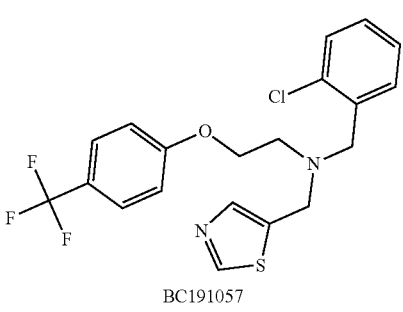
BC191057
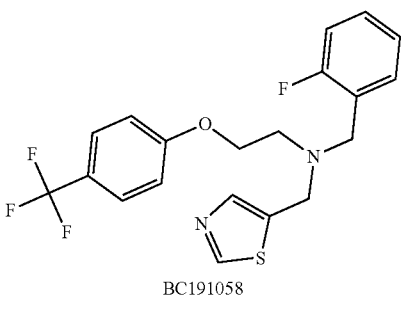
BC191058
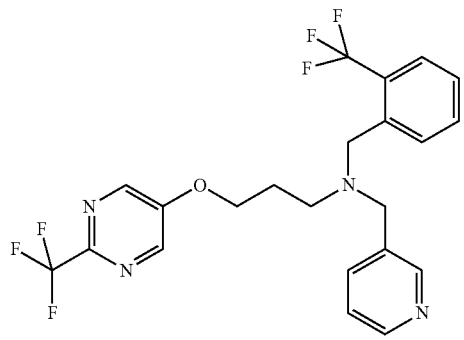
BC191059
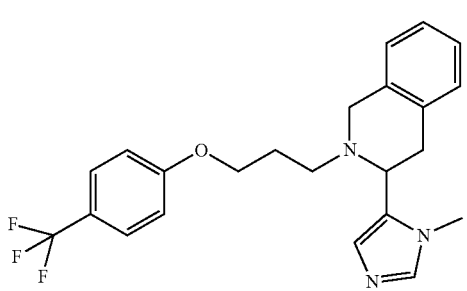
BC191060
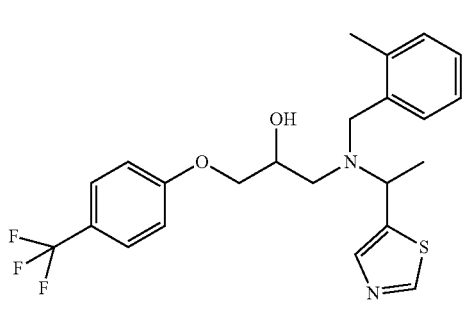
BC191061

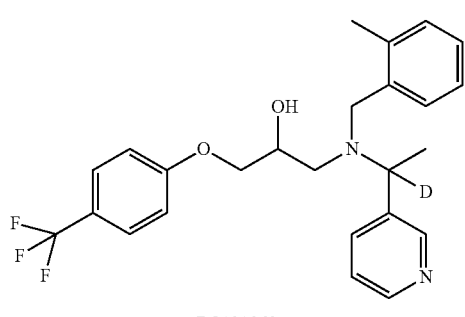
BC191062
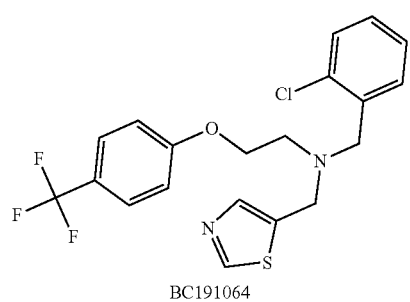
BC191064
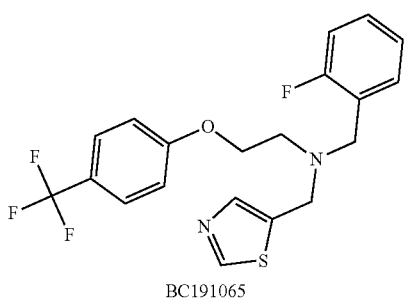
BC191065
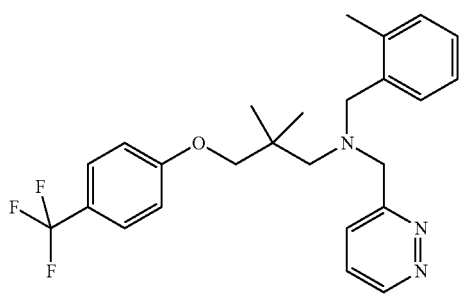
BC191066
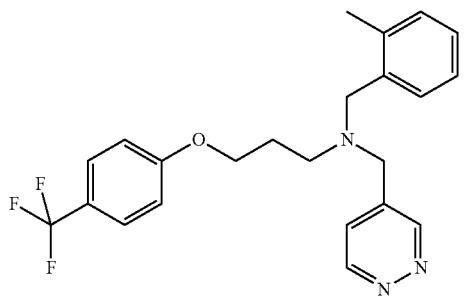
BC191067
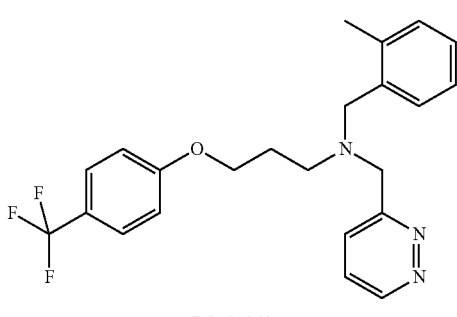
BC191068
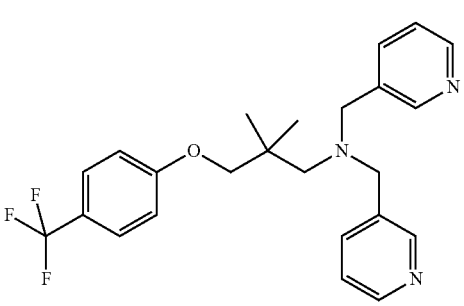
BC191069
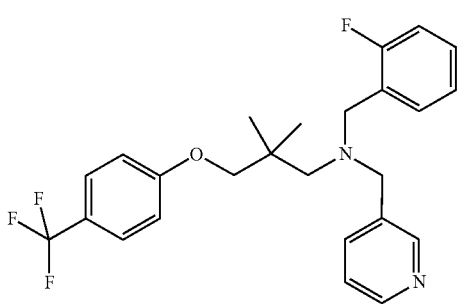
BC191070
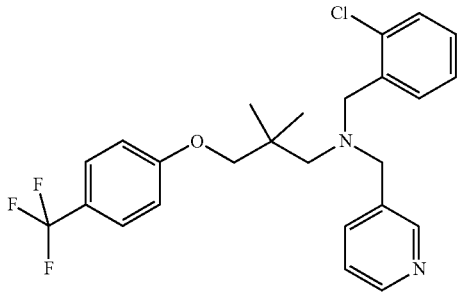
BC191071

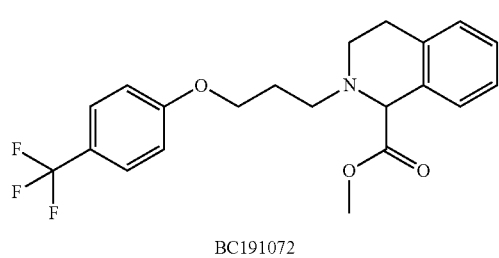
BC191072
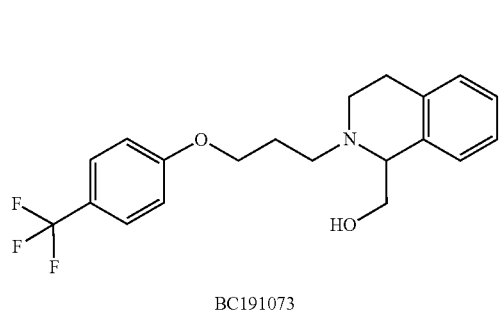
BC191073
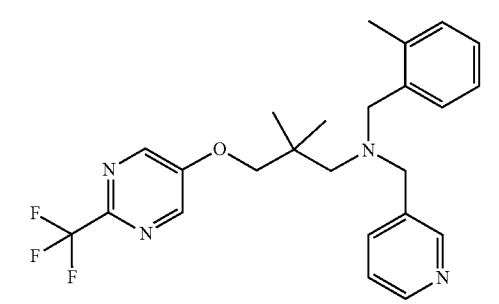
BC191075
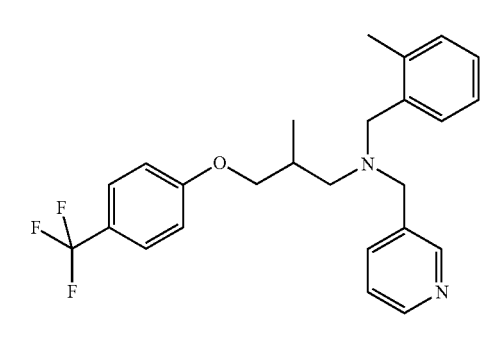
BC191076
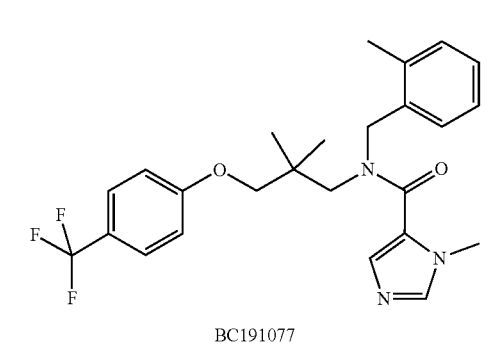
BC191077
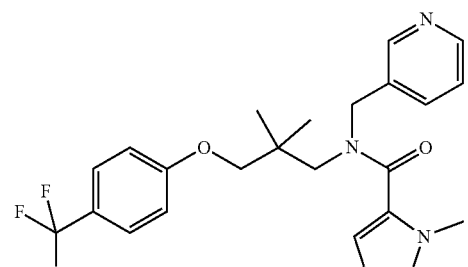
BC191078
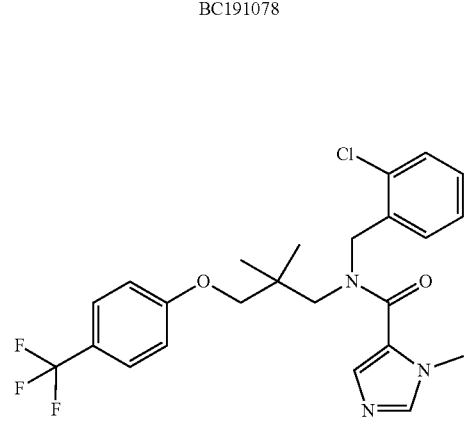
BC191079
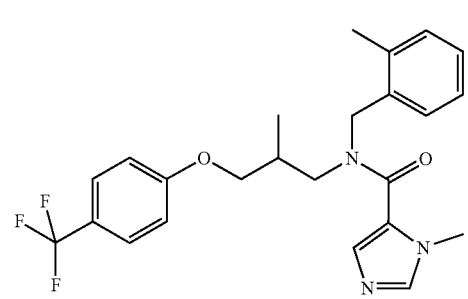
BC191080
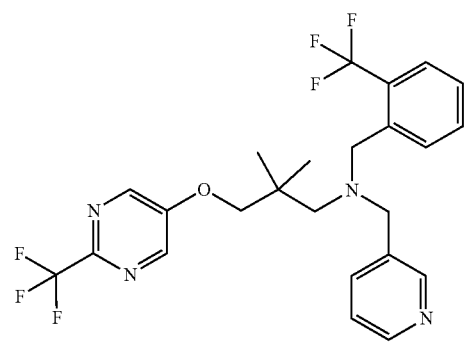
BC191081

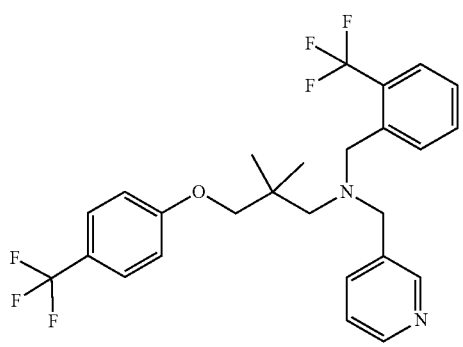

BC191082

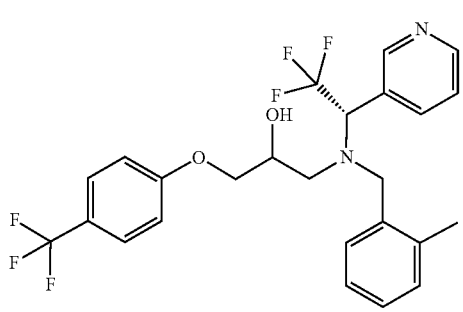

BC191083

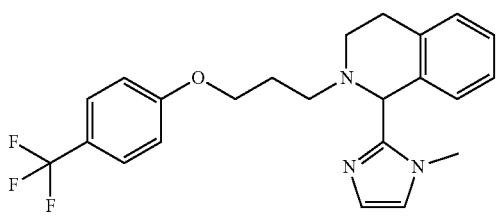

BC191084

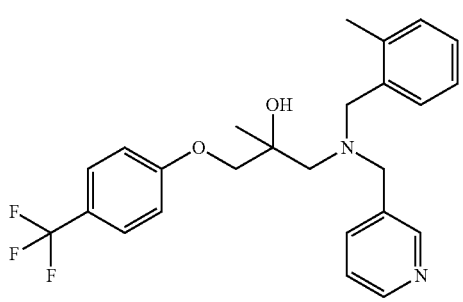

BC191085

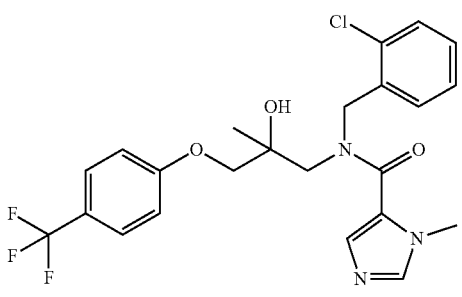

BC191086 or a pharmaceutically acceptable salt thereof.

In some embodiments, the present disclosure provides a compound of formula:

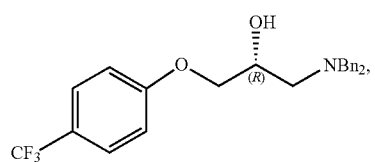

or a pharmaceutically acceptable salt thereof.

In some embodiments, the present disclosure provides a compound of formula:

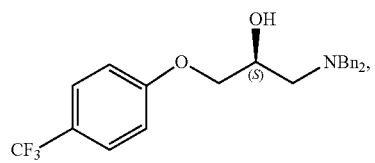

or a pharmaceutically acceptable salt thereof.

In some embodiments, the present disclosure provides a compound selected from:

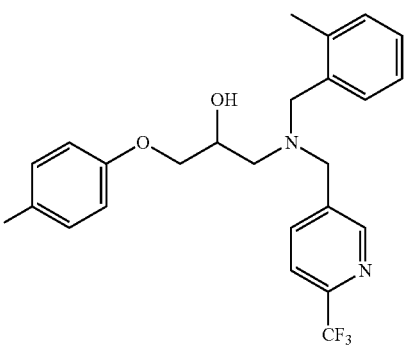

BC19844

-continued
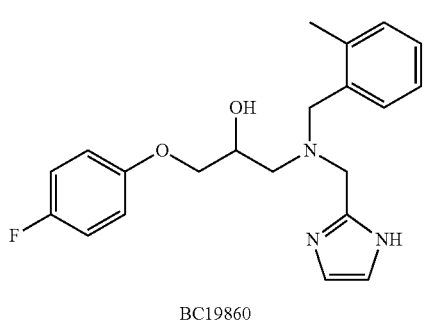
BC19860
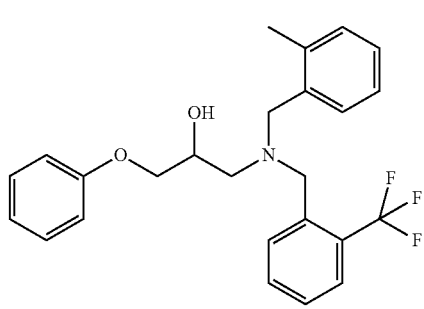
BC19887
or a pharmaceutically acceptable salt thereof.
In some embodiments, the present disclosure provides a compound selected from:
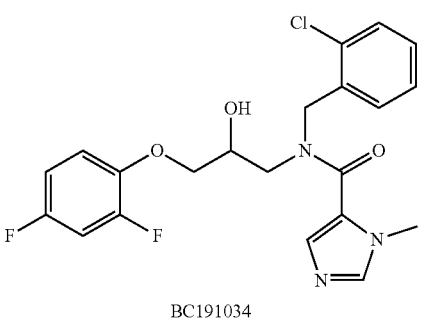
BC19888
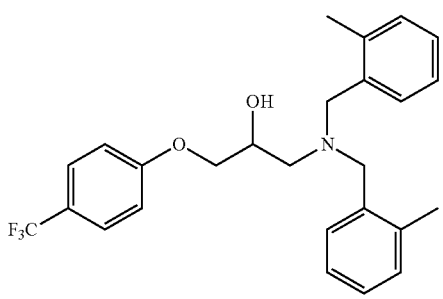
BC19802
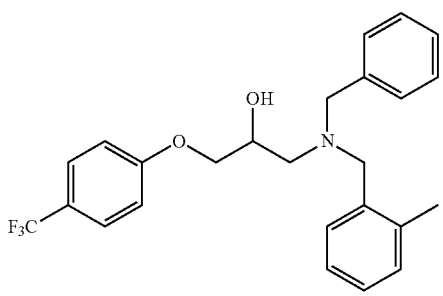
BC19803
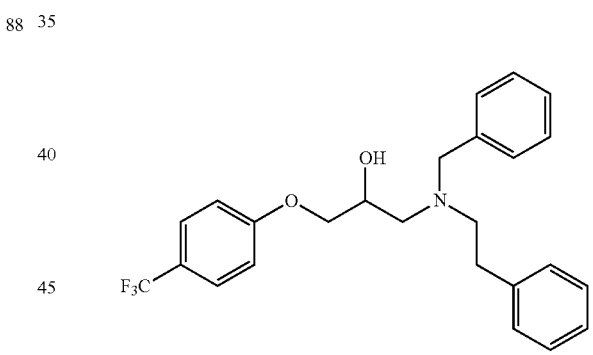
BC191034
or a pharmaceutically acceptable salt thereof.
In some embodiments, the present disclosure provides a compound selected from:
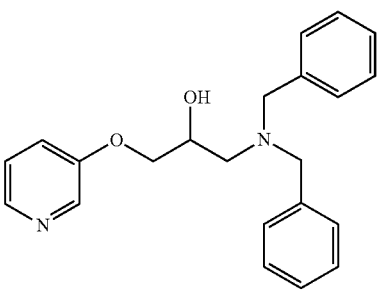
BC19807

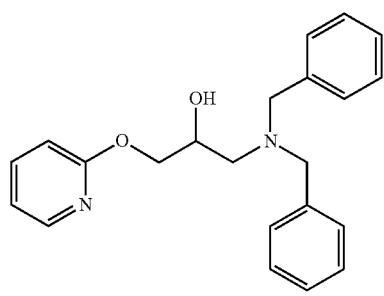
BC19808
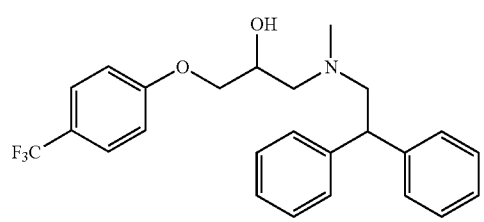
BC19809
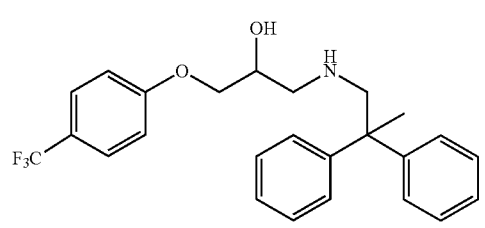
BC19810
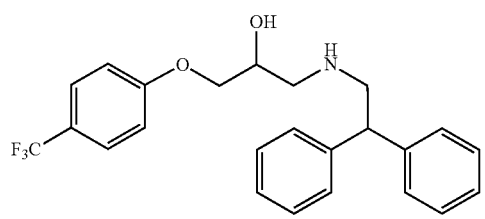
BC19812
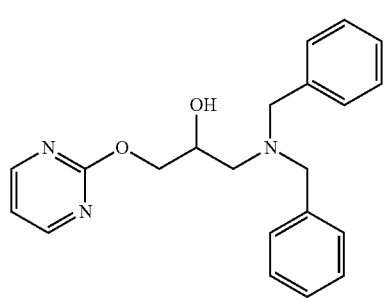
BC19813
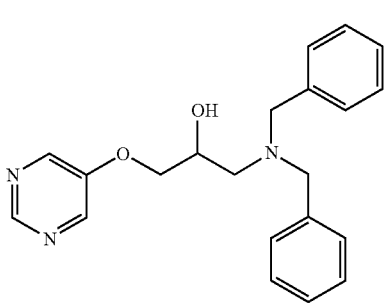
BC19814
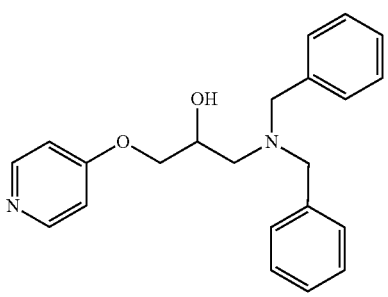
BC19815
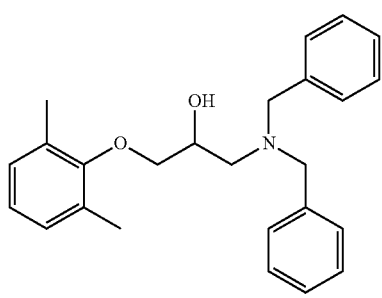
BC19816
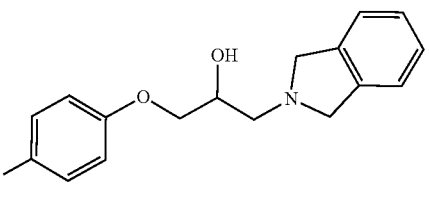
BC19819
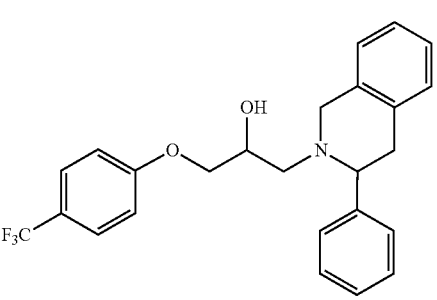
BC19820

-continued
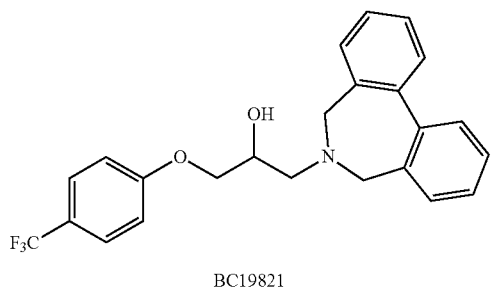
BC19821
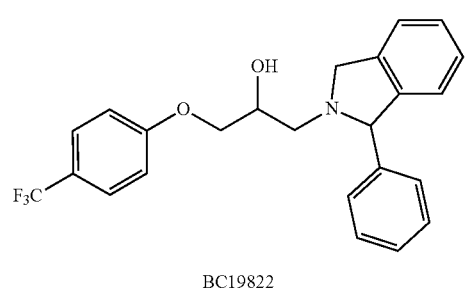
BC19822
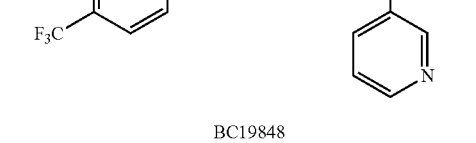
BC19848
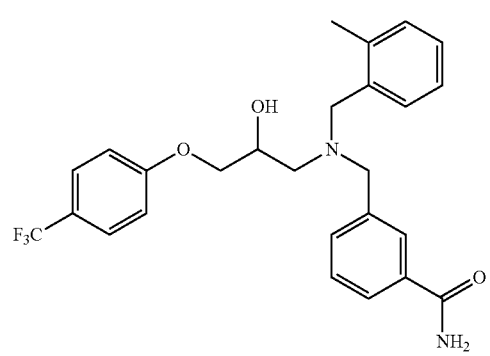
BC19849
-continued
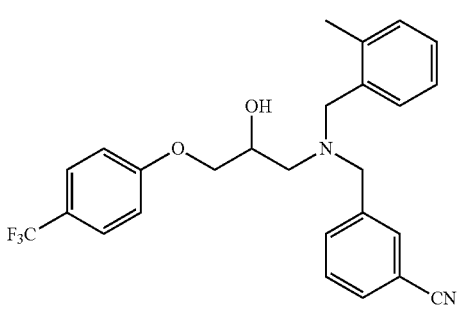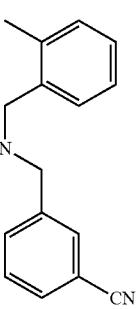
BC19850
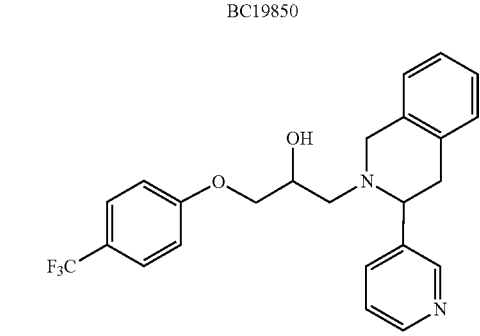
BC19856
or a pharmaceutically acceptable salt thereof.
In some embodiments, the present disclosure provides a compound selected from:
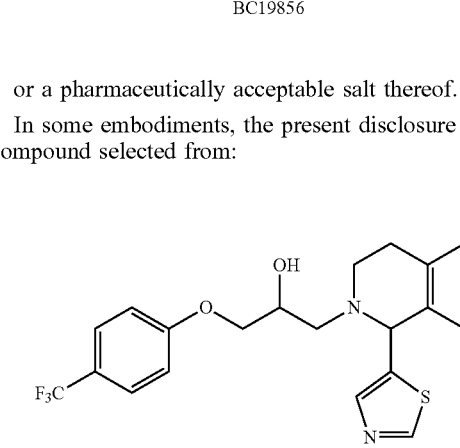
BC19893
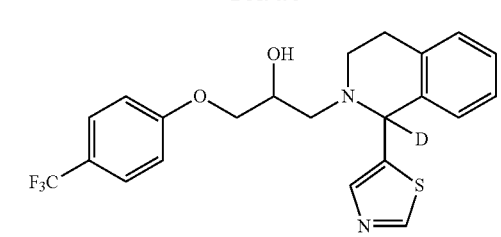
BC19894
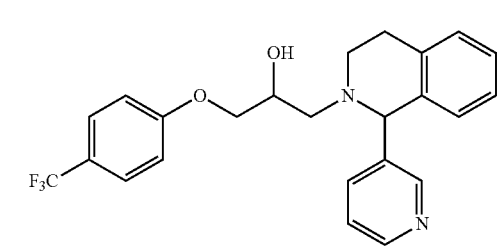
BC19895

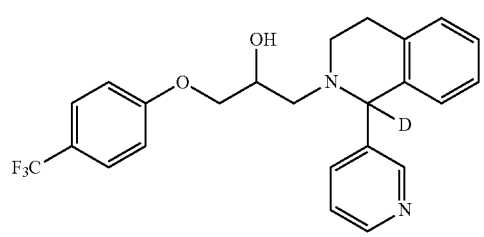
BC19896
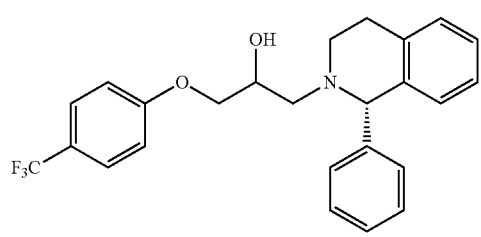
BC191011A
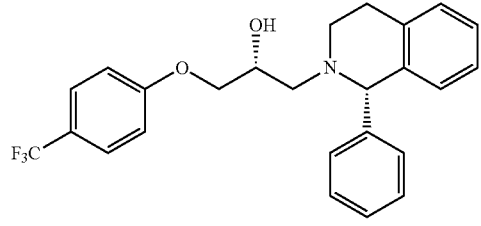
BC191011B
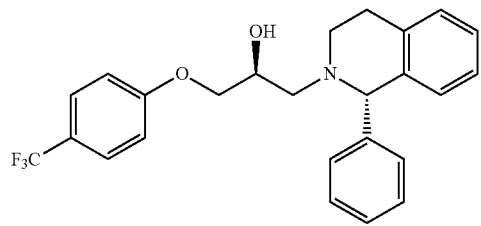
BC191011C
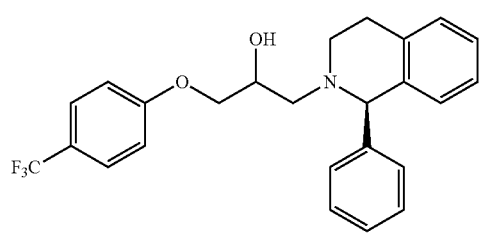
BC191011D
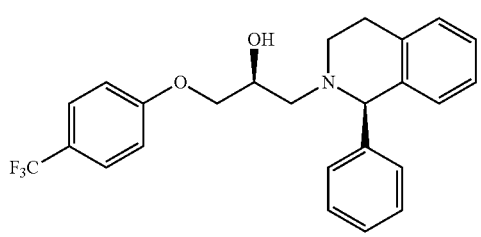
BC191011E
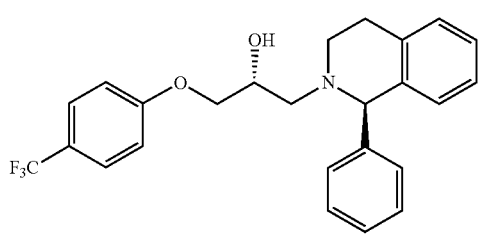
BC191011F
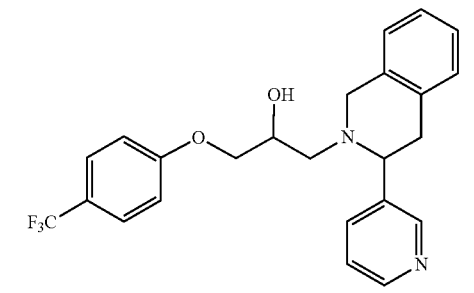
BC191023
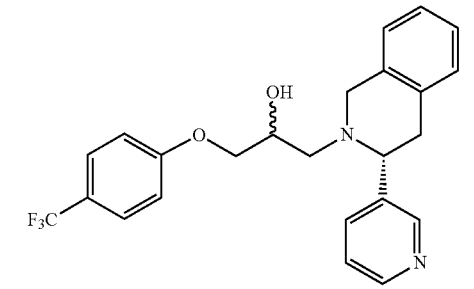
BC19856A
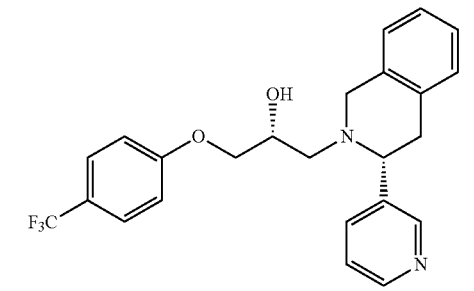
BC19856B

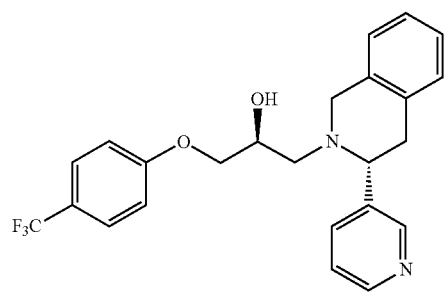
BC19856C

BC19856D
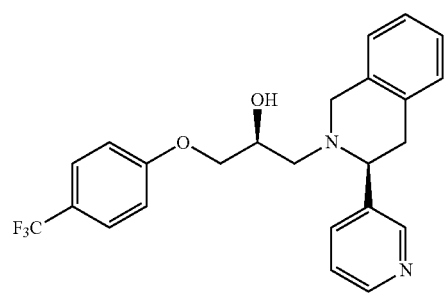
BC19856E
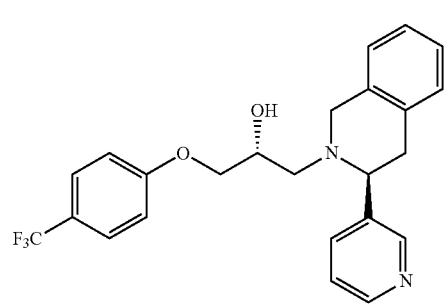
BC19856F
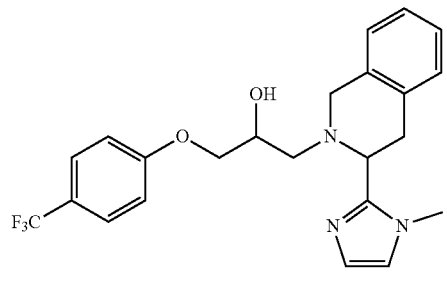
BC191036
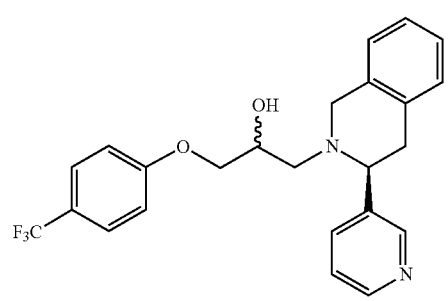
BC191063
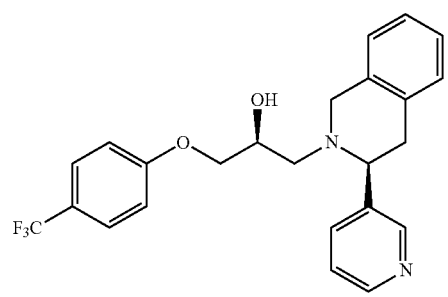
BC191074
or a pharmaceutically acceptable salt thereof.
In some embodiments, the present disclosure provides a compound selected from:
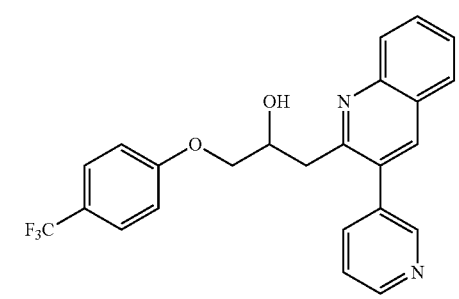
BC19857

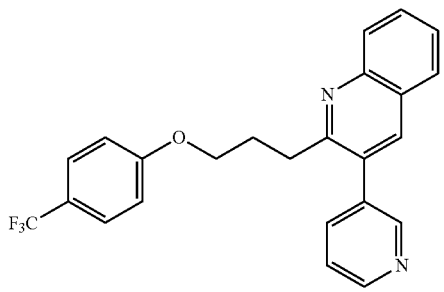

BC19892

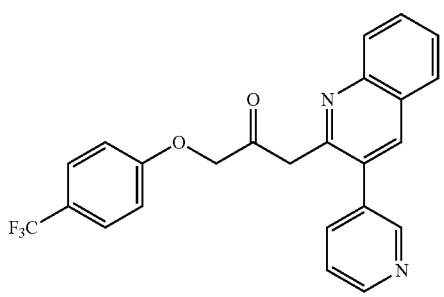

BC191003 or a pharmaceutically acceptable salt thereof.

In some embodiments, this document provides a pharmaceutical composition comprising any of the compounds described herein, or a pharmaceutically acceptable salt thereof, and a pharmaceutically acceptable carrier.

In some embodiments, this document provides a method for increasing the level of phosphorylated AMPK within a cell. The method comprises (or consists essentially of or consists of) administering, to a mammal (e.g., a human) containing the cell, a therapeutically effective amount of any one or more of the compounds described herein (or one or more pharmaceutically acceptable salts thereof).

In some embodiments, this document provides a method of treating a mammal having a disease, disorder, or condition responsive to an increase in the level of phosphorylated AMPK within cells, wherein said method comprises administering, to said mammal, any one of the compounds disclosed herein, or a pharmaceutically acceptable salt thereof, or a pharmaceutical composition comprising same.

In some embodiments, this document provides a method for treating a disease, disorder, or condition selected from the group consisting of inflammatory disorders, (including a cytokine-driven inflammation), sepsis, pneumonia, acute lung injury, metabolic syndrome, diabetic nephropathy, polycystic kidney disease, polycystic ovarian syndrome, and a neurological or neurodegenerative disease. The method comprises (or consists essentially of or consists of) administering, to a mammal (e.g., a human) having the disease, disorder, or condition, a therapeutically effective amount of any one or more of the compounds described herein (or one or more pharmaceutically acceptable salts thereof).

In some embodiments, said mammal is a human. In some embodiments, said method comprises treating a mammal having an inflammation. In some embodiments, the inflammation is a cytokine-driven inflammation. In some embodiments, said method comprises treating a mammal having a sepsis. In some embodiments, said method comprises treating a mammal having a pneumonia. In some embodiments, said method comprises treating a mammal having an acute lung injury. In some embodiments, said method comprises treating a mammal having a metabolic syndrome. In some embodiments, said method comprises treating a mammal having a diabetic nephropathy. In some embodiments, said method comprises treating a mammal having a polycystic kidney disease. In some embodiments, said method comprises treating a mammal having a polycystic ovarian syndrome. In some embodiments, said method comprises treating a mammal having a neurological disease.

In some embodiments, this disclosure provides a method of treating a mammal having a disease, disorder, or condition responsive to an increase in the level of phosphorylated AMPK within cells, wherein said method comprises administering, to said mammal, a compound having formula:

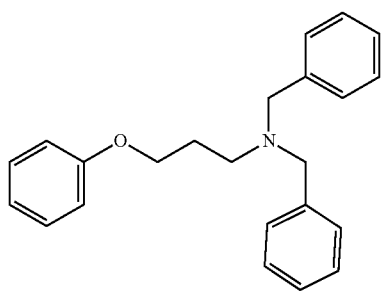

BC19861 or a pharmaceutically acceptable salt thereof.

In some embodiments, this disclosure provides a method for increasing a level of phosphorylated AMPK within cells of a mammal, wherein said method comprises administering, to said mammal, a compound having formula:

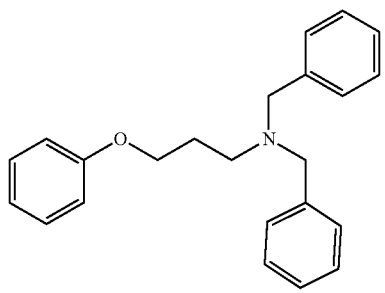

BC19861 or a pharmaceutically acceptable salt thereof.

In some embodiments, the present disclosure provides a method for treating cancer in a mammal, wherein said method comprises administering, to said mammal, any one of the compounds described herein, or a pharmaceutically acceptable salt thereof, or a pharmaceutical composition comprising the compound. In some embodiments, the method further comprises administering, to said mammal, a checkpoint inhibitor.

In some embodiments, the present disclosure provides a method for improving function of immune cells in a mammal, wherein said method comprises administering, to said mammal, any one of the compounds described herein, or a pharmaceutically acceptable salt thereof, or a pharmaceutical composition comprising the compound. In some embodiments, said immune cells are T cells. In some embodiments, said method further comprising administering, to said mammal, a checkpoint inhibitor.

In some embodiments, the present disclosure provides a method for expanding a population of immune cells, said method comprising obtaining a population of immune cells from a mammal and culturing said population of immune cells with any one of the compounds described herein, or a pharmaceutically acceptable salt thereof. In some embodiments, said immune cells are T cells.

In some embodiments, the present disclosure provides a method for treating an infection or reducing the risk of developing an infection in a mammal, said method comprising administering, to said mammal, any one of the compounds described herein, or a pharmaceutically acceptable salt thereof, or a pharmaceutical composition comprising the compound.

Unless otherwise defined, all technical and scientific terms used herein have the same meaning as commonly understood by one of ordinary skill in the art to which the present application pertains. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the present application will be apparent from the following detailed description and figures, and from the claims.

DETAILED DESCRIPTION

Figure 1A:
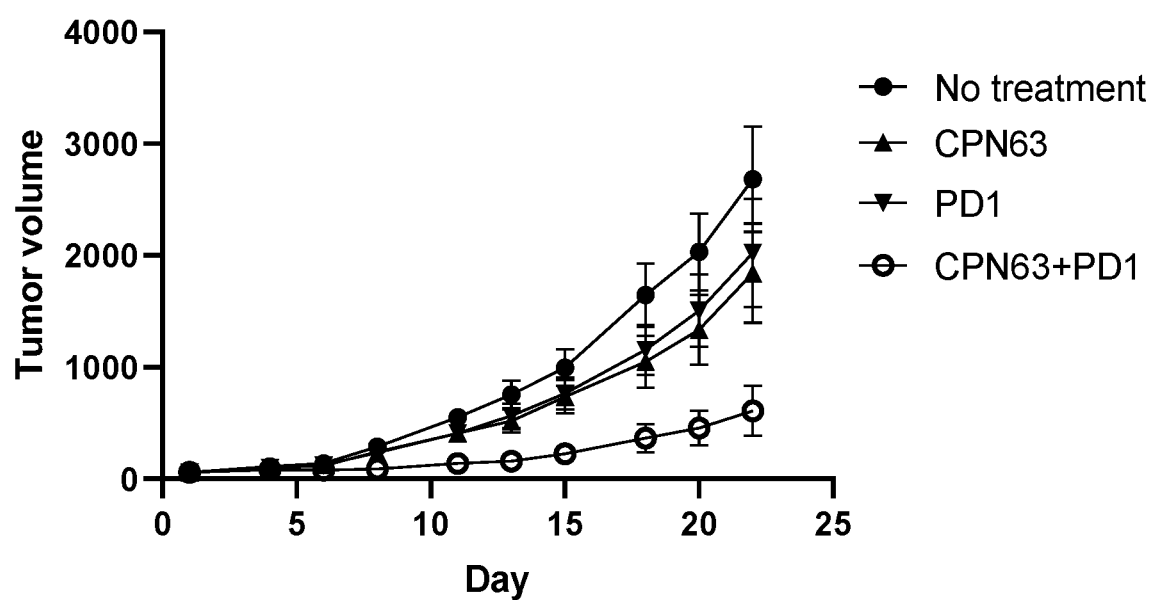
FIG. 1A is a graph of the tumor volume in mice over time with no treatment, treatment with an anti-PD-1 antibody, treatment with compound 63, or treated with a combination of an anti-PD-1 antibody and compound 63.

This document provides methods and materials for increasing the level of phosphorylated AMPK. For example, this document provides therapeutic compounds (e.g., therapeutic organic compounds) having the ability to increase the level of phosphorylated AMPK within cells, formulations containing therapeutic compounds having the ability to increase the level of phosphorylated AMPK, methods for making therapeutic compounds having the ability to increase the level of phosphorylated AMPK within cells, methods for making formulations containing therapeutic compounds having the ability to increase the level of phosphorylated AMPK within cells, methods for increasing the level of phosphorylated AMPK within cells, and methods for treating mammals (e.g., humans) having a condition responsive to an increase in the level of phosphorylated AMPK.

Methods of Treatment

Without being bound by theory, it is believed that AMPK is an enzyme involved in cellular energy homeostasis, largely to activate glucose and fatty acid uptake and oxidation when cellular energy is low. Increasing the level of phosphorylated AMPK within cells using a compound provided herein (e.g., a compound set forth in Formula (I), or a pharmaceutically acceptable salt thereof) as described herein can result in one or more benefits for the cell and/or mammal.

In some cases, this document provides methods for increasing the level of phosphorylated AMPK within cells by contacting the cell with one or more compounds provided herein (e.g., a compound set forth in Formula (I), or a pharmaceutically acceptable salt thereof).

The increase in phosphorylated AMPK levels can be as compared to the phosphorylated AMPK levels prior to the contacting step. In some cases, methods for increasing the level of phosphorylated AMPK within cells can be performed in vivo. For example, one or more compounds provided herein (e.g., a compound set forth in Formula (I), or a pharmaceutically acceptable salt thereof) can be administered to a mammal (e.g., a human) to increase the level of phosphorylated AMPK within cells within that mammal. In some cases, methods for increasing the level of phosphorylated AMPK within cells can be performed in vitro. For example, one or more compounds provided herein (e.g., a compound set forth in Formula (I), or a pharmaceutically acceptable salt thereof) can be added to a cell culture containing cells (e.g., human cells) to increase the level of phosphorylated AMPK within those cells. In some cases, such intervention can improve the quality of the cell while in culture or subsequently.

This document also provides methods for treating diseases, disorders, and conditions in a mammal by administering one or more compounds provided herein (e.g., a compound set forth in Formula (I), or a pharmaceutically acceptable salt thereof) to a mammal in need thereof. In some cases, the disease, disorder, or condition being treated can be a disease, disorder, or condition that is responsive to an increase in the level of phosphorylated AMPK within cells within the mammal. In some cases, the disease, disorder, or condition being treated can be a disease, disorder, or condition that is associated with a low level of phosphorylated AMPK within the mammal.

Examples of diseases, disorders, and conditions that can be treated with one or more compounds provided herein (e.g., a compound set forth in Formula (I), or a pharmaceutically acceptable salt thereof) as described herein can include, without limitation, inflammation disorders (including acute or chronic inflammation disorders, cytokine-driven inflammation disorders, or inflammation and tissue damage induced by pathogenic infection), sepsis, pneumonia, acute lung injury, metabolic syndrome, neurodegenerative or neurological conditions, diabetic nephropathy, chronic renal diseases, polycystic kidney disease, polycystic ovarian syndrome, chronic pain syndrome(s), atherosclerosis, atherosclerotic heart disease, malignancies of various cell types, age-related macular degeneration, other age-related pathologies including generalized frailty, sarcopenia, and muscular dystrophies.

Examples of inflammation disorders (e.g., acute or chronic) that can be treated with one or more compounds provided herein (e.g., a compound set forth in Formula (I), or a pharmaceutically acceptable salt thereof) include, without limitation, asthma, chronic obstructive lung disease, pulmonary fibrosis, pneumonitis (e.g., hypersensitivity pneumonitis or radiation pneumonitis), pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (e.g., Crohn's disease or ulcerative colitis), colitis, sepsis, vasculitis, bursitis, connective tissue disease, autoimmune diseases (e.g., systemic lupus erythematosis (SLE)), polymyalgia rheumatica, scleroderma, Wegener's granulomatosis, temporal arteritis, vasculitis, cryoglobulinemia, multiple sclerosis, viral or influenza-induced inflammation, edema, pneumonia, chronic bacterial colonization or persistent intracellular pathogen, and impaired responsiveness to antigenic challenge or vaccines administration. Other examples of inflammation disorders that can be treated with one or more compounds provided herein (e.g., a compound set forth in Formula (I), or a pharmaceutically acceptable salt thereof) include, without limitation, inflammation and tissue damage induced by pathogenic infection with, for example, *Pseudomonas aeruginosa, Staphylococcus aureus, Streptococcus pneumoniae, Haemophilus influenza,* or *Escherichia coli.*

In some cases, provided herein are methods to treat sepsis in a subject in need thereof, the method comprising administering to the subject a therapeutically effective amount of a compound described herein, or a pharmaceutically acceptable salt thereof (e.g., a compound set forth in Formula (I), or a pharmaceutically acceptable salt thereof).

In some cases, provided herein are methods for treating sepsis in a mammal by administering one or more compounds provided herein (e.g., a compound set forth in Formula (I), or a pharmaceutically acceptable salt thereof) to a mammal in need thereof.

In some cases, provided herein are methods for treating pneumonia in a mammal by administering one or more compounds provided herein (e.g., a compound set forth in Formula (I), or a pharmaceutically acceptable salt thereof) to a mammal in need thereof.

In some cases, provided herein are methods for treating acute lung injury in a mammal by administering one or more compounds provided herein (e.g., a compound set forth in Formula (I), or a pharmaceutically acceptable salt thereof) to a mammal in need thereof.

In some cases, provided herein are methods for treating metabolic disease (or an age-related condition) in a mammal by administering one or more compounds provided herein (e.g., a compound set forth in Formula (I), or a pharmaceutically acceptable salt thereof) to a mammal in need thereof. Examples of metabolic disease include metabolic syndrome, NASH, and diabetes. Examples of age-related conditions include sarcopenia, frailty, macular degeneration, other inherited or acquired retinal degenerative diseases, age-related hearing loss, early cognitive decline, osteoporosis, acute or age-related organ dysfunction (e.g., heart and/or kidney dysfunction), and age-related immune dysfunction (e.g., impaired response to vaccination or immunosenescence).

In some cases, provided herein are methods for treating diabetic nephropathy in a mammal by administering one or more compounds provided herein (e.g., a compound set forth in Formula (I), or a pharmaceutically acceptable salt thereof) to a mammal in need thereof.

In some cases, provided herein are methods for treating polycystic kidney disease in a mammal by administering one or more compounds provided herein (e.g., a compound set forth in Formula (I), or a pharmaceutically acceptable salt thereof) to a mammal in need thereof.

In some cases, provided herein are methods for treating polycystic ovarian syndrome in a mammal by administering one or more compounds provided herein (e.g., a compound set forth in Formula (I), or a pharmaceutically acceptable salt thereof) to a mammal in need thereof.

In some cases, provided herein are methods for treating neurodegenerative or neurological diseases in a mammal by administering one or more compounds provided herein (e.g., a compound set forth in Formula (I), or a pharmaceutically acceptable salt thereof) to a mammal in need thereof. Examples of neurodegenerative diseases includes Alzheimer's disease, ALS, Huntington's disease, Parkinson's disease, primary age-related tauopathy, progressive supranuclear palsy, chronic traumatic encephalopathy, acute or chronic traumatic brain injury, and frontotemporal dementia.

In another aspect, this document provides methods for treating cancer in a mammal in need thereof by administering a therapeutically effective amount of one or more compounds described herein (e.g., a compound set forth in Formula (I) or a pharmaceutically acceptable salt thereof) to the mammal. For example, a mammal (e.g., a human) can be treated for a cancer such as melanoma, non-small cell lung cancer, bladder cancer, renal cell cancer, colorectal cancer, or multiple myeloma. In some cases, methods described herein for treating cancer can include administering to a mammal in need thereof one or more compounds provided herein (e.g., a compound set forth in Formula (I) or a pharmaceutically acceptable salt thereof) in combination with a checkpoint inhibitor. Examples of checkpoint inhibitors that can be used in combination with a compound provided herein include, without limitation, PD-1 inhibitors such as Pembrolizumab (KEYTRUDA, Merck &Co., Inc.), Nivolumab (OPDIVO, Bristol-Myers Squibb), or Cemiplimab (LIBTAYO, Regeneron Pharmaceuticals, Inc. and Sanofi), or a small molecule inhibitor of PD-1/PD-L1 such as BMS-1001 or BMS-1166 (see, e.g., Skalniak et al., *Oncotarget,* 8(42):72167-72181 (2017)), a CTLA4 inhibitor such as Ipilimumab (YERVOY, Bristol-Myers Squibb), or a PD-L1 inhibitor such as Atezolizumab (TECENTRIQ, Genentech/Roche), Avelumab (BAVENCIO, Pfizer), or Durvalumab (IMFINZI, AstraZeneca Pharmaceuticals LP).

In some cases, methods described herein for treating cancer in a mammal (e.g., a human) in need thereof can include administering to the mammal a therapeutically effective amount of one or more compounds described herein such as a compound set forth in Formula (A):

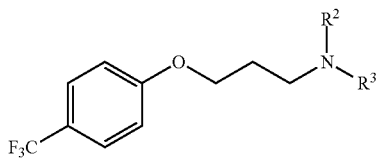

or a pharmaceutically acceptable salt thereof, wherein R² and R³ are as described herein. In some cases, methods described herein for treating cancer can include administering to a mammal in need thereof (e.g., a human) a therapeutically effective amount of one or more compounds provided herein (e.g., a compound set forth in Formula (A):

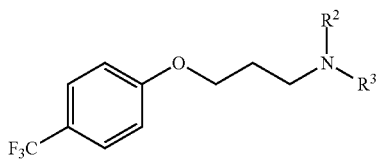

or a pharmaceutically acceptable salt thereof, wherein R² and R³ are each independently an C₁₋₆ alkyl, optionally substituted with Cy¹) in combination with a checkpoint inhibitor such as a PD-1 inhibitor, a CTLA4 inhibitor, or a PD-L1 inhibitor.

In some cases, methods described herein for treating cancer in a mammal (e.g., a human) can include administering a therapeutically effective amount of compound 63:

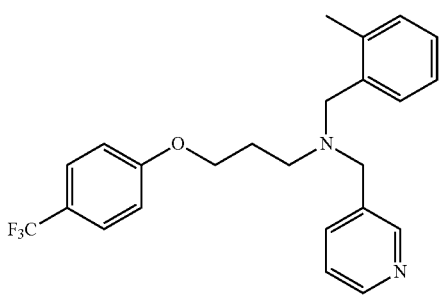 [SMILES: Cc1ccccc1CN(CCCOc1ccc(C(F)(F)F)cc1)Cc1cccnc1]

or a pharmaceutically acceptable salt thereof (e.g., a hydrochloride salt such as compound 139 or a tartrate salt such as compound 140). In some cases, methods described herein for treating cancer can include administering to a mammal in need thereof (e.g., a human) a therapeutically effective amount of one or more compounds provided herein such as compound 63 or a pharmaceutically acceptable salt thereof (e.g., a hydrochloride salt such as compound 139 or a tartrate salt such as compound 140) in combination with a checkpoint inhibitor (e.g., a PD-I inhibitor, a CTLA4 inhibitor, or a PD-L1 inhibitor). As shown in Example 3, the combination of compound 63 and a checkpoint inhibitor (e.g., an anti-PD-1 antibody) can result in a synergistic inhibition of tumor growth in an animal model of cancer (e.g., melanoma).

In another aspect, this document provides methods for improving function of immune cells (e.g., T cells) in a mammal (e.g., a human) by administering a therapeutically effective amount of one or more compounds described herein (e.g., a compound set forth in Formula (I) or a pharmaceutically acceptable salt thereof) to the mammal. In some cases, methods described herein for improving function of immune cells (e.g., T cells) can include administering to a mammal in need thereof a therapeutically effective amount of one or more compounds provided herein (e.g., a compound set forth in Formula (I) or a pharmaceutically acceptable salt thereof) in combination with a checkpoint inhibitor (e.g., a PD-1 inhibitor, a CTLA4 inhibitor, or a PD-L1 inhibitor).

In some cases, methods described herein for improving function of immune cells (e.g., T cells) in a mammal (e.g., a human) in need thereof can include administering a therapeutically effective amount of one or more compounds described herein such as a compound set forth in Formula (A):

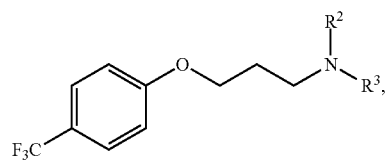

or a pharmaceutically acceptable salt thereof, wherein R² and R³ are as described herein. In some cases, methods described herein for improving function of immune cells (e.g., T cells) can include administering to a mammal (e.g., a human) in need thereof a therapeutically effective amount of one or more compounds provided herein (e.g., a compound set forth in Formula (A):

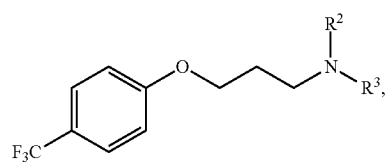

or a pharmaceutically acceptable salt thereof, wherein R² and R³ are as described herein (e.g., R² and R³ are each independently an C₁₋₆ alkyl, optionally substituted with Cy¹) in combination with a checkpoint inhibitor such as a PD-1 inhibitor, a CTLA4 inhibitor, or a PD-L1 inhibitor.

In some cases, methods described herein for improving function of immune cells (e.g., T cells) in a mammal can include administering a therapeutically effective amount of compound 63:

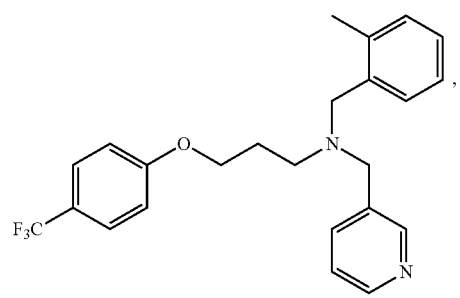

or a pharmaceutically acceptable salt thereof (e.g., a hydrochloride salt such as compound 139 or a tartrate salt such as compound 140). In some cases, methods described herein for improving function of immune cells (e.g. T cells) can include administering to a mammal in need thereof (e.g., a human) a therapeutically effective amount one or more compounds provided herein such as compound 63 or a pharmaceutically acceptable salt thereof (e.g., a hydrochloride salt such as compound 139 or a tartrate salt such as compound 140) in combination with a checkpoint inhibitor such as a PD-1 inhibitor, a CTLA4 inhibitor, or a PD-L1 inhibitor.

In another aspect, this document provides methods for expanding a population of immune cells (e.g., T cells) that can include obtaining a population of immune cells from a mammal (e.g., a mammal in need of treatment with a cell based immunotherapy) and culturing the population of immune cells with one or more compounds described herein (e.g., a compound set forth in Formula (I) or a pharmaceutically acceptable salt thereof) to increase the number of immune cells (e.g., T cells such as CD8+ cells).

In some cases, methods described herein for expanding a population of immune cells (e.g., T cells) can include obtaining a population of immune cells from a mammal (e.g., a mammal in need of treatment with a cell based immunotherapy) and culturing the population of immune cells with one or more compounds described herein such as a compound set forth in Formula (A):

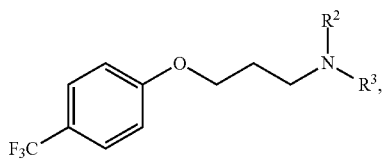

or a pharmaceutically acceptable salt thereof, wherein $R^2$ and $R^3$ are as described herein.

In some cases, methods described herein for expanding a population of immune cells (e.g., T cells) can include obtaining a population of immune cells from a mammal (e.g., a mammal in need of treatment with a cell based immunotherapy) and culturing the population of immune cells with compound 63:

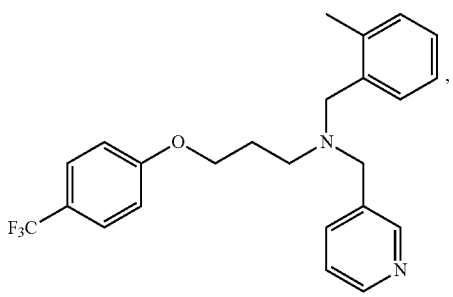 [SMILES: Cc1ccccc1CN(CCCOc1ccc(C(F)(F)F)cc1)Cc1cccnc1]

or a pharmaceutically acceptable salt thereof (e.g., a hydrochloride salt such as compound 139 or a tartrate salt such as compound 140).

In some cases, the population of immune cells can be obtained from a tumor and cultured to obtain tumor infiltrating lymphocytes. In some cases, the population of immune cells can be obtained from peripheral blood mononuclear cells. In some cases, the expanded immune cells (e.g., T cells) can be further manipulated ex vivo (e.g., to introduce a novel T cell receptor (TCR) or chimeric antigen receptor (CAR)) for a cell based immunotherapy using, for example, methods described elsewhere (see, e.g., Rohaan et al., Virchows Arch. 474(4): 449-461 (2019)).

In some cases, the expanded immune cells can be used for adoptive cell therapy and infused into the mammal in need of treatment with a cell based immunotherapy. In some cases, after adoptive cell therapy, a therapeutically effective amount of one or more compounds provided herein (e.g., a compound set forth in Formula (I) or a pharmaceutically acceptable salt thereof) can be administered to the mammal, optionally in combination with a checkpoint inhibitor (e.g., a PD-1 inhibitor, a CTLA4 inhibitor, or a PD-Li inhibitor). In some cases, after adoptive cell therapy, a therapeutically effective amount of one or more compounds provided herein such as a compound set forth in Formula (A):

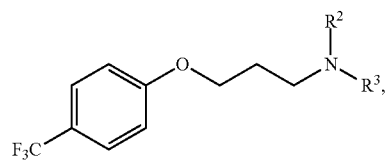

or a pharmaceutically acceptable salt thereof, wherein $R^2$ and $R^3$ are as described herein, can be administered to the mammal, optionally in combination with a checkpoint inhibitor (e.g., a PD-1 inhibitor, a CTLA4 inhibitor, or a PD-L1 inhibitor). In some cases, after adoptive cell therapy, a therapeutically effective amount of one or more compounds provided herein such as compound 63:

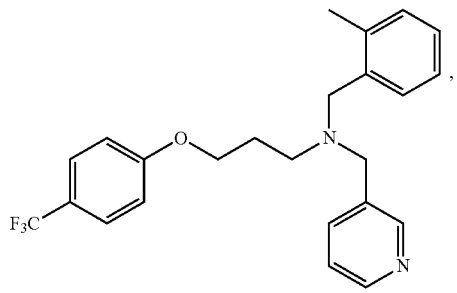 [SMILES: Cc1ccccc1CN(CCCOc1ccc(C(F)(F)F)cc1)Cc1cccnc1]

or a pharmaceutically acceptable salt thereof (e.g., a hydrochloride salt such as compound 139 or a tartrate salt such as compound 140) can be administered to the mammal, optionally in combination with a checkpoint inhibitor (e.g., a PD-1 inhibitor, a CTLA4 inhibitor, or a PD-L1 inhibitor).

In another aspect, this document provides methods for treating an infection and/or reducing the risk of developing an infection in a mammal by administering a therapeutically effective amount of one or more compounds described herein (e.g., a compound set forth in Formula (I) or a pharmaceutically acceptable salt thereof) to the mammal.

In some cases, methods described herein for treating an infection and/or reducing the risk of developing an infection in a mammal (e.g., a human) can include administering a therapeutically effective amount of one or more compounds described herein such as a compound set forth in Formula (A):

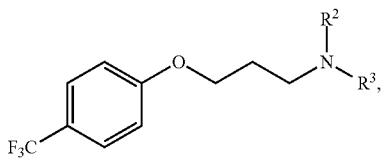

or a pharmaceutically acceptable salt thereof, wherein $R^2$ and $R^3$ are as described herein.

In some cases, methods described herein for treating an infection and/or reducing the risk of developing an infection in a mammal (e.g., a human) can include administering a therapeutically effective amount of compound 63:

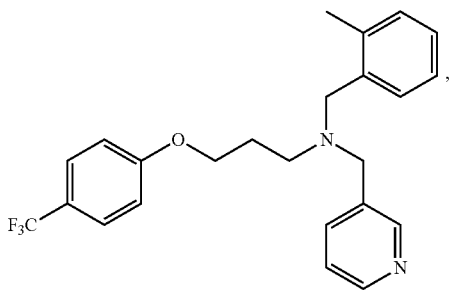 [SMILES: Cc1ccccc1CN(CCCOc1ccc(C(F)(F)F)cc1)Cc1cccnc1]

or a pharmaceutically acceptable salt thereof (e.g., a hydrochloride salt such as compound 139 or a tartrate salt such as compound 140) to the mammal.

In some cases, the infection can be a bacterial infection (e.g., with methicillin-resistant *Staphylococcus auereus* (MRSA)). In some cases, the infection can be a viral infection. In some cases, the methods provided herein can be used for treating, or reducing the risk of developing, an infection in the lungs of the mammal (e.g., a human). For example, the methods described herein can be used for improving clearance of bacteria, viruses, or fungus from the lungs of the mammal, by boosting the host defense through the activation of AMPK. In some cases, the mammal can have cystic fibrosis or chronic obstructive pulmonary disease (COPD). As shown in Example 4, compound 63 can be used to clear the MRSA infection from the lungs of a mouse model of MRSA infection. In some cases, one or more compounds provided herein (e.g., a compound set forth in Formula (I), or a pharmaceutically acceptable salt thereof) can be used as described herein (e.g., to increase the level of phosphorylated AMPK within cells and/or to treat a disease, disorder, or condition as described herein) as the sole active ingredient(s). For example, a composition containing a compound set forth in Formula (I), or a pharmaceutically acceptable salt thereof can lack any other active ingredients that increase the level of phosphorylated AMPK within cells. In some cases, a composition containing a compound set forth in Formula (I), or a pharmaceutically acceptable salt thereof can lack any other active ingredients that are effective to treat a disease, disorder, or condition as described herein.

Therapeutic compounds

As described herein, any one or more of the compounds provided herein can be used to increase the level of phosphorylated AMPK within cells, and/or to treat a disease, disorder, and condition described herein in a mammal.

In some embodiments, this document provides a compound of Formula (I):

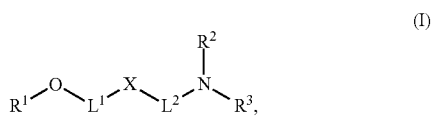

or a pharmaceutically acceptable salt thereof, wherein $R^1$, $L^1$, $X$, $L^2$, $R^2$, and $R^3$ are as described herein.

In some embodiments:

$R^1$ is selected from 5-6 membered heteroaryl and a group of formula:

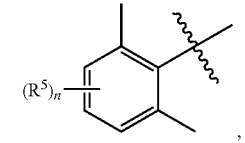

wherein said 5-6 membered heteroaryl of R is optionally substituted with 1, 2, 3, 4, or 5 substituents independently selected from $R^5$;

$L^1$ is $C_{1-4}$ alkylene, which is optionally substituted with halo or $OR^4$;

$L^2$ is $C_{1-4}$ alkylene or $L^2$ is absent;

X is selected from $CR^7(OR^4)$, C=O, and $C_{3-6}$ cycloalkylene; or X is absent;

$R^7$ is selected from H, $C_{1-6}$ alkyl, $C_{1-6}$ haloalkyl, $C_{2-6}$ alkenyl, and $C_{2-6}$ alkynyl;

$R^2$ and $R^3$ are each independently selected from H, $C_{1-6}$ alkyl, $Cy^1$, $C_{1-6}$ haloalkyl, $C_{2-6}$ alkenyl, $C_{2-6}$ alkynyl, C(=O)$Cy^1$, and S(=O)$_2Cy^1$, wherein said $C_{1-6}$ alkyl, $C_{2-6}$ alkenyl, $C_{2-6}$ alkynyl, and $C_{1-6}$ haloalkyl are each optionally substituted with 1 or 2 independently selected $Cy^1$;

provided that at least one of $R^2$ and $R^3$ is other than H;

$R^4$ is selected from H, C(O)$R^{b1}$, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;

or $R^4$ and $R^2$ together with the O atom to which $R^4$ is attached and N atom to which $R^2$ is attached form 5-10 membered heterocycloalkyl, which is optionally substituted with 1 or 2 independently selected $Cy^1$;

or $R^2$ and $R^3$, together with the N atom to which they are attached, form 4-16 membered heterocycloalkyl ring, which is optionally substituted with 1 or 2 substituents independently selected from $R^6$;

each $R^6$ is independently selected from $C_{1-6}$ alkyl, $OR^{a1}$, C(O)$NR^{c1}R^{d1}$, C(O)$OR^{a1}$, $C_{1-6}$ haloalkyl, and $Cy^1$, wherein said $C_{1-6}$ alkyl is optionally substituted with a substituent selected from $OR^{a1}$, C(O)$NR^{c1}R^{d1}$, and C(O)$OR^{a1}$;

m is 0, 1, 2, 3, or 4;

n is 0, 1, 2, or 3;

each $R^5$ is independently selected from OH, $NO_2$, CN, halo, $C_{1-6}$ alkyl, $C_{1-4}$ haloalkyl, $C_{1-6}$alkoxy, $C_{1-6}$ haloalkoxy, thio, $C_{1-6}$ alkylthio, carboxy, amino, $C_{1-6}$ alkylamino, and di($C_{1-6}$ alkyl)amino;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}lS(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-6}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylsulfonylamino, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$ is selected from 5-6 membered heteroaryl and a group of formula:

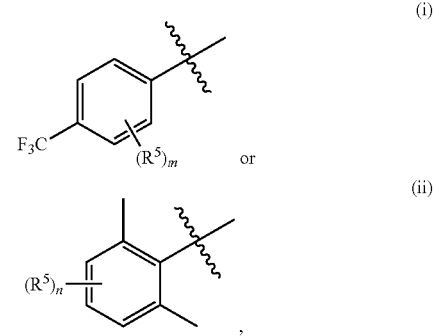

wherein said 5-6 membered heteroaryl of $R^1$ is optionally substituted with 1, 2, 3, 4, or 5 substituents independently selected from $R^5$;

$L^1$ is $C_{1-4}$ alkylene;

$L^2$ is $C_{1-4}$ alkylene or $L^2$ is absent;

X is selected from CH($OR^4$) and C=O; or X is absent;

$R^2$ and $R^3$ are each independently selected from H, $C_{1-6}$ alkyl, $Cy^1$, $C_{1-6}$ haloalkyl, $C_{2-6}$ alkenyl, $C_{2-6}$ alkynyl, C(=O)$Cy^1$, and S(=O)$_2Cy^1$, wherein said $C_{1-6}$ alkyl, $C_{2-6}$ alkenyl, and $C_{2-6}$ alkynyl are each optionally substituted with 1 or 2 independently selected $Cy^1$;

provided that at least one of $R^2$ and $R^3$ is other than H;

$R^4$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;

or $R^4$ and $R^2$ together with the O atom to which $R^4$ is attached and N atom to which $R^2$ is attached form 5-10 membered heterocycloalkyl, which is optionally substituted with 1 or 2 independently selected $Cy^1$;

or $R^2$ and $R^3$, together with the N atom to which they are attached, form 4-16 membered heterocycloalkyl ring, which is optionally substituted with 1 or 2 independently selected $Cy^1$;

m is 0, 1, 2, 3, or 4;

n is 0, 1, 2, or 3;

each $R^5$ is independently selected from OH, $NO_2$, CN, halo, $C_{1-6}$ alkyl, $C_{1-4}$ haloalkyl, $C_{1-6}$alkoxy, $C_{1-6}$haloalkoxy, thio, $C_{1-6}$ alkylthio, carboxy, amino, $C_{1-6}$ alkylamino, and di($C_{1-6}$ alkyl)amino;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a1}$, $C(O)R^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

each Cy$^2$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy2}$;

each R$^{Cy2}$ is independently selected from halo, CN, NO$_2$, C$_{1-6}$ alkyl, C$_{1-6}$ haloalkyl, C$_{2-6}$ alkenyl, C$_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

each R$^{a1}$, R$^{b1}$, R$^{c1}$, and R$^{d1}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{3-10}$ alkylene, C$_{3-10}$ cycloalkyl-CIA alkylene, (5-10 membered heteroaryl)-C$_{1-4}$ alkylene, and (4-10 membered heterocycloalkyl)-C$_{1-4}$ alkylene, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene are each optionally substituted with 1, 2, 3, 4, or 5 substituents independently selected from R$^g$;

or any R$^{c1}$ and R$^{d1}$ together with the N atom to which they are attached form a 4-7 membered heterocycloalkyl, which is optionally substituted with 1, 2, or 3 substituents independently selected from R$^g$; and each R$^g$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkylene, HO—C$_{1-3}$ alkylene, C$_{6-10}$ aryl, C$_{6-10}$ aryloxy, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$alkylene, (4-10 membered heterocycloalkyl)-C$_{1-4}$ alkylene, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$alkyl)aminosulfonylamino, aminocarbonylamino, C$_{1-6}$ alkylaminocarbonylamino, and di(C$_{1-6}$ alkyl)aminocarbonylamino.

In some embodiments, when R$^4$ is H, then at least one of R$^2$ and R$^3$ is selected from C$_{1-6}$ alkyl, C$_{1-6}$ haloalkyl, C$_{2-6}$ alkenyl, C$_{2-6}$ alkynyl, C(=O)Cy$^3$, and S(=O)$_2$Cy$^3$, wherein said C$_{1-6}$ alkyl, C$_{1-6}$ haloalkyl, C$_{2-6}$ alkenyl, and C$_{2-6}$ alkynyl are each substituted with 1 or 2 independently selected Cy$^3$, and each of said Cy$^3$ is independently selected from C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$.

In some embodiments, when R$^4$ is H, then R$^2$ and R$^3$ are both independently selected from C$_{1-6}$ alkyl, C$_{1-6}$ haloalkyl, C$_{2-6}$ alkenyl, C$_{2-6}$ alkynyl, Cy$^3$, C(=O)Cy$^3$, and S(=O)$_2$Cy$^3$, wherein said C$_{1-6}$ alkyl, C$_{1-6}$ haloalkyl, C$_{2-6}$ alkenyl, and C$_{2-6}$ alkynyl are each substituted with 1 or 2 independently selected Cy$^3$, and each of said Cy$^3$ is independently selected from C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$.

In some embodiments, when R$^4$ is H, then at least one of R$^2$ and R$^3$ is selected from C$_{1-6}$ alkyl, Cy$^3$, C$_{1-6}$ haloalkyl, C$_{2-6}$ alkenyl, C$_{2-6}$ alkynyl, C(=O)Cy$^3$, and S(=O)$_2$Cy$^3$, wherein said C$_{1-6}$ alkyl, C$_{2-6}$ alkenyl, and C$_{2-6}$ alkynyl are each optionally substituted with 1 or 2 independently selected Cy$^3$, and each of said Cy$^3$ is independently selected from C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$.

In some embodiments, the compound of Formula (I) is not any one of the following compounds:

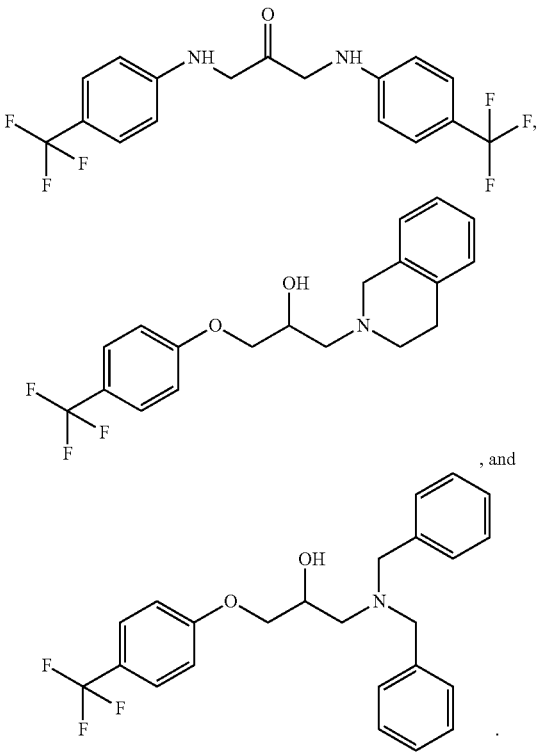

In some embodiments, the compound of Formula (I) is not the following compound:

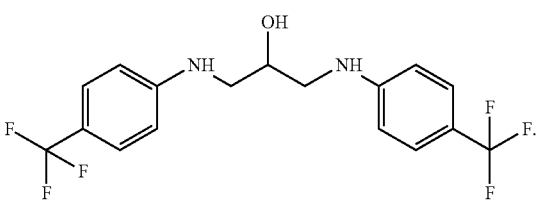 [SMILES: OC(CNc1ccc(C(F)(F)F)cc1)CNc1ccc(C(F)(F)F)cc1]

In some embodiments, the compound of Formula (I) is not any one of the following compounds:

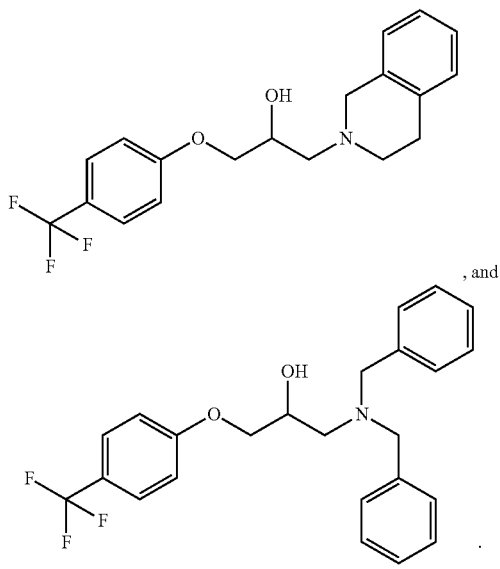

, and

In some embodiments:
L¹ is $C_{1-4}$ alkylene;
X is selected from $CH(OR^4)$ and $C=O$; or X is absent;
R⁴ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;
R² and R³, together with the N atom to which they are attached, form 4-16 membered heterocycloalkyl ring, which is optionally substituted with 1 or 2 independently selected $Cy^1$.

In some embodiments, the compound of Formula (I) has formula:

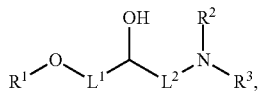

or a pharmaceutically acceptable salt thereof.

In some embodiments, the compound of Formula (I) has formula:

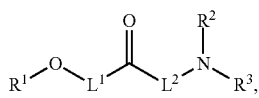

or a pharmaceutically acceptable salt thereof.

In some embodiments, the compound of Formula (I) has formula:

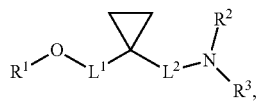

or a pharmaceutically acceptable salt thereof.

In some embodiments, the compound of Formula (I) has formula:

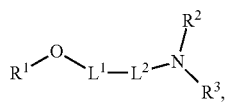

or a pharmaceutically acceptable salt thereof.

In some embodiments, the compound of Formula (I) has formula:

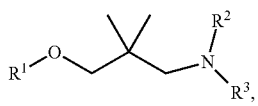

or a pharmaceutically acceptable salt thereof.

In some embodiments, $R^7$ is H. In some embodiments, $R^7$ is $C_{1-6}$ alkyl.

In some embodiments, $Cy^3$ is $C_{3-10}$ cycloalkyl, optionally substituted with 1, 2, or 3 substituents independently selected from $R^{Cy1}$.

In some embodiments, $Cy^3$ is 5-10 membered heteroaryl, optionally substituted with 1, 2, or 3 substituents independently selected from $R^{Cy1}$.

In some embodiments, $Cy^3$ is 4-10 membered heterocycloalkyl, optionally substituted with 1, 2, or 3 substituents independently selected from $R^{Cy1}$.

In some embodiments, $L^2$ is $C_{1-4}$ alkylene (e.g., methylene, ethylene, or propylene). In some embodiments, $L^2$ is methylene.

In some embodiments, the compound of Formula (I) has formula:

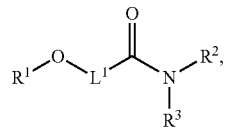

or a pharmaceutically acceptable salt thereof.

In some embodiments, the compound of Formula (I) has formula:

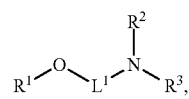

or a pharmaceutically acceptable salt thereof.

In some embodiments, $L^1$ is selected from methylene, ethylene, and propylene. In some embodiments, $L^1$ is selected from methylene and ethylene. In some embodiments, $L^1$ is selected from methylene and ethylene. In some embodiments, $L^1$ is methylene.

In some embodiments, $L^1$ is methylene and $L^2$ is methylene. In some embodiments, $L^1$ is methylene and $L^2$ is ethylene. In some embodiments, $L^1$ is ethylene and $L^2$ is methylene. In some embodiments, $L^1$ is methylene and $L^2$ is propylene. In some embodiments, $L^1$ is propylene and $L^2$ is methylene.

In some embodiments, $R^1$ is 5-6 membered heteroaryl, optionally substituted with 1, 2, or 3 substituents independently selected from $R^5$. In some embodiments, is $R^1$ is selected from pyridinyl (e.g., pyridin-2-yl, pyridin-3-yl, and pyridin-4-yl) and pyrimidinyl (e.g., pyrimidin-2-yl, pyrimidin-4-yl, pyrimidin-5-yl, and pyrimidin-6-yl), each of which is optionally substituted with 1, 2, or 3 substituents independently selected from $R^5$. In some aspects of these embodiments, at least one $R^5$ is $C_{1-3}$ haloalkyl (e.g., trifluoromethyl).

In some embodiments, $R^1$ is a group of formula:

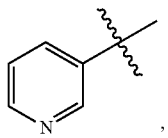 [SMILES: *c1cccnc1]

which is optionally substituted with 1, 2, 3, or 4 independently selected $R^5$ groups.

In some embodiments, $R^1$ is a group of formula:

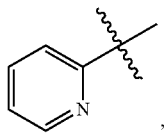 [SMILES: *c1ccccn1]

which is optionally substituted with 1, 2, 3, or 4 independently selected $R^5$ groups.

In some embodiments, $R^1$ is a group of formula:

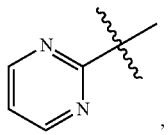 [SMILES: *c1ncccn1]

which is optionally substituted with 1, 2, or 3 independently selected $R^5$ groups.

In some embodiments, $R^1$ is a group of formula:

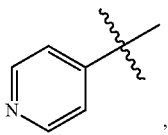

which is optionally substituted with 1, 2, 3, or 4 independently selected $R^5$ groups.

In some embodiments, $R^1$ is a group of formula:

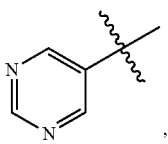

which is optionally substituted with 1, 2, or 3 independently selected $R^5$ groups.

In some embodiments, $R^1$ is a group of formula:

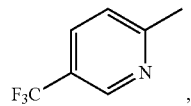

which is optionally substituted with 1, 2, or 3 independently selected $R^5$ groups.

In some embodiments, $R^1$ is a group of formula:

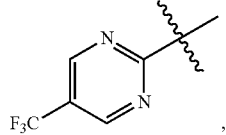

which is optionally substituted with 1, 2, or 3 independently selected $R^5$ groups.

In some embodiments, $R^1$ is a group of formula:

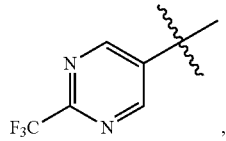

which is optionally substituted with 1, 2, or 3 independently selected $R^5$ groups.

In some embodiments, $R^1$ is a group of formula (i):

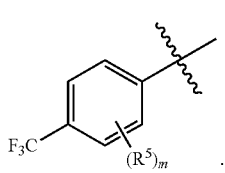

(i)

In some embodiments, m is 0, 1, or 2. In some embodiments, m is 1. In some embodiments, m is 2. In some embodiments, m is 3.

In some embodiments, $R^1$ is a group of formula (ii):

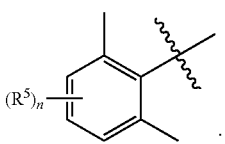

(ii)

In some embodiments, n is 0, 1, or 2. In some embodiments, n is 1. In some embodiments, n is 2. In some embodiments, n is 3.

In some embodiments, $R^5$ is selected from halo, $C_{1-6}$ alkyl, $C_{1-4}$ haloalkyl, $C_{1-6}$alkoxy, and $C_{1-6}$ haloalkoxy. In some embodiments, $R^5$ is halo (e.g., F or Cl). In some embodiments, $R^5$ is selected from $C_{1-6}$ alkyl, $C_{1-4}$ haloalkyl and $C_{1-6}$ alkoxy. In some embodiments, $R^5$ is $C_{1-4}$ haloalkyl (e.g., trifluoromethyl). In some embodiments, $R^5$ is $C_{1-6}$ alkoxy (e.g., methoxy).

In some embodiments, $R^1$ is a group of formula:

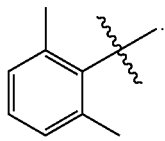 [SMILES: *c1c(C)cccc1C]

In some embodiments, $R^1$ is a group of formula:

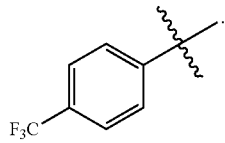

In some embodiments, the compound of Formula (I) has formula:

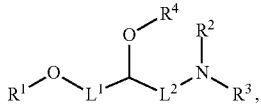

or a pharmaceutically acceptable salt thereof.

In some embodiments, the compound of Formula (I) has formula:

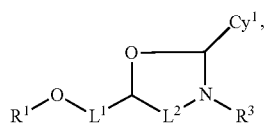

or a pharmaceutically acceptable salt thereof.

In some embodiments, the compound of Formula (I) has formula:

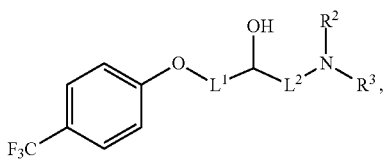

or a pharmaceutically acceptable salt thereof.

In some embodiments, the compound of Formula (I) has formula:

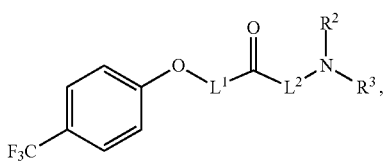

or a pharmaceutically acceptable salt thereof.

In some embodiments, the compound of Formula (I) has formula:

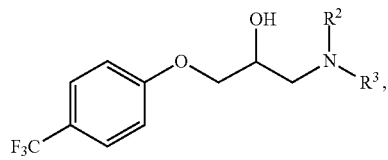

or a pharmaceutically acceptable salt thereof.

In some embodiments, the compound of Formula (I) has formula:

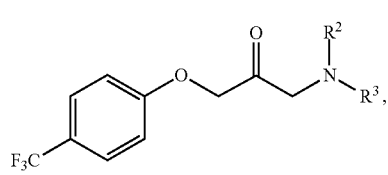

or a pharmaceutically acceptable salt thereof.

In some embodiments, the compound of Formula (I) has formula:

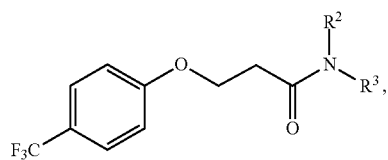

or a pharmaceutically acceptable salt thereof.

In some embodiments, the compound of Formula (I) has formula:

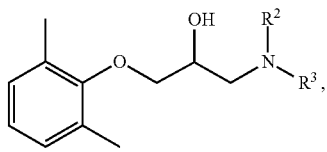

or a pharmaceutically acceptable salt thereof.

In some embodiments, the compound of Formula (I) has formula:

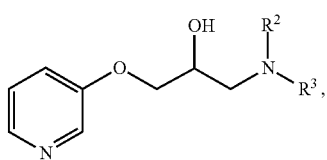

or a pharmaceutically acceptable salt thereof.

In some embodiments, the compound of Formula (I) has formula:

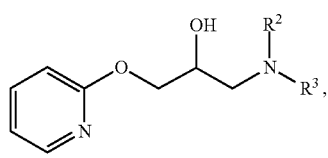

or a pharmaceutically acceptable salt thereof.

In some embodiments, the compound of Formula (I) has formula:

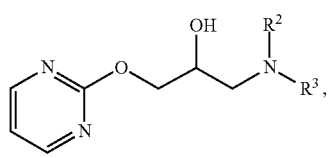

or a pharmaceutically acceptable salt thereof.

In some embodiments, the compound of Formula (I) has formula:

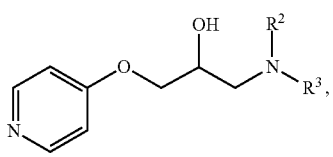

or a pharmaceutically acceptable salt thereof.

In some embodiments, the compound of Formula (I) has formula:

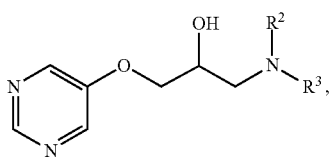

or a pharmaceutically acceptable salt thereof.

In some embodiments, the compound of Formula (I) has formula:

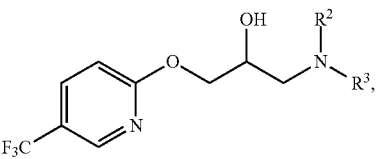

or a pharmaceutically acceptable salt thereof.

In some embodiments, the compound of Formula (I) has formula:

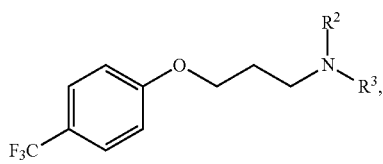

or a pharmaceutically acceptable salt thereof.

In some embodiments, the compound of Formula (I) has formula:

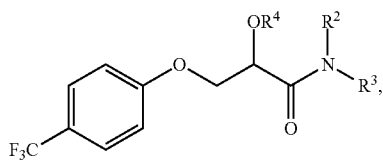

or a pharmaceutically acceptable salt thereof.

In some embodiments, the compound of Formula (I) has formula:

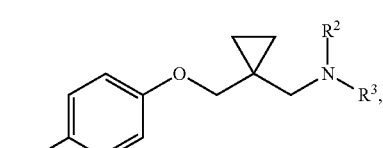

or a pharmaceutically acceptable salt thereof.

In some embodiments, the compound of Formula (I) has formula:

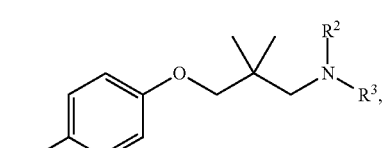

or a pharmaceutically acceptable salt thereof.

In some embodiments, the compound of Formula (I) has formula:

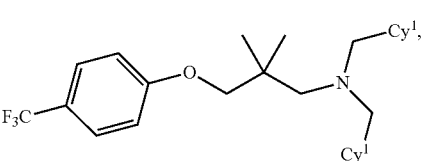

or a pharmaceutically acceptable salt thereof.

In some embodiments:
$R^2$ is $C_{1-6}$ alkyl substituted with $C_{6-10}$ aryl group, which is optionally substituted with 1, 2, or 3 substituents independently selected from $R^{Cy1}$; and
$R^3$ is $C_{1-6}$ alkyl substituted with 5-10 membered heteroaryl group, which is optionally substituted with 1, 2, or 3 substituents independently selected from $R^{Cy1}$.

In some embodiments, the compound of Formula (I) has formula:

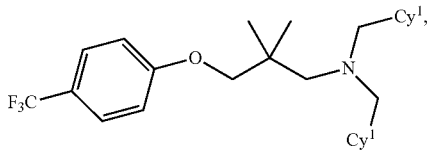

or a pharmaceutically acceptable salt thereof.

In some embodiments, each $Cy^1$ is independently selected from $C_{6-10}$ aryl and 5-10 membered heteroaryl, each of which is optionally substituted with 1, 2, or 3 substituents independently selected from $R^{Cy1}$.

In some embodiments, the compound of Formula (I) has formula:

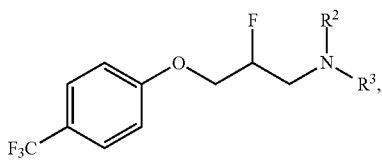

or a pharmaceutically acceptable salt thereof.

In some embodiments, the compound of Formula (I) has formula:

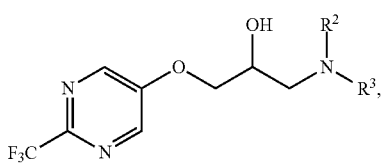

or a pharmaceutically acceptable salt thereof.

In some embodiments, the compound of Formula (I) has formula:

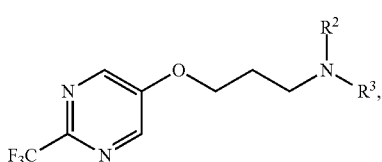

or a pharmaceutically acceptable salt thereof.

In some embodiments, the compound of Formula (I) has formula:

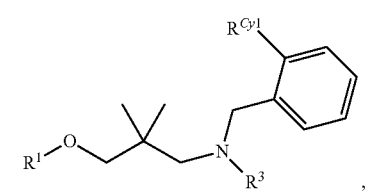

or a pharmaceutically acceptable salt thereof.

In some embodiments, $R^{Cy1}$ is selected from $C_{1-6}$ alkyl, halo, and $C_{1-6}$ haloalkyl.

In some embodiments, $R^{Cy1}$ is $C_{1-6}$ alkyl.

In some embodiments, the compound of Formula (I) has formula:

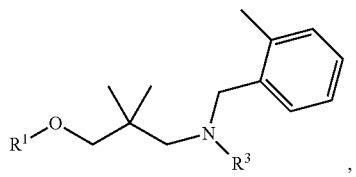

or a pharmaceutically acceptable salt thereof.

In some embodiments, the compound of Formula (I) has formula:

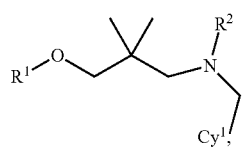

or a pharmaceutically acceptable salt thereof.

In some embodiments, $Cy^1$ is pyridinyl, optionally substituted with 1, 2, or 3 substituents independently selected from $R^{Cy1}$.

In some embodiments, the compound of Formula (I) has formula:

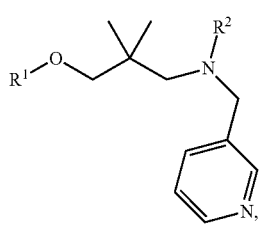

or a pharmaceutically acceptable salt thereof.

In some embodiments, $R^2$ is $C_{1-6}$ alkyl substituted with $C_{6-10}$ aryl group, which is optionally substituted with 1, 2, or 3 substituents independently selected from $R^{Cy1}$.

In some embodiments, the compound of Formula (I) has formula:

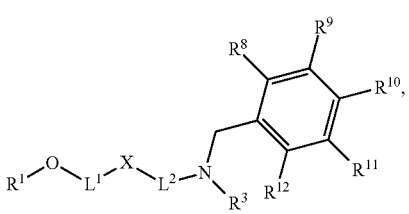

or a pharmaceutically acceptable salt thereof, wherein each $R^8$, $R^9$, $R^{10}$, $R^{11}$, and $R^{12}$ is independently selected from H and $R^{Cy1}$.

In some embodiments, the compound of Formula (I) has formula:

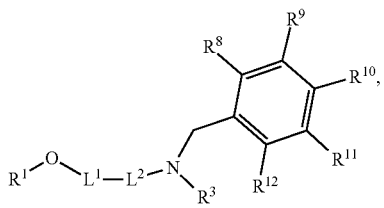

or a pharmaceutically acceptable salt thereof.

In some embodiments, the compound of Formula (I) has formula:

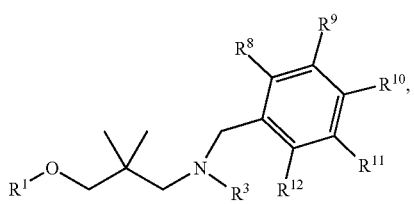

or a pharmaceutically acceptable salt thereof.

In some embodiments, at least one of $R^8$, $R^9$, $R^{10}$, $R^{11}$, and $R^{12}$ is $R^{Cy1}$.

In some embodiments, at least one of $R^8$, $R^9$, $R^{10}$, $R^{11}$, and $R^{12}$ is $C_{1-6}$ alkyl, optionally substituted with 1, 2, or 3 substituents independently selected from $Cy^2$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{d1}$, and $S(O)_2NR^{c1}R^{d1}$.

In some embodiments, at least one of $R^8$, $R^9$, $R^{10}$, $R^{11}$, and $R^{12}$ is $C_{1-6}$ alkyl.

In some embodiments, at least one of $R^8$, $R^9$, $R^{10}$, $R^{11}$, and $R^{12}$ is $C_{1-3}$ alkyl.

In some embodiments:
$R^8$ is $C_{1-6}$ alkyl; and
each $R^9$, $R^{10}$, $R^{11}$, and $R^{12}$ is independently selected from H and $R^{Cy1}$.

In some embodiments, the compound of Formula (I) has formula:

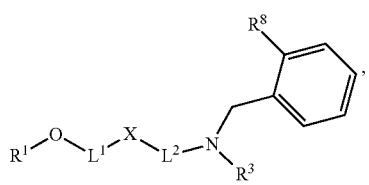

or a pharmaceutically acceptable salt thereof.

In some embodiments, the compound of Formula (I) has formula:

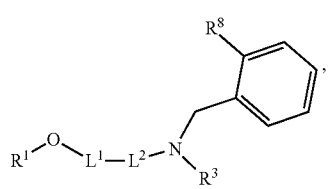

or a pharmaceutically acceptable salt thereof.

In some embodiments, $R^8$ is $R^{Cy1}$.

In some embodiments, $R^8$ is $C_{1-6}$ alkyl.

In some embodiments, the compound of Formula (I) has formula:

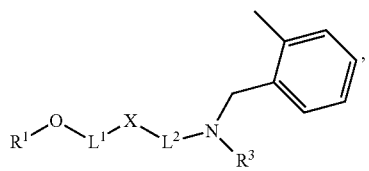

or a pharmaceutically acceptable salt thereof.

In some embodiments, the compound of Formula (I) has formula:

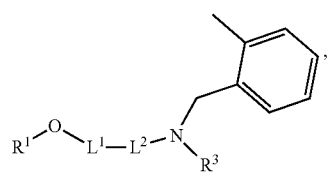

or a pharmaceutically acceptable salt thereof.

In some embodiments, the compound of Formula (I) has formula:

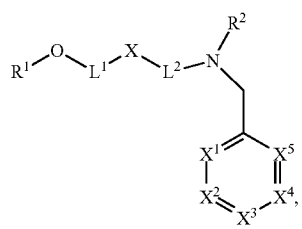

or a pharmaceutically acceptable salt thereof, wherein:

$X^1$ is selected from N and $CR^{13}$;

$X^2$ is selected from N and $CR^{14}$;

$X^3$ is selected from N and $CR^{15}$;

$X^4$ is selected from N and $CR^{16}$;

$X^5$ is selected from N and $CR^{17}$; and each $R^{13}$, $R^{14}$, $R^{15}$, $R^{16}$, and $R^{17}$ is independently selected from H and $R^{Cy1}$.

In some embodiments, not more than three of $X^1$, $X^2$, $X^3$, $X^4$, and $X^5$ are N.

In some embodiments, not more than two of $X^1$, $X^2$, $X^3$, $X^4$, and $X^5$ are N.

In some embodiments, only one of $X^1$, $X^2$, $X^3$, $X^4$, and $X^5$ is N.

In some embodiments, the compound of Formula (I) has formula:

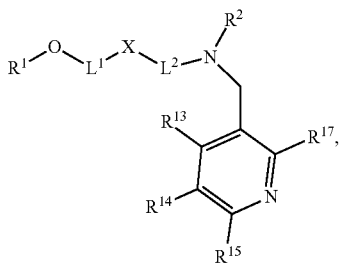

or a pharmaceutically acceptable salt thereof.

In some embodiments, the compound of Formula (I) has formula:

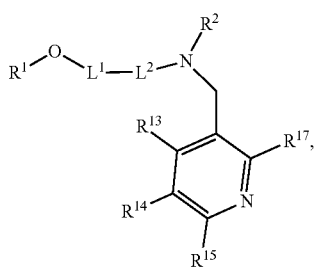

or a pharmaceutically acceptable salt thereof.

In some embodiments, each $R^{13}$, $R^{14}$, $R^{15}$, and $R^{17}$ is independently selected from H and $R^{Cy1}$. In some embodiments, at least one of $R^{13}$, $R^{14}$, $R^{15}$, and $R^{17}$ is $R^{Cy1}$. In some embodiments, at least one of $R^{13}$, $R^{14}$, $R^{15}$, and $R^{17}$ is $C_{1-6}$ alkyl.

In some embodiments, $R^{13}$ is $C_{1-6}$ alkyl, and $R^{14}$, $R^{15}$, and $R^{17}$ are each H.

In some embodiments, $R^{17}$ is $C_{1-6}$ alkyl, and $R^{14}$, $R^{15}$, and $R^{13}$ are each H.

In some embodiments, the compound of Formula (I) has formula:

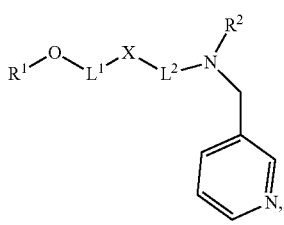

or a pharmaceutically acceptable salt thereof.

In some embodiments, the compound of Formula (I) has formula:

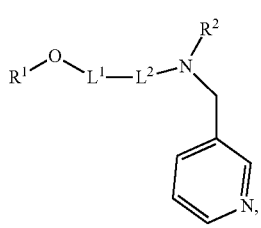

or a pharmaceutically acceptable salt thereof.

In some embodiments, the compound of Formula (I) has formula:

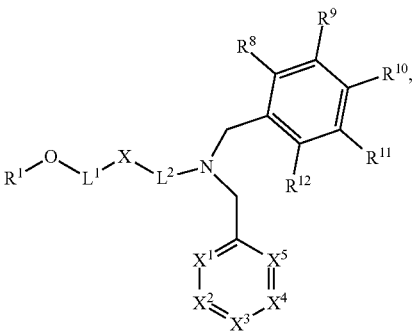

or a pharmaceutically acceptable salt thereof.

In some embodiments, the compound of Formula (I) has formula:

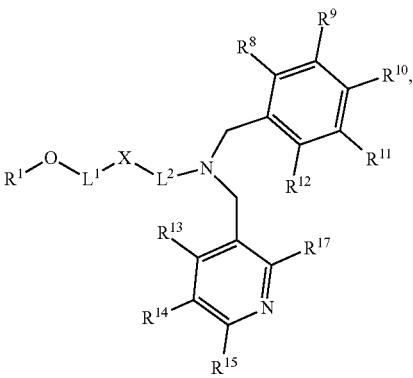

or a pharmaceutically acceptable salt thereof.

In some embodiments, the compound of Formula (I) has formula:

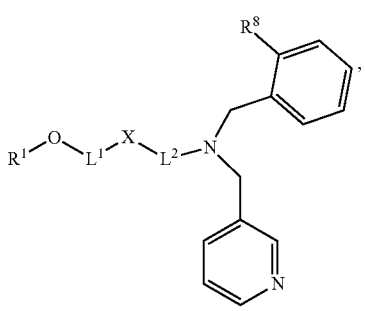

or a pharmaceutically acceptable salt thereof.

In some embodiments, the compound of Formula (I) has formula:

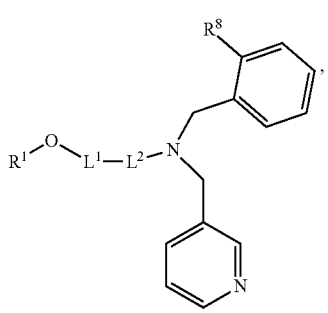

or a pharmaceutically acceptable salt thereof.

In some embodiments, the compound of Formula (I) has formula:

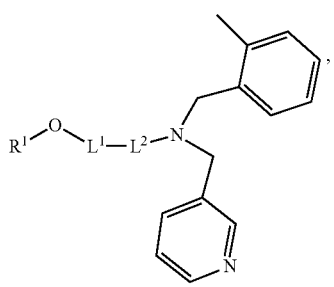

or a pharmaceutically acceptable salt thereof.

In some embodiments, $R^2$ and $R^3$ are each independently selected from H, $C_{1-6}$ alkyl, $Cy^1$, $C(=O)Cy^1$, and $S(=O)_2Cy^1$, wherein said $C_{1-6}$ alkyl, is optionally substituted with 1 or 2 independently selected $Cy^1$.

In some embodiments, $R^2$ is H. In some embodiments, $R^2$ is $C_{1-6}$ alkyl. In some embodiments, $R^2$ is $Cy^1$. In some embodiments, $R^2$ is $C(=O)Cy^1$. In some embodiments, $R^2$ is $S(=O)_2Cy^1$. In some embodiments, $R^2$ is $C_{1-6}$ alkyl substituted with 1 or 2 independently selected $Cy^1$. In some embodiments, $R^2$ is $C_{1-6}$ alkyl substituted with $Cy^1$. In some embodiments, $R^2$ is $C_{1-6}$ alkyl substituted with 2 independently selected $Cy^1$.

In some embodiments, $R^3$ is H. In some embodiments, $R^3$ is $C_{1-6}$ alkyl. In some embodiments, $R^3$ is $Cy^1$. In some embodiments, $R^3$ is $C(=O)Cy^1$. In some embodiments, $R^3$ is $S(=O)_2Cy^1$. In some embodiments, $R^3$ is $C_{1-6}$ alkyl substituted with 1 or 2 independently selected $Cy^1$. In some embodiments, $R^3$ is $C_{1-6}$ alkyl substituted with $Cy^1$. In some embodiments, $R^3$ is $C_{1-6}$ alkyl substituted with 2 independently selected $Cy^1$.

In some embodiments, $R^2$ and $R^3$ are each independently an $C_{1-6}$ alkyl substituted with 1 or 2 independently selected $Cy^1$.

In some embodiments:
$R^2$ is $C_{1-6}$ alkyl substituted with $Cy^1$; and
$R^3$ is $C_{1-6}$ alkyl substituted with $Cy^1$.

In some embodiments:
$R^2$ is $C_{1-6}$ alkyl substituted with 1 or 2 independently selected $C_{6-10}$ aryl groups, each of which is optionally substituted with 1, 2, or 3 substituents independently selected from $R^{Cy1}$; and
$R^3$ is $C_{1-6}$ alkyl substituted with 1 or 2 independently selected $C_{6-10}$ aryl groups, each of which is optionally substituted with 1, 2, or 3 substituents independently selected from $R^{Cy1}$.

In some embodiments:
$R^2$ is $C_{1-6}$ alkyl substituted with 1 or 2 independently selected $C_{3-10}$ cycloalkyl groups, each of which is optionally substituted with 1, 2, or 3 substituents independently selected from $R^{Cy1}$; and
$R^3$ is $C_{1-6}$ alkyl substituted with 1 or 2 independently selected $C_{3-10}$ cycloalkyl groups, each of which is optionally substituted with 1, 2, or 3 substituents independently selected from $R^{Cy1}$.

In some embodiments:
$R^2$ is $C_{1-6}$ alkyl substituted with 1 or 2 independently selected 5-10 membered heteroaryl groups, each of which is optionally substituted with 1, 2, or 3 substituents independently selected from $R^{Cy1}$; and
$R^3$ is $C_{1-6}$ alkyl substituted with 1 or 2 independently selected 5-10 membered heteroaryl groups, each of which is optionally substituted with 1, 2, or 3 substituents independently selected from $R^{Cy1}$.

In some embodiments:
$R^2$ is $C_{1-6}$ alkyl substituted with 1 or 2 independently selected $C_{6-10}$ aryl groups, each of which is optionally substituted with 1, 2, or 3 substituents independently selected from $R^{Cy1}$; and
$R^3$ is $C_{1-6}$ alkyl substituted with 1 or 2 independently selected 5-10 membered heteroaryl groups, each of which is optionally substituted with 1, 2, or 3 substituents independently selected from $R^{Cy1}$.

In some embodiments:
$R^2$ is selected from H and $C_{1-6}$ alkyl; and
$R^3$ is $C_{1-6}$ alkyl substituted with 1 or 2 independently selected $Cy^1$.

In some embodiments:
$R^2$ is $C_{1-6}$ alkyl substituted with 1 or 2 independently selected $Cy^1$; and
$R^3$ is selected from $Cy^1$, $C(=O)Cy^1$ and $S(=O)_2Cy^1$.

In some embodiments:
$R^2$ is $C_{1-6}$ alkyl substituted with 1 or 2 independently selected $Cy^1$; and
$R^3$ is $C(=O)Cy^1$.

In some embodiments, $R^2$ and $R^3$, together with the N atom to which they are attached, form 4-16 membered heterocycloalkyl ring, which is optionally substituted with $Cy^1$.

In some embodiments, the 4-16 membered heterocycloalkyl ring is selected from tetrahydroisoquinolinyl, isoindolinyl, and dihydrodibenzoazepinyl.

In some embodiments, $R^2$ and $R^3$, together with the N atom to which they are attached, form a ring of formula selected from:

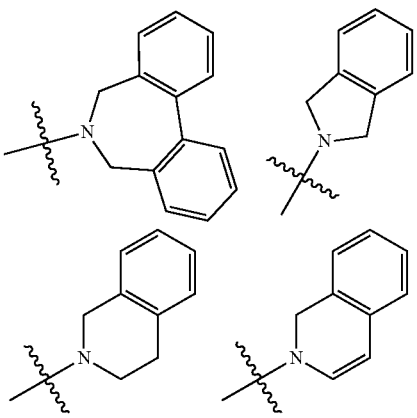

each of which is optionally substituted with a substituent selected from Cy$^1$, C(O)OR$^{a1}$, and an C$_{1-6}$ alkyl optionally substituted with OR$^{a1}$.

In some embodiments, R$^2$ and R$^3$, together with the N atom to which they are attached, form a ring of formula:

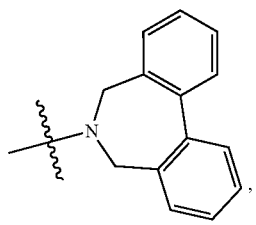 [SMILES: *N1Cc2ccccc2-c2ccccc2C1]

which is optionally substituted with Cy$^1$.

In some embodiments, R$^2$ and R$^3$, together with the N atom to which they are attached, form a ring of formula:

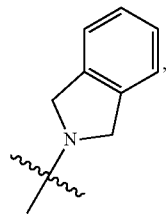 [SMILES: *N1Cc2ccccc2C1]

which is optionally substituted with Cy$^1$.

In some embodiments, R$^2$ and R$^3$, together with the N atom to which they are attached, form a ring of formula:

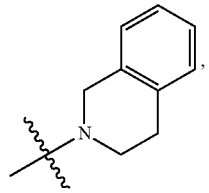 [SMILES: *N1CCc2ccccc2C1]

which is optionally substituted with Cy$^1$.

In some embodiments, R$^2$ and R$^3$, together with the N atom to which they are attached, form a ring of formula:

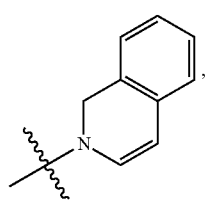 [SMILES: *N1C=Cc2ccccc2C1]

which is optionally substituted with Cy$^1$.

In some embodiments, the compound of Formula (I) is has formula:

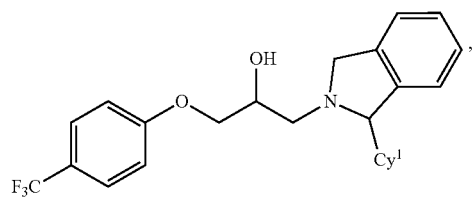

or a pharmaceutically acceptable salt thereof.

In some embodiments, the compound of Formula (I) is has formula:

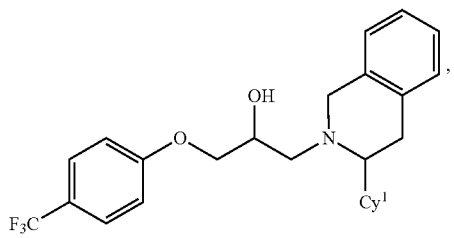

or a pharmaceutically acceptable salt thereof.

In some embodiments, the compound of Formula (I) is has formula:

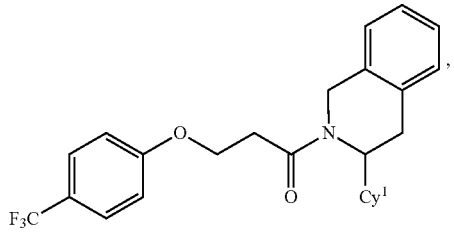

or a pharmaceutically acceptable salt thereof.

In some embodiments, the compound of Formula (I) is has formula:

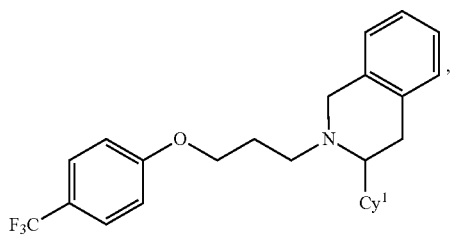

or a pharmaceutically acceptable salt thereof.

In some embodiments, the compound of Formula (I) is has formula:

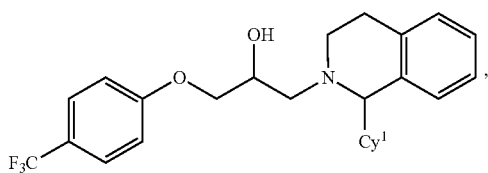

or a pharmaceutically acceptable salt thereof.

In some embodiments, the compound of Formula (I) is has formula:

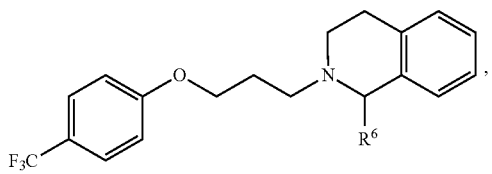

or a pharmaceutically acceptable salt thereof.

In some embodiments, the compound of Formula (I) is has formula:

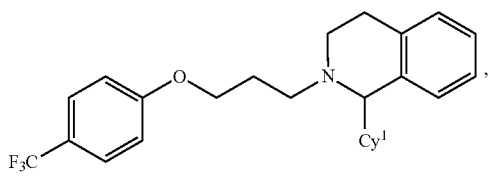

or a pharmaceutically acceptable salt thereof.

In some embodiments, the compound of Formula (I) is has formula:

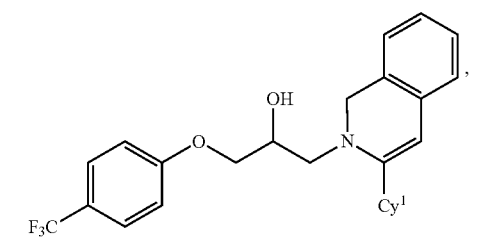

or a pharmaceutically acceptable salt thereof.

In some embodiments, $R^4$ and $R^2$ together with the O atom to which $R^4$ is attached and N atom to which $R^2$ is attached form 5-10 membered heterocycloalkyl, which is optionally substituted with 1 or 2 independently selected $Cy^1$.

In some embodiments, the compound of Formula (I) has formula:

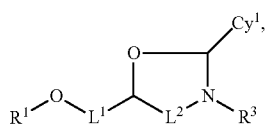

or a pharmaceutically acceptable salt thereof.

In some embodiments, the compound of Formula (I) has formula:

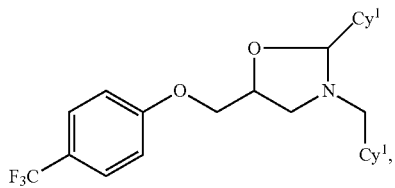

or a pharmaceutically acceptable salt thereof.

In some embodiments. $Cy^1$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy1}$.

In some embodiments, $Cy^1$ is selected from $C_{6-10}$ aryl, $C_{3-10}$ cycloalkyl, and 5-10 membered heteroaryl, each of which is optionally substituted with 1, 2, or 3 substituents independently selected from $R^{Cy1}$.

In some embodiments, $Cy^1$ is $C_{6-10}$ aryl, optionally substituted with 1, 2, or 3 substituents independently selected from $R^{Cy1}$. In some embodiments, $Cy^1$ is phenyl, optionally substituted with 1, 2, or 3 substituents independently selected from $R^{Cy1}$.

In some embodiments, $Cy^1$ is $C_{3-10}$ cycloalkyl, optionally substituted with 1, 2, or 3 substituents independently selected from $R^{Cy1}$. In some embodiments, $Cy^1$ is selected from cyclopropyl and cyclohexyl, each of which is optionally substituted with 1, 2, or 3 substituents independently selected from $R^{Cy1}$.

In some embodiments, $Cy^1$ is 5-10 membered heteroaryl, optionally substituted with 1, 2, or 3 substituents independently selected from $R^{Cy1}$.

In some embodiments, $Cy^1$ is selected from phenyl, cyclopropyl, cyclohexyl, pyridinyl, pyrimidinyl, pyridazinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

In some embodiments, $Cy^3$ is selected from cyclopropyl, cyclohexyl, pyridinyl, pyrimidinyl, pyridazinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

In some embodiments, $Cy^1$ is selected from phenyl, cyclopropyl, cyclohexyl, pyridinyl, pyrimidinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

In some embodiments, $Cy^1$ is selected from pyridinyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-6-yl), imidazolyl, pyrazolyl, and thiazolyl, each of which is optionally substituted with 1, 2, or 3 substituents independently selected from $R^{Cy1}$.

In some embodiments, $Cy^1$ is selected from phenyl, cyclopropyl, cyclohexyl, pyridinyl, pyrimidinyl, imidazolyl, pyrazolyl, and thiazolyl, each of which is optionally substituted with 1, 2, or 3 substituents independently selected from $R^{Cy1}$.

In some embodiments, each $R^{Cy1}$ is independently selected from halo, CN, $C(O)NR^{c1}R^{d1}$, $C_{1-6}$ alkyl, $C_{1-6}$ haloalkyl, and 5-10 membered heteroaryl, wherein said 5-10 membered heteroaryl is optionally substituted with halo, $C_{1-6}$ alkyl, $C_{1-6}$ alkoxy, $C_{1-6}$ haloalkyl, and $C_{1-6}$ haloalkoxy.

In some embodiments, each $R^{Cy1}$ is independently selected from halo, $C_{1-6}$ alkyl, $C_{1-6}$ haloalkyl, and 5-10 membered heteroaryl, wherein said 5-10 membered heteroaryl is optionally substituted with halo, $C_{1-6}$ alkyl, $C_{1-6}$ alkoxy, $C_{1-6}$ haloalkyl, and $C_{1-6}$ haloalkoxy.

In some embodiments, each $R^{Cy1}$ is independently selected from halo, $C_{1-6}$ alkyl, and $C_{1-6}$ haloalkyl. In some embodiments, $R^{Cy1}$ is 5-10 membered heteroaryl, optionally substituted with halo, $C_{1-6}$ alkyl, $C_{1-6}$ alkoxy, $C_{1-6}$ haloalkyl, and $C_{1-6}$ haloalkoxy. In some embodiments, $R^{Cy1}$ is 5-10 membered heteroaryl, optionally substituted with halo or C 1.6 haloalkyl.

In some embodiments, the compound of Formula (I) is selected from any one of the following compounds:

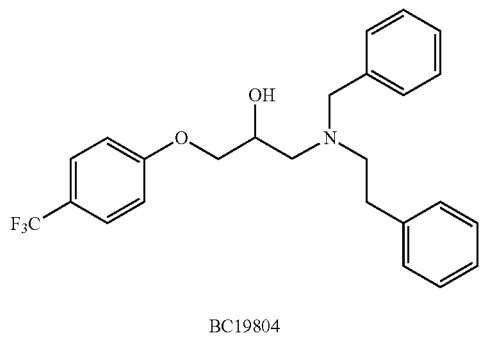

BC19804

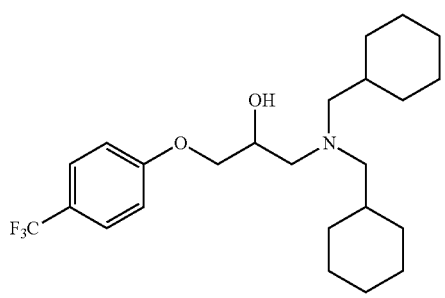

BC19801

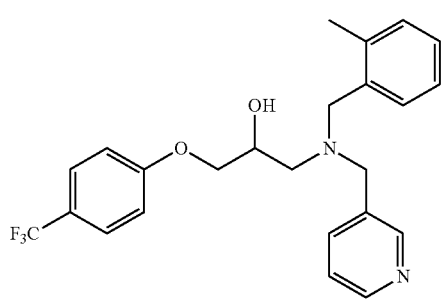

BC19805

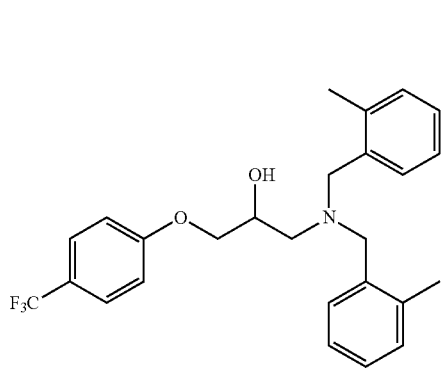

BC19802

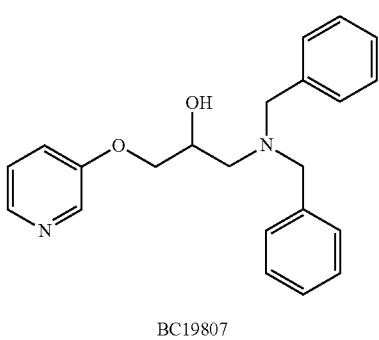

BC19806

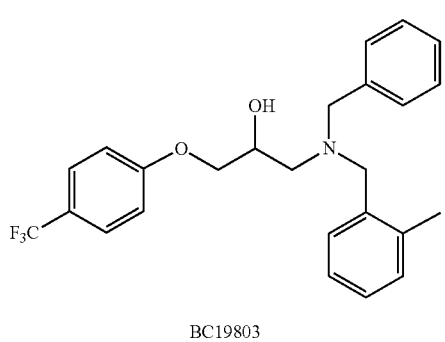

BC19803

BC19807

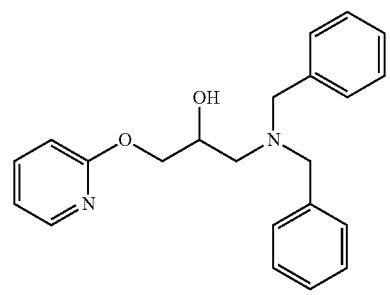
BC19808
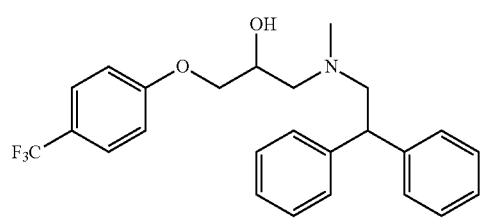
BC19809
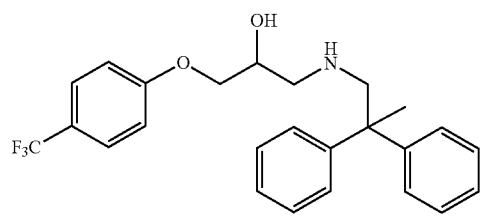
BC19810
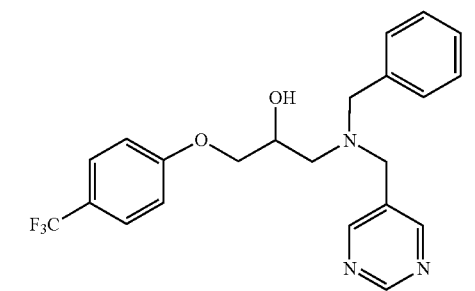
BC19811
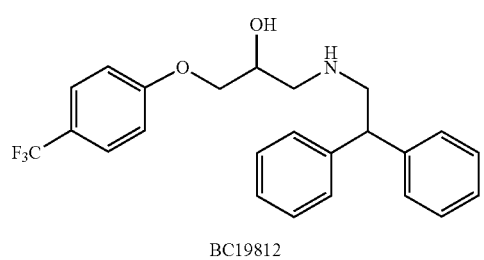
BC19812
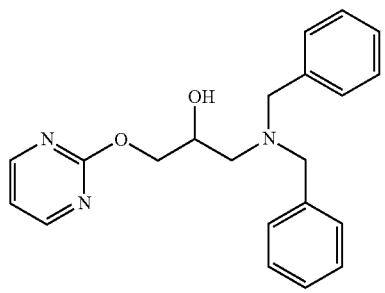
BC19813
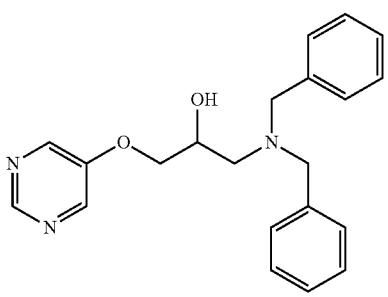
BC19814
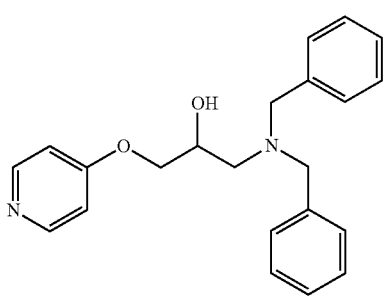
BC19815
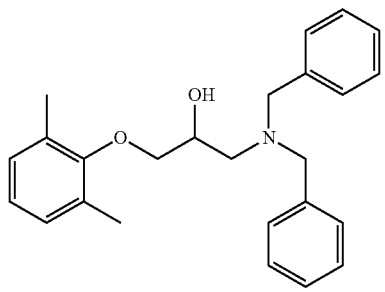
BC19816
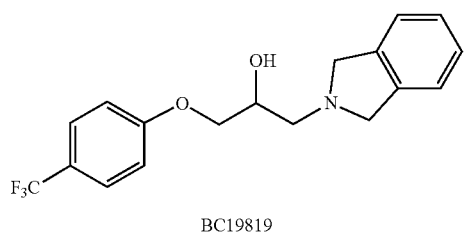
BC19819

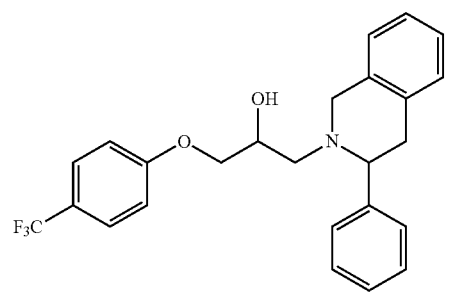
BC19820
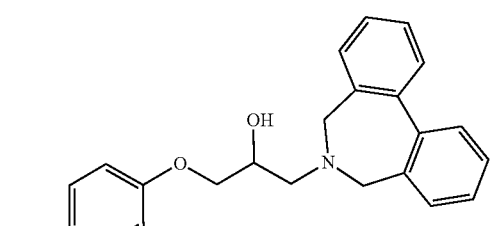
BC19821
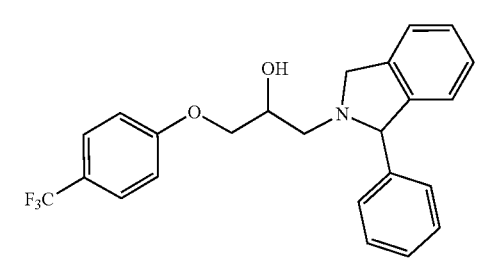
BC19822
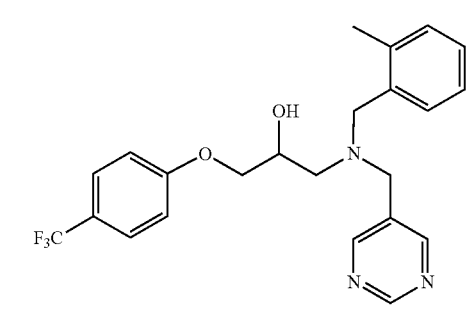
BC19823
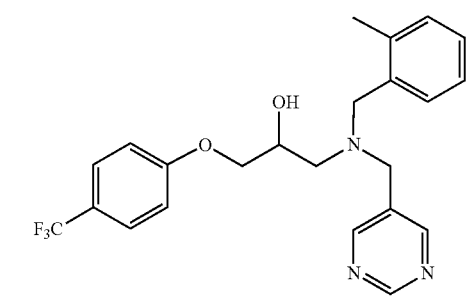
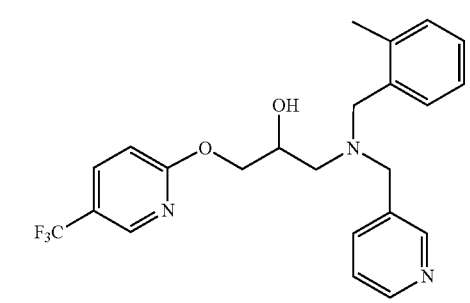
BC19824
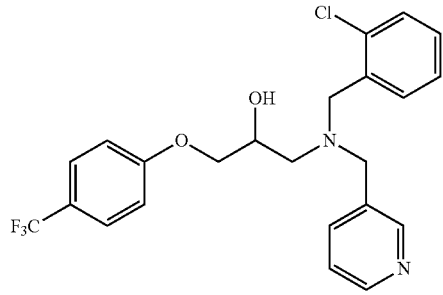
BC19825
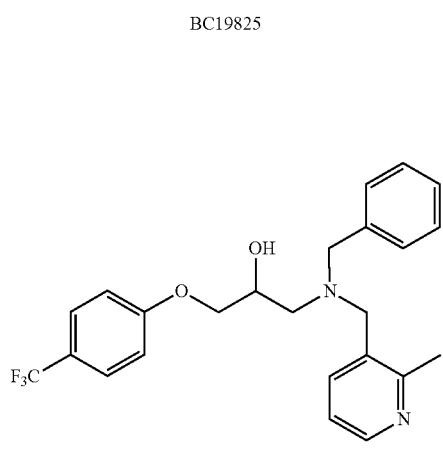
BC19826
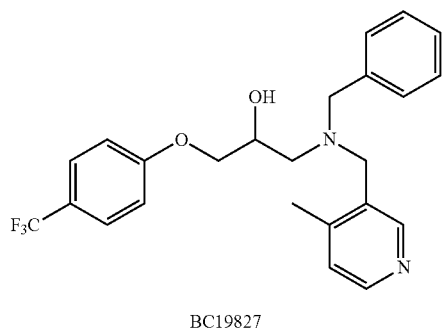
BC19827
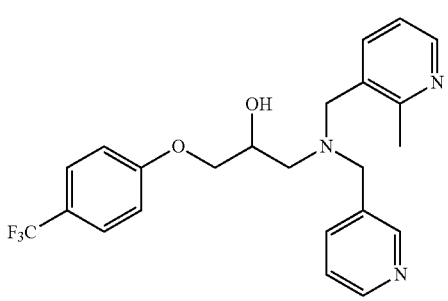
BC19828

-continued
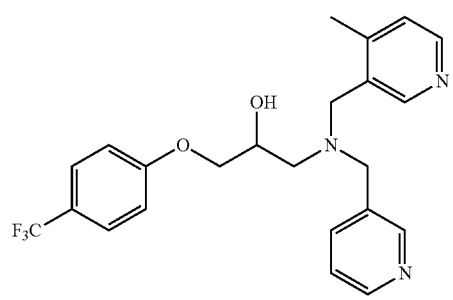
BC19829
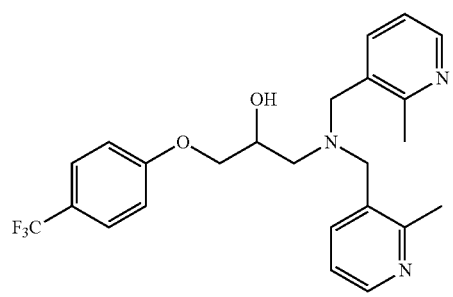
BC19830
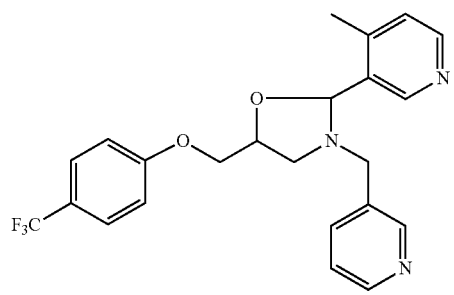
BC19831
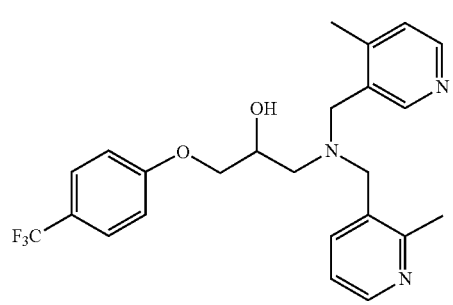
BC19832
-continued
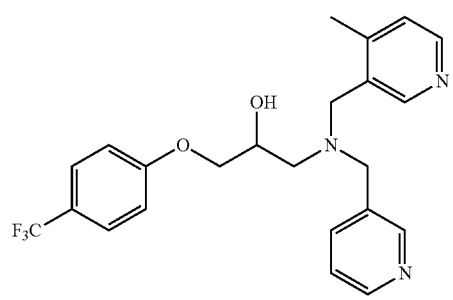
BC19833
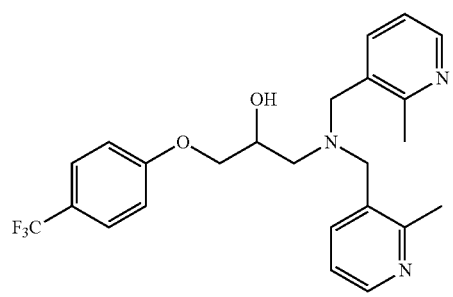
BC19834
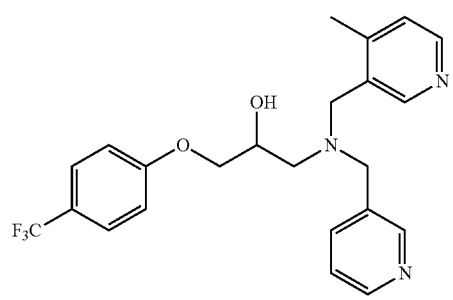
BC19835
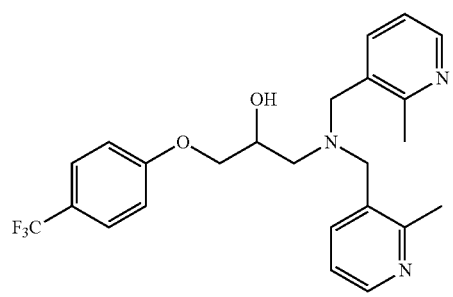
BC19836
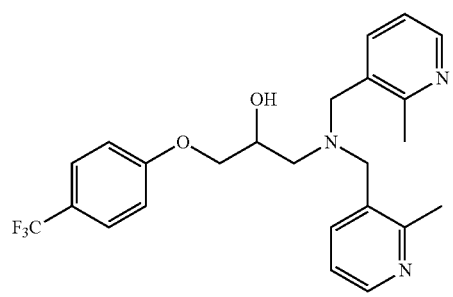
BC19837

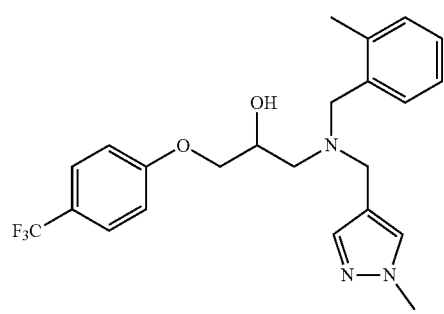
BC19838
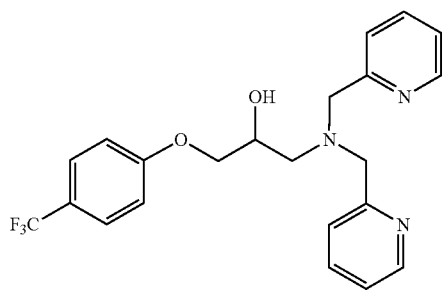
BC19842
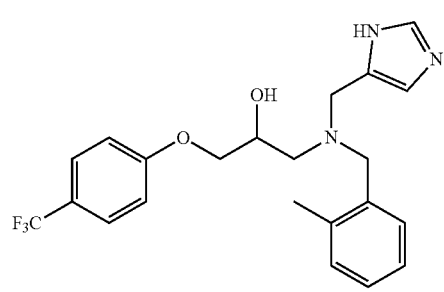
BC19839
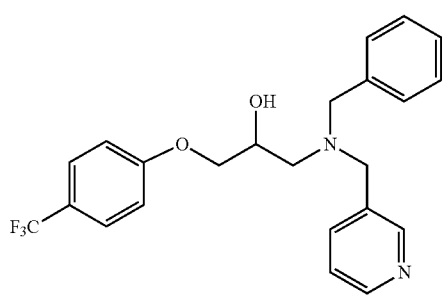
BC19843
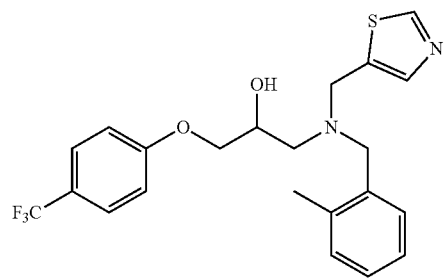
BC19840
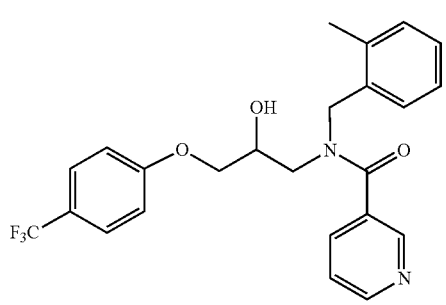
BC19845
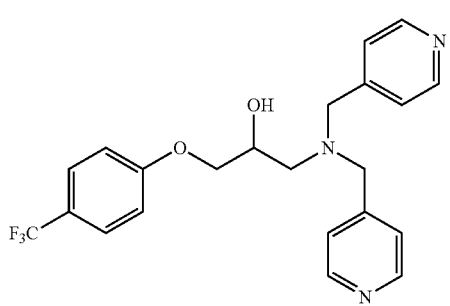
BC19841
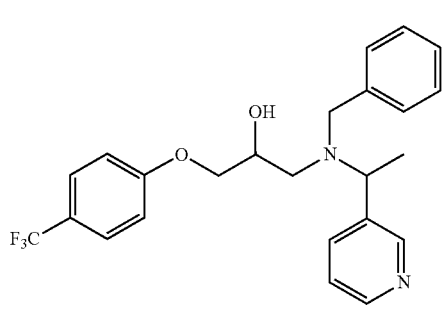
BC19846

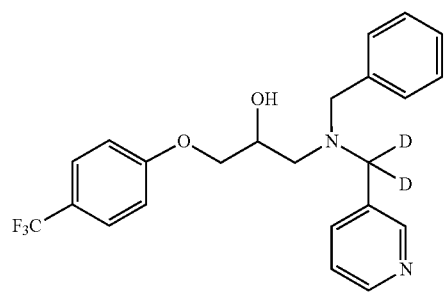
BC19847
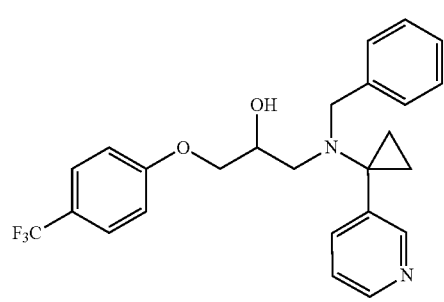
BC19848
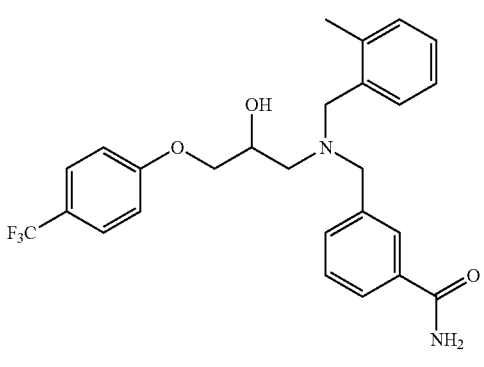
BC19849
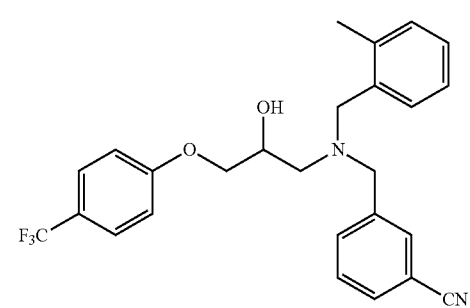
BC19850
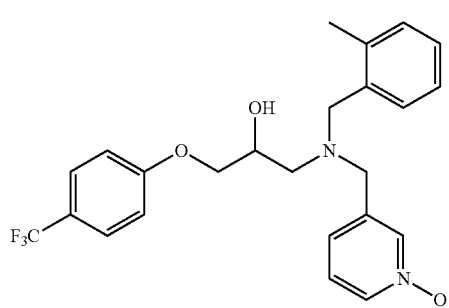
BC19851
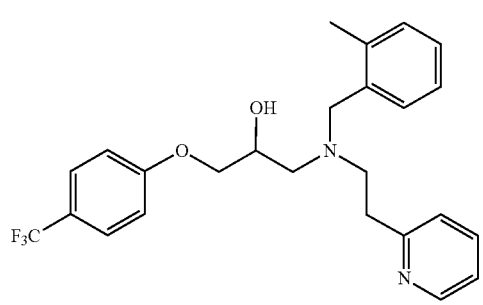
BC19852
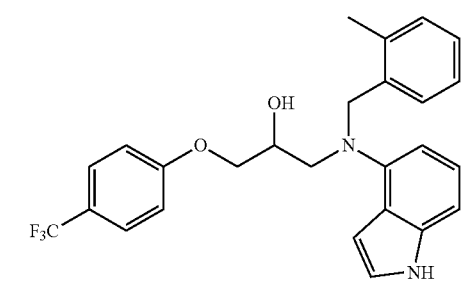
BC19853
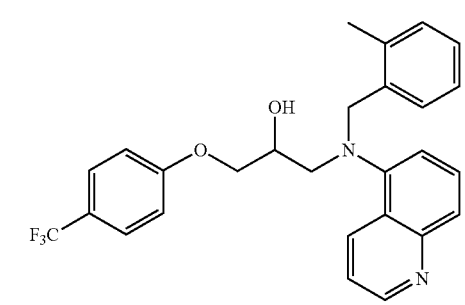
BC19854
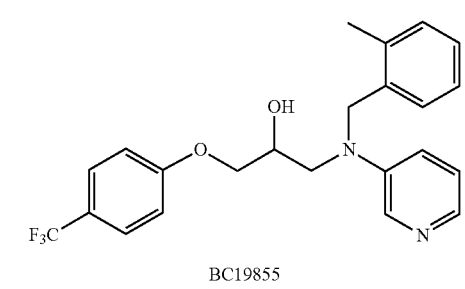
BC19855

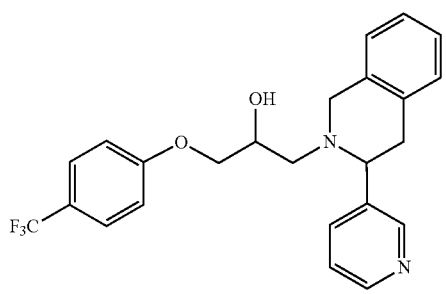
BC19856
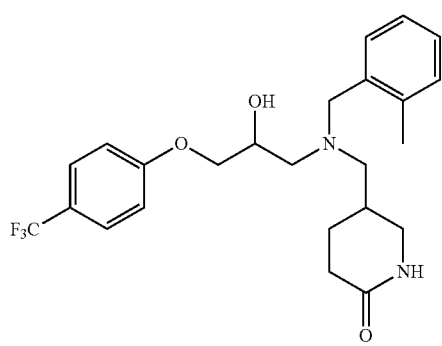
BC19858
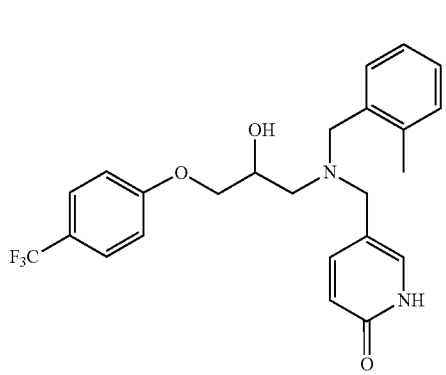
BC19859
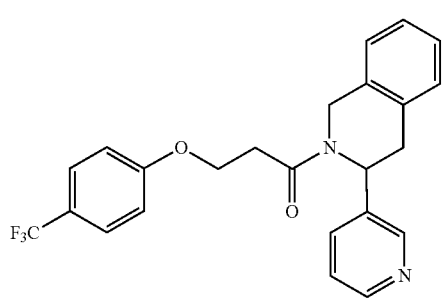
BC19862
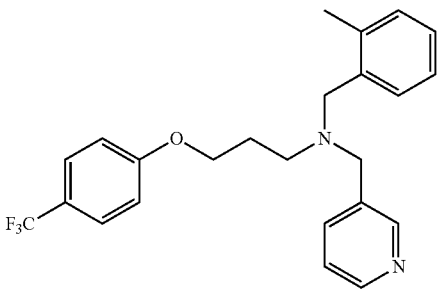
BC19863
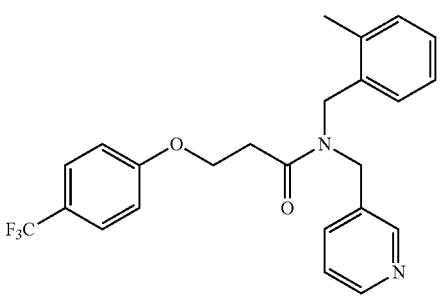
BC19864
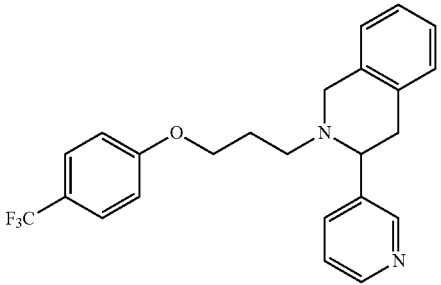
BC19865
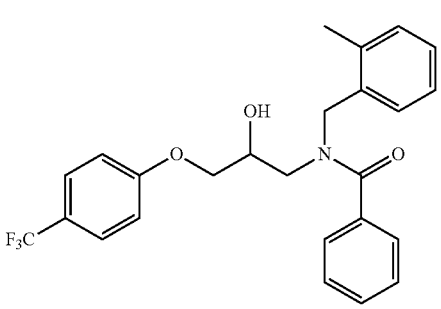
BC19866

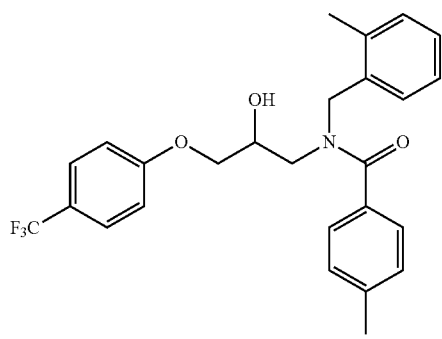
BC19867
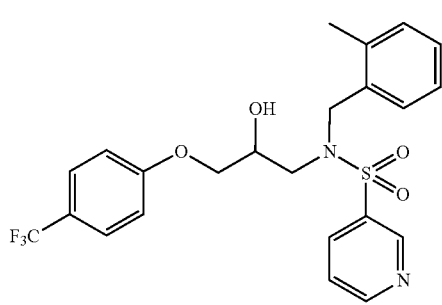
BC19868
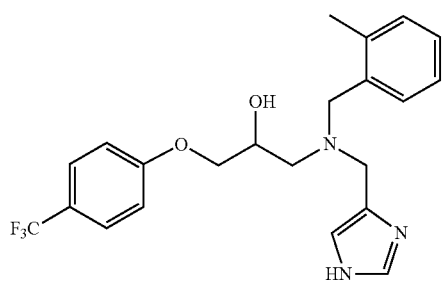
BC19869
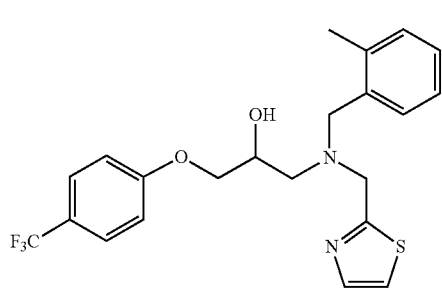
BC19870
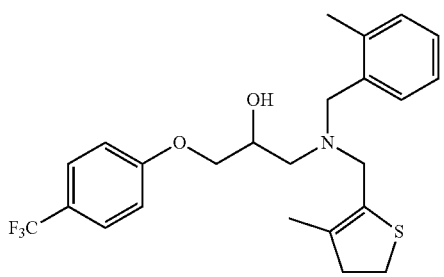
BC19871
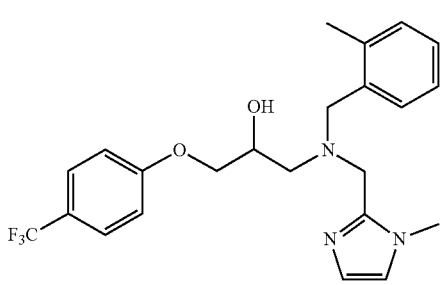
BC19872
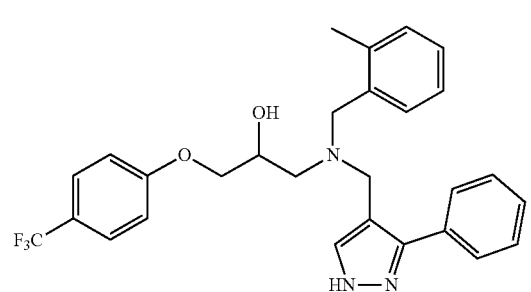
BC19873
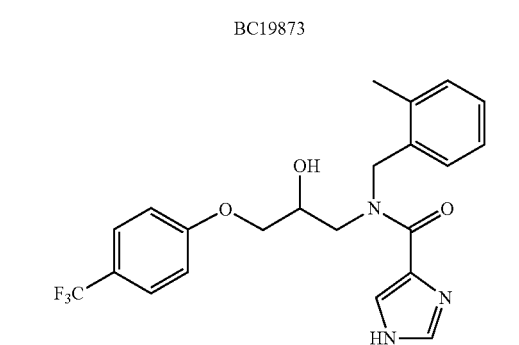
BC19874
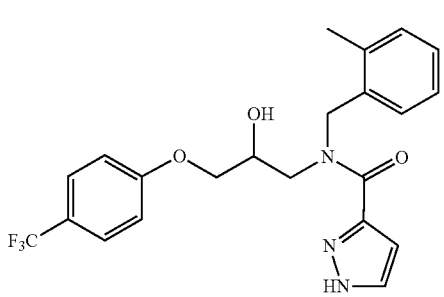
BC19875

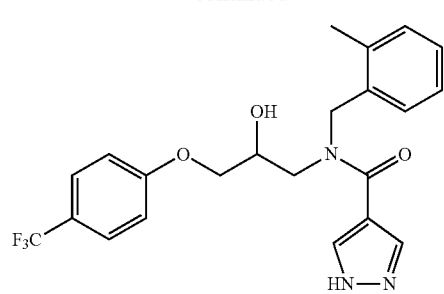
BC19876
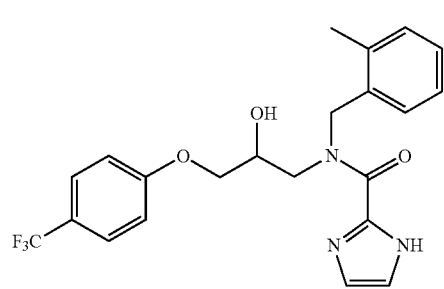
BC19877
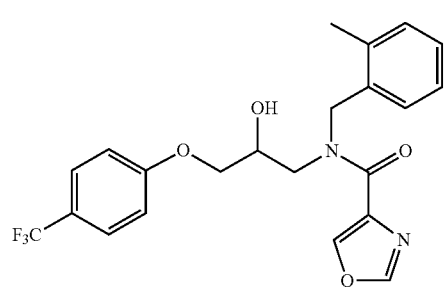
BC19878
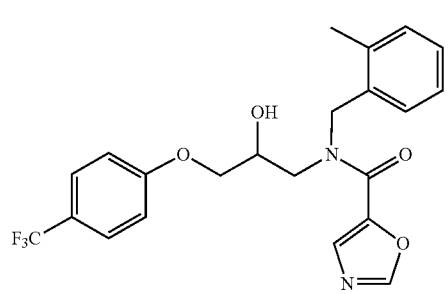
BC19879
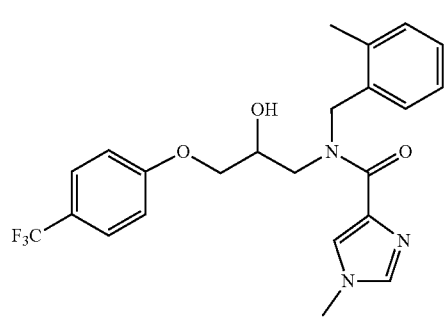
BC19880
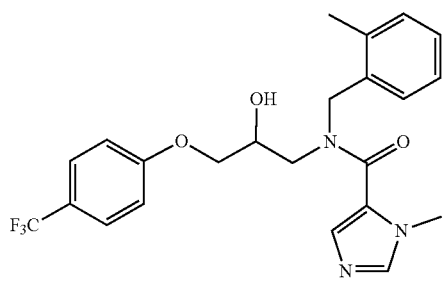
BC19881
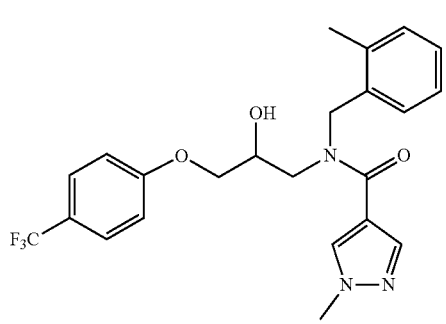
BC19882
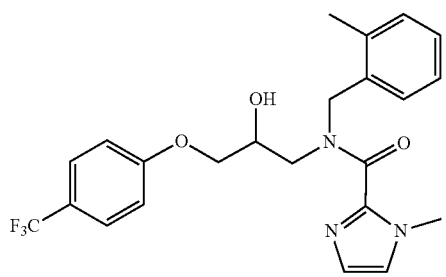
BC19883
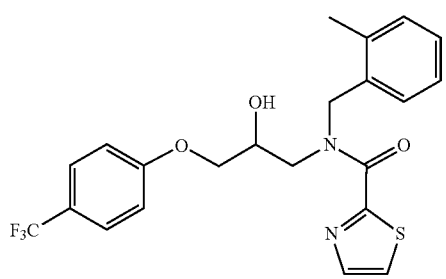
BC19884

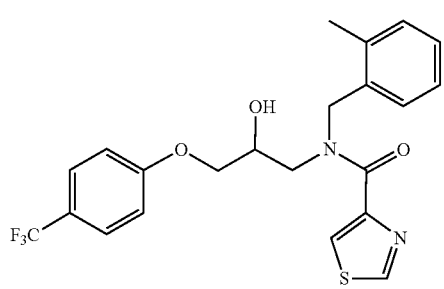
BC19885
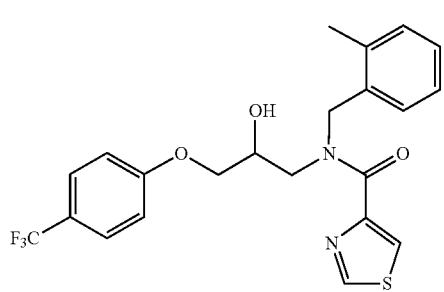
BC19886
or a pharmaceutically acceptable salt thereof.
In some embodiments, the compound of Formula (I) is selected from any one of the following compounds:
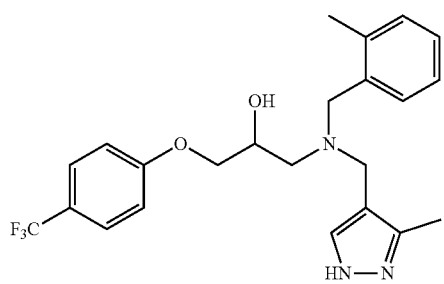
BC19889
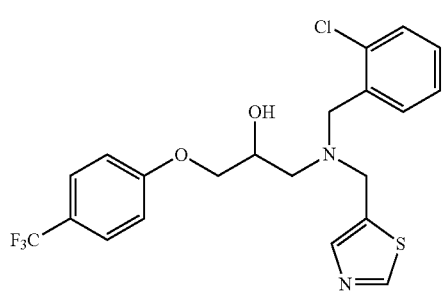
BC19890
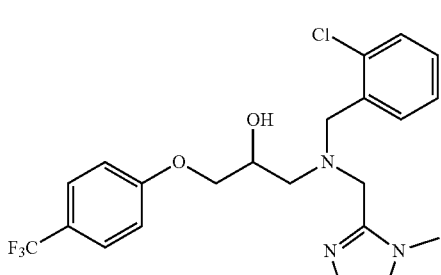
BC19891
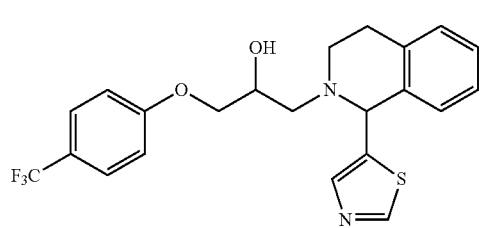
BC19893
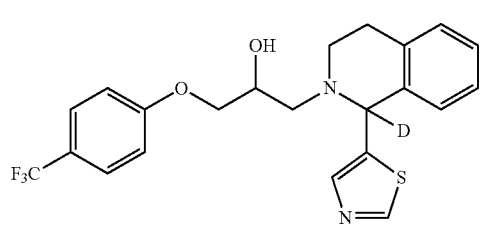
BC19894
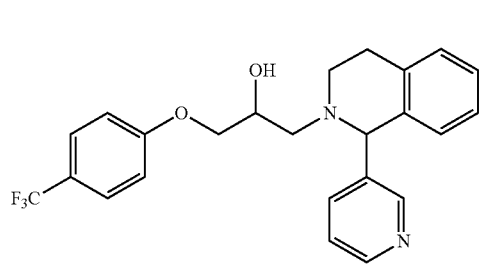
BC19895
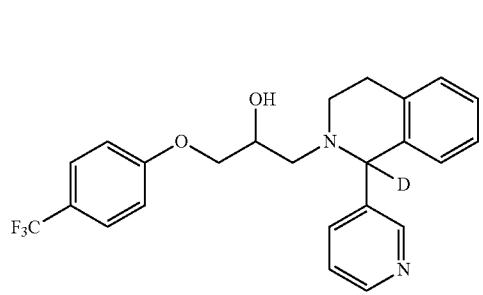
BC19896

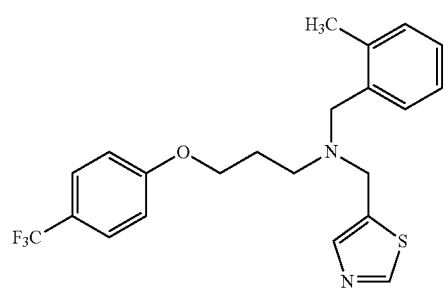
BC19897
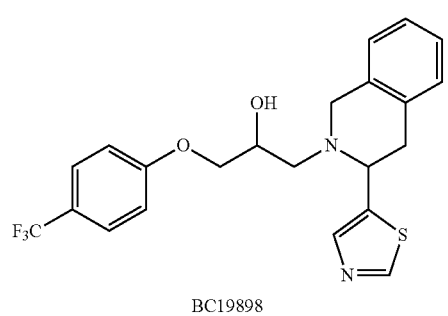
BC19898
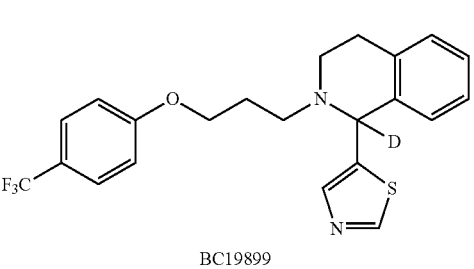
BC19899
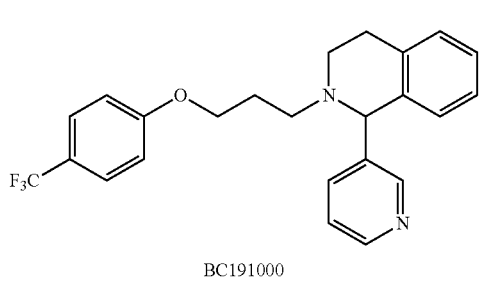
BC191000
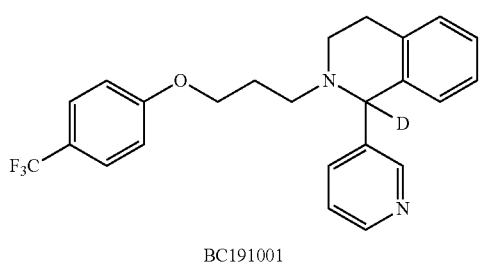
BC191001
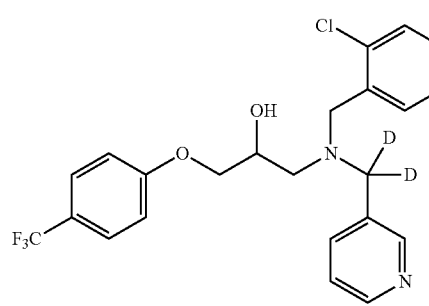
BC191002
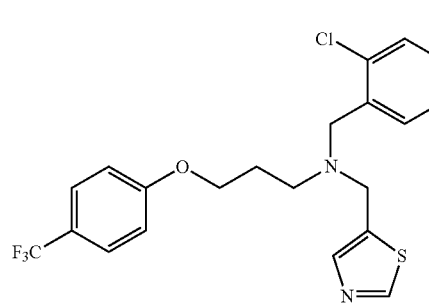
BC191004
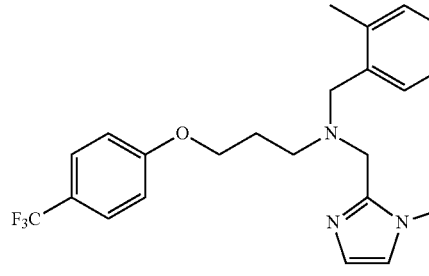
BC191005
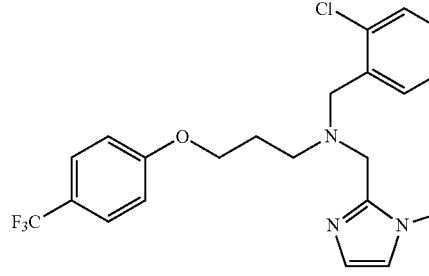
BC191006
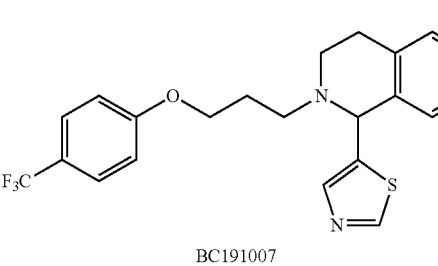
BC191007

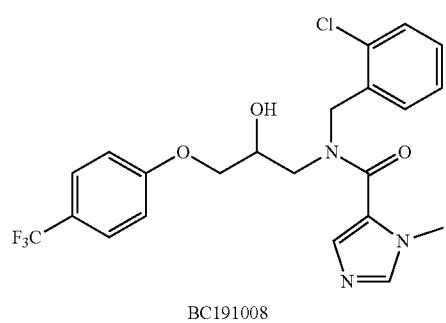
BC191008
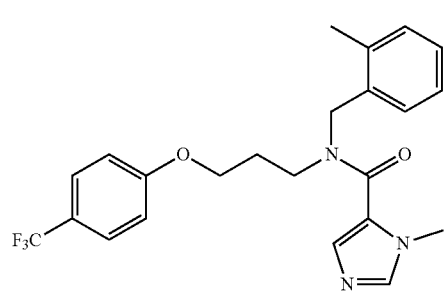
BC191009
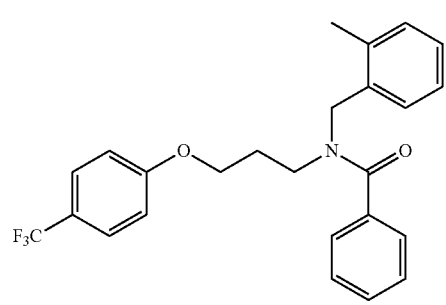
BC191010
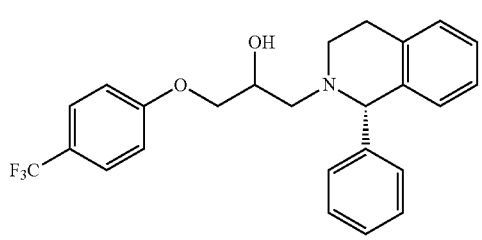
BC191011A
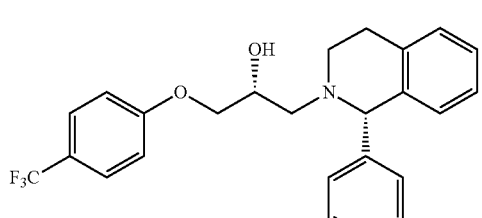
BC191011B
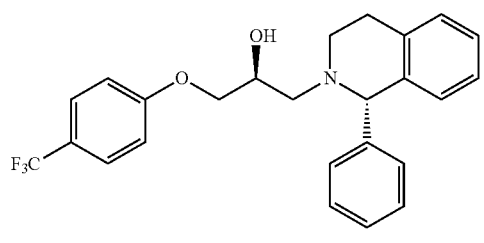
BC191011C
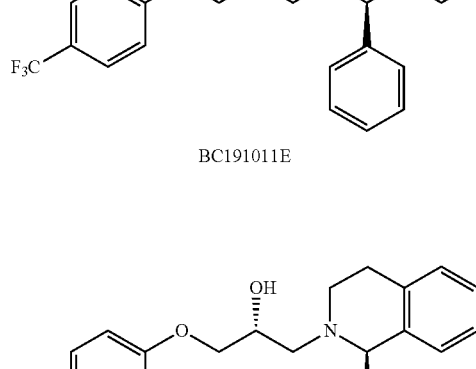
BC191011D
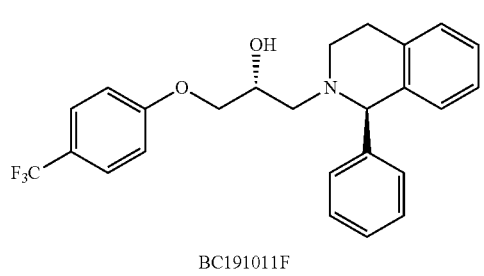
BC191011E
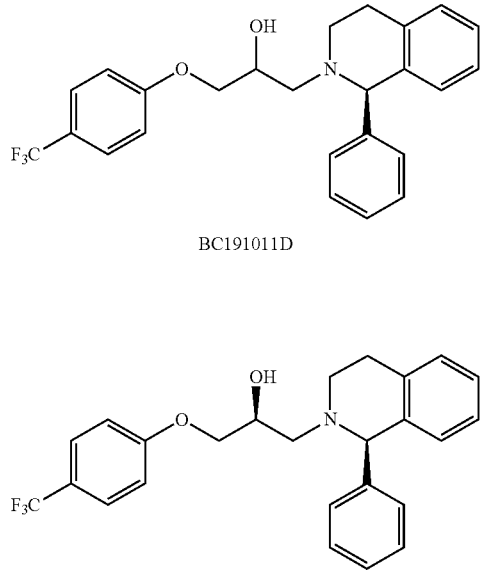
BC191011F
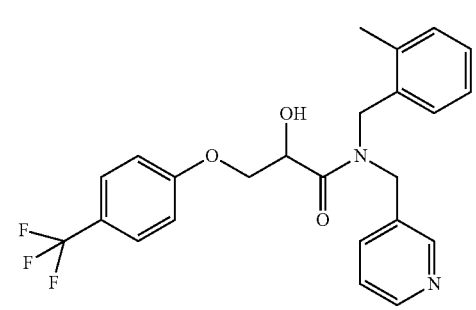
BC191012

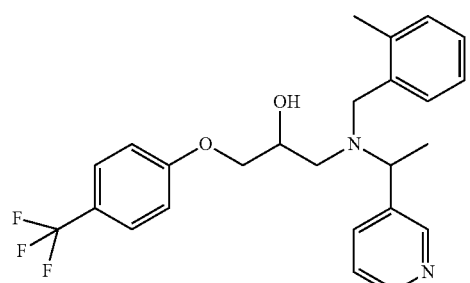
BC191013
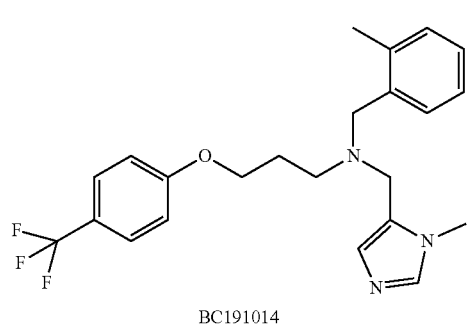
BC191014
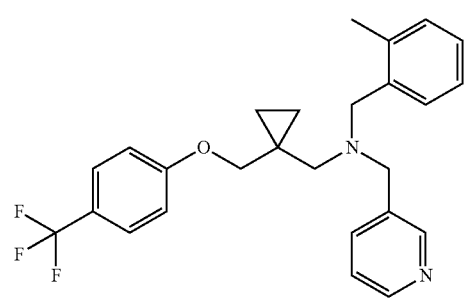
BC191015
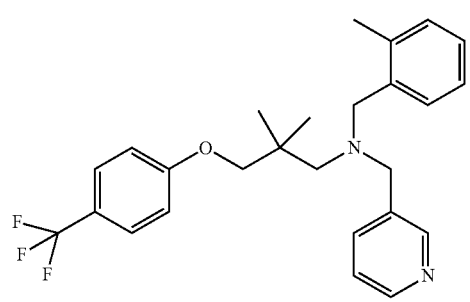
BC191016
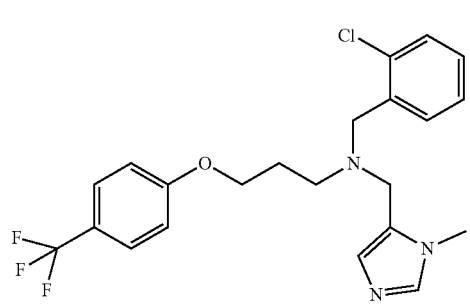
BC191017
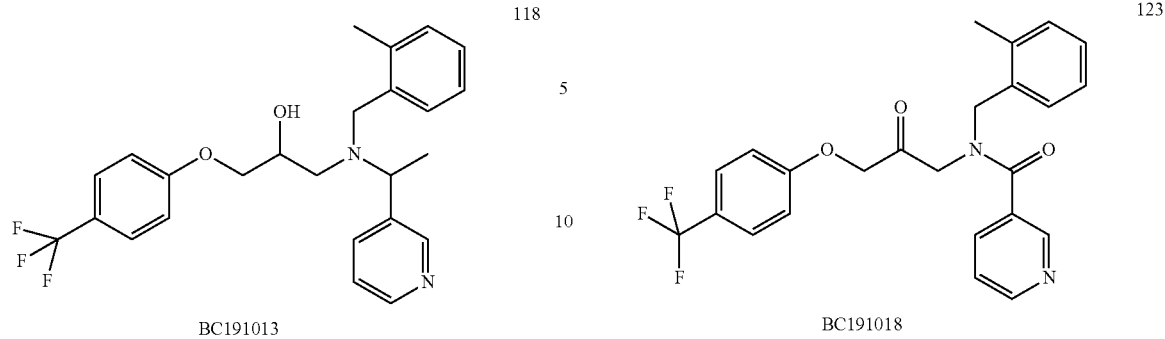
BC191018
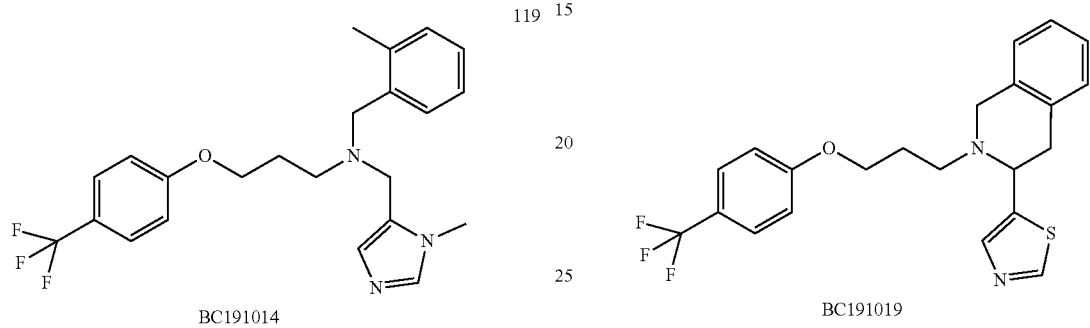
BC191019
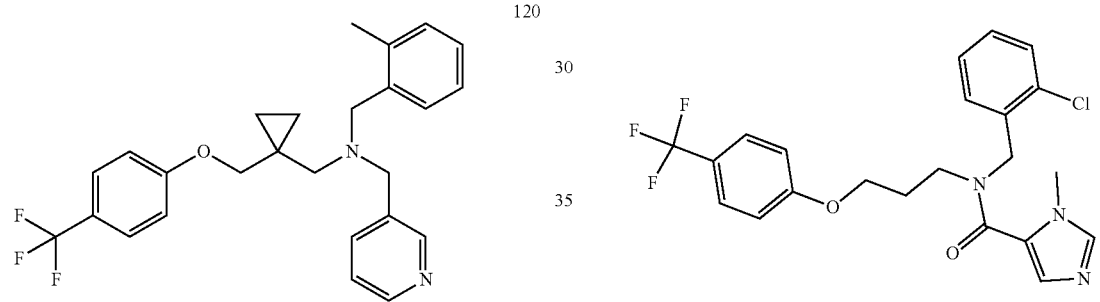
BC191020
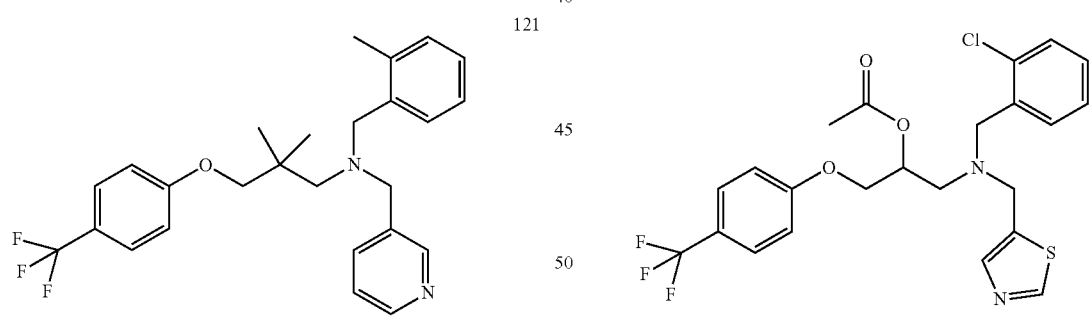
BC191021
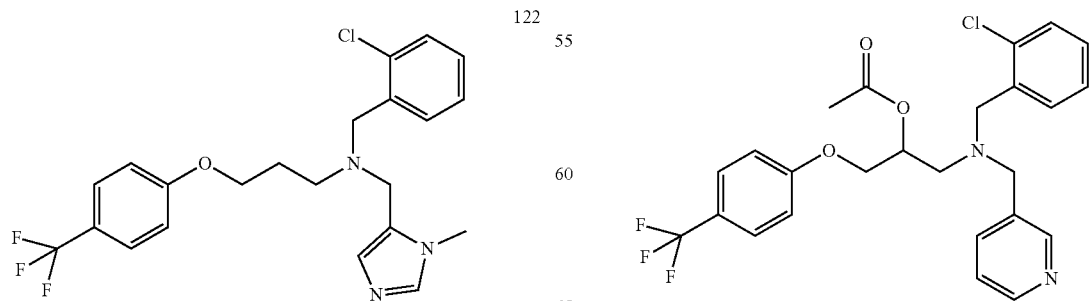
BC191022

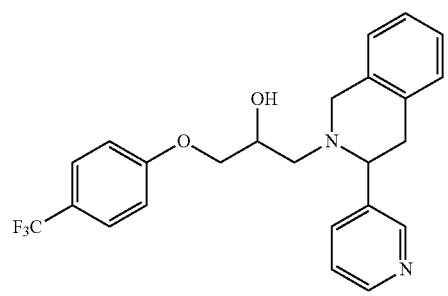
BC191023
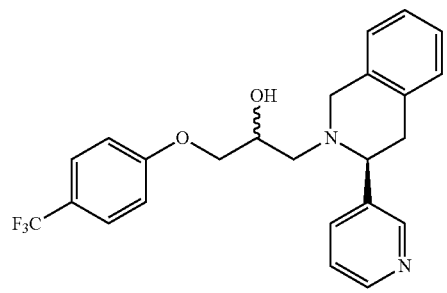
BC19856D
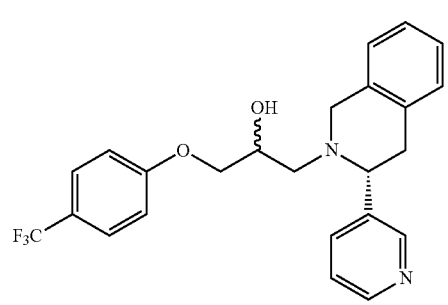
BC19856A
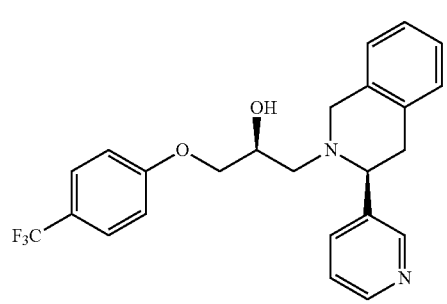
BC19856E
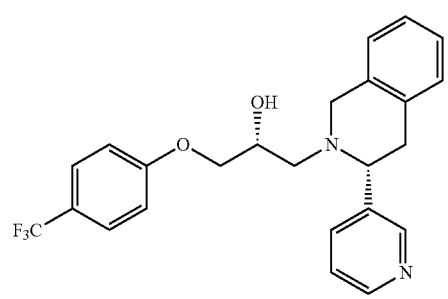
BC19856B
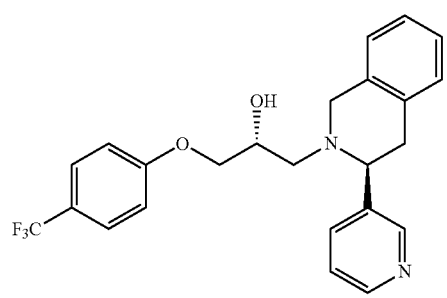
BC19856F
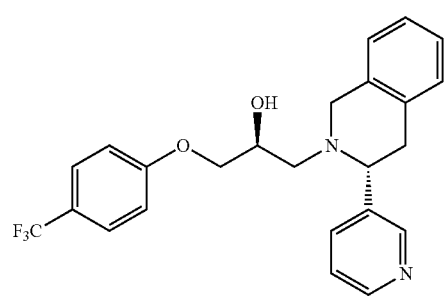
BC19856C
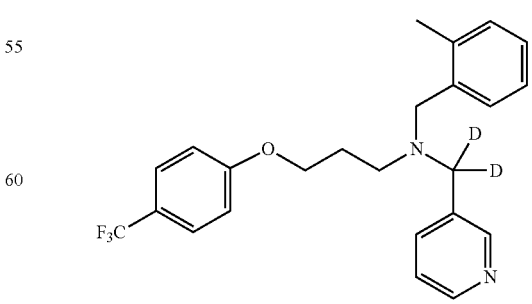
BC191024

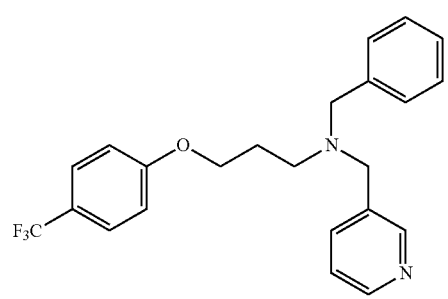
BC191025
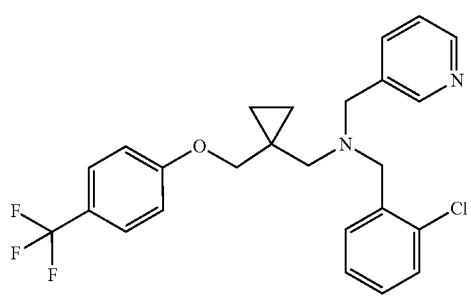
BC191029
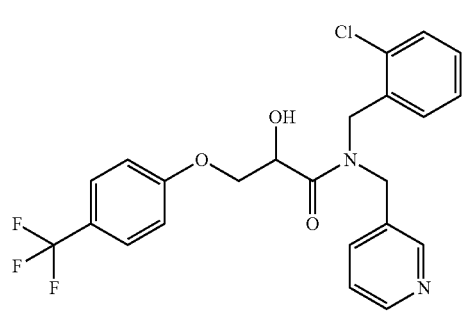
BC191026
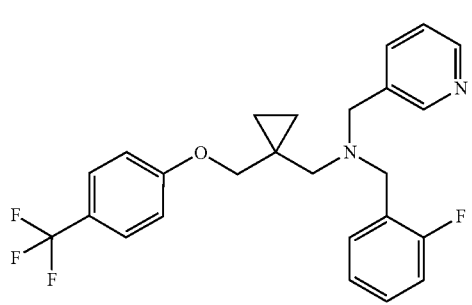
BC191030
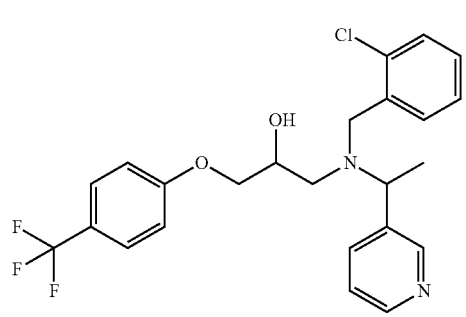
BC191027
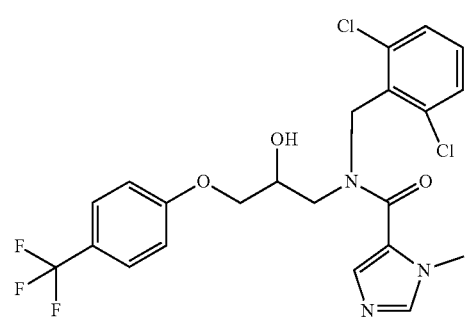
BC191031
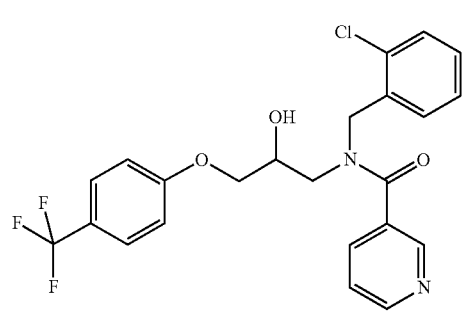
BC191028
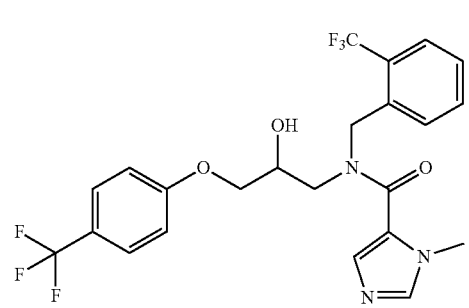
BC191032

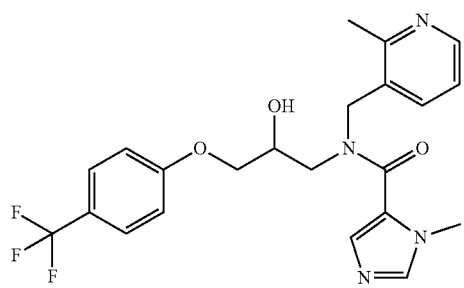
BC191033
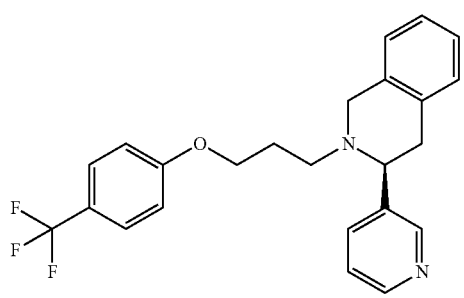
BC19865B
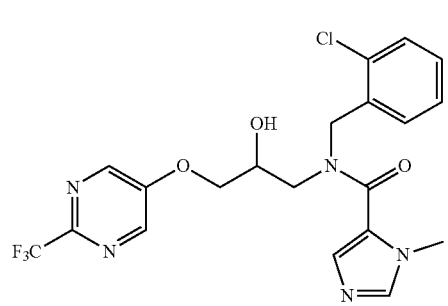
BC191035
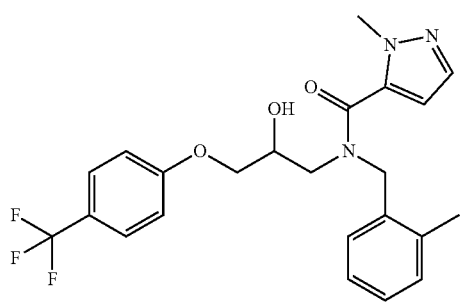
BC191037
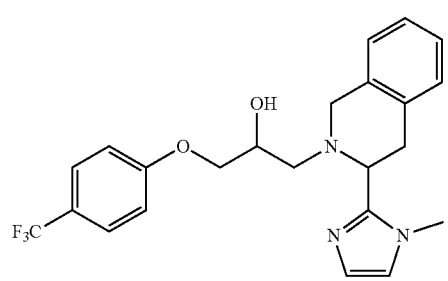
BC191036
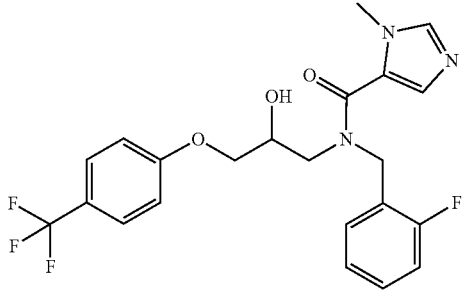
BC191038
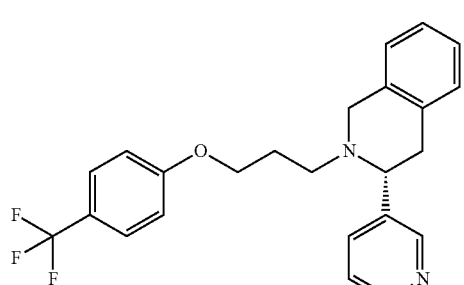
BC19865A
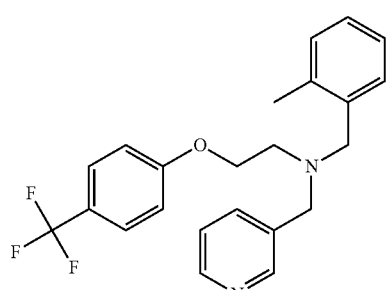
BC191039

155 BC191040

156 BC191041

157 BC191042

158 BC191043

159 BC191044

160 BC191045

161 BC191046

162 BC191047

-continued

BC191048

BC191049

BC191050

BC191051

BC191052

BC191053

BC191054

BC191055

BC191056

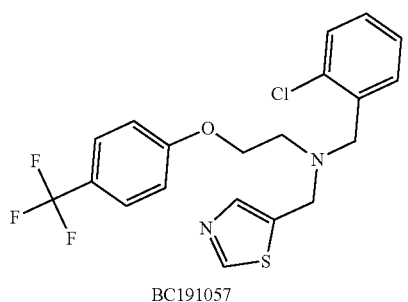
BC191057
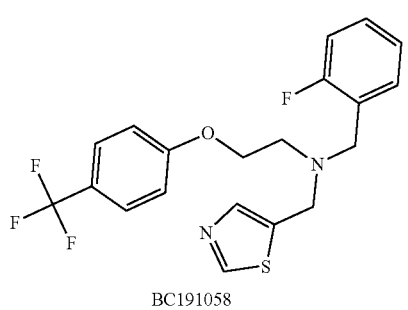
BC191058
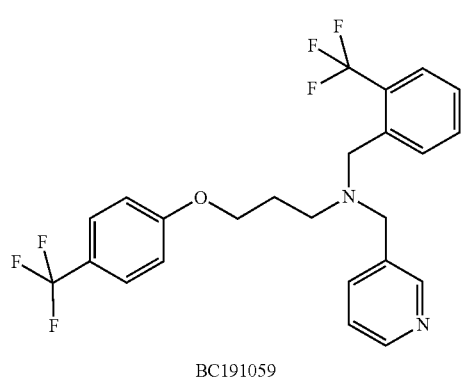
BC191059
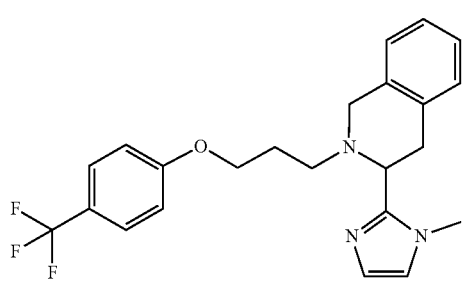
BC191060
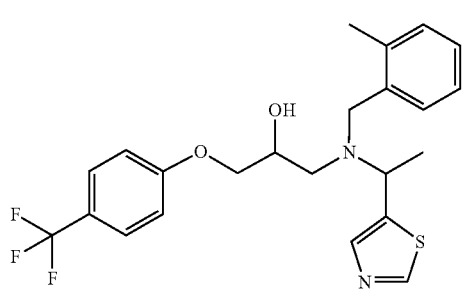
BC191061
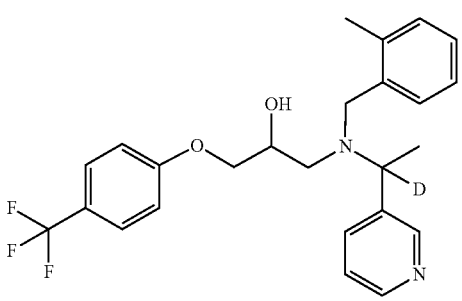
BC191062
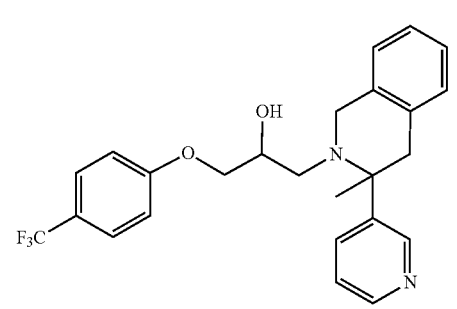
BC191063
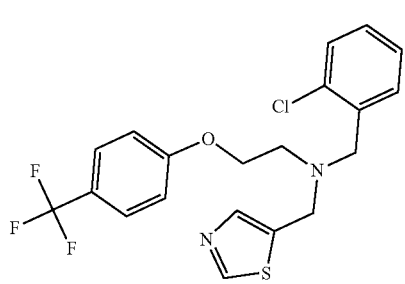
BC191064
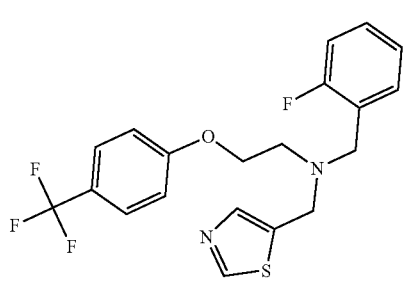
BC191065
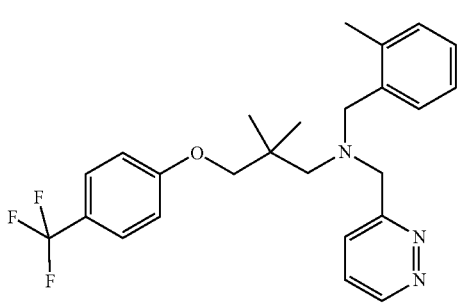
BC191066

| | |
|---|---|
| 182 BC191067 | 186 BC191071 |
| 183 BC191068 | 187 BC191072 |
| 184 BC191069 | 188 BC191073 |
| 185 BC191070 | 189 BC191074 |
| | 190 BC191075 |

191 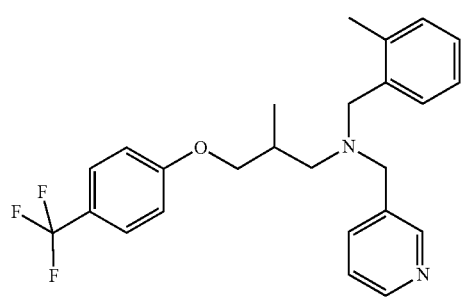
BC191076
192 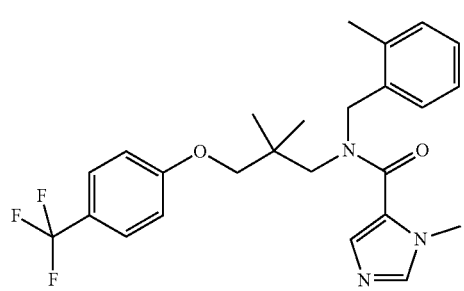
BC191077
193 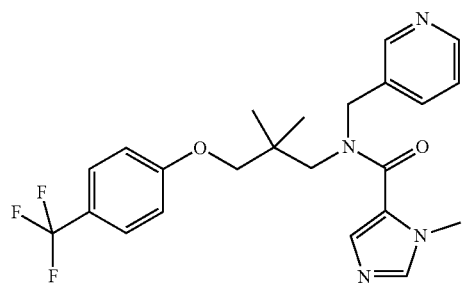
BC191078
194 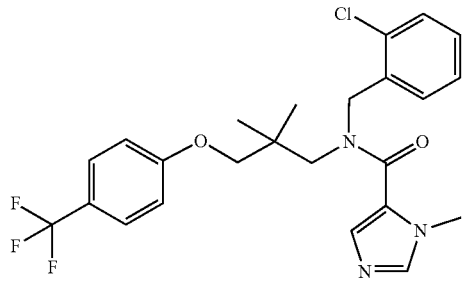
BC191079
195 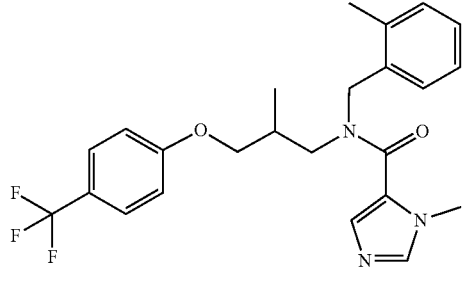
BC191080
196 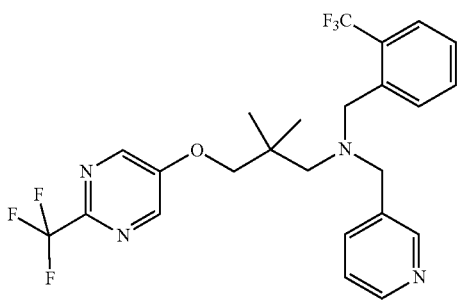
BC191081
197 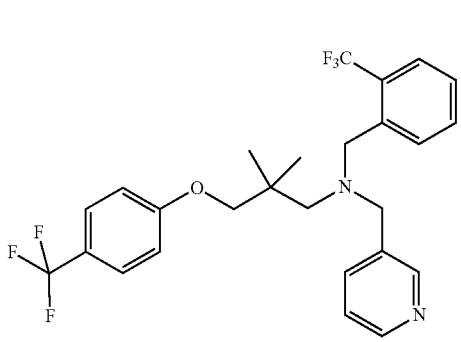
BC191082
198 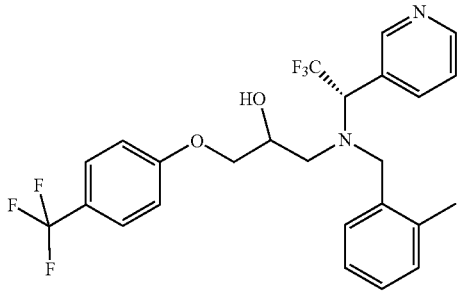
BC191083
199 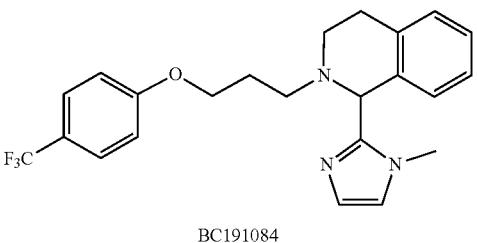
BC191084
200 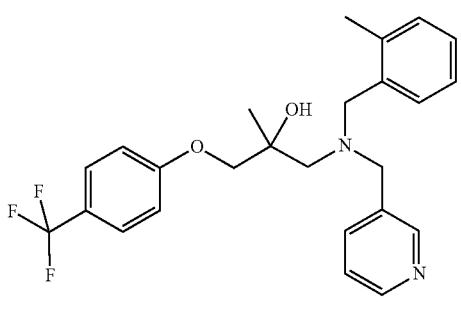
BC191085

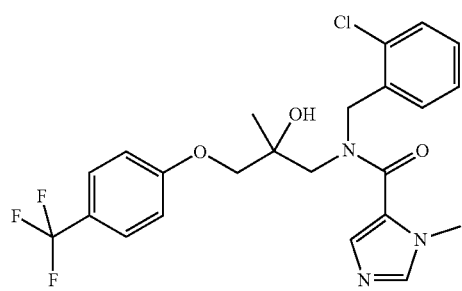

BC191086 or a pharmaceutically acceptable salt thereof.

In some embodiments, the present application provides a compound of formula:

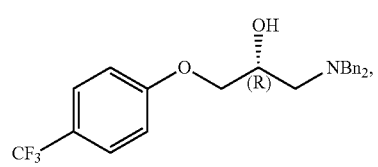

or a pharmaceutically acceptable salt thereof.

In some embodiments, the present application provides a compound of formula:

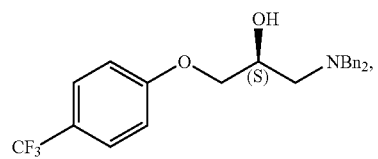

or a pharmaceutically acceptable salt thereof.

In some embodiments, the present application provides a compound selected from:

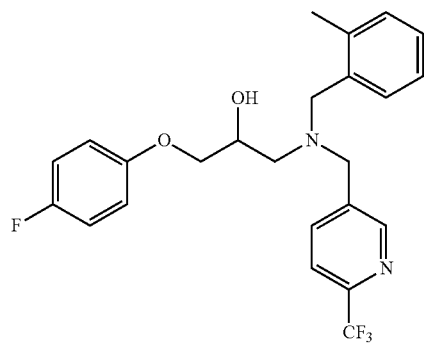

BC19844

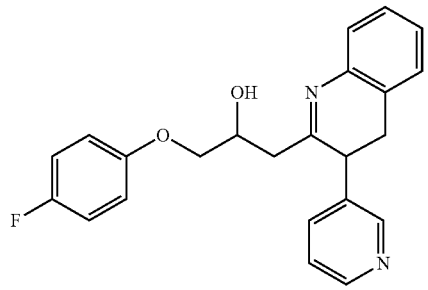

BC19857

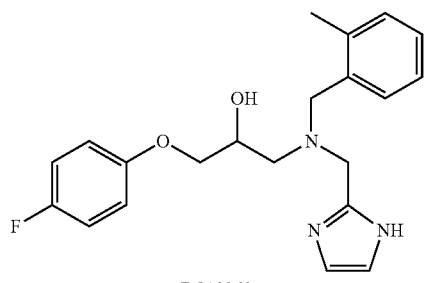

BC19860

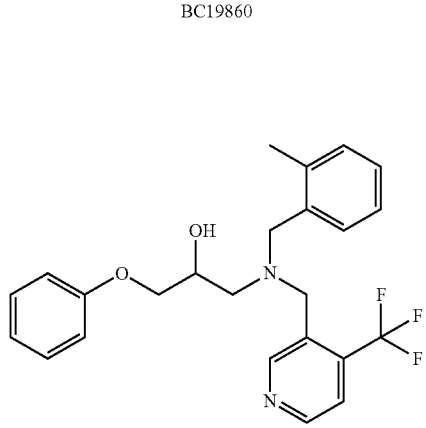

BC19887 or a pharmaceutically acceptable salt thereof.

In some embodiments, the present application provides a compound selected from:

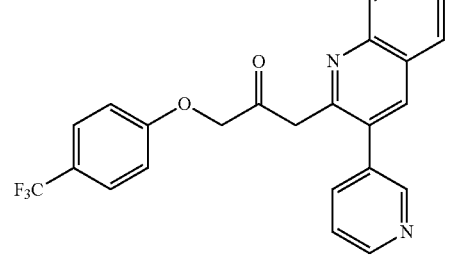

BC191003

88

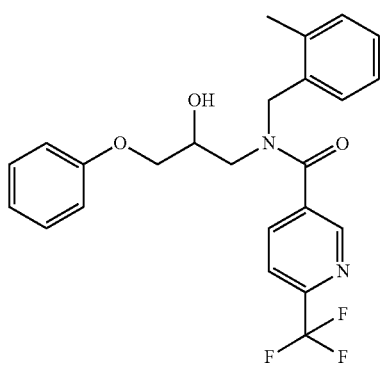

BC19888

92

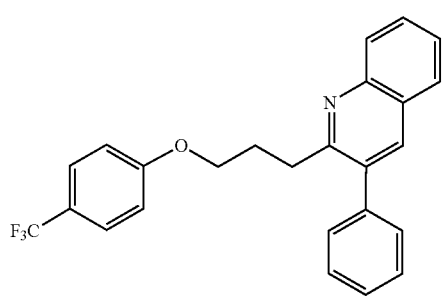

BC19892

147

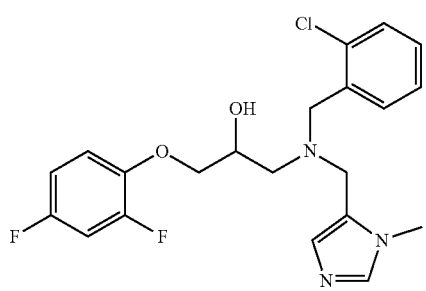

BC191034 or a pharmaceutically acceptable salt thereof.

In some embodiments, the present application provides a compound of formula:

61

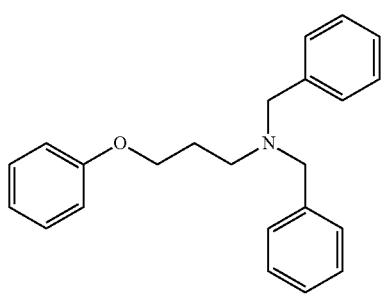

BC19861 or a pharmaceutically acceptable salt thereof.

In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of any Formulae disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, p-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compounds of any Formulae include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH-(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of any Formulae disclosed herein, or pharmaceutically acceptable salts thereof, are substantially isolated.

In some embodiments, a compound of any Formulae disclosed herein, or a pharmaceutically acceptable salt thereof, can have the ability to increase the level of phosphorylated AMPK within a cell. Such cells can be in vitro or in vivo. For example, a compound of any Formulae disclosed herein, or a pharmaceutically acceptable salt thereof, can have the ability to increase the level of phosphorylated AMPK within cells present within a mammal (e.g., a human) following administration to that mammal.

Methods of Making Therapeutic Compounds

Compounds of any one of the Formulae disclosed herein, including salts thereof, can be prepared using one or more appropriate organic synthesis techniques and can be synthesized according to any of numerous appropriate synthetic routes. Any appropriate method can be used to select and implement appropriate synthetic protocols. The processes described herein are not the exclusive means by which compounds provided herein may be synthesized, and a broad repertoire of synthetic organic reactions is available to be potentially employed in synthesizing compounds provided herein.

Suitable synthetic methods of starting materials, intermediates, and products can be identified by reference to the literature, including reference sources such as: Advances in Heterocyclic Chemistry, Vols. 1-107 (Elsevier, 1963-2012); *Journal of Heterocyclic Chemistry* Vols. 1-49 (*J. Heterocyclic Chemistry,* 1964-2012); Carreira et al., (Ed.) *Science of Synthesis*, Vols. 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, $2^{nd}$ Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.) *Comprehensive Organic Synthesis* (Pergamon Press, 1991).

The reactions for preparing the compounds provided herein can be carried out in suitable solvents that can be appropriately selected. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be appropriately selected.

Preparation of the compounds provided herein can involve the protection and deprotection of various chemical groups. The need for protection and deprotection, and the selection of appropriate protecting groups, can be appropriately determined. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Pharmaceutical Compositions and Formulations

This document also provides pharmaceutical compositions comprising an effective amount of a compound of Formula (I) disclosed herein, or a pharmaceutically acceptable salt thereof; and a pharmaceutically acceptable carrier. The pharmaceutical composition also can comprise any one of the additional therapeutic agents and/or therapeutic molecules described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds set forth in Formula (I), or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intramenigeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., a compound set forth in Formula (I), or a pharmaceutically acceptable salt thereof) with a suitable non-irritating excipient that is solid at room temperature but liquid at the rectal temperature and therefore will melt in the rectum to release the active component(s). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J. Pharm. Pharmacol.*, 56:3-17 (2004); and Ilium, L., *Eur J. Pharm. Sci.*, 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound set forth in Formula (I), or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., a compound set forth in Formula (I), or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos. 6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., a compound set forth in Formula (I), or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein (e.g., a compound set forth in Formula (I), or a pharmaceutically acceptable salt thereof) can include that compound in an effective amount (e.g., a therapeutically effective amount).

Effective doses can vary, depending on the diseases being treated, the severity of the disease, the route of administration, the sex, age and general health condition of the subject, excipient usage, the possibility of co-usage with other therapeutic treatments such as use of other agents, and the judgment of the treating physician.

In some embodiments, an effective amount of a compound of Formula (I), or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated as described herein.

In some cases, an effective amount of a compound of Formula (I), or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound of Formula (I), or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to increase the level of phosphorylated AMPK within cells and/or within the nucleus of cells within a mammal (e.g., a human). In some cases, this document provides pharmaceutical kits useful, for example, to treat diseases, disorders, and conditions referred to herein. Such pharmaceutical kits can include one or more containers containing a pharmaceutical composition that includes a therapeutically effective amount of a compound provided herein (e.g., a compound set forth in Formula (I), or a pharmaceutically acceptable salt thereof). In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein.

Combination Therapy

In some cases, one or more compounds provided herein (e.g., a compound set forth in Formula (I), or a pharmaceutically acceptable salt thereof) can be combined with one or more therapeutic molecules. Examples of therapeutic molecules that can be used in combination with one or more compounds provided herein (e.g., a compound set forth in Formula (I), or a pharmaceutically acceptable salt thereof) include, without limitation, anti-inflammatory agents (e.g., steroids and antibodies against IL-6 or TNF-alpha), antimicrobial agents (e.g., antibiotics, anti-mycobacterial drugs, and anti-viral agents), anti-cancer agents (e.g., chemotherapeutic agents such as immune checkpoint inhibitors (e.g., anti-PD1 antibodies or anti-PD-L1 antibodies) and cellular products such as engineered T cells), anti-aging agents (e.g., nicotinamide riboside, or rapamycin), neurological agents (e.g., L-DOPA, memantine, and riluzole), therapies for a neurodegenerative disease (e.g., edaravone or tetrabenazine), agents used to treat chronic organ dysfunction (e.g., ACE inhibitor and lactulose), therapies for atherosclerosis (e.g. lipid-lowering agents, platelet inhibitors), agents to treat polycystic kidney disease (e.g. tolvaptan), therapies used for metabolic syndrome (e.g. insulin, glucose-lowering therapies), therapies for polycystic ovarian syndrome (e.g. metformin), treatment for muscular dystrophies (e.g. steroids, gene therapy approaches) and therapies for pain relief (e.g., non-steroidal anti-inflammatory medicines, opioids, regional nerve blocks).

One or more compounds provided herein (e.g., a compound set forth in Formula (I), or a pharmaceutically acceptable salt thereof) and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in this document, substituents of compounds provided herein are disclosed in groups or in ranges. It is specifically intended that these groups and ranges include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in this document various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features described herein, which are, for clarity, described in the context of separate embodiments, can also be provided in combination in a single embodiment. Conversely, various features described herein which are, for brevity, described in the context of a single embodiment, also can be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridinyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, without limitation, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, without limitation, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl-linking group having n to m carbons. Examples of alkylene groups include, without limitation, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, without limitation, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, without limitation, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, without limitation, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms. Examples of alkylcarbonyl groups include, without limitation, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)NH$_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(=O)— group, which may also be written as C(O).

As used herein, the term "carboxy" refers to a —C(O)OH group. In some embodiments, the "carboxy" group also refers to a bioisostere replacement group selected from the group consisting of:

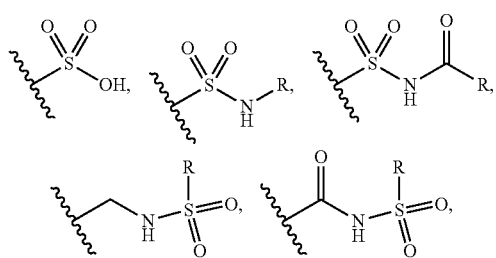

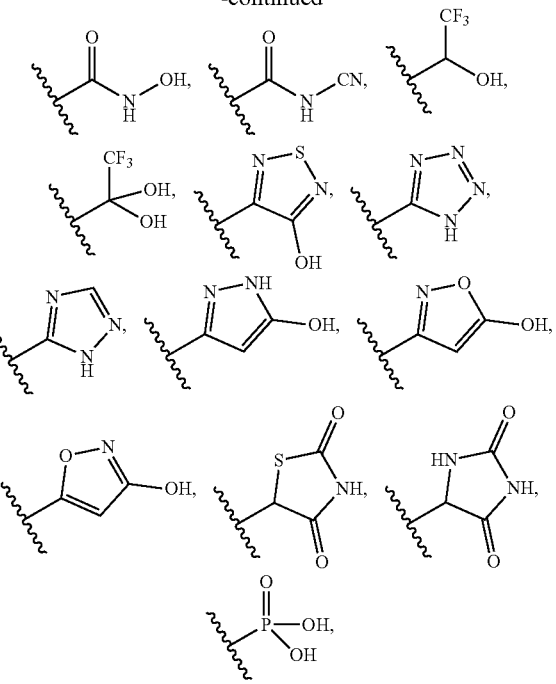

and the like, where R refers to a hydrogen, (C$_1$-C$_8$) alkyl, or C$_6$ aryl.

As used herein, the term "cyano-C$_{1-3}$ alkyl" refers to a group of formula —(C$_{1-3}$ alkylene)-CN.

As used herein, the term "HO—C$_{1-3}$ alkyl" refers to a group of formula —(C$_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which can be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups can have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3, or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (C$_{3-10}$). In some embodiments, the cycloalkyl is a C$_{3-10}$ monocyclic or bicyclic cycloalkyl. In some embodiments, the cycloalkyl is a C$_{3-7}$ monocyclic cycloalkyl. Example cycloalkyl groups include, without limitation, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl. The term "$C_{n-m}$ cycloalkylene" refers to a divalent $C_{n-m}$ cycloalkyl group. Examples of cycloalkylene groups include, without limitation, cyclopropylene (e.g., 1,1-cyclopropylene, 1,2,-cyclopropylene), cyclobutylene (1,1,-cyclobutylene, 1,2-cyclobutylene, 1,3-cyclobutylene), cyclopentylene, and cyclohexylene. An example of a cyclopropylene group is shown below:

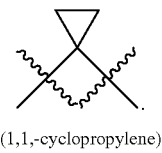

(1,1,-cyclopropylene)

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from nitrogen, sulfur, and oxygen. In some embodiments, the heteroaryl is a 5-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1, 2, 3-triazolyl, tetrazolyl, 1, 2, 3-thiadiazolyl, 1, 2, 3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, 10-, 11-, 12-, 13-, 14-, 15-, or 16-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-16 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring can be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Any appropriate method can be used to prepare optically active forms from, for example, optically inactive starting materials. For example, techniques such as resolution of racemic mixtures or stereoselective synthesis can be used to prepare optically active forms of a compound provided herein. Many geometric isomers of olefins, C=N double bonds, N=N double bonds, and the like also can be present in a compound described herein, and all such stable isomers are contemplated herein. Cis and trans geometric isomers of the compounds provided herein are described and can be isolated as a mixture of isomers or as separated isomeric forms. In some embodiments, a compound provided herein has the (R)-configuration. In some embodiments, a compound provided herein has the (S)-configuration.

Compounds provided herein also include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include, without limitation, ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution. For example, in aqueous solution, pyrazoles can exhibit the following isomeric forms, which are referred to as tautomers of each other:

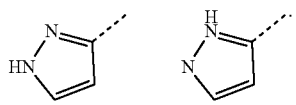

As readily understood by one skilled in the art, a wide variety of functional groups and other structures can exhibit tautomerism, and all tautomers of compounds as described herein are within the scope provided herein.

In the compounds of the present disclosure any atom not specifically designated as a particular isotope is meant to represent any stable isotope of that atom. Unless otherwise stated, when a position is not specifically designated as "H" or "hydrogen", the position is understood to have hydrogen at its natural abundance isotopic composition, or deuterium at an abundance that is at least 3340 times greater than the natural abundance of deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium). In some embodiments, a compound of the present disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein, the term "cell" is meant to refer to a cell that is in vitro, ex vivo, or in vivo. In some embodiments, an ex vivo cell can be part of a tissue sample excised from an organism such as a mammal (e.g., a human). In some embodiments, an in vitro cell can be a cell in cell culture. In some embodiments, an in vivo cell is a cell living in an organism such as a mammal (e.g., a human).

As used herein, the term "contacting" refers to the bringing together of indicated moieties or items in an in vitro system, an ex vivo system, or an in vivo system. For example, "contacting" a cell with a compound provided herein includes the act of administering that compound to a mammal (e.g., a human) containing that cell as well as, for example, introducing that compound into a cell culture containing that cell.

As used herein, the term "mammal" includes, without limitation, mice, rats, other rodents, rabbits, dogs, cats, swine, cattle, sheep, horses, elephants, deer, non-human primates (e.g., monkeys and apes), house pets, and humans.

As used herein, the phrase "effective amount" or "therapeutically effective amount" refers to the amount of active compound or pharmaceutical agent that elicits the biological or medicinal response in a tissue, system, mammal, or human that is being sought by a researcher, veterinarian, medical doctor, or other clinician.

As used herein, the term "treating" or "treatment" refers to (a) inhibiting a disease, disorder, or condition, for example, inhibiting a disease, disorder, or condition in a mammal (e.g., human) that is experiencing or displaying the pathology or symptomatology of the disease, disorder, or condition (e.g., arresting further development of the pathology and/or symptomatology), or (b) ameliorating the disease, disorder, or condition, for example, ameliorating a disease, disorder, or condition in a mammal (e.g., a human) that is experiencing or displaying the pathology or symptomatology of the disease, disorder, or condition (e.g., reversing the pathology and/or symptomatology).

As used herein, the term "preventing" or "prevention" of a disease, disorder, or condition refers to decreasing the risk of occurrence of the disease, disorder, or condition in a mammal or group of mammals (e.g., a mammal or group of mammals predisposed to or susceptible to the disease, disorder, or condition). In some embodiments, preventing a disease, disorder, or condition refers to decreasing the possibility of acquiring the disease, disorder, or condition and/or its associated symptoms. In some embodiments, preventing a disease, disorder, or condition refers to completely or almost completely stopping the disease, disorder, or condition from occurring.

EXAMPLES

Material and Methods

All non-aqueous reactions were carried out under a nitrogen atmosphere in oven- or flame-dried glassware unless otherwise noted. Anhydrous tetrahydrofuran and diethyl ether were distilled from sodium benzophenone ketyl solutions; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 F254 plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g $Ce(NH_4)_2(NO_3)_6$, 12 g $(NH_4)_6Mo_7O_{24} \cdot 4H_2O$, and 28 mL conc. $H_2SO_4$ in 235 mL water), or vanillin (6 g vanillin and 1.5 mL conc. $H_2SO_4$ in 100 mL EtOH). Flash chromatography was performed with SiliCycle silica gel 60 (230-400 mesh) or with ISCO MPLC. $^1H$ and $^{13}C$ NMR spectra were recorded on Bruker Avance 300, 400, or 500 MHz spectrometers, using the residual solvent as an internal standard. IR spectra were obtained on a Smiths IdentifyIR or PerkinElmer Spectrum 100. HRMS data were obtained on a Thermo Scientific Exactive HRMS coupled to a Thermo Scientific Accela HPLC system using a 2.1×50 mm 3.5 μm Waters XTerra C18 column eluting with $MeCN/H_2O$ containing 0.1% formic acid. Purity of compounds was assessed using the same HPLC system with either the PDA or an Agilent 385 ELSD. All final screening samples passed QC based on >95% purity by LC/MS/ELSD analysis.

Synthetic Methods

The preparation of the compounds of Formula (I) can be exemplified by the following synthesis of compound BC19856 shown in Scheme 1 from the readily available starting materials.

Scheme 1
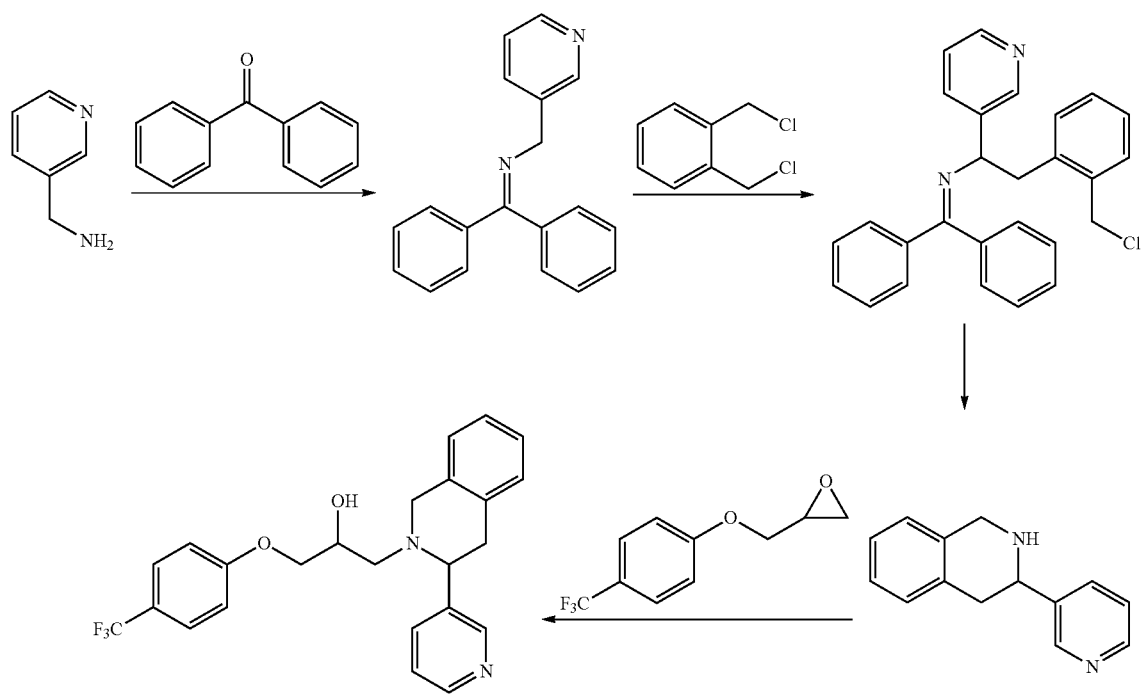
Example 1—Compound Structures
The compounds in Table 1 and Table 1a were prepared from readily available starting materials using methods and procedures similar to those described above for compound BC19856.
TABLE 1
| No. | BC code | Structure |
|-----|---------|-----------|
| 1 | BC1618R | 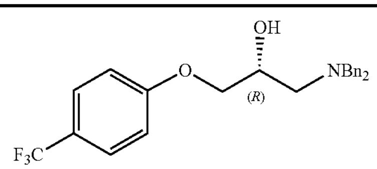 |
| 2 | BC1618S | 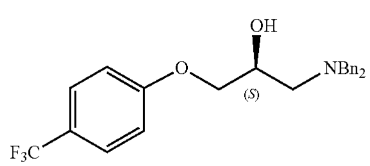 |
| 3 | BC19801 | 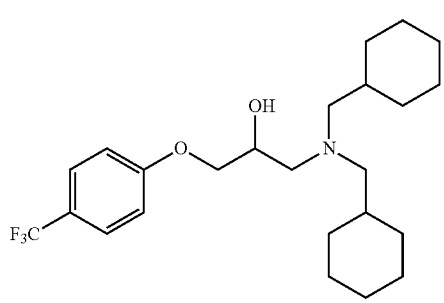 [SMILES: OC(COc1ccc(C(F)(F)F)cc1)CN(CC1CCCCC1)CC1CCCCC1] |

TABLE 1-continued

| No. | BC code | Structure |
|---|---|---|
| 4 | BC19802 | 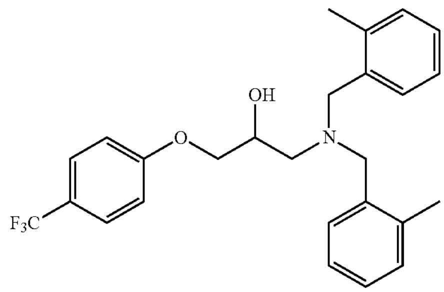 [SMILES: Cc1ccccc1CN(Cc1ccccc1C)CC(O)COc1ccc(C(F)(F)F)cc1] |
| 5 | BC19803 | 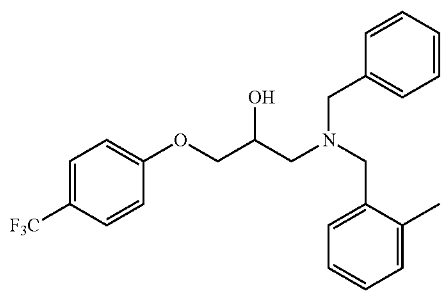 [SMILES: Cc1ccccc1CN(Cc1ccccc1)CC(O)COc1ccc(C(F)(F)F)cc1] |
| 6 | BC19804 | 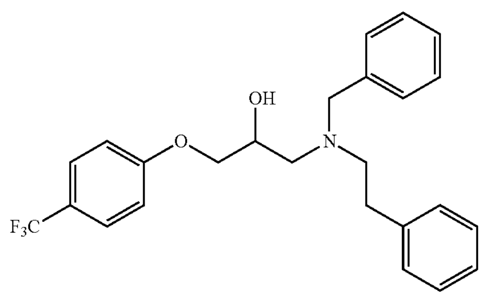 [SMILES: OC(COc1ccc(C(F)(F)F)cc1)CN(CCc1ccccc1)Cc1ccccc1] |
| 7 | BC19805 | 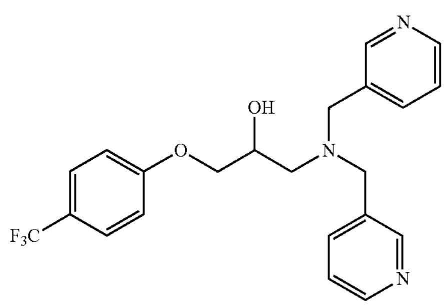 [SMILES: OC(COc1ccc(C(F)(F)F)cc1)CN(Cc1cccnc1)Cc1cccnc1] |
| 8 | BC19806 | 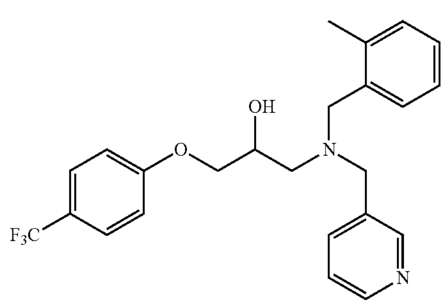 |

TABLE 1-continued
| No. | BC code | Structure |
|---|---|---|
| 9 | BC19807 | 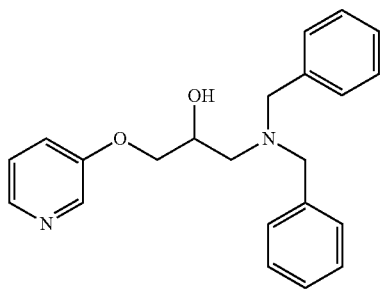 [SMILES: OC(COc1cccnc1)CN(Cc1ccccc1)Cc1ccccc1] |
| 10 | BC19808 | 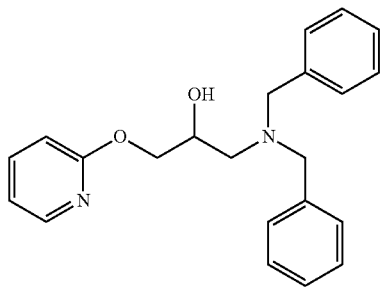 [SMILES: OC(COc1ccccn1)CN(Cc1ccccc1)Cc1ccccc1] |
| 11 | BC19809 | 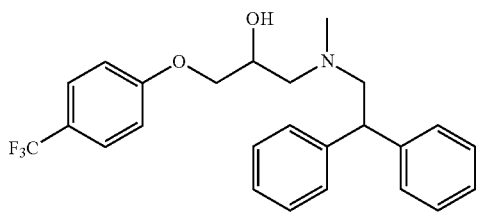 [SMILES: CN(CC(O)COc1ccc(C(F)(F)F)cc1)CC(c1ccccc1)c1ccccc1] |
| 12 | BC19810 | 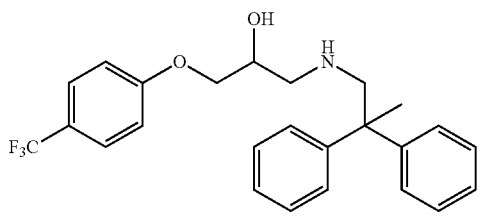 [SMILES: CC(CNCC(O)COc1ccc(C(F)(F)F)cc1)(c1ccccc1)c1ccccc1] |
| 13 | BC19811 | 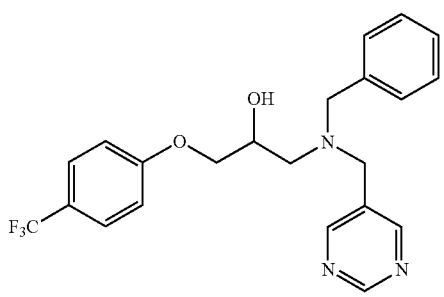 [SMILES: OC(COc1ccc(C(F)(F)F)cc1)CN(Cc1ccccc1)Cc1cncnc1] |
| 14 | BC19812 | 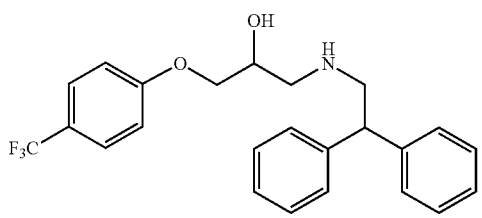 [SMILES: OC(CNCC(c1ccccc1)c1ccccc1)COc1ccc(C(F)(F)F)cc1] |

TABLE 1-continued

| No. | BC code | Structure |
|---|---|---|
| 15 | BC19813 | 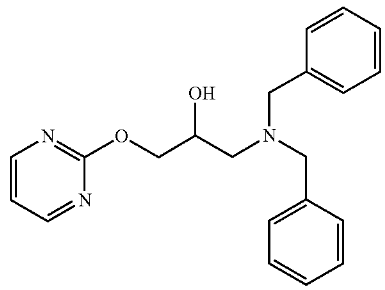 [SMILES: OC(COc1ncccn1)CN(Cc1ccccc1)Cc1ccccc1] |
| 16 | BC19814 | 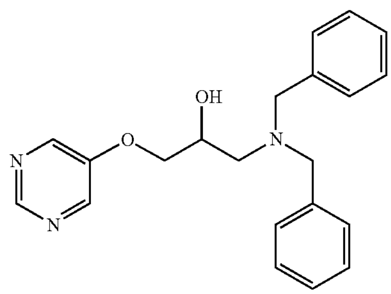 [SMILES: OC(COc1cncnc1)CN(Cc1ccccc1)Cc1ccccc1] |
| 17 | BC19815 | 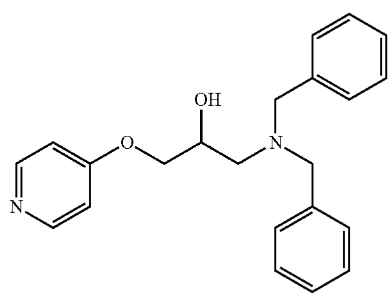 [SMILES: OC(COc1ccncc1)CN(Cc1ccccc1)Cc1ccccc1] |
| 18 | BC19816 | 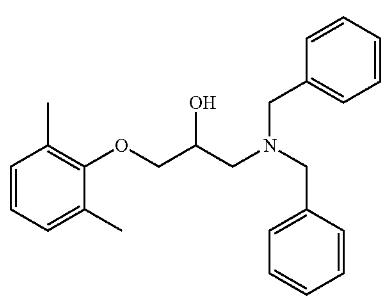 [SMILES: Cc1cccc(C)c1OCC(O)CN(Cc1ccccc1)Cc1ccccc1] |
| 19 | BC19819 | 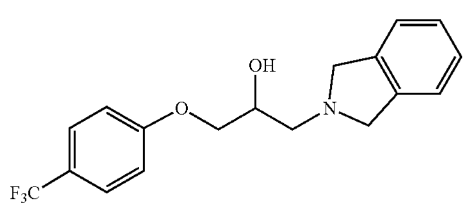 [SMILES: OC(COc1ccc(C(F)(F)F)cc1)CN1Cc2ccccc2C1] |

TABLE 1-continued
| No. | BC code | Structure |
|---|---|---|
| 20 | BC19820 | 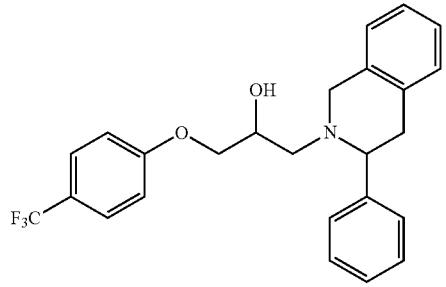 [SMILES: OC(COc1ccc(C(F)(F)F)cc1)CN1Cc2ccccc2CC1c1ccccc1] |
| 21 | BC19821 | 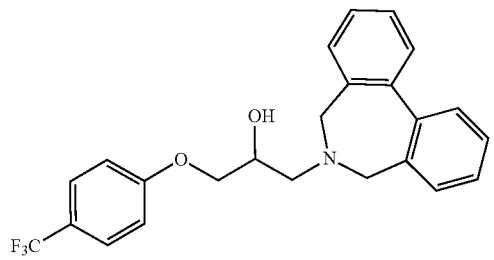 [SMILES: OC(COc1ccc(C(F)(F)F)cc1)CN1Cc2ccccc2-c2ccccc2C1] |
| 22 | BC19822 | 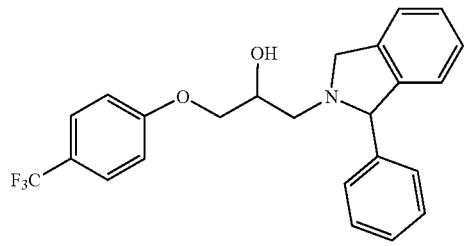 [SMILES: OC(COc1ccc(C(F)(F)F)cc1)CN1Cc2ccccc2C1c1ccccc1] |
| 23 | BC19823 | 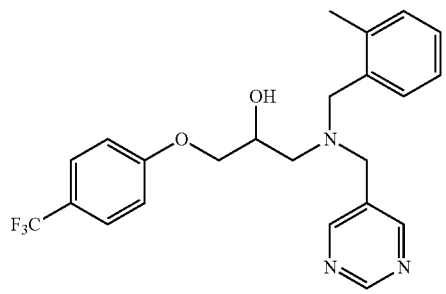 [SMILES: Cc1ccccc1CN(Cc1cncnc1)CC(O)COc1ccc(C(F)(F)F)cc1] |
| 24 | BC19824 | 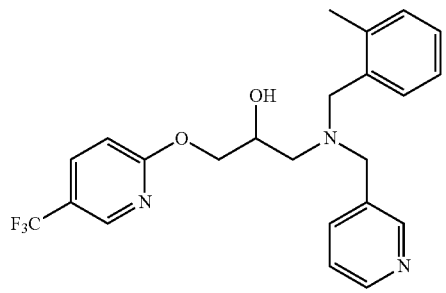 [SMILES: Cc1ccccc1CN(Cc1cccnc1)CC(O)COc1ccc(C(F)(F)F)cn1] |

TABLE 1-continued
| No. | BC code | Structure |
|---|---|---|
| 25 | BC19825 | 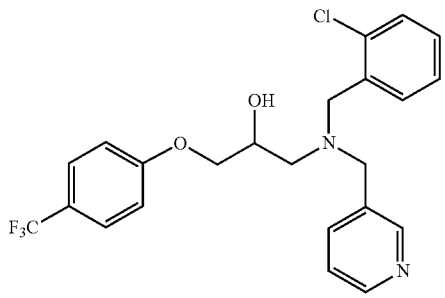 [SMILES: OC(COc1ccc(C(F)(F)F)cc1)CN(Cc1cccnc1)Cc1ccccc1Cl] |
| 26 | BC19826 | 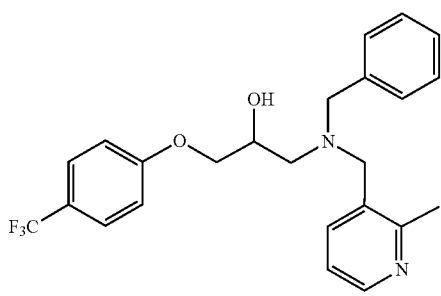 [SMILES: Cc1ncccc1CN(Cc1ccccc1)CC(O)COc1ccc(C(F)(F)F)cc1] |
| 27 | BC19827 | 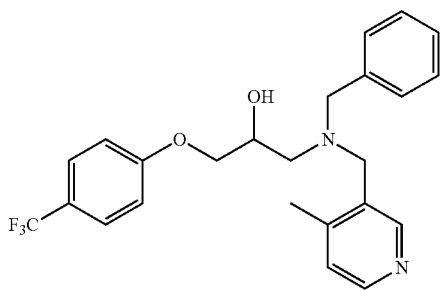 [SMILES: Cc1ccncc1CN(Cc1ccccc1)CC(O)COc1ccc(C(F)(F)F)cc1] |
| 28 | BC19828 | 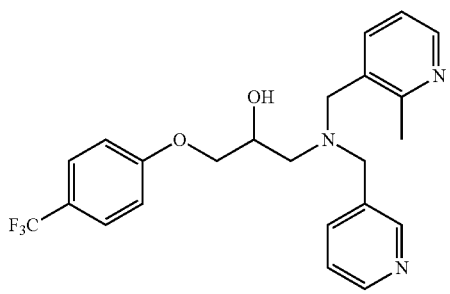 [SMILES: Cc1ncccc1CN(Cc1cccnc1)CC(O)COc1ccc(C(F)(F)F)cc1] |
| 29 | BC19829 | 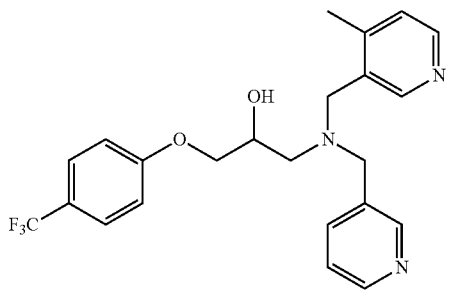 [SMILES: Cc1ccncc1CN(Cc1cccnc1)CC(O)COc1ccc(C(F)(F)F)cc1] |

TABLE 1-continued
| No. | BC code | Structure |
|---|---|---|
| 30 | BC19830 | 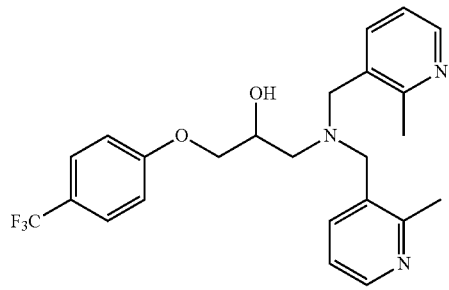 [SMILES: Cc1ncccc1CN(Cc1cccnc1C)CC(O)COc1ccc(C(F)(F)F)cc1] |
| 31 | BC19831 | 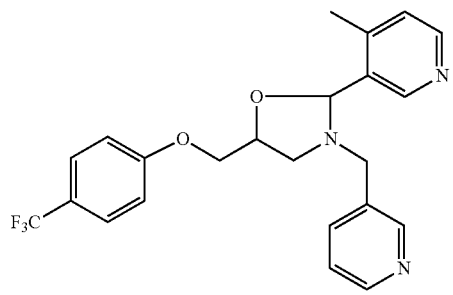 [SMILES: Cc1ccncc1C1OC(COc2ccc(C(F)(F)F)cc2)CN1Cc1cccnc1] |
| 32 | BC19832 | 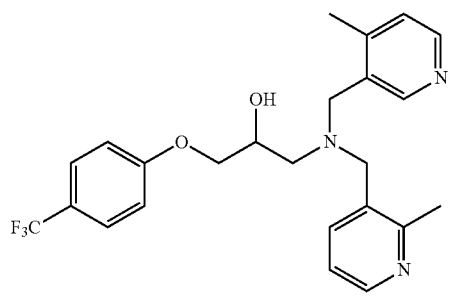 [SMILES: Cc1ccncc1CN(Cc1cccnc1C)CC(O)COc1ccc(C(F)(F)F)cc1] |
| 33 | BC19833 | 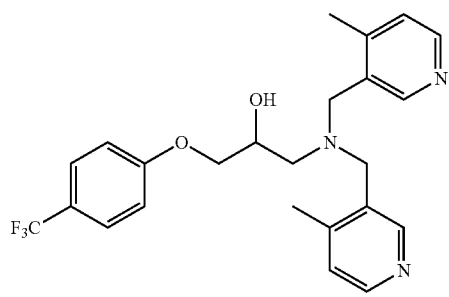 [SMILES: Cc1ccncc1CN(Cc1cnccc1C)CC(O)COc1ccc(C(F)(F)F)cc1] |
| 34 | BC19834 | 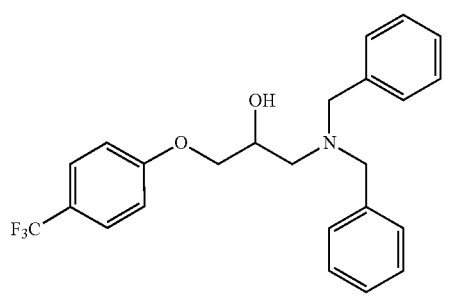 |

TABLE 1-continued
| No. | BC code | Structure |
|---|---|---|
| 35 | BC19835 | 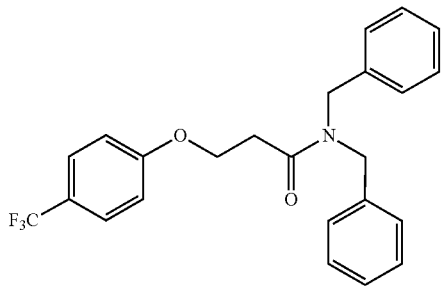 [SMILES: O=C(CCOc1ccc(C(F)(F)F)cc1)N(Cc1ccccc1)Cc1ccccc1] |
| 36 | BC19836 | 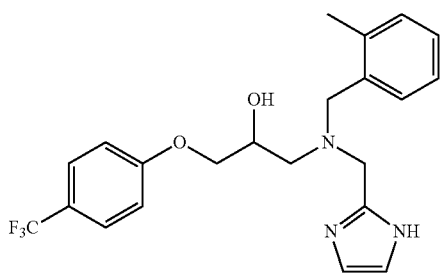 |
| 37 | BC19837 | 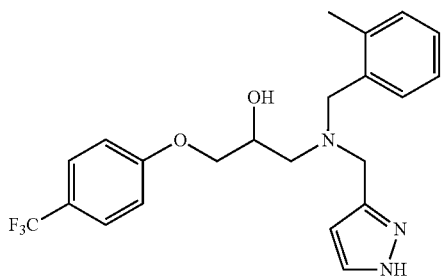 [SMILES: Cc1ccccc1CN(Cc1cc[nH]n1)CC(O)COc1ccc(C(F)(F)F)cc1] |
| 38 | BC19838 | 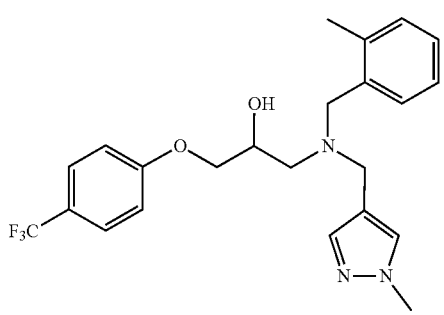 [SMILES: Cc1ccccc1CN(Cc1cnn(C)c1)CC(O)COc1ccc(C(F)(F)F)cc1] |
| 39 | BC19839 | 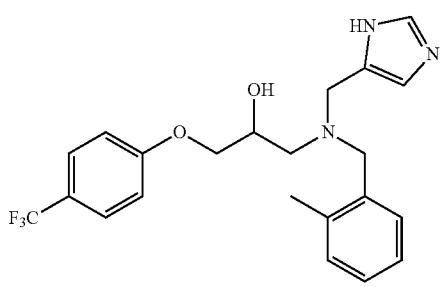 |

TABLE 1-continued
| No. | BC code | Structure |
|---|---|---|
| 40 | BC19840 | 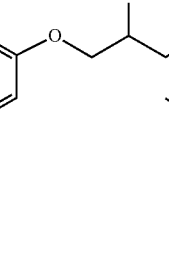 |
| 41 | BC19841 | 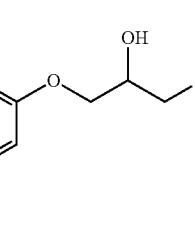 |
| 42 | BC19842 | 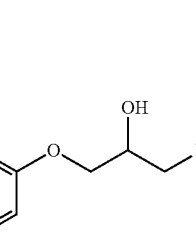 |
| 43 | BC19843 | 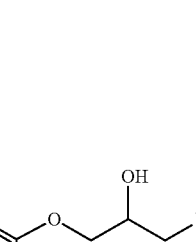 |
| 44 | BC19844 | 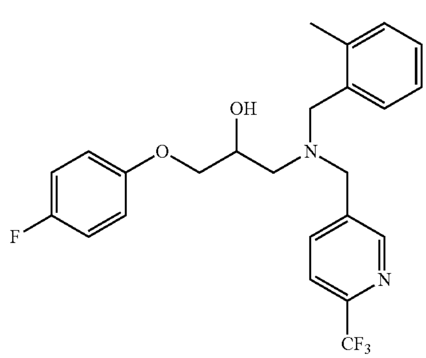 [SMILES: Cc1ccccc1CN(Cc1ccc(C(F)(F)F)nc1)CC(O)COc1ccc(F)cc1] |

TABLE 1-continued

| No. | BC code | Structure |
| --- | --- | --- |
| 45 | BC19845 | 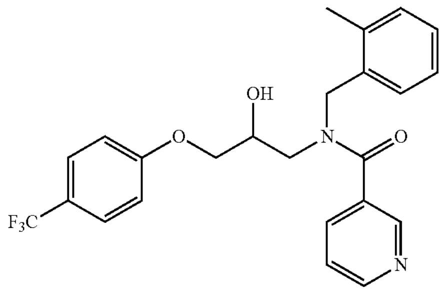 [SMILES: Cc1ccccc1CN(CC(O)COc1ccc(C(F)(F)F)cc1)C(=O)c1cccnc1] |
| 46 | BC19846 | 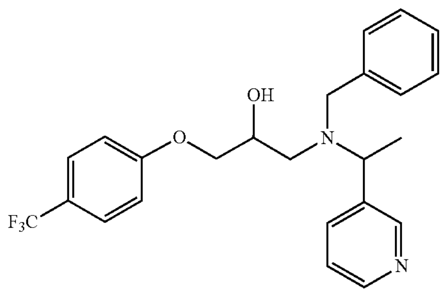 [SMILES: CC(c1cccnc1)N(Cc1ccccc1)CC(O)COc1ccc(C(F)(F)F)cc1] |
| 47 | BC19847 | 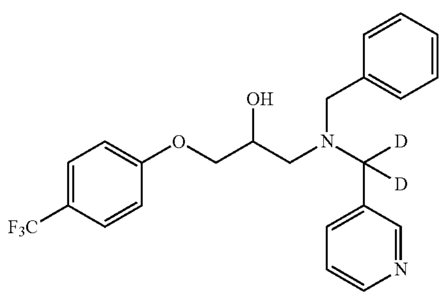 [SMILES: [2H]C([2H])(c1cccnc1)N(Cc1ccccc1)CC(O)COc1ccc(C(F)(F)F)cc1] |
| 48 | BC19848 | 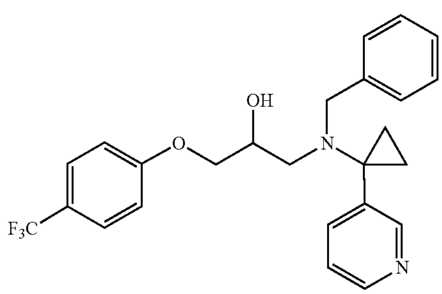 [SMILES: OC(COc1ccc(C(F)(F)F)cc1)CN(Cc1ccccc1)C1(c2cccnc2)CC1] |
| 49 | BC19849 | 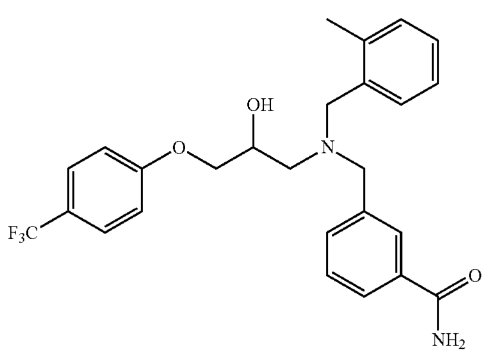 [SMILES: Cc1ccccc1CN(Cc1cccc(C(N)=O)c1)CC(O)COc1ccc(C(F)(F)F)cc1] |

TABLE 1-continued

| No. | BC code | Structure |
|-----|---------|-----------|
| 50 | BC19850 | 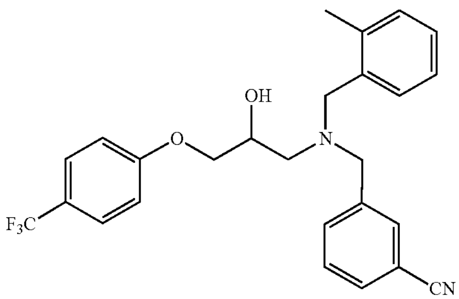 [SMILES: Cc1ccccc1CN(Cc1cccc(C#N)c1)CC(O)COc1ccc(C(F)(F)F)cc1] |
| 51 | BC19851 | 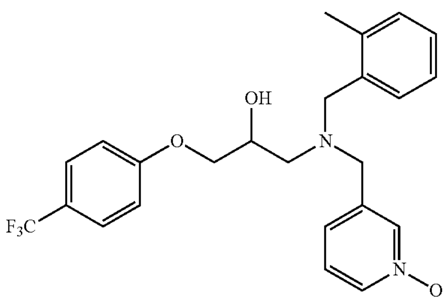 |
| 52 | BC19852 | 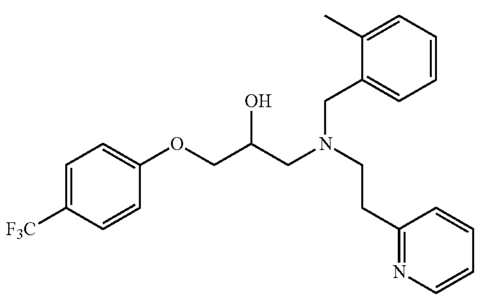 [SMILES: Cc1ccccc1CN(CCc1ccccn1)CC(O)COc1ccc(C(F)(F)F)cc1] |
| 53 | BC19853 | 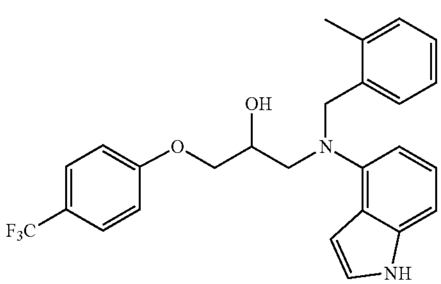 [SMILES: Cc1ccccc1CN(CC(O)COc1ccc(C(F)(F)F)cc1)c1cccc2[nH]ccc12] |
| 54 | BC19854 | 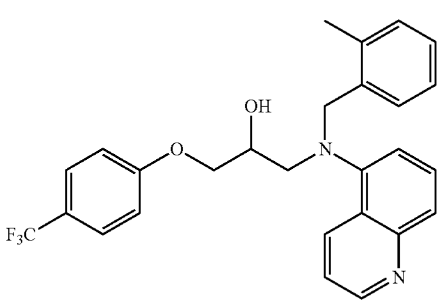 [SMILES: Cc1ccccc1CN(CC(O)COc1ccc(C(F)(F)F)cc1)c1cccc2ncccc12] |

TABLE 1-continued
| No. | BC code | Structure |
|---|---|---|
| 55 | BC19855 | 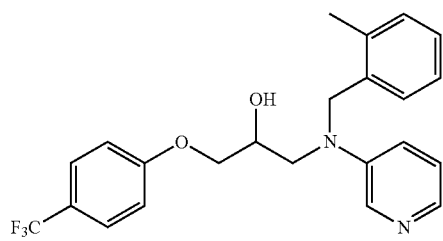 [SMILES: Cc1ccccc1CN(CC(O)COc1ccc(C(F)(F)F)cc1)c1cccnc1] |
| 56 | BC19856 | 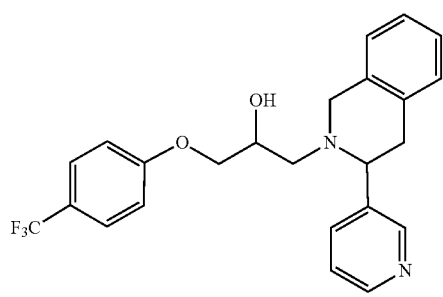 [SMILES: OC(COc1ccc(C(F)(F)F)cc1)CN1Cc2ccccc2CC1c1cccnc1] |
| 57 | BC19857 | 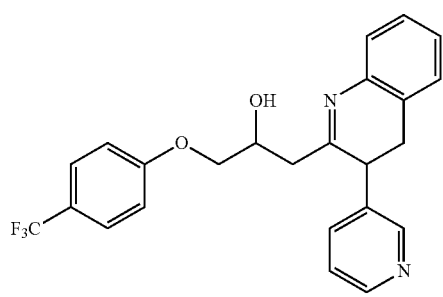 [SMILES: OC(COc1ccc(C(F)(F)F)cc1)CC1=Nc2ccccc2CC1c1cccnc1] |
| 58 | BC19858 | 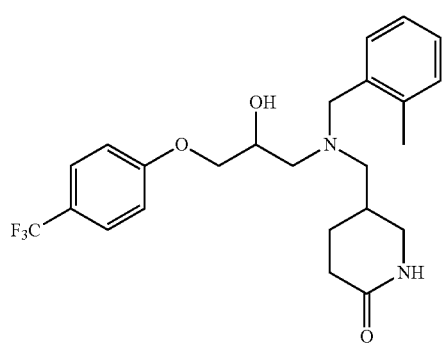 [SMILES: Cc1ccccc1CN(CC(O)COc1ccc(C(F)(F)F)cc1)CC1CCC(=O)NC1] |
| 59 | BC19859 | 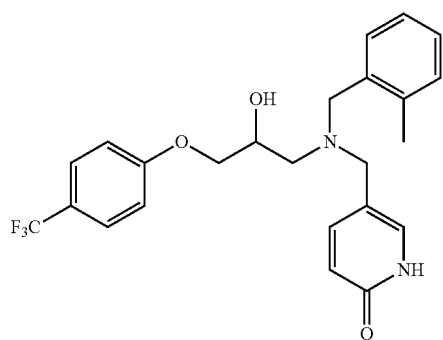 [SMILES: Cc1ccccc1CN(Cc1ccc(=O)[nH]c1)CC(O)COc1ccc(C(F)(F)F)cc1] |

TABLE 1-continued
| No. | BC code | Structure |
|---|---|---|
| 60 | BC19860 | 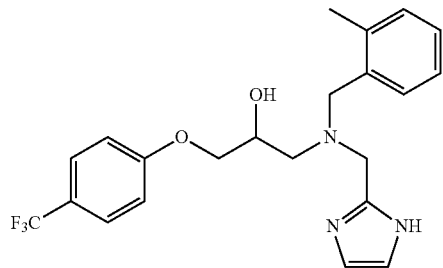 |
| 61 | BC19861 | 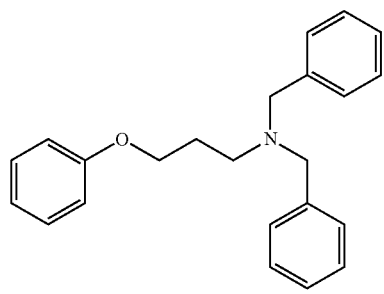 [SMILES: c1ccc(CN(CCCOc2ccccc2)Cc2ccccc2)cc1] |
| 62 | BC19862 | 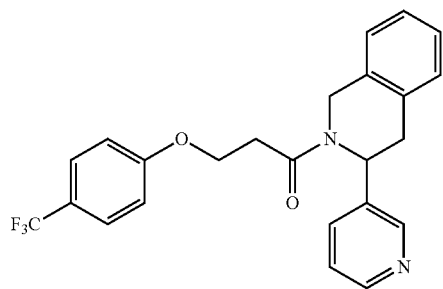 [SMILES: O=C(CCOc1ccc(C(F)(F)F)cc1)N1Cc2ccccc2CC1c1cccnc1] |
| 63 | BC19863 | 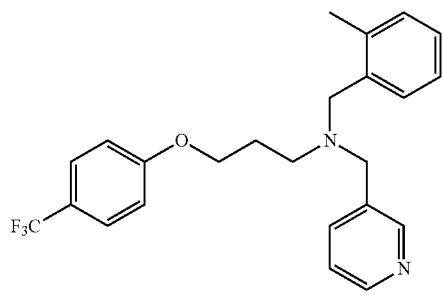 |
| 64 | BC19864 | 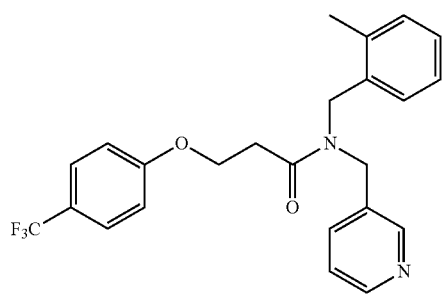 [SMILES: Cc1ccccc1CN(Cc1cccnc1)C(=O)CCOc1ccc(C(F)(F)F)cc1] |

TABLE 1-continued
| No. | BC code | Structure |
|---|---|---|
| 65 | BC19865 | 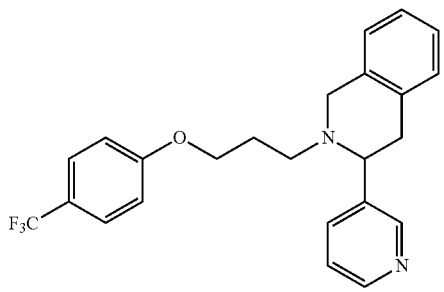 [SMILES: FC(F)(F)c1ccc(OCCCN2Cc3ccccc3CC2c2cccnc2)cc1] |
| 66 | BC19866 | 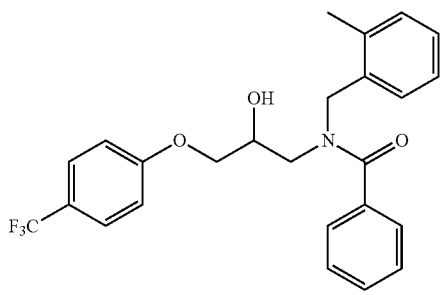 [SMILES: Cc1ccccc1CN(CC(O)COc1ccc(C(F)(F)F)cc1)C(=O)c1ccccc1] |
| 67 | BC19867 | 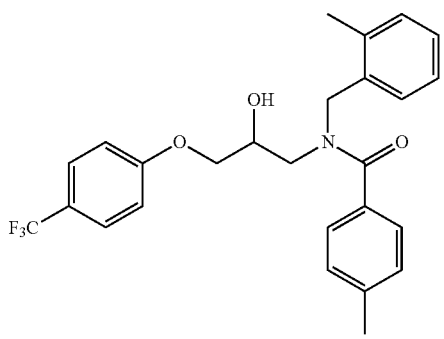 [SMILES: Cc1ccc(C(=O)N(Cc2ccccc2C)CC(O)COc2ccc(C(F)(F)F)cc2)cc1] |
| 68 | BC19868 | 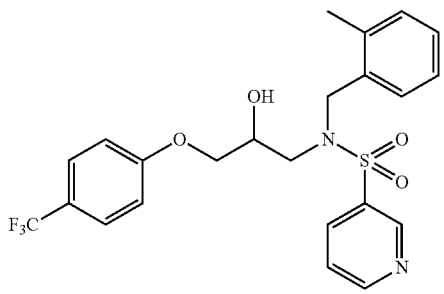 [SMILES: Cc1ccccc1CN(CC(O)COc1ccc(C(F)(F)F)cc1)S(=O)(=O)c1cccnc1] |
| 69 | BC19869 | 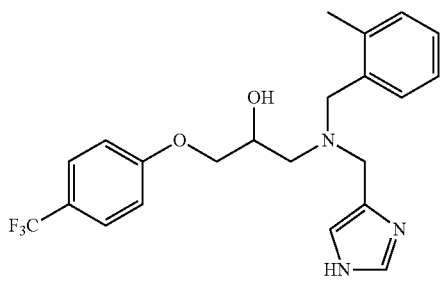 [SMILES: Cc1ccccc1CN(Cc1c[nH]cn1)CC(O)COc1ccc(C(F)(F)F)cc1] |

TABLE 1-continued
| No. | BC code | Structure |
|---|---|---|
| 70 | BC19870 | 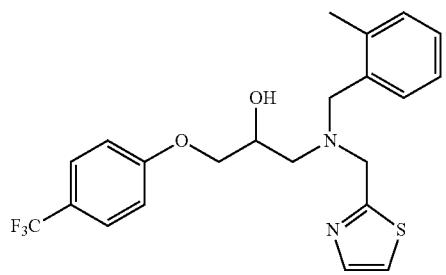 [SMILES: Cc1ccccc1CN(Cc1nccs1)CC(O)COc1ccc(C(F)(F)F)cc1] |
| 71 | BC19871 | 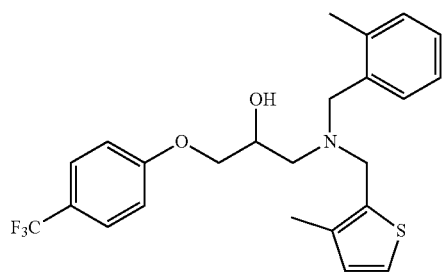 [SMILES: Cc1ccccc1CN(Cc1sccc1C)CC(O)COc1ccc(C(F)(F)F)cc1] |
| 72 | BC19872 | 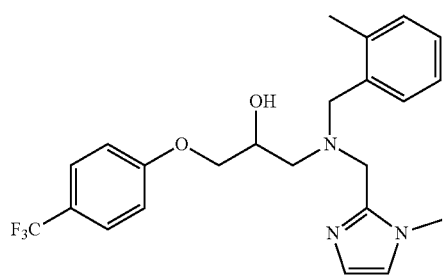 [SMILES: Cc1ccccc1CN(Cc1nccn1C)CC(O)COc1ccc(C(F)(F)F)cc1] |
| 73 | BC19873 | 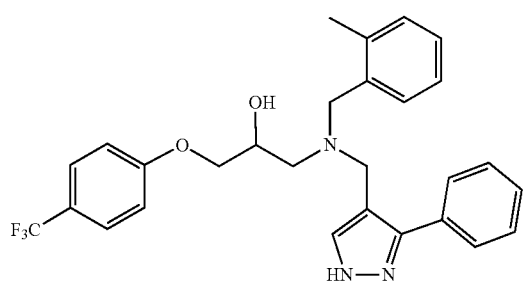 [SMILES: Cc1ccccc1CN(Cc1c[nH]nc1-c1ccccc1)CC(O)COc1ccc(C(F)(F)F)cc1] |
| 74 | BC19874 | 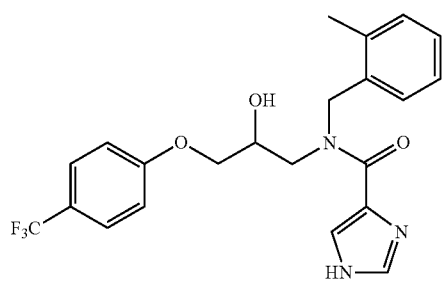 |

TABLE 1-continued
| No. | BC code | Structure |
|---|---|---|
| 75 | BC19875 | 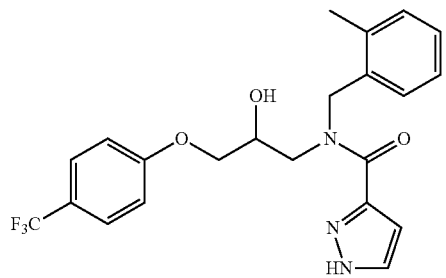 [SMILES: Cc1ccccc1CN(CC(O)COc1ccc(C(F)(F)F)cc1)C(=O)c1cc[nH]n1] |
| 76 | BC19876 | 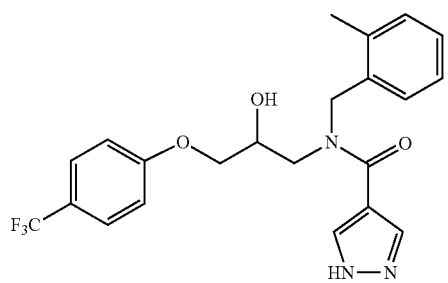 [SMILES: Cc1ccccc1CN(CC(O)COc1ccc(C(F)(F)F)cc1)C(=O)c1cn[nH]c1] |
| 77 | BC19877 | 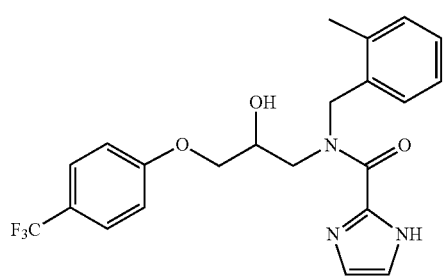 [SMILES: Cc1ccccc1CN(CC(O)COc1ccc(C(F)(F)F)cc1)C(=O)c1ncc[nH]1] |
| 78 | BC19878 | 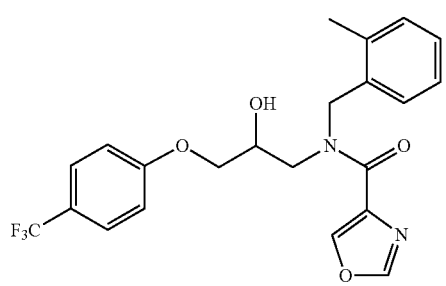 [SMILES: Cc1ccccc1CN(CC(O)COc1ccc(C(F)(F)F)cc1)C(=O)c1cocn1] |
| 79 | BC19879 | 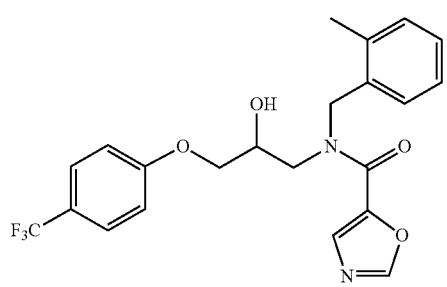 [SMILES: Cc1ccccc1CN(CC(O)COc1ccc(C(F)(F)F)cc1)C(=O)c1cnco1] |

TABLE 1-continued
| No. | BC code | Structure |
|---|---|---|
| 80 | BC19880 | 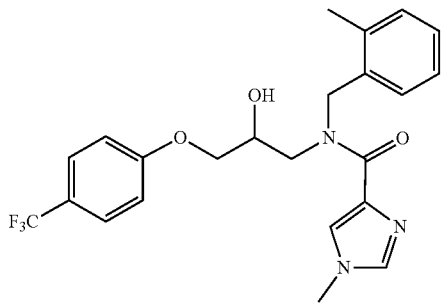 [SMILES: Cc1ccccc1CN(CC(O)COc1ccc(C(F)(F)F)cc1)C(=O)c1cn(C)cn1] |
| 81 | BC19881 | 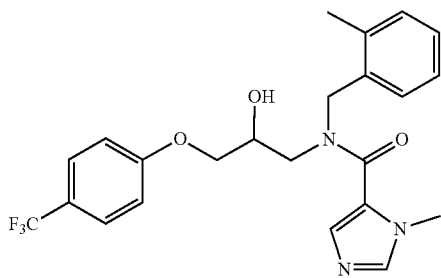 [SMILES: Cc1ccccc1CN(CC(O)COc1ccc(C(F)(F)F)cc1)C(=O)c1cncn1C] |
| 82 | BC19882 | 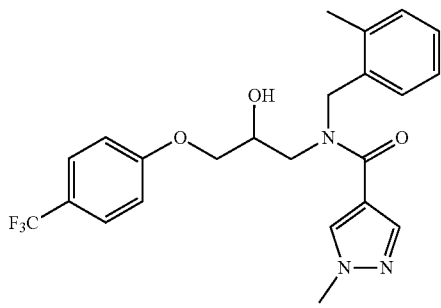 [SMILES: Cc1ccccc1CN(CC(O)COc1ccc(C(F)(F)F)cc1)C(=O)c1cnn(C)c1] |
| 83 | BC19883 | 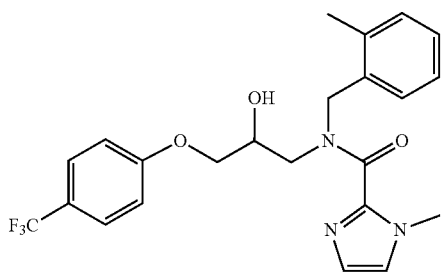 [SMILES: Cc1ccccc1CN(CC(O)COc1ccc(C(F)(F)F)cc1)C(=O)c1nccn1C] |
| 84 | BC19884 | 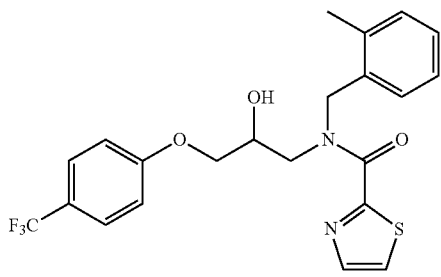 [SMILES: Cc1ccccc1CN(CC(O)COc1ccc(C(F)(F)F)cc1)C(=O)c1nccs1] |

TABLE 1-continued
| No. | BC code | Structure |
|-----|---------|-----------|
| 85 | BC19885 | 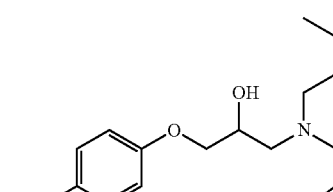 |
| 86 | BC19886 | 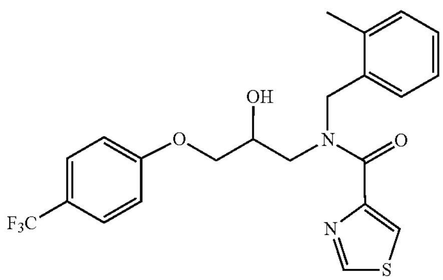 [SMILES: Cc1ccccc1CN(CC(O)COc1ccc(C(F)(F)F)cc1)C(=O)c1cscn1] |
| 87 | BC19887 | 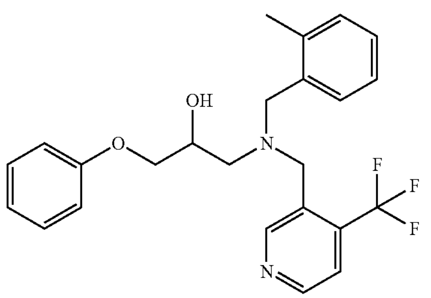 [SMILES: Cc1ccccc1CN(Cc1cnccc1C(F)(F)F)CC(O)COc1ccccc1] |
Compounds 3-34, 36-44, and 47-60 were isolated and tested as HCl salts.
TABLE 1a
| No. | BC code | Structure |
|-----|---------|-----------|
| 88 | BC19888 | 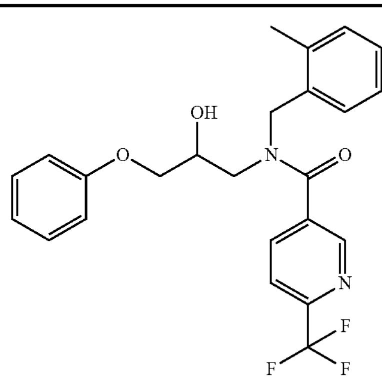 |
TABLE 1a-continued
| No. | BC code | Structure |
|-----|---------|-----------|
| 89 | BC19889 | 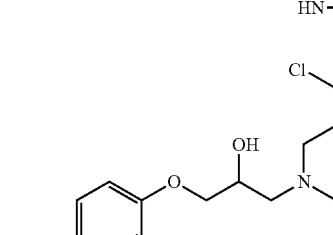 |
| 90 | BC19890 | 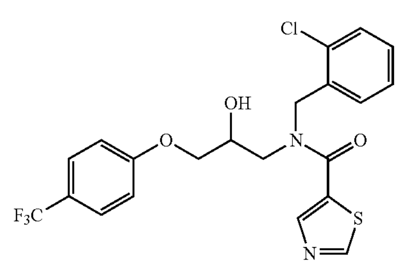 [SMILES: O=C(c1cncs1)N(Cc1ccccc1Cl)CC(O)COc1ccc(C(F)(F)F)cc1] |

TABLE 1a-continued
| No. | BC code | Structure |
|---|---|---|
| 91 | BC19891 | 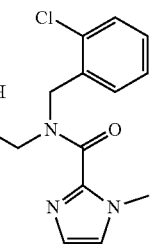 |
| 92 | BC19892 | 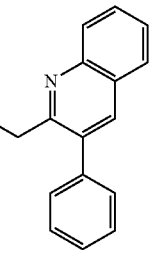 |
| 93 | BC19893 | 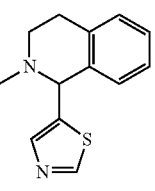 |
| 94 | BC19894 | 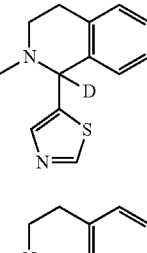 |
| 95 | BC19895 | 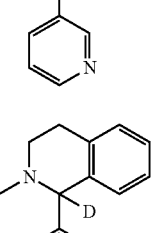 |
| 96 | BC19896 | 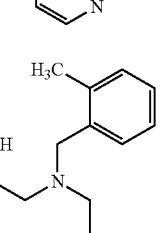 |
| 97 | BC19897 | 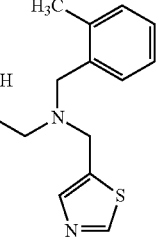 |
TABLE 1a-continued
| No. | BC code | Structure |
|---|---|---|
| 98 | BC19898 | 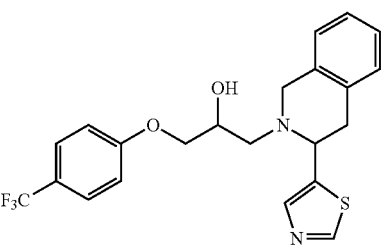 [SMILES: OC(COc1ccc(C(F)(F)F)cc1)CN1Cc2ccccc2CC1c1cncs1] |
| 99 | BC19899 | 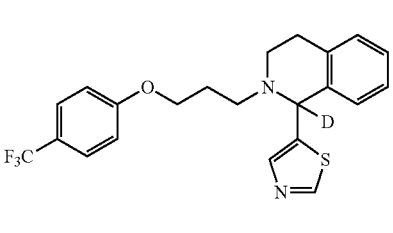 [SMILES: [2H]C1(c2cncs2)c2ccccc2CCN1CCCOc1ccc(C(F)(F)F)cc1] |
| 100 | BC191000 | 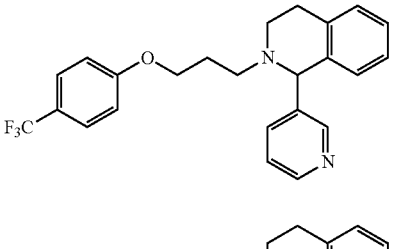 |
| 101 | BC191001 | 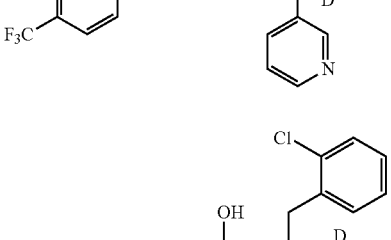 |
| 102 | BC191002 | 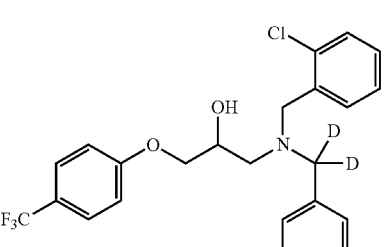 |
| 103 | BC191003 | 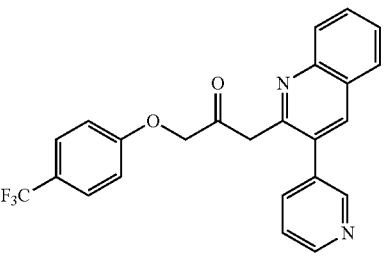 [SMILES: O=C(COc1ccc(C(F)(F)F)cc1)Cc1nc2ccccc2cc1-c1cccnc1] |

TABLE 1a-continued

| No. | BC code | Structure |
|---|---|---|
| 104 | BC191004 | |
| 105 | BC191005 | |
| 106 | BC191006 | |
| 107 | BC191007 | |
| 108 | BC191008 | |
| 109 | BC191009 | |
| 110 | BC191010 | 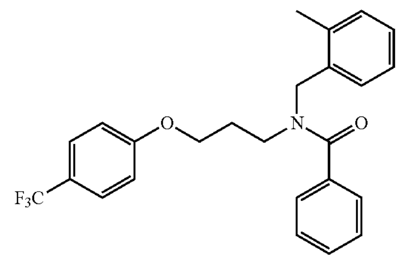 [SMILES: Cc1ccccc1CN(CCCOc1ccc(C(F)(F)F)cc1)C(=O)c1ccccc1] |
| 111 | BC191011A | 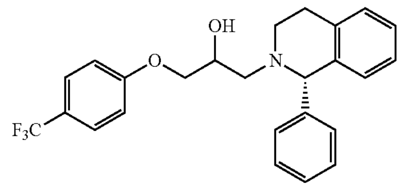 [SMILES: OC(COc1ccc(C(F)(F)F)cc1)CN1CCc2ccccc2[C@@H]1c1ccccc1] |
| 112 | BC191011B | 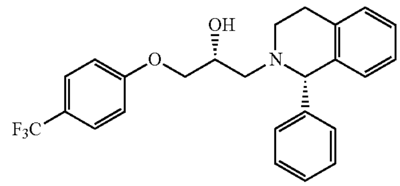 [SMILES: O[C@@H](COc1ccc(C(F)(F)F)cc1)CN1CCc2ccccc2[C@@H]1c1ccccc1] |
| 113 | BC191011C | 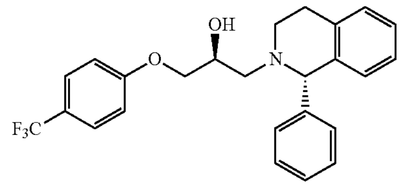 [SMILES: O[C@H](COc1ccc(C(F)(F)F)cc1)CN1CCc2ccccc2[C@@H]1c1ccccc1] |
| 114 | BC191011D | 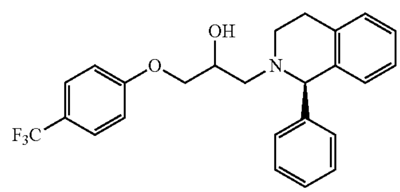 [SMILES: OC(COc1ccc(C(F)(F)F)cc1)CN1CCc2ccccc2[C@H]1c1ccccc1] |
| 115 | BC191011E | 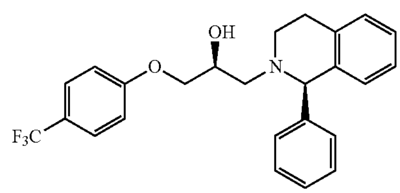 [SMILES: O[C@H](COc1ccc(C(F)(F)F)cc1)CN1CCc2ccccc2[C@H]1c1ccccc1] |
| 116 | BC191011F | 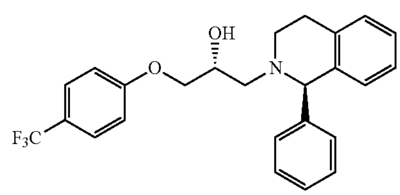 [SMILES: O[C@@H](COc1ccc(C(F)(F)F)cc1)CN1CCc2ccccc2[C@H]1c1ccccc1] |

TABLE 1a-continued

| No. | BC code | Structure |
|-----|---------|-----------|
| 117 | BC191012 | 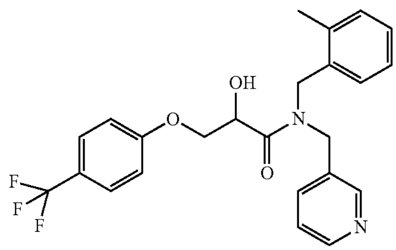 [SMILES: Cc1ccccc1CN(Cc1cccnc1)C(=O)C(O)COc1ccc(C(F)(F)F)cc1] |
| 118 | BC191013 | 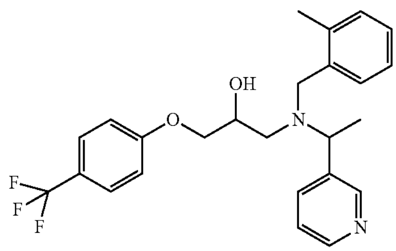 [SMILES: Cc1ccccc1CN(CC(O)COc1ccc(C(F)(F)F)cc1)C(C)c1cccnc1] |
| 119 | BC191014 | 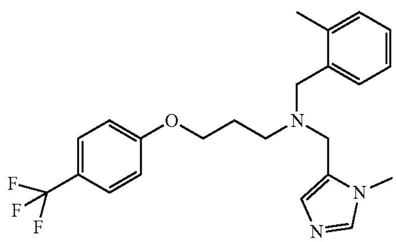 [SMILES: Cc1ccccc1CN(CCCOc1ccc(C(F)(F)F)cc1)Cc1cncn1C] |
| 120 | BC191015 | 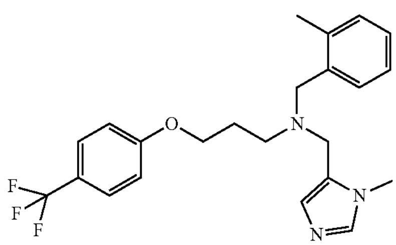 [SMILES: Cc1ccccc1CN(CCCOc1ccc(C(F)(F)F)cc1)Cc1cncn1C] |
| 121 | BC191016 | 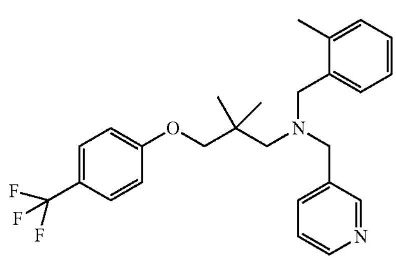 [SMILES: Cc1ccccc1CN(Cc1cccnc1)CC(C)(C)COc1ccc(C(F)(F)F)cc1] |
| 122 | BC191017 | 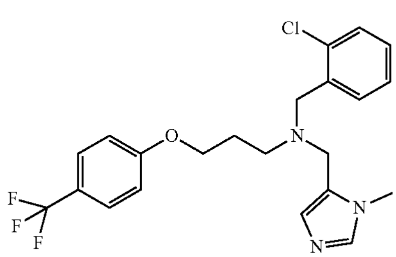 [SMILES: Cn1cncc1CN(CCCOc1ccc(C(F)(F)F)cc1)Cc1ccccc1Cl] |
| 123 | BC191018 | |
| 124 | BC191019 | |
| 125 | BC191020 | |
| 126 | BC191021 | |
| 127 | BC191022 | |
| 128 | BC191023 | |

TABLE 1a-continued

| No. | BC code | Structure |
|---|---|---|
| 129 | BC19856A | (structure) |
| 130 | BC19856B | (structure) |
| 131 | BC19856C | (structure) |
| 132 | BC19856D | (structure) |
| 133 | BC19856E | (structure) |
| 134 | BC19856F | (structure) |
| 135 | BC191024 | (structure) |
| 136 | BC191025 | (structure) |
| 137 | BC191026 | (structure) |
| 138 | BC191027 | (structure) |
| 139 | BC19863A | BC 19863 isolated as HCl salt |
| 140 | BC19863B | BC19863 isolated as tartrate salt |
| 141 | BC191028 | (structure) |
| 142 | BC191029 | (structure) |

TABLE 1a-continued
| No. | BC code | Structure |
|---|---|---|
| 143 | BC191030 | 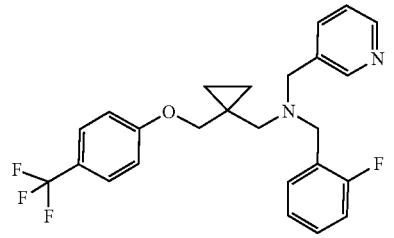 [SMILES: Fc1ccccc1CN(Cc1cccnc1)CC1(COc2ccc(C(F)(F)F)cc2)CC1] |
| 144 | BC191031 | 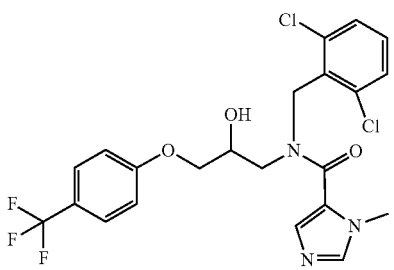 [SMILES: Cn1cncc1C(=O)N(Cc1c(Cl)cccc1Cl)CC(O)COc1ccc(C(F)(F)F)cc1] |
| 145 | BC191032 | 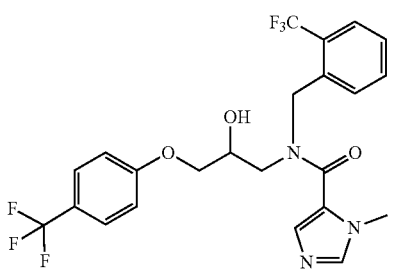 [SMILES: Cn1cncc1C(=O)N(Cc1ccccc1C(F)(F)F)CC(O)COc1ccc(C(F)(F)F)cc1] |
| 146 | BC191033 | 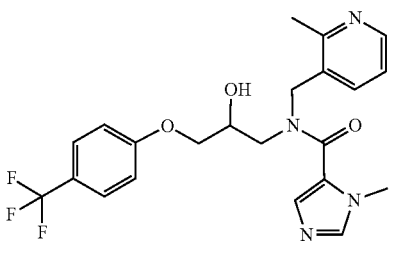 [SMILES: Cc1ncccc1CN(CC(O)COc1ccc(C(F)(F)F)cc1)C(=O)c1cncn1C] |
| 147 | BC191034 | 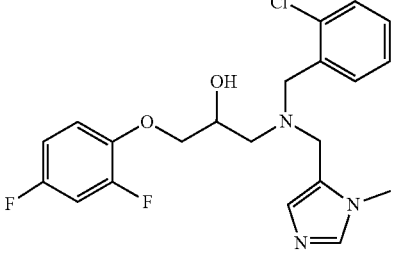 |
| 148 | BC191035 | 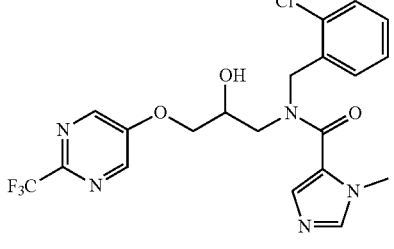 |
| 149 | BC191036 | 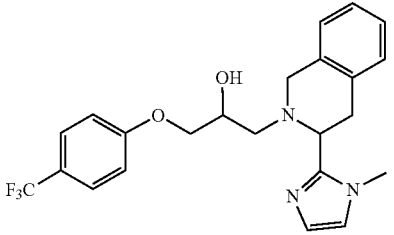 [SMILES: Cn1ccnc1C1Cc2ccccc2CN1CC(O)COc1ccc(C(F)(F)F)cc1] |
| 150 | BC19865A | 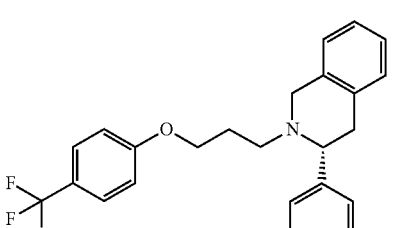 |
| 151 | BC19865B | 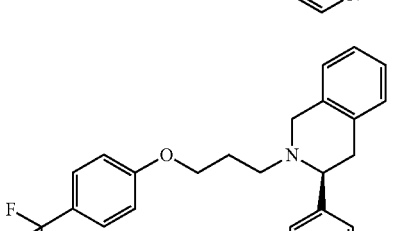 |
| 152 | BC191037 | 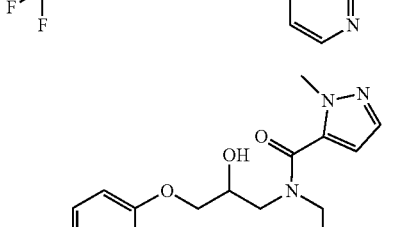 |
| 153 | BC191038 | 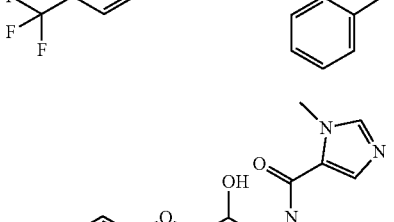 |
| 154 | BC191039 | 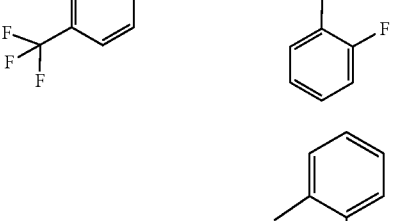 |

TABLE 1a-continued

| No. | BC code | Structure |
|-----|---------|-----------|
| 155 | BC191040 | |
| 156 | BC191041 | |
| 157 | BC191042 | |
| 158 | BC191043 | |
| 159 | BC191044 | |
| 160 | BC191045 | 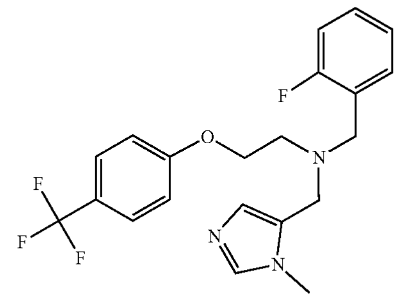 [SMILES: Cn1cncc1CN(CCOc1ccc(C(F)(F)F)cc1)Cc1ccccc1F] |
| 161 | BC191046 | 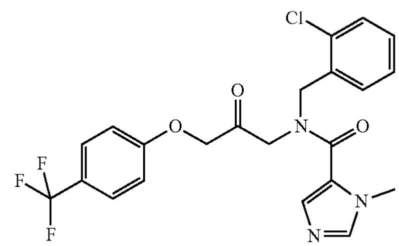 [SMILES: Cn1cncc1C(=O)N(CC(=O)COc1ccc(C(F)(F)F)cc1)Cc1ccccc1Cl] |
| 162 | BC191047 | 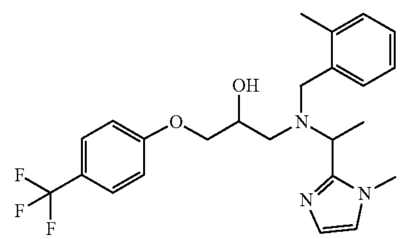 [SMILES: Cc1ccccc1CN(CC(O)COc1ccc(C(F)(F)F)cc1)C(C)c1nccn1C] |
| 163 | BC191048 | 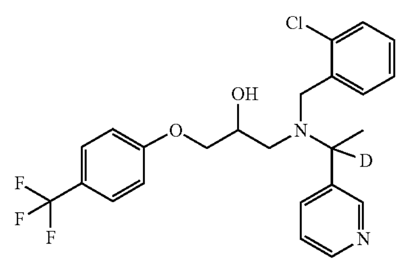 [SMILES: [2H]C(C)(c1cccnc1)N(Cc1ccccc1Cl)CC(O)COc1ccc(C(F)(F)F)cc1] |
| 164 | BC191049 | 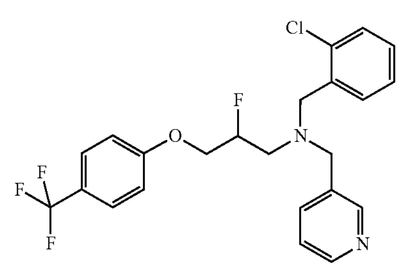 [SMILES: FC(COc1ccc(C(F)(F)F)cc1)CN(Cc1cccnc1)Cc1ccccc1Cl] |
| 165 | BC191050 | 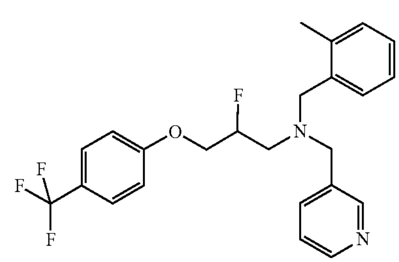 [SMILES: Cc1ccccc1CN(Cc1cccnc1)CC(F)COc1ccc(C(F)(F)F)cc1] |

TABLE 1a-continued
| No. | BC code | Structure |
|---|---|---|
| 166 | BC191051 | 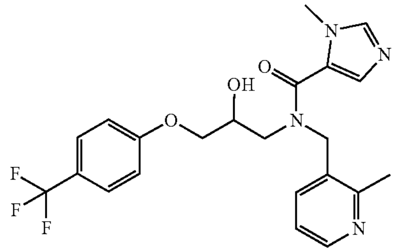 [SMILES: Cc1ncccc1CN(CC(O)COc1ccc(C(F)(F)F)cc1)C(=O)c1cncn1C] |
| 167 | BC191052 | 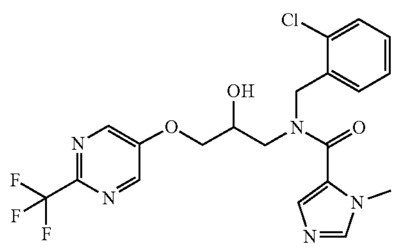 [SMILES: Cn1cncc1C(=O)N(Cc1ccccc1Cl)CC(O)COc1cnc(C(F)(F)F)nc1] |
| 168 | BC191053 | 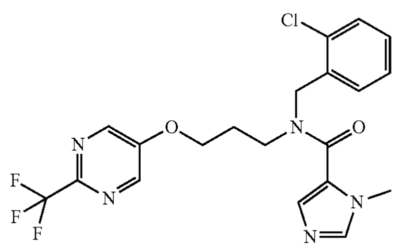 [SMILES: Cn1cncc1C(=O)N(CCCOc1cnc(C(F)(F)F)nc1)Cc1ccccc1Cl] |
| 169 | BC191054 | 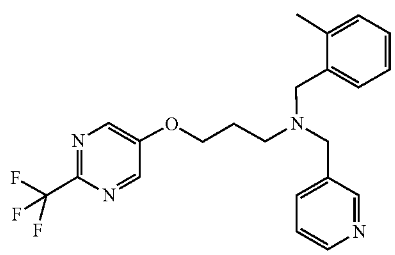 [SMILES: Cc1ccccc1CN(CCCOc1cnc(C(F)(F)F)nc1)Cc1cccnc1] |
| 170 | BC191055 | 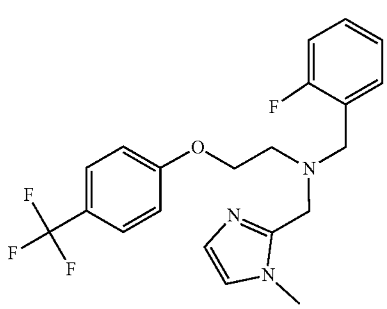 [SMILES: Cn1ccnc1CN(CCOc1ccc(C(F)(F)F)cc1)Cc1ccccc1F] |
| 171 | BC191056 | 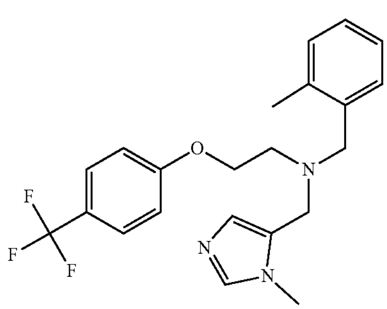 [SMILES: Cc1ccccc1CN(CCOc1ccc(C(F)(F)F)cc1)Cc1cncn1C] |
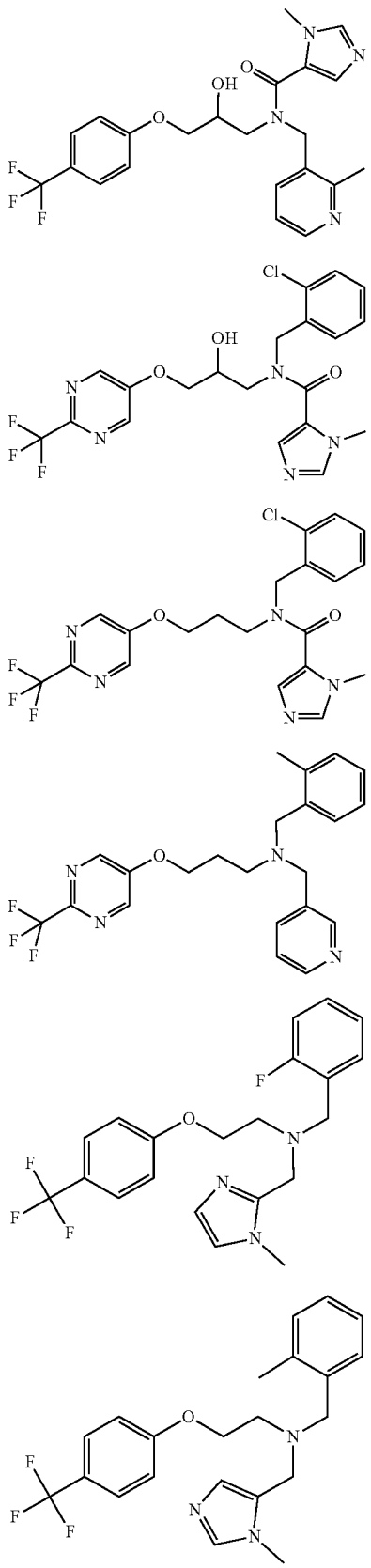
TABLE 1a-continued
| No. | BC code | Structure |
|---|---|---|
| 172 | BC191057 | 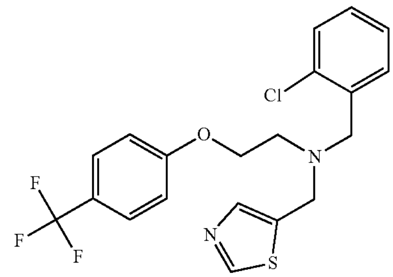 [SMILES: FC(F)(F)c1ccc(OCCN(Cc2cncs2)Cc2ccccc2Cl)cc1] |
| 173 | BC191058 | 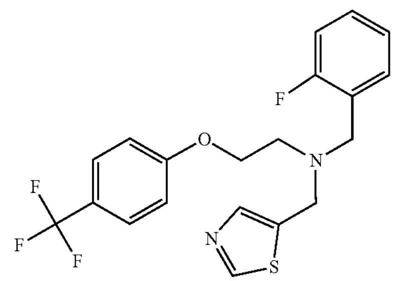 [SMILES: Fc1ccccc1CN(CCOc1ccc(C(F)(F)F)cc1)Cc1cncs1] |
| 174 | BC191059 | 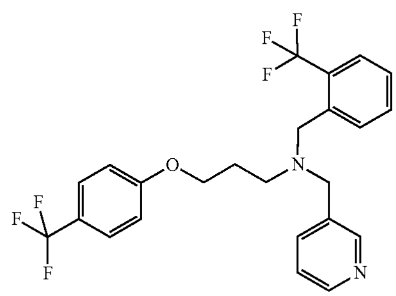 [SMILES: FC(F)(F)c1ccc(OCCCN(Cc2cccnc2)Cc2ccccc2C(F)(F)F)cc1] |
| 175 | BC191060 | 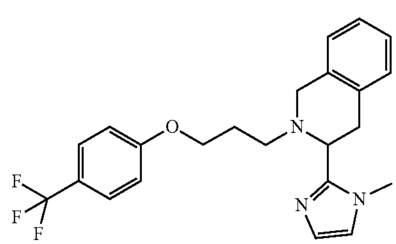 [SMILES: Cn1ccnc1C1Cc2ccccc2CN1CCCOc1ccc(C(F)(F)F)cc1] |
| 176 | BC191061 | 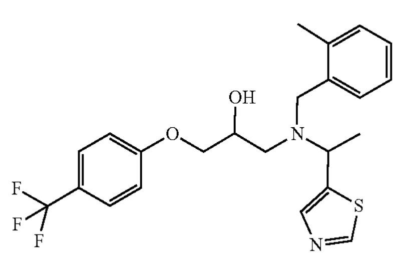 [SMILES: Cc1ccccc1CN(CC(O)COc1ccc(C(F)(F)F)cc1)C(C)c1cncs1] |
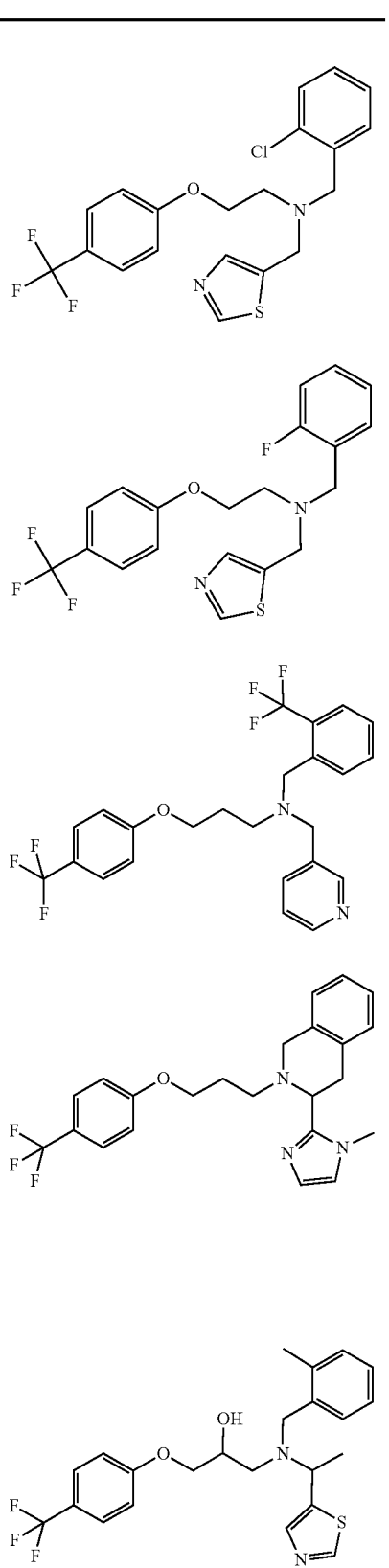

TABLE 1a-continued

| No. | BC code | Structure |
|---|---|---|
| 177 | BC191062 | (structure) |
| 178 | BC191063 | (structure) |
| 179 | BC191064 | (structure) |
| 180 | BC191065 | (structure) |
| 181 | BC191066 | (structure) |
| 182 | BC191067 | (structure) |
| 183 | BC191068 | (structure) |
| 184 | BC191069 | (structure) |
| 185 | BC191070 | (structure) |
| 186 | BC191071 | (structure) |
| 187 | BC191072 | (structure) |
| 188 | BC191073 | (structure) |

TABLE 1a-continued
| No. | BC code | Structure |
|-----|---------|-----------|
| 189 | BC191074 | 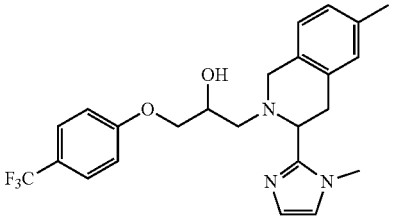 [SMILES: Cc1ccc2c(c1)CC(c1nccn1C)N(CC(O)COc1ccc(C(F)(F)F)cc1)C2] |
| 190 | BC191075 | 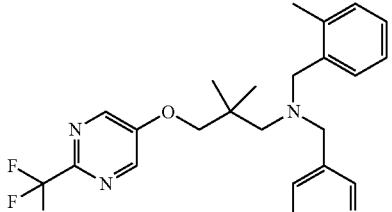 |
| 191 | BC191076 | 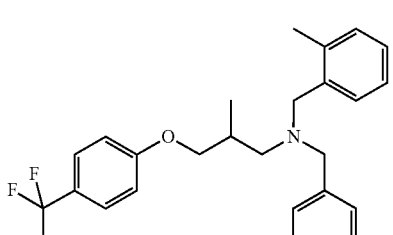 |
| 192 | BC191077 | 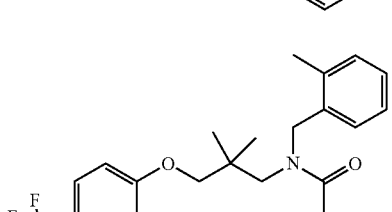 |
| 193 | BC191078 | 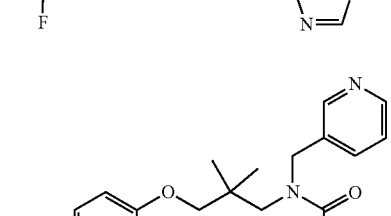 |
| 194 | BC191079 | 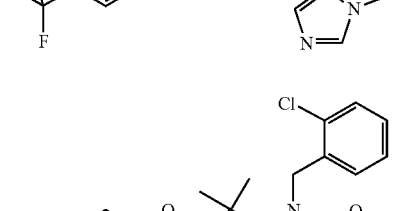 |
TABLE 1a-continued
| No. | BC code | Structure |
|-----|---------|-----------|
| 195 | BC191080 | 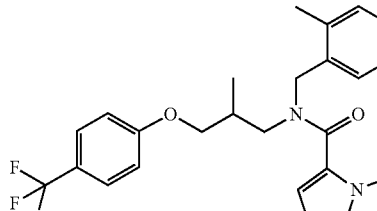 |
| 196 | BC191081 | 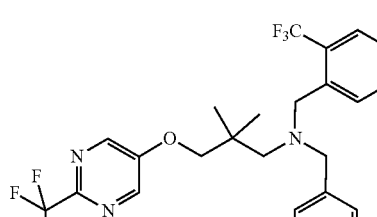 |
| 197 | BC191082 | 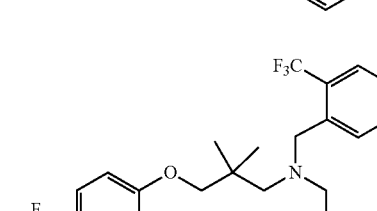 |
| 198 | BC191083 | 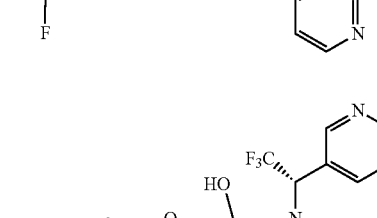 |
| 199 | BC191084 | 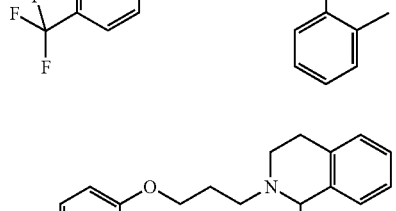 |
| 200 | BC191085 | 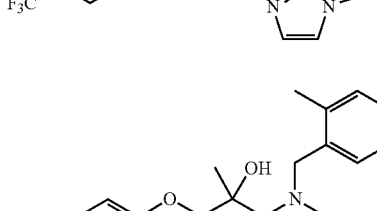 |

TABLE 1a-continued

| No. | BC code | Structure |
|---|---|---|
| 201 | BC191086 | 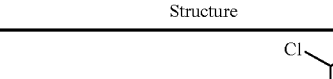 |

Example 2—Assay Results

Assay Protocol

Beas2B cells were plated in 384 white nunc plate (4000 cells per well) for overnight. Compounds were serially diluted in DMEM no glucose media using the liquid handler. Cells were washed once using Biotek EL406 before compound addition for additional 18 hours. Cells were washed and fixed with PFA before immunostained with pAMPK primary antibody and anti-Rabbit HRP secondary antibody. Finally, 25 µl of ECL reagent will be added to cells, and chemical luminescence signal will be counted using plate reader.

Compounds efficacies (µM) were determined by the minimal compound concentration needed to increase pAMPK by 30%. Activity: "+" equals >10 µM; "++" equals between ≤10 µM and >1 µM; and "+++" equals ≤1 µM. The assay results for compounds 1-87 are shown in Table A. The assay results for compounds 88-201 are shown in Table B.

TABLE A

Compound efficacy results

| No. | BC code | efficacy |
|---|---|---|
| 1 | BC1618R | ++ |
| 2 | BC1618S | ++ |
| 3 | BC19801 | ++ |
| 4 | BC19802 | +++ |
| 5 | BC19803 | ++ |
| 6 | BC19804 | ++ |
| 7 | BC19805 | +++ |
| 8 | BC19806 | +++ |
| 9 | BC19807 | + |
| 10 | BC19808 | ++ |
| 11 | BC19809 | ++ |
| 12 | BC19810 | ++ |
| 13 | BC19811 | +++ |
| 14 | BC19812 | + |
| 15 | BC19813 | + |
| 16 | BC19814 | ++ |
| 17 | BC19815 | + |
| 18 | BC19816 | +++ |
| 19 | BC19819 | + |
| 20 | BC19820 | ++ |
| 21 | BC19821 | |
| 22 | BC19822 | ++ |
| 23 | BC19823 | +++ |
| 24 | BC19824 | + |
| 25 | BC19825 | +++ |
| 26 | BC19826 | +++ |
| 27 | BC19827 | +++ |
| 28 | BC19828 | +++ |
| 29 | BC19829 | +++ |
| 30 | BC19830 | ++ |
| 31 | BC19831 | ++ |
| 32 | BC19832 | +++ |
| 33 | BC19833 | ++ |
| 34 | BC19834 | |
| 35 | BC19835 | ++ |
| 36 | BC19836 | +++ |
| 37 | BC19837 | ++ |
| 38 | BC19838 | ++ |
| 39 | BC19839 | ++ |
| 40 | BC19840 | +++ |
| 41 | BC19841 | ++ |
| 42 | BC19842 | +++ |
| 43 | BC19843 | +++ |
| 44 | BC19844 | +++ |
| 45 | BC19845 | +++ |
| 46 | BC19846 | +++ |
| 47 | BC19847 | +++ |
| 48 | BC19848 | +++ |
| 49 | BC19849 | ++ |
| 50 | BC19850 | + |
| 51 | BC19851 | ++ |
| 52 | BC19852 | ++ |
| 53 | BC19853 | ++ |
| 54 | BC19854 | ++ |
| 55 | BC19855 | ++ |
| 56 | BC19856 | +++ |
| 57 | BC19857 | ++ |
| 58 | BC19858 | |
| 59 | BC19859 | ++ |
| 60 | BC19860 | ++ |
| 61 | BC19861 | ++ |
| 62 | BC19862 | ++ |
| 63 | BC19863 | +++ |
| 64 | BC19864 | ++ |
| 65 | BC19865 | +++ |
| 66 | BC19866 | +++ |
| 67 | BC19867 | +++ |
| 68 | BC19868 | +++ |
| 69 | BC19869 | +++ |
| 70 | BC19870 | +++ |
| 71 | BC19871 | ++ |
| 72 | BC19872 | +++ |
| 73 | BC19873 | ++ |
| 74 | BC19874 | ++ |
| 75 | BC19875 | ++ |
| 76 | BC19876 | ++ |
| 77 | BC19877 | ++ |
| 78 | BC19878 | +++ |
| 79 | BC19879 | ++ |
| 80 | BC19880 | ++ |
| 81 | BC19881 | +++ |
| 82 | BC19882 | +++ |
| 83 | BC19883 | +++ |
| 84 | BC19884 | +++ |
| 85 | BC19885 | ++ |
| 86 | BC19886 | +++ |
| 87 | BC19887 | ++ |

TABLE B

Compound efficacy results.

| No. | BC code | efficacy |
|---|---|---|
| 88 | BC19888 | +++ |
| 89 | BC19889 | ++ |
| 90 | BC19890 | +++ |
| 91 | BC19891 | +++ |
| 92 | BC19892 | ++ |
| 93 | BC19893 | ++ |
| 94 | BC19894 | ++ |
| 95 | BC19895 | +++ |
| 96 | BC19896 | +++ |
| 97 | BC19897 | +++ |
| 98 | BC19898 | ++ |

TABLE B-continued

Compound efficacy results.

| No. | BC code | efficacy |
|---|---|---|
| 99 | BC19899 | +++ |
| 100 | BC191000 | +++ |
| 101 | BC191001 | +++ |
| 102 | BC191002 | +++ |
| 103 | BC191003 | + |
| 104 | BC191004 | +++ |
| 105 | BC191005 | +++ |
| 106 | BC191006 | +++ |
| 107 | BC191007 | +++ |
| 108 | BC191008 | +++ |
| 109 | BC191009 | +++ |
| 110 | BC191010 | +++ |
| 111 | BC191011A | ++ |
| 112 | BC191011B | +++ |
| 113 | BC191011C | ++ |
| 114 | BC191011D | + |
| 115 | BC191011E | ++ |
| 116 | BC191011F | + |
| 117 | BC191012 | ++ |
| 118 | BC191013 | + |
| 119 | BC191014 | +++ |
| 120 | BC191015 | +++ |
| 121 | BC191016 | +++ |
| 122 | BC191017 | +++ |
| 123 | BC191018 | ++ |
| 124 | BC191019 | ++ |
| 125 | BC191020 | +++ |
| 126 | BC191021 | + |
| 127 | BC191022 | +++ |
| 128 | BC191023 | ++ |
| 129 | BC19856A | +++ |
| 130 | BC19856B | +++ |
| 131 | BC19856C | +++ |
| 132 | BC19856D | +++ |
| 133 | BC19856E | +++ |
| 134 | BC19856F | +++ |
| 135 | BC191024 | +++ |
| 136 | BC191025 | +++ |
| 137 | BC191026 | +++ |
| 138 | BC191027 | + |
| 139 | BC19863A | +++ |
| 140 | BC19863B | +++ |
| 141 | BC191028 | +++ |
| 142 | BC191029 | +++ |
| 143 | BC191030 | +++ |
| 144 | BC191031 | ++ |
| 145 | BC191032 | ++ |
| 146 | BC191033 | + |
| 147 | BC191034 | + |
| 148 | BC191035 | + |
| 149 | BC191036 | ++ |
| 150 | BC19865A | ++ |
| 151 | BC19865B | +++ |
| 152 | BC191037 | ++ |
| 153 | BC191038 | ++ |
| 154 | BC191039 | +++ |
| 155 | BC191040 | +++ |
| 156 | BC191041 | +++ |
| 157 | BC191042 | +++ |
| 158 | BC191043 | +++ |
| 159 | BC191044 | +++ |
| 160 | BC191045 | +++ |
| 161 | BC191046 | +++ |
| 162 | BC191047 | + |
| 163 | BC191048 | + |
| 164 | BC191049 | +++ |
| 165 | BC191050 | +++ |
| 166 | BC191051 | + |
| 167 | BC191052 | + |
| 168 | BC191053 | + |
| 169 | BC191054 | +++ |
| 170 | BC191055 | +++ |
| 171 | BC191056 | ++ |
| 172 | BC191057 | +++ |
| 173 | BC191058 | +++ |
| 174 | BC191059 | +++ |
| 175 | BC191060 | +++ |
| 176 | BC191061 | ++ |
| 177 | BC191062 | + |
| 178 | BC191063 | +++ |
| 179 | BC191064 | ++ |
| 180 | BC191065 | ++ |
| 181 | BC191066 | +++ |
| 182 | BC191067 | +++ |
| 183 | BC191068 | +++ |
| 184 | BC191069 | +++ |
| 185 | BC191070 | +++ |
| 186 | BC191071 | +++ |
| 187 | BC191072 | +++ |
| 188 | BC191073 | +++ |
| 189 | BC191074 | + |
| 190 | BC191075 | ++ |
| 191 | BC191076 | +++ |
| 192 | BC191077 | +++ |
| 193 | BC191078 | +++ |
| 194 | BC191079 | +++ |
| 195 | BC191080 | +++ |
| 196 | BC191081 | ++ |
| 197 | BC191082 | +++ |
| 198 | BC191083 | + |
| 199 | BC191084 | ++ |
| 200 | BC191085 | +++ |
| 201 | BC191086 | ++ |

Example 3—Therapeutic Efficacy in Syngeneic A20 Murine Lymphoma in BALB/c Mice

Groups of (8) immunocompetent (7-8 weeks old), specific pathogen-free (SPF) BALB/c female mice bred in an animal isolator (IVC racks) under specific pathogen free (SPF) condition at 22±2° C. were used in this study. Viable A20 murine melanoma cells (ATCC TIB-208, $1.0 \times 10^6$ in 0.1 mL), syngeneic for BALB/c mice, were injected subcutaneously into the right flank of the mice. When group mean tumor volumes reached approximately 40-80 mm$^3$, animals were randomized into five groups, and dosing (denoted as Day 1) was initiated as shown in the following table. For group 1, the animals received no treatment. For Group 2, the animals were administered compound 63 orally, once a day for 21 days. For Group 3, the animals were administered anti-mPD-1 (Clone: RMP1-14, Bio X Cell, Catalog No. BE0146), formulated in phosphate buffered saline (PBS), intraperitoneally (IP) once every four days (repeated three times). For Groups 4 and 5, the animals were administered compound 63 orally, once a day for 21 days, and administered anti-mPD-1 (Clone: RMP1-14, Bio X Cell, Catalog No. BE0146), formulated in PBS, IP, once every four days (repeated three times). Half-life of the antibody is 9 days.

Tumor volumes, body weights, and signs of overt dose related toxicity were monitored in the mice and recorded three times weekly starting on Day 1 and continuing to Day 28 or when the mean tumor volume in the negative control group reached 3000 mm$^3$, whichever came first. Therapeutic efficacy was evaluated for Tumor Growth Inhibition (TGI), or Tumor Growth Delay (TGD), or both TGI and TGD.

| | Treatment 1 | | | | Treatment 2 | | | | |
|---|---|---|---|---|---|---|---|---|---|
| Group | Test Article | Route | Schedule | mL/kg | mg/kg | Test Article | Route | Schedule | mL/kg | mg/kg | Mice (n) |
| 1[#] | No Treatment | — | — | — | — | No Treatment | — | — | — | — | 8 |
| 2 | Compound 63 | Oral | qd x 21 | | 25 | — | | | | | 8 |
| 3 | PD-1 | IP | q4d x 3 | 10 | 20 | — | | | | | 8 |
| 4 | Compound 63 | Oral | qd x 21 | 10 | 25 | PD-1 | IP | q4d x 3 | 10 | 20 | 8 |
| 5 | Compound 63 | Oral | qd x 21 | 10 | 25 | PD-1 | IP | q4d x 3 | 10 | 20 | 2 |

[#]Negative control

For group 5, in-life blood samples (40 μL whole blood per time-point) were collected from both mice via mandibular bleed prior to administering the last dose of compound 63, and at 30 min, 1 hour, 2 hours, and 4 hours post last dose. Terminal blood samples were collected via cardiac puncture from all mice 24 hours post last dose. All blood samples were processed for plasma, flash frozen and stored at −80° C. until analysis. Whole blood samples were analyzed using fluorescence-activated cell sorting (FACS) to determine the percentage of CD4+, CD8+, and T-reg cells.

Upon termination of the mice, tumor samples were collected from all mice, and the tumors divided into two parts. One part was flash frozen and stored at −80° C. until analysis. The second part was homogenized and evaluated for CD4+, CD8+, and T-reg cells using FACS.

Tumor growth inhibition (T/C) was calculated by the following formula: % T/C=(Tn/Cn)×100%, where Cn is the tumor weight measured on Day n in the control group, Tn is the tumor weight measured on Day n in the treated group. % T/C value <42% was considered significant antitumor activity (NCI standards).

Percent tumor growth inhibition (% TGI) also was calculated using the following formula: % TGI=(1−(Tn/Cn))×100%. A % TGI value >58% was considered significant antitumor activity.

Percent Tumor Growth Delay (% TGD) was expressed as the percentage by which the treated group median tumor volume was delayed in reaching the established tumor volume endpoint compared to the controls using the formula ((T−C)/C))×100, where T and C are median times (days) to reach the established tumor volume endpoint for the treated and control group, respectively. Animal were monitored individually. The tumor volume endpoint for individual animals is 3000 mm$^3$. Responders can be followed longer.

Tumor volume (mm$^3$) was estimated according to the formula for a prolate ellipsoid: length (mm)×[width (mm)]$^2$×0.5.

Figure 1B:
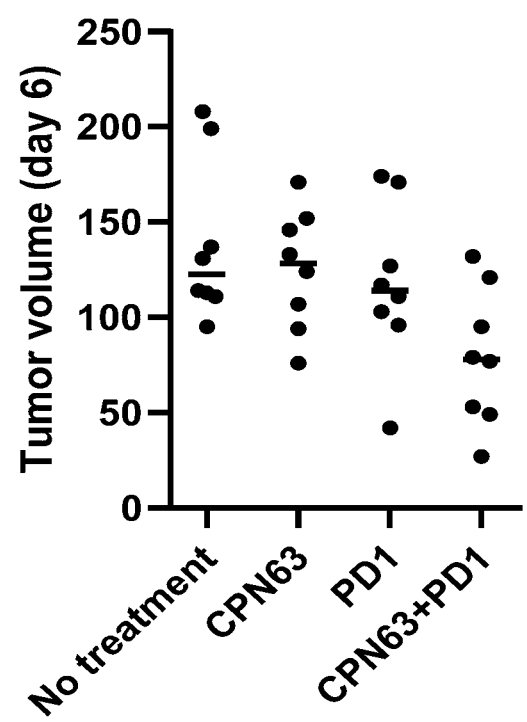
In FIGS. 1B, 1C, and 1D, tumor volume is shown for days 6, 13, and 22, respectively.
Figure 1C:
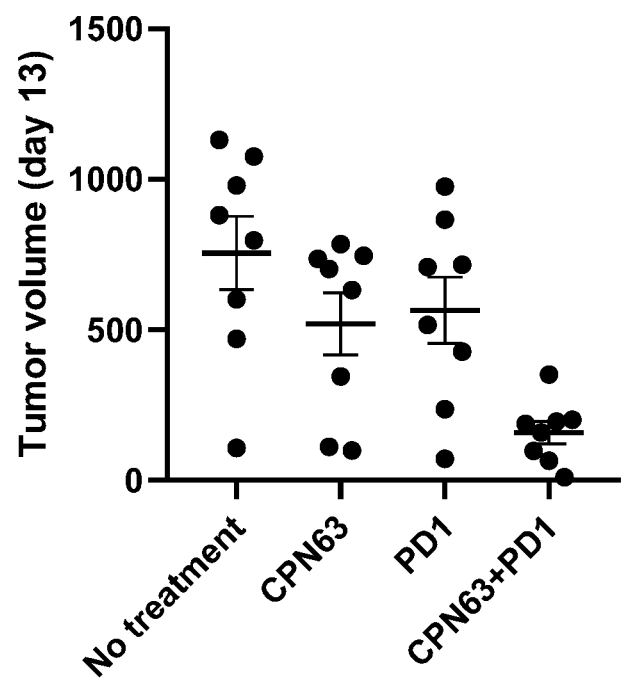
Figure 1D:
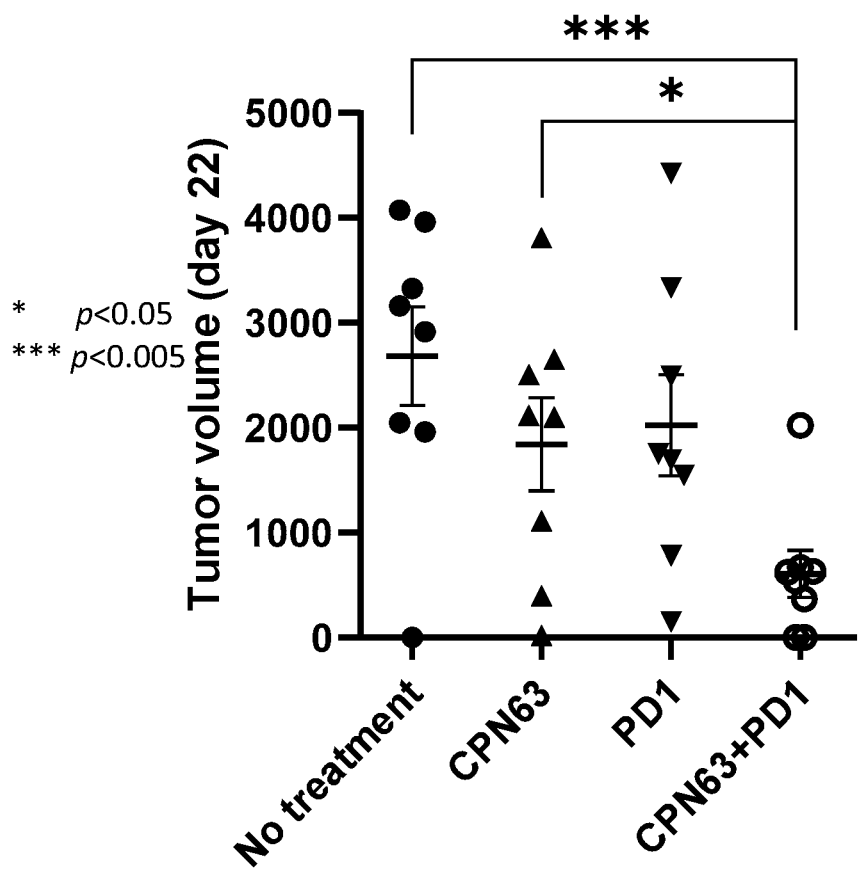

Tumor volume data is shown in FIGS. 1A-1D. FIG. 1A compares tumor volume over the course of the study, while FIGS. 1B, 1C, and 1D show tumor volume on days 6, 13, and 22, respectively. In mice treated with either compound 63 or anti-PD-1 antibody, tumor volume was reduced but did not reach the >58% TGI threshold. However, when mice were treated with a combination of compound 63 and anti-PD-1 antibody, a significant (p<0.005 compared to vehicle and p<0.05 compared to compound 63 alone) decrease in tumor growth was observed (76% TGI), indicating that compound 63 and anti-PD-1 antibody had a synergistic effect. This may underestimate the value of compound 63 since higher doses may be more effective. Similarly, PD-1 therapy was not given after day 12 in this model (q4d×3 dosing). Continuation of PD-1 therapy for longer periods might result in higher levels of synergy.

Figure 2A:
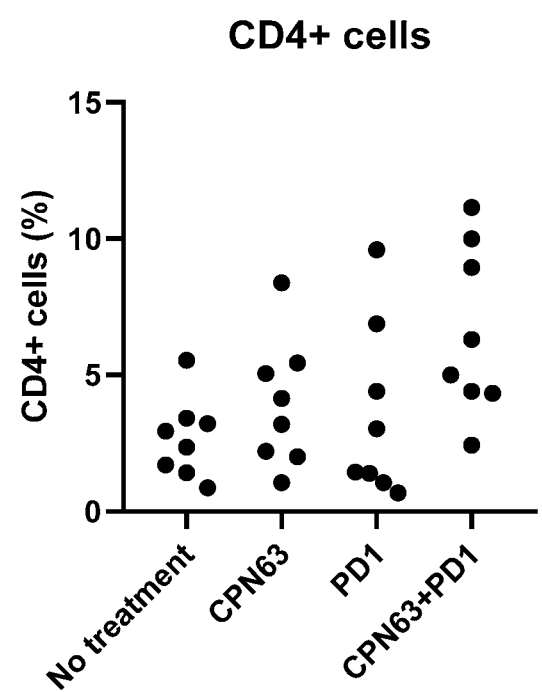
FIGS. 2A-2D depict the percentage of CD4+ cells (A), CD8+ cells (B), regulatory T cells (C), and leukocytes (D) as determined by fluorescence-activated cell sorting (FACS) of blood from mice with no treatment (1), treatment with 25 mg/kg compound 63 (3), treatment with 20 mg/kg anti-PD-1 antibody (4), or treated with a combination of 20 mg/kg anti-PD-1 antibody and 25 mg/kg compound 63 (6). Leukocytes can include monocytes, neutrophils, granulocytes, natural killer cells (NKCs), and myeloid-derived suppressor cells (MDSCs).
Figure 2B:
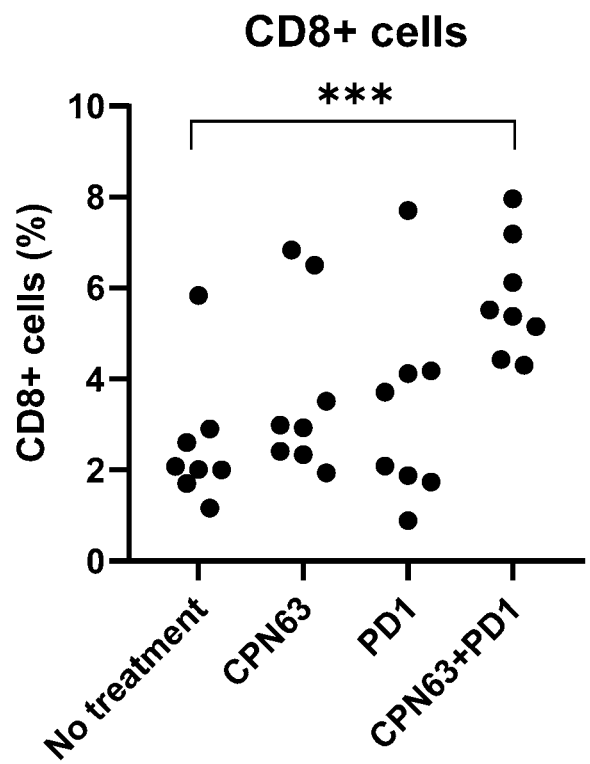
Figure 2C:
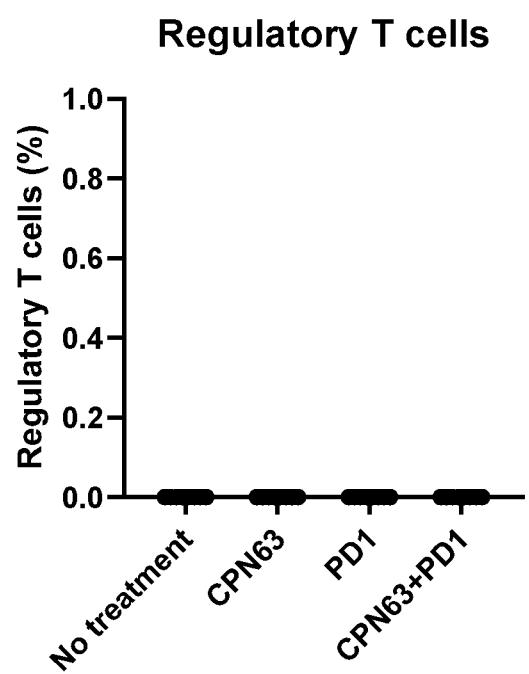
Figure 2D:
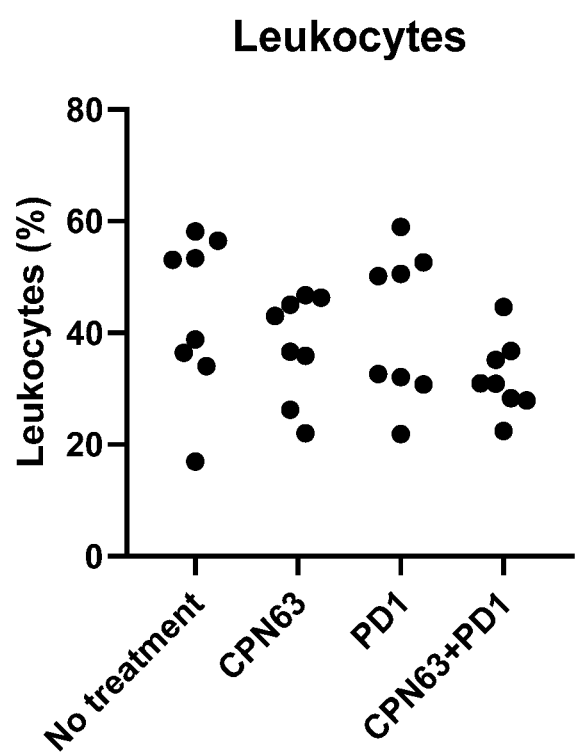

FIGS. 2A-2D depict the percentage of CD4+ cells (FIG. 2A), CD8+ cells (FIG. 2B), regulatory T cells (FIG. 2C), and leukocytes (FIG. 2D) found in the blood of mice after termination of the study. As shown in FIG. 2B, a significant (p<0.001 compared to vehicle treatment) increase in circulating CD8+ cells was observed in the mice treated with the combination of compound 63 and anti-PD-1 antibody.

Example 4—Antimicrobial Efficacy Against Methicillin Resistant *Staphylococcus aureus* (MRSA)

Groups of 5-10 female BALB/c mice weighing 20±2 g were used in this study. Animals were rendered immune suppressed by treatment with 250 mg/kg of cyclophosphamide IP at 4 and 2 days before infection (Day −4 and −2). Vehicle 10% DMA (N,N-dimethylacetamide):40% PEG300: 50% H$_2$O) and/or test substances were administered on days −4, −3, −2, −1 and 0.

| Group | Test Article | Schedule Route | Conc. mg/mL | Dosage mL/kg | Dosage mg/kg | Mice (Female) |
|---|---|---|---|---|---|---|
| 1 | Initial counts, 30 min Post infection | — | — | — | — | 5 |
| 2 | Vehicle[a,b] | Once a day, orally | — | 10 | — | 10 |
| 3 | Vancomycin | Twice a day, IV | 1.6 | 10 | 16 | 10 |
| 4 | Compound 63 | Once a day, orally | 2.5 | 10 | 25 | 10 |

On day 0, immediately following the final dose, animals were inoculated intranasally (0.02 mL/lung) with 1-5×10$^6$ colony forming units (CFU)/mouse of MRSA (ATCC 33591) after being anaesthetized by etomidate (20 mg/kg dose, IV). In addition, following the final dose, blood was collected at 0, 0.5 h, 1 h, 2 h, 4 h and 24 h from three animals of each group, via facial veins. Terminal blood samples were taken by cardiac puncture. Blood samples were drawn into K2EDTA anti-coagulant coated mini collection tubes. The blood was collected from group 1 after sacrifice as the blank for PK analysis. Samples were stored on ice for no more than one hour then centrifuged at 2500×g for 15 min at 4° C. Plasma (~50 μL) was stored at −80° C. until analysis.

Figure 3:
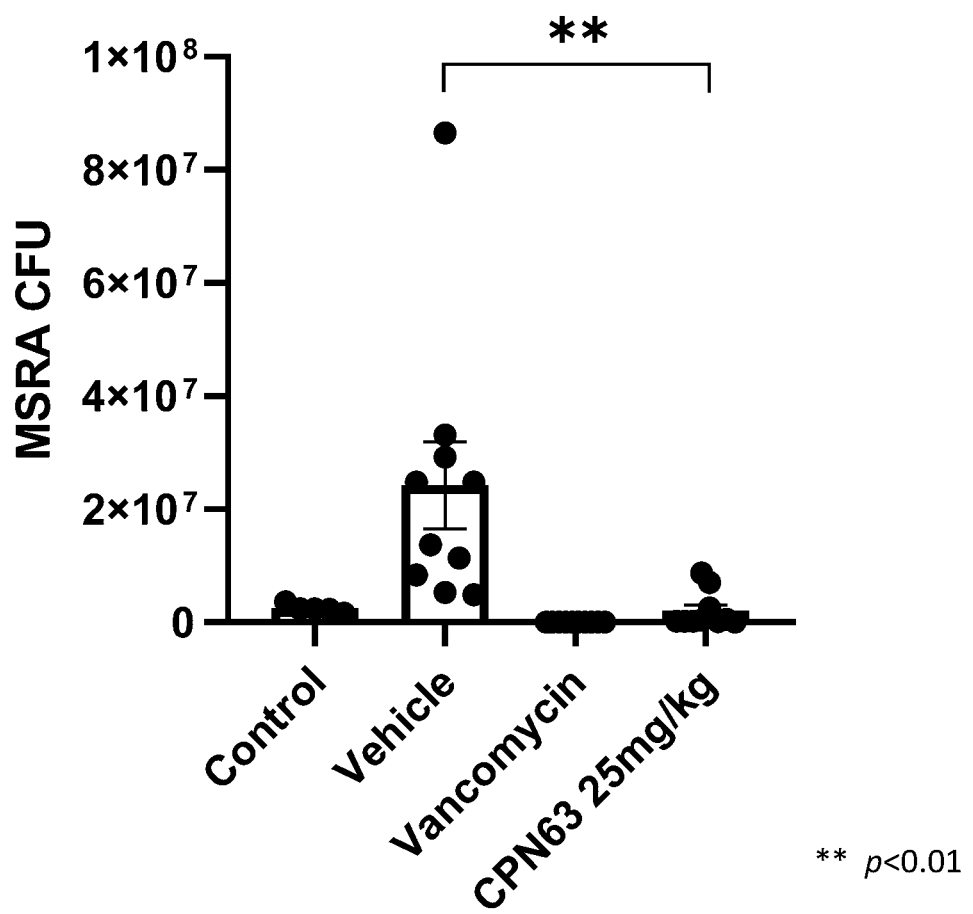
FIG. 3 is a graph of the clearance of methicillin resistant *Staphylococcus aureus* (strain ATCC 33591) from the lungs of neutropenic BALB/c mice treated with vehicle, vancomycin (16 mg/kg), or compound 63 (25 mg/kg).
Figure 4:
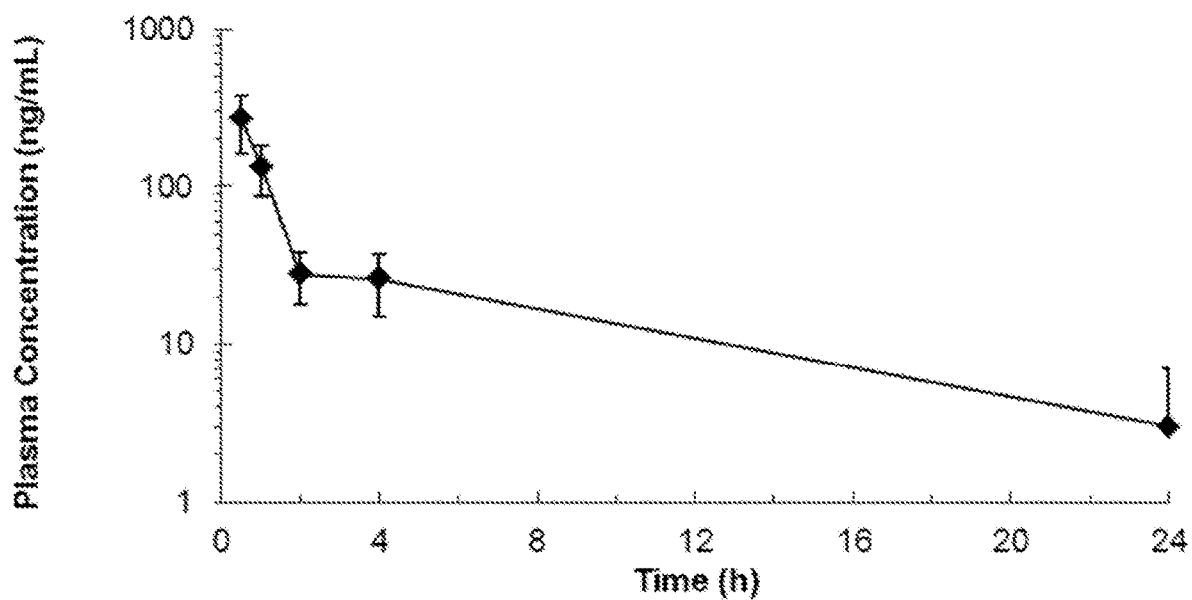
FIG. 4 contains a line plot showing mean exposure levels of compound 63 in plasma samples vs. time (semi-log plots).

At 24 hours after inoculation, the animals were humanely euthanized with CO$_2$ asphyxiation, and the lung tissue was harvested from each of the test animals. The tissues were homogenized in 1 mL of PBS. Homogenates, 0.1 mL, were used for serial 10-fold dilutions and plated on mannitol salt agar plates for CFU determination. As shown in FIG. 3, compound 63 cleared MRSA from the lung (p<0.01 compared to vehicle treatment).

The plasma samples are processed using acetonitrile precipitation and analyzed by HPLC-MS/MS. A plasma calibration curve is generated. Aliquots of drug-free plasma are spiked with the test compound at the specified concentration levels. The spiked plasma samples are processed together with the unknown plasma samples using the same procedure. The processed plasma samples are stored at −20° C. until the HPLC-MS/MS analysis, at which time peak areas were recorded, and the concentrations of the test compound in the unknown plasma samples are determined using the respective calibration curve. The reportable linear range of the assay is determined, along with the lower limit of quantitation (LLQ).

TABLE 2

The exposure levels of compound 63 in mouse plasma samples-compound 63 (25 mg/kg, PO QD × 5) group:

| Time (h) | Sample concentration (ng/mL) | | | mean | SD |
|---|---|---|---|---|---|
| 0 | 3 | 0 | 0 | 1* | 2 |
| 0.5 | 180 | 243 | 390 | 271 | 108 |
| 1 | 184 | 95 | 120 | 133 | 46 |
| 2 | 16 | 36 | 31 | 28 | 10 |
| 4 | 22 | 38 | 18 | 26 | 11 |
| 24 | 7 | 0 | 3 | 3 | 4 |

*The data was excluded from the PK calculation

TABLE 3

The PK parameters of compound 63 in mouse plasma samples

| Dose, PO (mg/kg) | $T_{max}$ (h) | $C_{max}$ (ng/mL) | $AUC_{last}$ (h × ng/mL) | $AUC_{inf}$ (h × ng/mL) | AUC/D (h × kg × ng/mL/mg) | $AUC_{Extr}$ (%) | MTR (h) |
|---|---|---|---|---|---|---|---|
| 25 | 0.5 | 271 | 593 | 622 | 25 | 5 | 4.96 |

ADDITIONAL EMBODIMENTS

Embodiment 1. A compound of Formula (I):

$$R^1\text{—}O\text{—}L^1\text{—}X\text{—}L^2\text{—}N(R^2)R^3 \quad (I)$$

or a pharmaceutically acceptable salt thereof, wherein:
$R^1$ is selected from 5-6 membered heteroaryl and a group of formula:

(i) a para-CF$_3$-phenyl group with $(R^5)_m$ substituents or (ii) a 2,6-dimethylphenyl group with $(R^5)_n$ substituents, wherein said 5-6 membered heteroaryl of $R^1$ is optionally substituted with 1, 2, 3, 4, or 5 substituents independently selected from $R^5$;
$L^1$ is $C_{1-4}$ alkylene;
$L^2$ is $C_{1-4}$ alkylene or $L^2$ is absent;
X is selected from CH(OR$^4$) and C=O; or X is absent;
$R^2$ and $R^3$ are each independently selected from H, $C_{1-6}$ alkyl, Cy$^1$, $C_{1-6}$ haloalkyl, $C_{2-6}$ alkenyl, $C_{2-6}$ alkynyl, C(=O)Cy$^1$, and S(=O)$_2$Cy$^1$, wherein said $C_{1-6}$ alkyl, $C_{2-6}$ alkenyl, and $C_{2-6}$ alkynyl are each optionally substituted with 1 or 2 independently selected Cy$^1$;
provided that at least one of $R^2$ and $R^3$ is other than H;
$R^4$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;
or $R^4$ and $R^2$ together with the O atom to which $R^4$ is attached and N atom to which $R^2$ is attached form 5-10 membered heterocycloalkyl, which is optionally substituted with 1 or 2 independently selected Cy$^1$;
or $R^2$ and $R^3$, together with the N atom to which they are attached, form 4-16 membered heterocycloalkyl ring, which is optionally substituted with 1 or 2 independently selected Cy$^1$;
m is 0, 1, 2, 3, or 4;
n is 0, 1, 2, or 3;
each $R^5$ is independently selected from OH, NO$_2$, CN, halo, $C_{1-6}$ alkyl, Cia haloalkyl, $C_{1-6}$ alkoxy, $C_{1-6}$ haloalkoxy, thio, $C_{1-6}$ alkylthio, carboxy, amino, $C_{1-6}$ alkylamino, and di($C_{1-6}$ alkyl)amino;
each Cy$^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;
each $R^{Cy1}$ is independently selected from halo, CN, NO$_2$, $C_{1-6}$ alkyl, $C_{1-6}$ haloalkyl, $C_{2-6}$ alkenyl, $C_{2-6}$ alkynyl, Cy$^2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said $C_{1-6}$ alkyl, $C_{2-6}$ alkenyl, and $C_{2-6}$ alkynyl are each optionally substituted with 1, 2, or 3 substituents independently selected from Cy$^2$, halo, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;
each Cy$^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;
each $R^{Cy2}$ is independently selected from halo, CN, NO$_2$, $C_{1-6}$ alkyl, $C_{1-6}$ haloalkyl, $C_{2-6}$ alkenyl, $C_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said $C_{1-6}$ alkyl, $C_{2-6}$ alkenyl, and $C_{2-6}$ alkynyl are each optionally substituted with 1, 2, or 3 substituents independently selected from halo, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;
each $R^{a1}$, $R^{b1}$, $R^{c1}$, and $R^{d1}$ is independently selected from H, $C_{1-6}$ alkyl, $C_{1-4}$haloalkyl, $C_{2-6}$ alkenyl, $C_{2-6}$ alkynyl, $C_{6-10}$aryl, $C_{3-10}$cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{11}$ and $R^{d1}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, provided that the compound of Formula (I) is not any one of the following compounds:

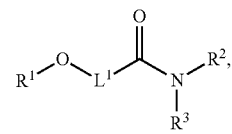

and

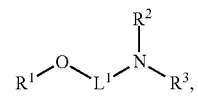

Embodiment 2. The compound of embodiment 1, wherein the compound of Formula (I) has formula:

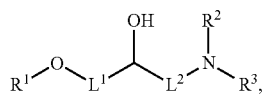

or a pharmaceutically acceptable salt thereof.

Embodiment 3. The compound of embodiment 1, wherein the compound of Formula (I) has formula:

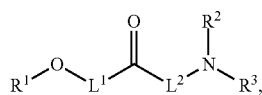

or a pharmaceutically acceptable salt thereof.

Embodiment 4. The compound of any one of embodiments 1-3, wherein $L^2$ is $C_{1-4}$ alkylene.

Embodiment The compound of any one of embodiments 1-4, wherein $L^2$ is methylene.

Embodiment 6. The compound of embodiment 1, wherein the compound of Formula (I) has formula:

or a pharmaceutically acceptable salt thereof.

Embodiment 7. The compound of embodiment 1, wherein the compound of Formula (I) has formula:

or a pharmaceutically acceptable salt thereof.

Embodiment 8. The compound of any one of embodiments 1-7, wherein $L^1$ is selected from methylene and ethylene.

Embodiment 9. The compound of embodiment 8, wherein $L^1$ is methylene.

Embodiment 10. The compound of any one of embodiments 1-9, wherein $R^1$ is 5-6 membered heteroaryl, optionally substituted with 1, 2, or 3 substituents independently selected from $R^5$.

Embodiment 11. The compound of embodiment 10, wherein the 5-6 membered heteroaryl is selected from pyridinyl and pyrimidinyl.

Embodiment 12. The compound of any one of embodiments 1-9, wherein m is 0, 1, or 2.

Embodiment 13. The compound of any one of embodiments 1-9, wherein n is 0, 1, or 2.

Embodiment The compound of any one of embodiments 1-13, wherein $R^5$ is selected from halo, $C_{1-6}$ alkyl, $C_{1-4}$ haloalkyl, $C_{1-6}$ alkoxy, and $C_{1-6}$ haloalkoxy.

Embodiment 15. The compound of any one of embodiments 1-9, wherein $R^1$ is a group of formula:

215

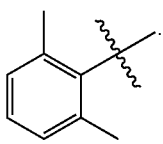 [SMILES: *c1c(C)cccc1C]

Embodiment 16. The compound of any one of embodiments 1-9, wherein $R^1$ is a group of formula:

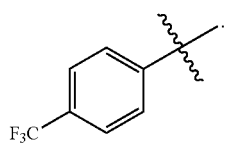

Embodiment The compound of embodiment 1, wherein the compound of Formula (I) is selected from:

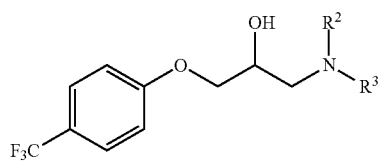

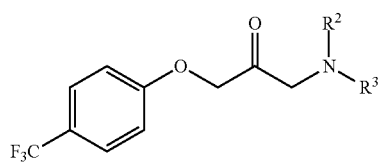

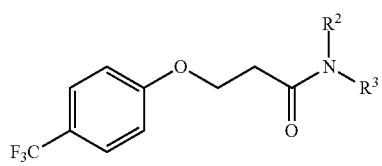

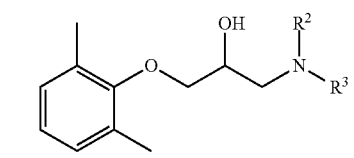

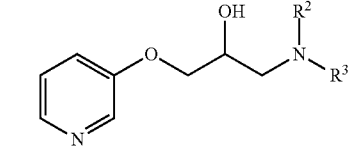

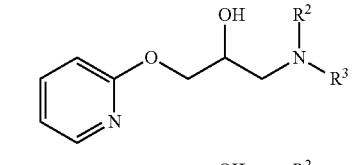

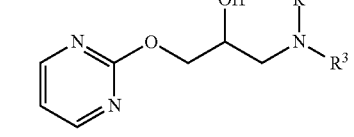

216

-continued

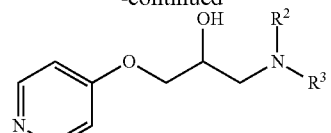

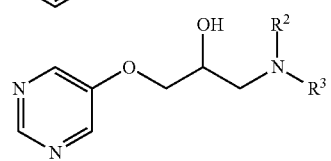

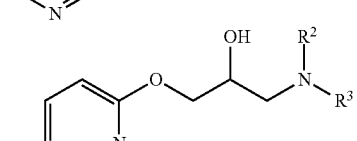

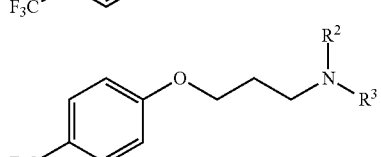

or a pharmaceutically acceptable salt thereof.

Embodiment 18. The compound of any one of embodiments 1-17, wherein $R^2$ and $R^3$ are each independently selected from H, $C_{1-6}$ alkyl, $Cy^1$, $C(=O)Cy^1$, and $S(=O)_2Cy^1$, wherein said $C_{1-6}$ alkyl, is optionally substituted with 1 or 2 independently selected $Cy^1$.

Embodiment 19. The compound of embodiment 18, wherein $R^2$ and $R^3$ are each independently an $C_{1-6}$ alkyl substituted with 1 or 2 independently selected $Cy^1$.

Embodiment 20. The compound of embodiment 18, wherein:
  $R^2$ is selected from H and $C_{1-6}$ alkyl; and
  $R^3$ is $C_{1-6}$ alkyl substituted with 1 or 2 independently selected $Cy^1$.

Embodiment 21. The compound of embodiment 18, wherein:
  $R^2$ is $C_{1-6}$ alkyl substituted with 1 or 2 independently selected $Cy^1$; and
  $R^3$ is selected from $Cy^1$, $C(=O)Cy^1$ and $S(=O)_2Cy^1$.

Embodiment 22. The compound of any one of embodiments 1-17, wherein $R^2$ and $R^3$, together with the N atom to which they are attached, form 4-16 membered heterocycloalkyl ring, which is optionally substituted with $Cy^1$.

Embodiment 23. The compound of embodiment 22, wherein the 4-16 membered heterocycloalkyl ring is selected from tetrahydroisoquinolinyl, isoindolinyl, and dihydrodibenzoazepinyl.

Embodiment 24. The compound of any one of embodiments 1-17, wherein $R^2$ and $R^3$, together with the N atom to which they are attached, form a ring of formula selected from:

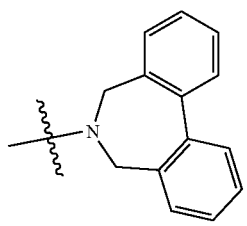

217
-continued

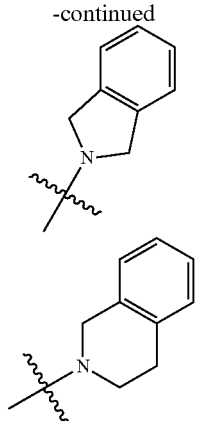

each of which is optionally substituted with $Cy^1$.

Embodiment 25. The compound of embodiment 1, wherein the compound of Formula (I) is selected from:

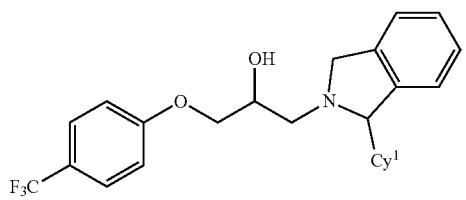

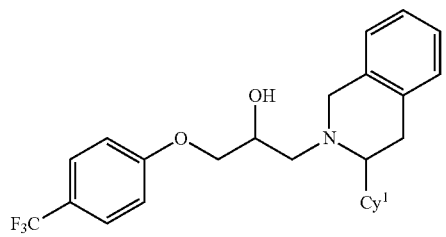

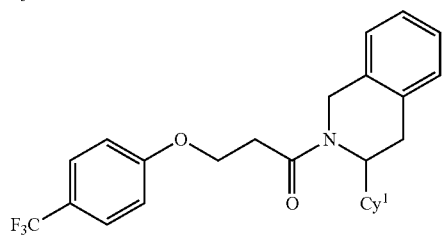

218
-continued

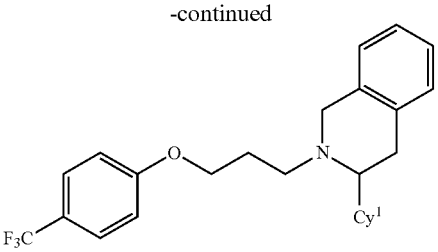

or a pharmaceutically acceptable salt thereof.

Embodiment 26. The compound of embodiment 1, wherein the compound of Formula (I) has formula:

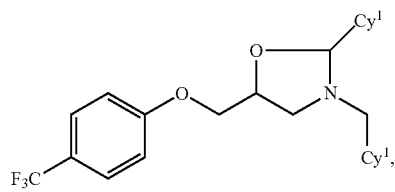

or a pharmaceutically acceptable salt thereof.

Embodiment 27. The compound of any one of embodiments 1-26, wherein $Cy^1$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy1}$.

Embodiment 28. The compound of embodiment 27, wherein $Cy^1$ is selected from phenyl, cyclopropyl, cyclohexyl, pyridinyl, pyrimidinyl, imidazolyl, pyrazolyl, thiazolyl, indolyl, quinolinyl, piperidinyl, dihydropyridinyl, each of which is optionally substituted with 1, 2, or 3 substituents independently selected from $R^{Cy1}$.

Embodiment 29. The compound of any one of embodiments 1-28, wherein each $R^{Cy1}$ is independently selected from halo, CN, $C(O)NR^{c1}R^{d1}$, $C_{1-6}$ alkyl, $C_{1-6}$ haloalkyl, and 5-10 membered heteroaryl, wherein said 5-10 membered heteroaryl is optionally substituted with halo, $C_{1-6}$ alkyl, $C_{1-6}$ alkoxy, $C_{1-6}$ haloalkyl, and $C_{1-6}$ haloalkoxy.

Embodiment 30. The compound of embodiment 1, wherein the compound of Formula (I) is selected from any one of the following compounds:

| No. | BC code | Structure |
|---|---|---|
| 3 | BC19801 | 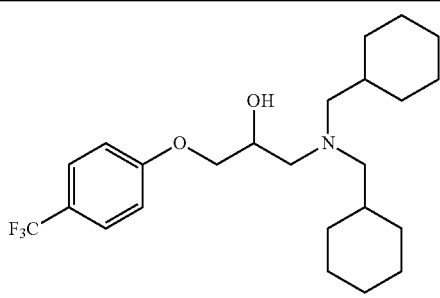 |

| No. | BC code | Structure |
|---|---|---|
| 4 | BC19802 | 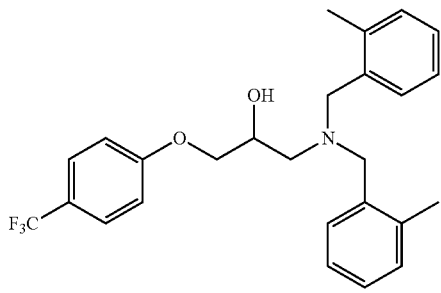 [SMILES: Cc1ccccc1CN(Cc1ccccc1C)CC(O)COc1ccc(C(F)(F)F)cc1] |
| 5 | BC19803 | 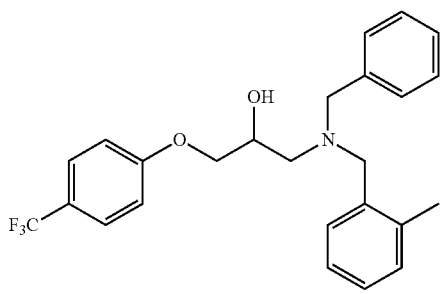 [SMILES: Cc1ccccc1CN(Cc1ccccc1)CC(O)COc1ccc(C(F)(F)F)cc1] |
| 6 | BC19804 | 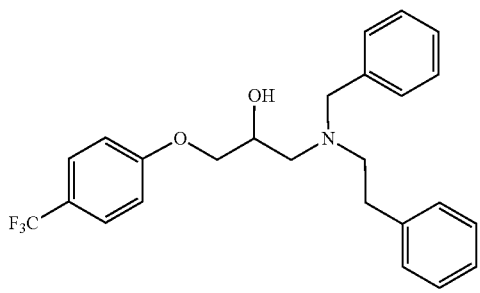 [SMILES: OC(COc1ccc(C(F)(F)F)cc1)CN(CCc1ccccc1)Cc1ccccc1] |
| 7 | BC19805 | 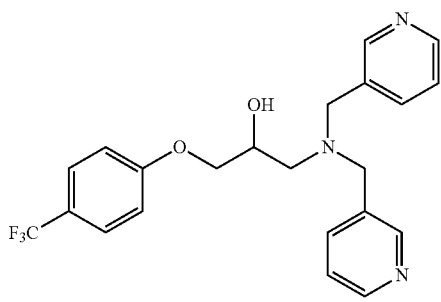 [SMILES: OC(COc1ccc(C(F)(F)F)cc1)CN(Cc1cccnc1)Cc1cccnc1] |
| 8 | BC19806 | 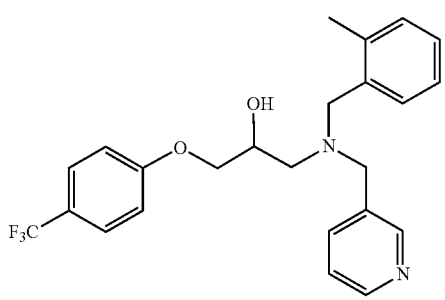 |

-continued
| No. | BC code | Structure |
|---|---|---|
| 9 | BC19807 | 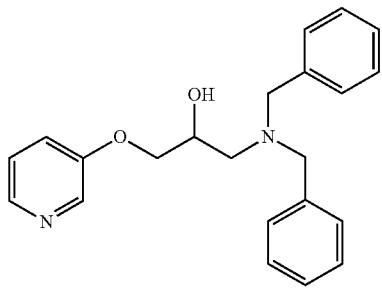 [SMILES: OC(COc1cccnc1)CN(Cc1ccccc1)Cc1ccccc1] |
| 10 | BC19808 | 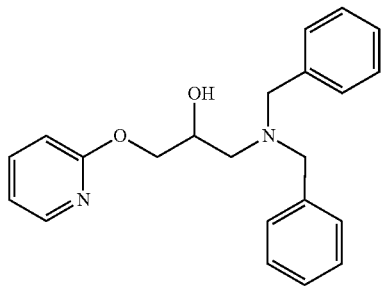 [SMILES: OC(COc1ccccn1)CN(Cc1ccccc1)Cc1ccccc1] |
| 11 | BC19809 | 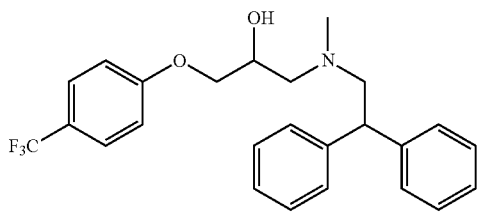 [SMILES: CN(CC(O)COc1ccc(C(F)(F)F)cc1)CC(c1ccccc1)c1ccccc1] |
| 12 | BC19810 | 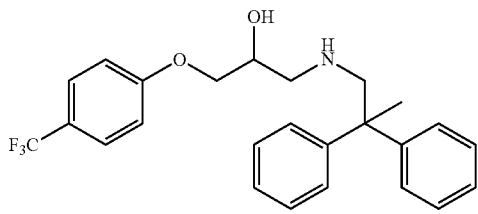 [SMILES: CC(CNCC(O)COc1ccc(C(F)(F)F)cc1)(c1ccccc1)c1ccccc1] |
| 13 | BC19811 | 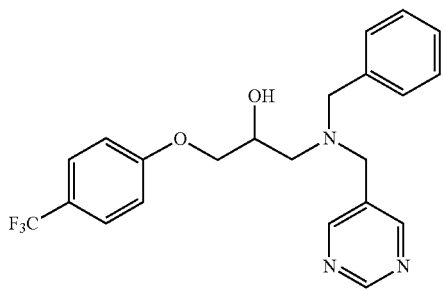 [SMILES: OC(COc1ccc(C(F)(F)F)cc1)CN(Cc1ccccc1)Cc1cncnc1] |
| 14 | BC19812 | 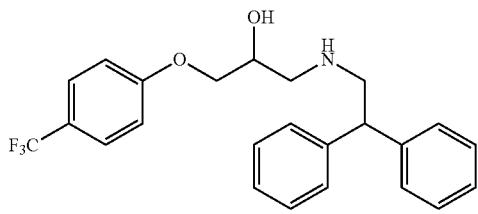 |

-continued
| No. | BC code | Structure |
|---|---|---|
| 15 | BC19813 | 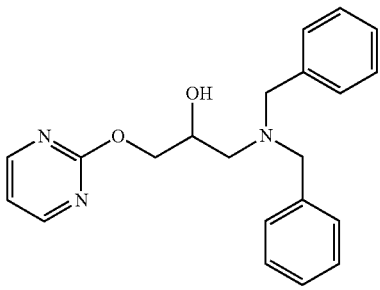 [SMILES: OC(COc1ncccn1)CN(Cc1ccccc1)Cc1ccccc1] |
| 16 | BC19814 | 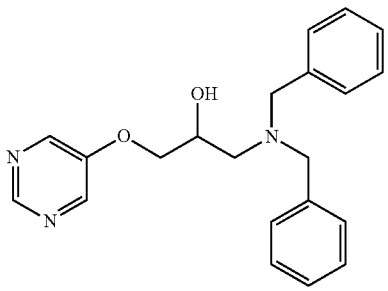 |
| 17 | BC19815 | 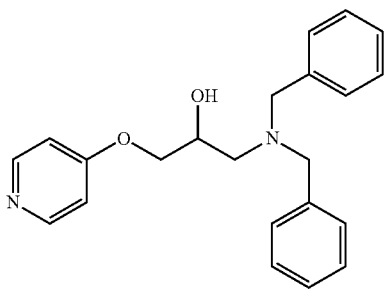 [SMILES: OC(COc1ccncc1)CN(Cc1ccccc1)Cc1ccccc1] |
| 18 | BC19816 | 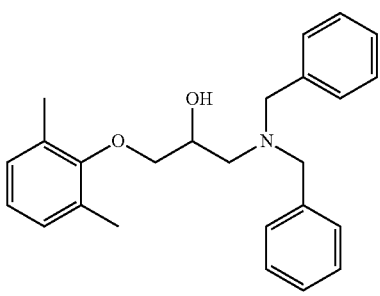 [SMILES: Cc1cccc(C)c1OCC(O)CN(Cc1ccccc1)Cc1ccccc1] |
| 19 | BC19819 | 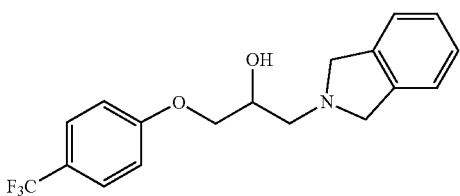 [SMILES: OC(COc1ccc(C(F)(F)F)cc1)CN1Cc2ccccc2C1] |

-continued
| No. | BC code | Structure |
|---|---|---|
| 20 | BC19820 | 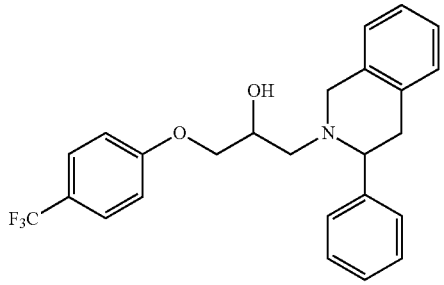 [SMILES: OC(COc1ccc(C(F)(F)F)cc1)CN1Cc2ccccc2CC1c1ccccc1] |
| 21 | BC19821 | 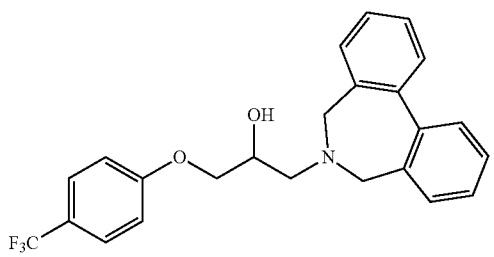 [SMILES: OC(COc1ccc(C(F)(F)F)cc1)CN1Cc2ccccc2-c2ccccc2C1] |
| 22 | BC19822 | 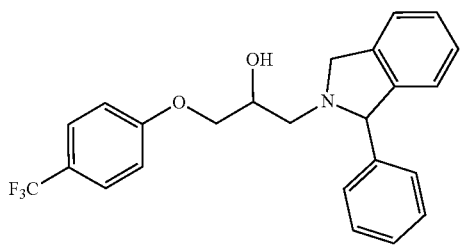 [SMILES: OC(COc1ccc(C(F)(F)F)cc1)CN1Cc2ccccc2C1c1ccccc1] |
| 23 | BC19823 | 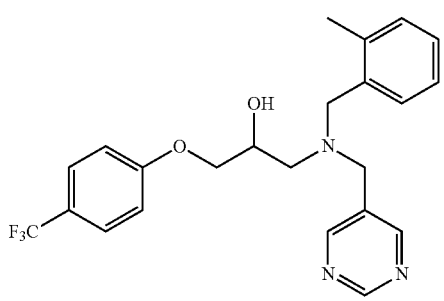 [SMILES: Cc1ccccc1CN(Cc1cncnc1)CC(O)COc1ccc(C(F)(F)F)cc1] |
| 24 | BC19824 | 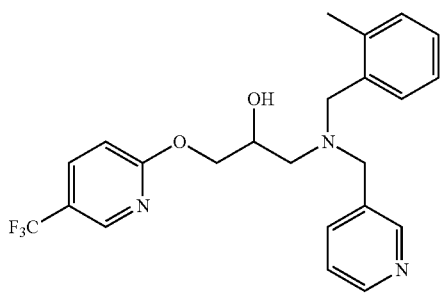 |

-continued
| No. | BC code | Structure |
|-----|---------|-----------|
| 25 | BC19825 | 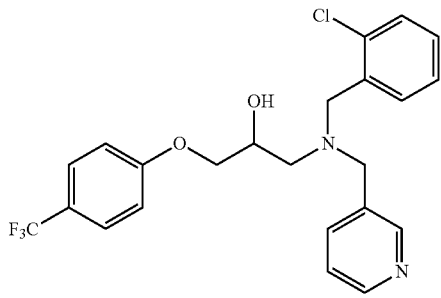 [SMILES: OC(COc1ccc(C(F)(F)F)cc1)CN(Cc1cccnc1)Cc1ccccc1Cl] |
| 26 | BC19826 | 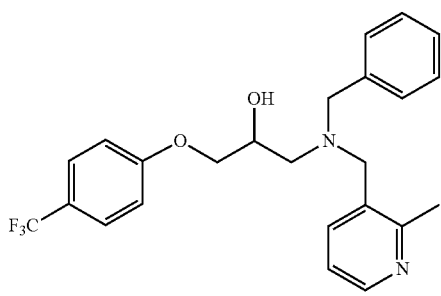 [SMILES: Cc1ncccc1CN(Cc1ccccc1)CC(O)COc1ccc(C(F)(F)F)cc1] |
| 27 | BC19827 | 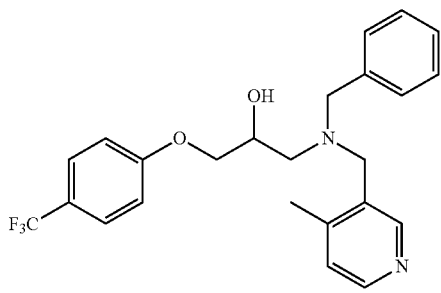 [SMILES: Cc1ccncc1CN(Cc1ccccc1)CC(O)COc1ccc(C(F)(F)F)cc1] |
| 28 | BC19828 | 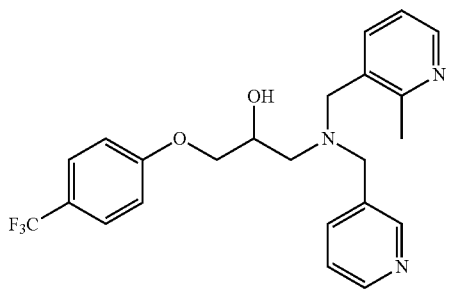 [SMILES: Cc1ncccc1CN(Cc1cccnc1)CC(O)COc1ccc(C(F)(F)F)cc1] |
| 29 | BC19829 | 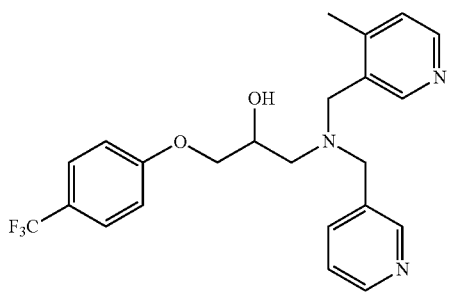 [SMILES: Cc1ccncc1CN(Cc1cccnc1)CC(O)COc1ccc(C(F)(F)F)cc1] |

| No. | BC code | Structure |
|---|---|---|
| 30 | BC19830 | 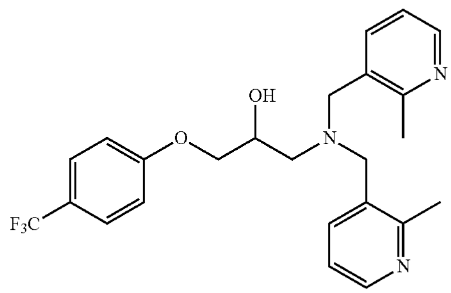 [SMILES: Cc1ncccc1CN(Cc1cccnc1C)CC(O)COc1ccc(C(F)(F)F)cc1] |
| 31 | BC19831 | 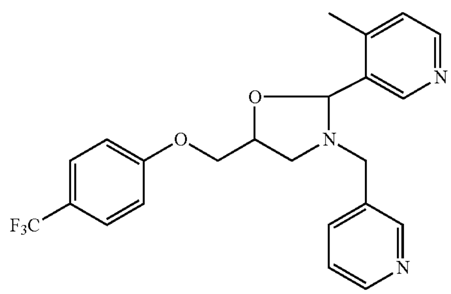 [SMILES: Cc1ccncc1C1OC(COc2ccc(C(F)(F)F)cc2)CN1Cc1cccnc1] |
| 32 | BC19832 | 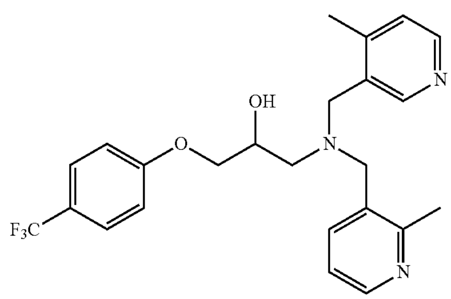 [SMILES: Cc1ccncc1CN(Cc1cccnc1C)CC(O)COc1ccc(C(F)(F)F)cc1] |
| 33 | BC19833 | 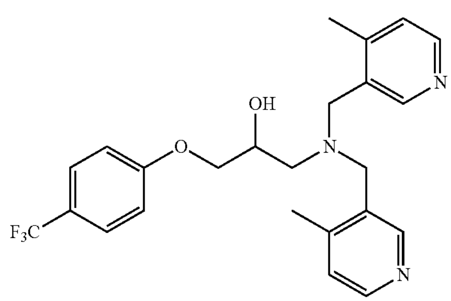 [SMILES: Cc1ccncc1CN(Cc1cnccc1C)CC(O)COc1ccc(C(F)(F)F)cc1] |
| 34 | BC19834 | 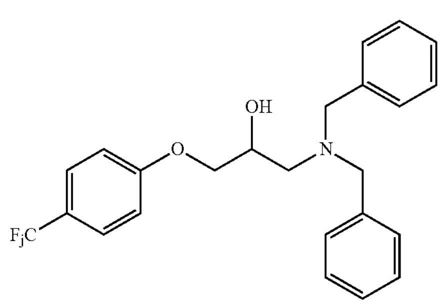 |

| No. | BC code | Structure |
|---|---|---|
| 35 | BC19835 | 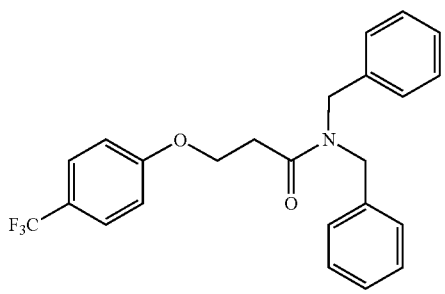 [SMILES: O=C(CCOc1ccc(C(F)(F)F)cc1)N(Cc1ccccc1)Cc1ccccc1] |
| 36 | BC19836 | 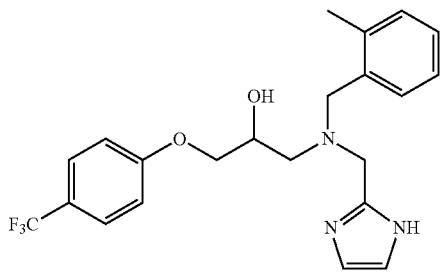 |
| 37 | BC19837 | 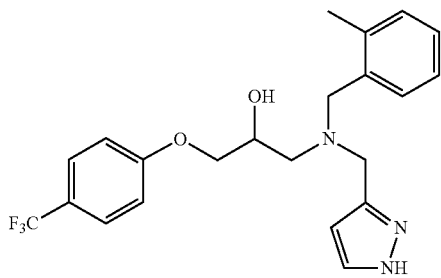 [SMILES: Cc1ccccc1CN(Cc1cc[nH]n1)CC(O)COc1ccc(C(F)(F)F)cc1] |
| 38 | BC19838 | 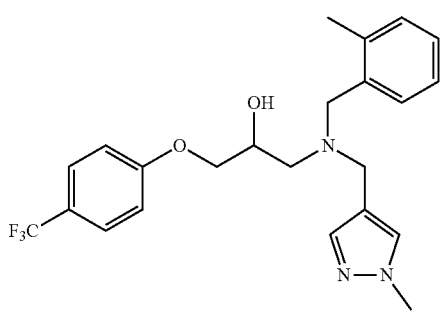 [SMILES: Cc1ccccc1CN(Cc1cnn(C)c1)CC(O)COc1ccc(C(F)(F)F)cc1] |
| 39 | BC19839 | 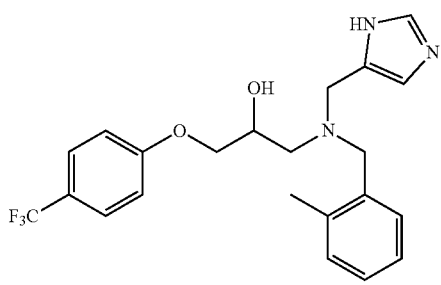 [SMILES: Cc1ccccc1CN(Cc1cnc[nH]1)CC(O)COc1ccc(C(F)(F)F)cc1] |

-continued
| No. | BC code | Structure |
|---|---|---|
| 40 | BC19840 | 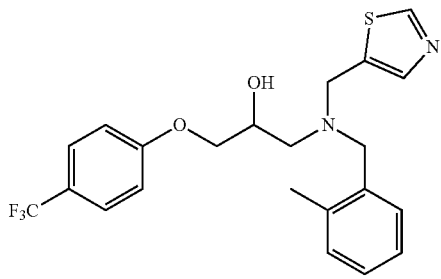 [SMILES: Cc1ccccc1CN(Cc1cncs1)CC(O)COc1ccc(C(F)(F)F)cc1] |
| 41 | BC19841 | 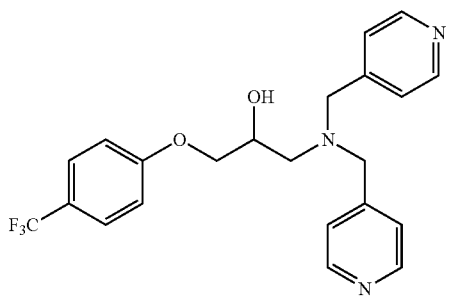 [SMILES: OC(COc1ccc(C(F)(F)F)cc1)CN(Cc1ccncc1)Cc1ccncc1] |
| 42 | BC19842 | 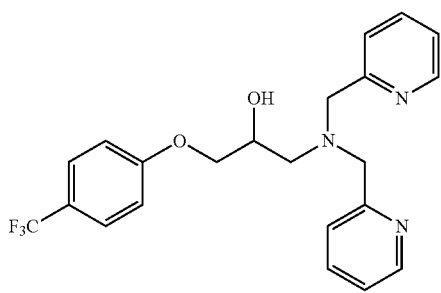 [SMILES: OC(COc1ccc(C(F)(F)F)cc1)CN(Cc1ccccn1)Cc1ccccn1] |
| 43 | BC19843 | 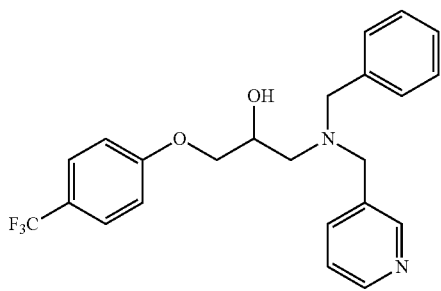 [SMILES: OC(COc1ccc(C(F)(F)F)cc1)CN(Cc1ccccc1)Cc1cccnc1] |
| 45 | BC19845 | 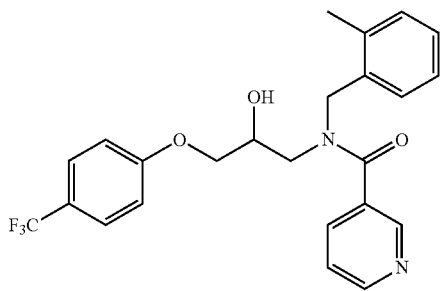 [SMILES: Cc1ccccc1CN(CC(O)COc1ccc(C(F)(F)F)cc1)C(=O)c1cccnc1] |

-continued
| No. | BC code | Structure |
|---|---|---|
| 46 | BC19846 | 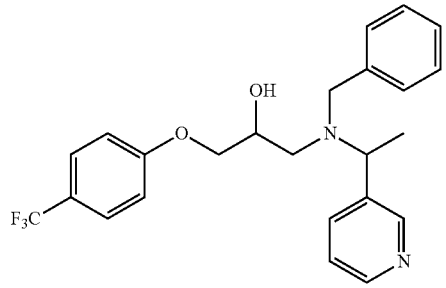 [SMILES: CC(c1cccnc1)N(Cc1ccccc1)CC(O)COc1ccc(C(F)(F)F)cc1] |
| 47 | BC19847 | 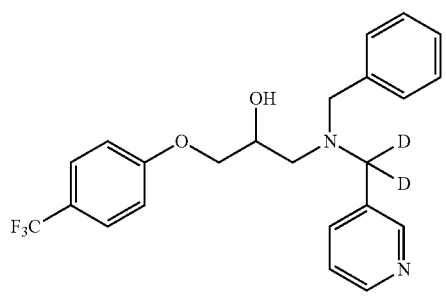 [SMILES: [2H]C([2H])(c1cccnc1)N(Cc1ccccc1)CC(O)COc1ccc(C(F)(F)F)cc1] |
| 48 | BC19848 | 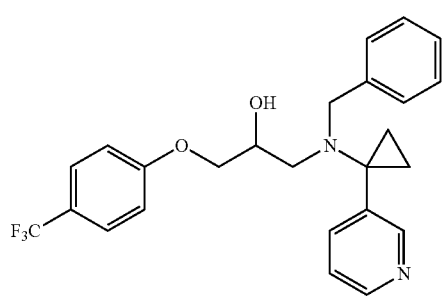 [SMILES: OC(COc1ccc(C(F)(F)F)cc1)CN(Cc1ccccc1)C1(c2cccnc2)CC1] |
| 49 | BC19849 | 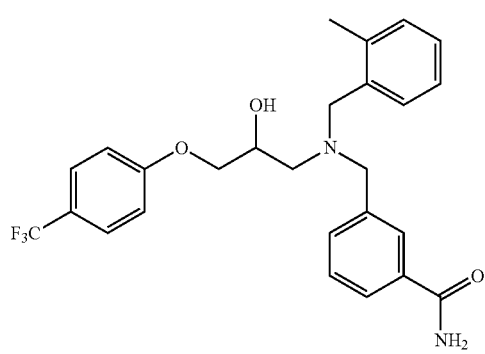 [SMILES: Cc1ccccc1CN(Cc1cccc(C(N)=O)c1)CC(O)COc1ccc(C(F)(F)F)cc1] |
| 50 | BC19850 | 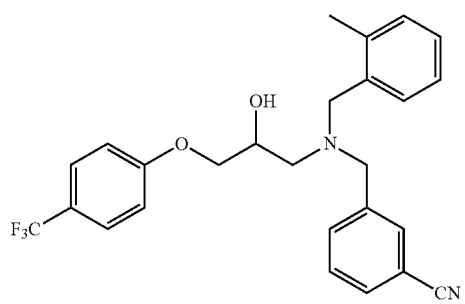 [SMILES: Cc1ccccc1CN(Cc1cccc(C#N)c1)CC(O)COc1ccc(C(F)(F)F)cc1] |

| No. | BC code | Structure |
|---|---|---|
| 51 | BC19851 | 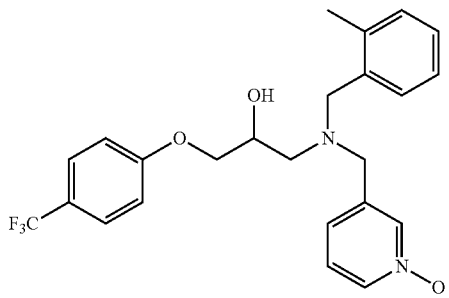 |
| 52 | BC19852 | 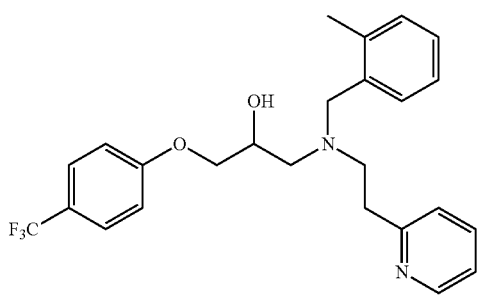 |
| 53 | BC19853 | 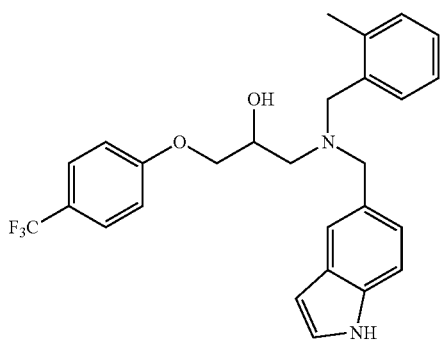 [SMILES: Cc1ccccc1CN(Cc1ccc2[nH]ccc2c1)CC(O)COc1ccc(C(F)(F)F)cc1] |
| 54 | BC19854 | 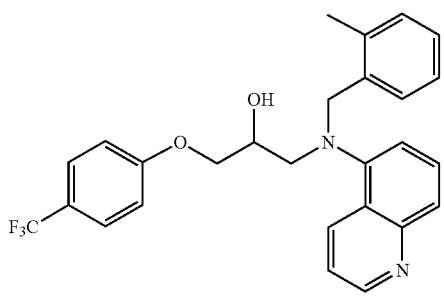 [SMILES: Cc1ccccc1CN(CC(O)COc1ccc(C(F)(F)F)cc1)c1cccc2ncccc12] |
| 55 | BC19855 | 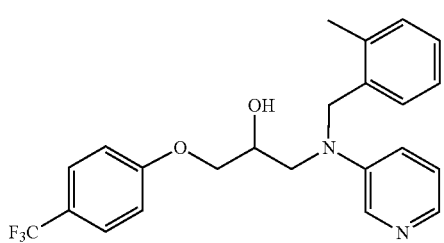 [SMILES: Cc1ccccc1CN(CC(O)COc1ccc(C(F)(F)F)cc1)c1cccnc1] |

-continued
| No. | BC code | Structure |
|---|---|---|
| 56 | BC19856 | 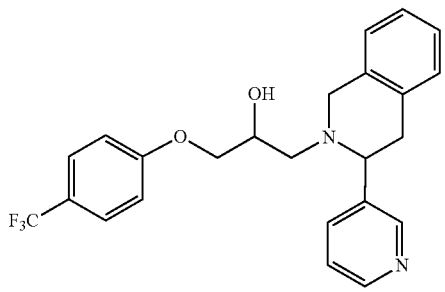 [SMILES: OC(COc1ccc(C(F)(F)F)cc1)CN1Cc2ccccc2CC1c1cccnc1] |
| 58 | BC19858 | 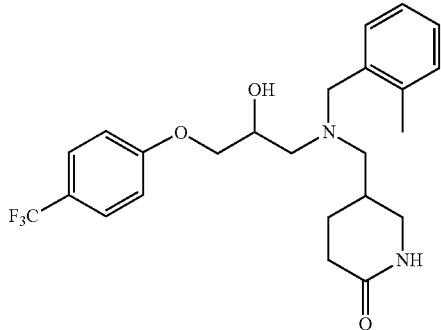 [SMILES: Cc1ccccc1CN(CC(O)COc1ccc(C(F)(F)F)cc1)CC1CCC(=O)NC1] |
| 59 | BC19859 | 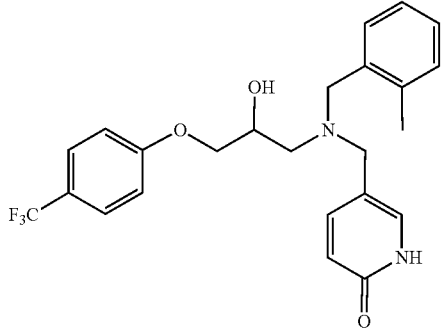 [SMILES: Cc1ccccc1CN(Cc1ccc(=O)[nH]c1)CC(O)COc1ccc(C(F)(F)F)cc1] |
| 62 | BC19862 | 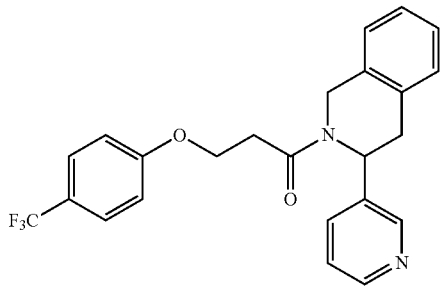 [SMILES: O=C(CCOc1ccc(C(F)(F)F)cc1)N1Cc2ccccc2CC1c1cccnc1] |
| 63 | BC19863 | 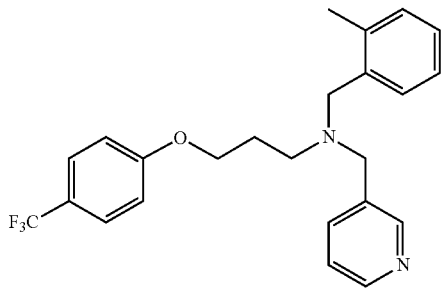 [SMILES: Cc1ccccc1CN(CCCOc1ccc(C(F)(F)F)cc1)Cc1cccnc1] |

| No. | BC code | Structure |
|---|---|---|
| 64 | BC19864 | 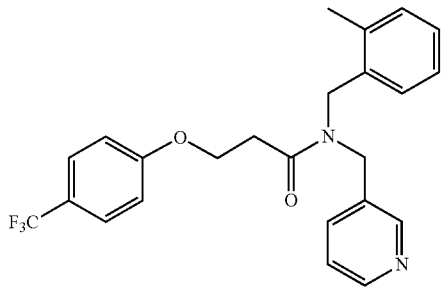 [SMILES: Cc1ccccc1CN(Cc1cccnc1)C(=O)CCOc1ccc(C(F)(F)F)cc1] |
| 65 | BC19865 | 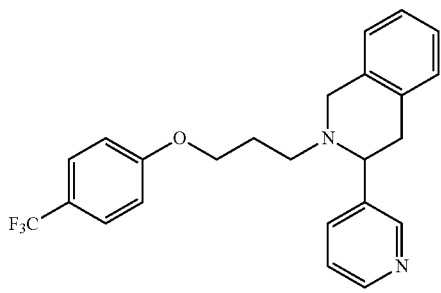 [SMILES: FC(F)(F)c1ccc(OCCCN2Cc3ccccc3CC2c2cccnc2)cc1] |
| 66 | BC19866 | 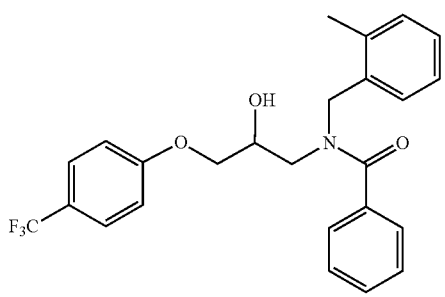 [SMILES: Cc1ccccc1CN(CC(O)COc1ccc(C(F)(F)F)cc1)C(=O)c1ccccc1] |
| 67 | BC19867 | 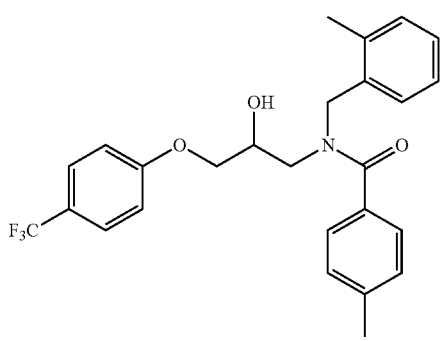 [SMILES: Cc1ccc(C(=O)N(Cc2ccccc2C)CC(O)COc2ccc(C(F)(F)F)cc2)cc1] |
| 68 | BC19868 | 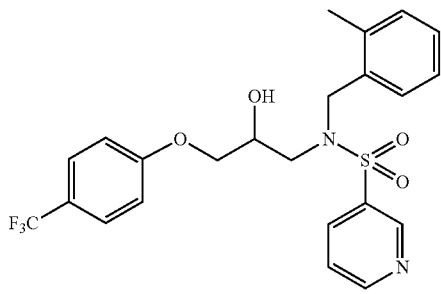 [SMILES: Cc1ccccc1CN(CC(O)COc1ccc(C(F)(F)F)cc1)S(=O)(=O)c1cccnc1] |

| No. | BC code | Structure |
|---|---|---|
| 69 | BC19869 | 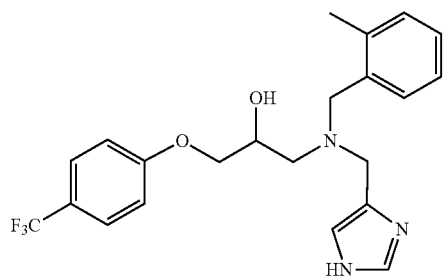 [SMILES: Cc1ccccc1CN(Cc1c[nH]cn1)CC(O)COc1ccc(C(F)(F)F)cc1] |
| 70 | BC19870 | 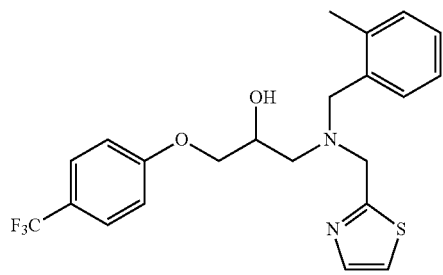 |
| 71 | BC19871 | 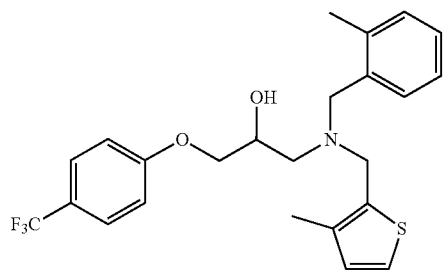 [SMILES: Cc1ccccc1CN(Cc1sccc1C)CC(O)COc1ccc(C(F)(F)F)cc1] |
| 72 | BC19872 | 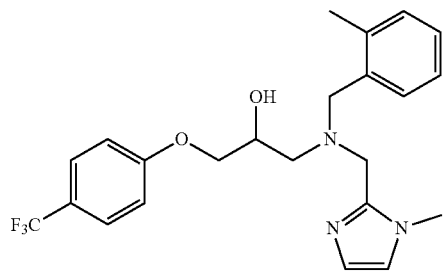 [SMILES: Cc1ccccc1CN(Cc1nccn1C)CC(O)COc1ccc(C(F)(F)F)cc1] |
| 73 | BC19873 | 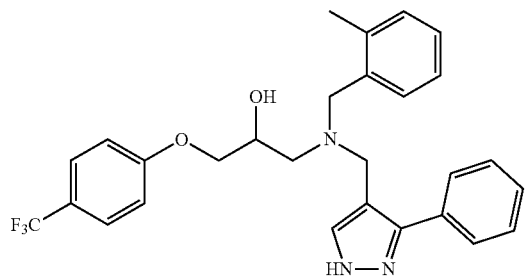 [SMILES: Cc1ccccc1CN(Cc1c[nH]nc1-c1ccccc1)CC(O)COc1ccc(C(F)(F)F)cc1] |

| No. | BC code | Structure |
|---|---|---|
| 74 | BC19874 | 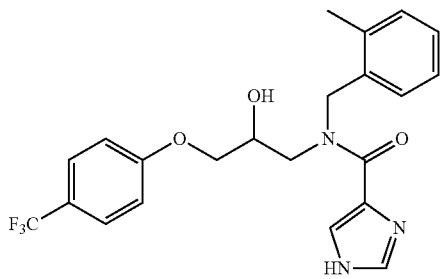 |
| 75 | BC19875 | 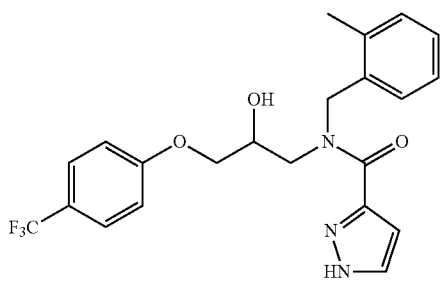 |
| 76 | BC19876 | 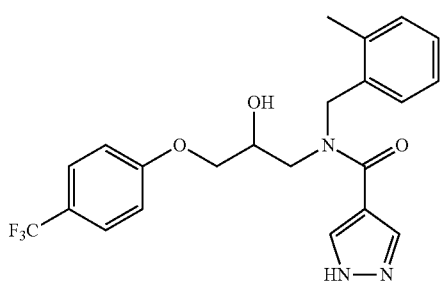 |
| 77 | BC19877 | 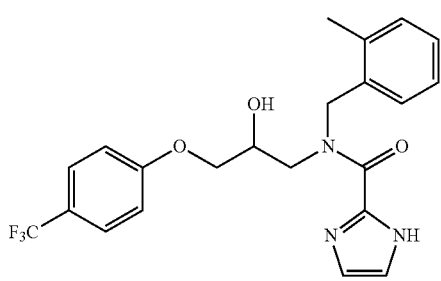 |
| 78 | BC19878 | 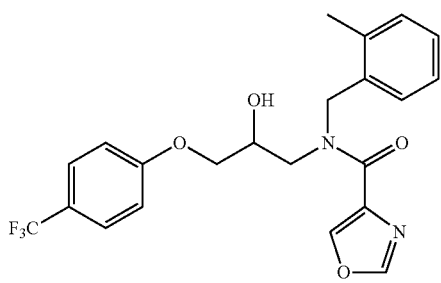 |

| No. | BC code | Structure |
|---|---|---|
| 79 | BC19879 | 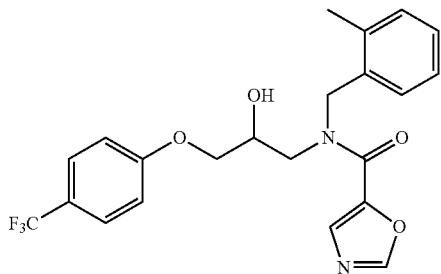 |
| 80 | BC19880 | 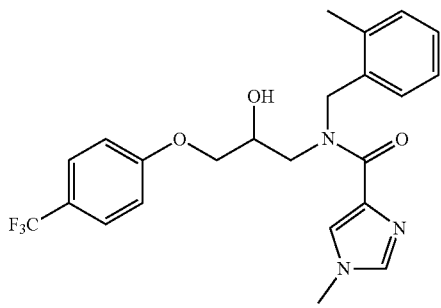 |
| 81 | BC19881 | 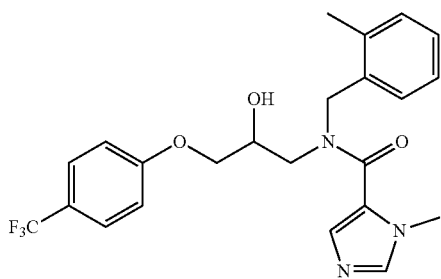 [SMILES: Cc1ccccc1CN(CC(O)COc1ccc(C(F)(F)F)cc1)C(=O)c1cncn1C] |
| 82 | BC19882 | 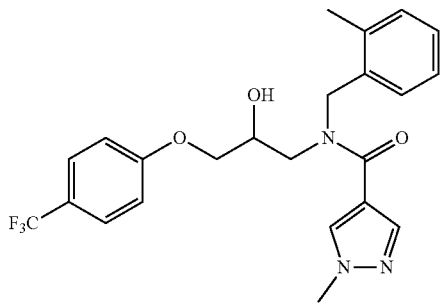 [SMILES: Cc1ccccc1CN(CC(O)COc1ccc(C(F)(F)F)cc1)C(=O)c1cnn(C)c1] |
| 83 | BC19883 | 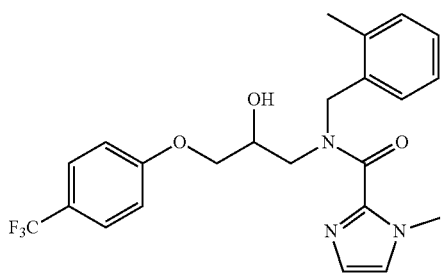 [SMILES: Cc1ccccc1CN(CC(O)COc1ccc(C(F)(F)F)cc1)C(=O)c1nccn1C] |

-continued
| No. | BC code | Structure |
|---|---|---|
| 84 | BC19884 | 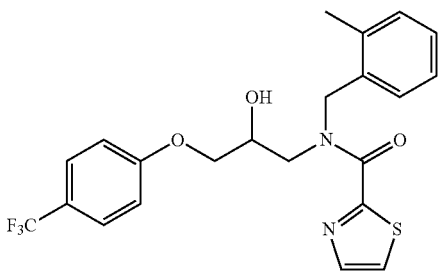 [SMILES: Cc1ccccc1CN(CC(O)COc1ccc(C(F)(F)F)cc1)C(=O)c1nccs1] |
| 85 | BC19885 | 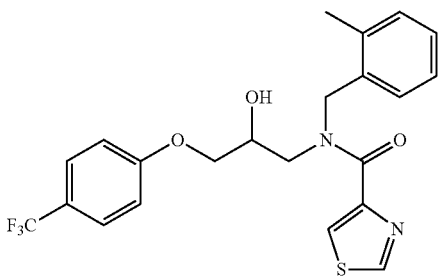 |
| 86 | BC19886 | 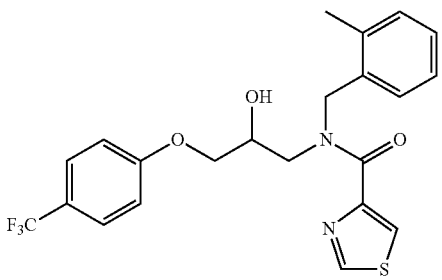 |
or a pharmaceutically acceptable salt thereof.
Embodiment 31. A compound of formula:
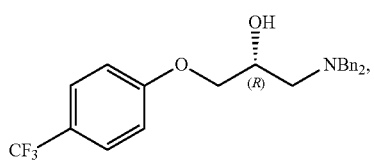
or a pharmaceutically acceptable salt thereof.
Embodiment 32. A compound of formula:
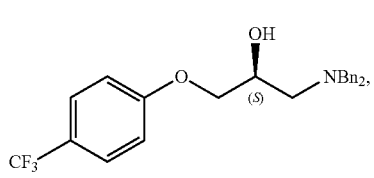
or a pharmaceutically acceptable salt thereof.
Embodiment 33. A compound selected from:
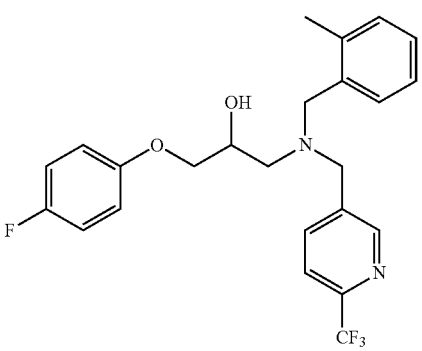
44
BC19844

-continued

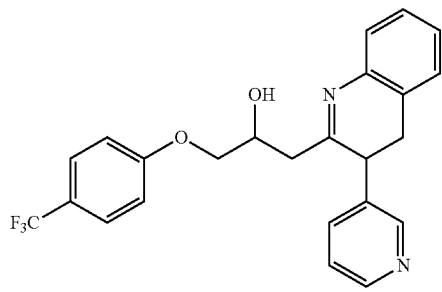

BC19857

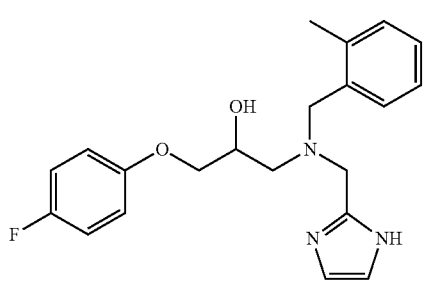

BC19860

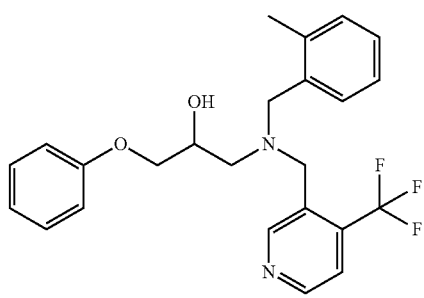

BC19887 or a pharmaceutically acceptable salt thereof.

Embodiment 34. A pharmaceutical composition comprising a compound of any one of embodiments 1-33, or a pharmaceutically acceptable salt thereof, and a pharmaceutically acceptable carrier.

Embodiment 35. A method of treating a mammal having a disease, disorder, or condition responsive to an increase in the level of phosphorylated AMPK within cells, wherein said method comprises administering, to said mammal, a compound of any one of embodiments 1-33, or a pharmaceutically acceptable salt thereof, or a pharmaceutical composition of embodiment 34.

Embodiment 36. The method of embodiment 35, wherein said mammal is a human.

Embodiment 37. The method of embodiment 35, wherein said method comprises treating a mammal having an inflammation.

Embodiment 38. The method of embodiment 37, wherein the inflammation is a cytokine-driven inflammation.

Embodiment 39. The method of embodiment 35, wherein said method comprises treating a mammal having a sepsis.

Embodiment 40. The method of embodiment 35, wherein said method comprises treating a mammal having a pneumonia.

Embodiment 41. The method of embodiment 35, wherein said method comprises treating a mammal having an acute lung injury.

Embodiment 42. The method of embodiment 35, wherein said method comprises treating a mammal having a metabolic syndrome.

Embodiment 43. The method of embodiment 35, wherein said method comprises treating a mammal having a diabetic nephropathy.

Embodiment 44. The method of embodiment 35, wherein said method comprises treating a mammal having a polycystic kidney disease.

Embodiment 45. The method of embodiment 35, wherein said method comprises treating a mammal having a polycystic ovarian syndrome.

Embodiment 46. The method of embodiment 35, wherein said method comprises treating a mammal having a neurological disease.

Embodiment 47. A method for increasing a level of phosphorylated AMPK within cells of a mammal, wherein said method comprises administering, to said mammal, a compound of any one of embodiments 1-33, or a pharmaceutically acceptable salt thereof, or a pharmaceutical composition of embodiment 34.

Embodiment 48. The method of embodiment 47, wherein said mammal is a human.

Embodiment 49. A method of treating a mammal having a disease, disorder, or condition responsive to an increase in the level of phosphorylated AMPK within cells, wherein said method comprises administering, to said mammal, a compound having formula:

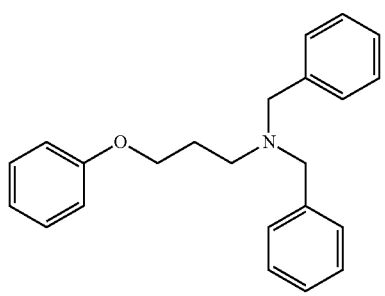

BC19861 or a pharmaceutically acceptable salt thereof.

Embodiment 50. A method for increasing a level of phosphorylated AMPK within cells of a mammal, wherein said method comprises administering, to said mammal, a compound having formula:

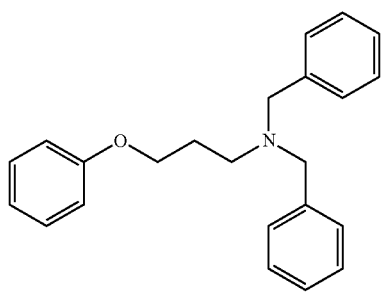

BC19861 or a pharmaceutically acceptable salt thereof.

Embodiment 51. A method for treating cancer in a mammal, wherein said method comprises administering, to said mammal, a compound of any one of embodiments 1-33, or a pharmaceutically acceptable salt thereof, or a pharmaceutical composition of embodiment 34.

Embodiment 52. The method of embodiment 51, said method further comprising administering, to said mammal, a checkpoint inhibitor.

Embodiment 53. The method of embodiment 51 or embodiment 52, wherein said compound is a compound set forth in Formula (A):

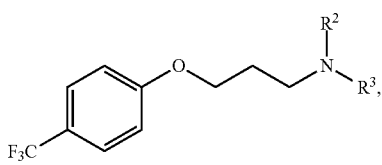

or a pharmaceutically acceptable salt thereof.

Embodiment 54. The method of any one of embodiments 51-53, wherein said compound is:

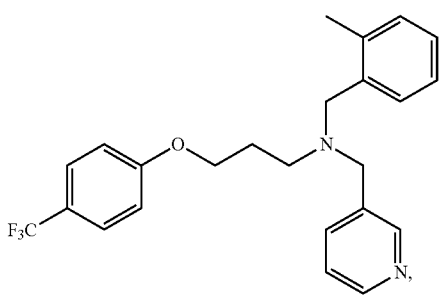 [SMILES: Cc1ccccc1CN(CCCOc1ccc(C(F)(F)F)cc1)Cc1cccnc1]

or a pharmaceutically acceptable salt thereof.

Embodiment 55. A method for improving function of immune cells in a mammal, wherein said method comprises administering, to said mammal, a compound of any one of embodiments 1-33, or a pharmaceutically acceptable salt thereof, or a pharmaceutical composition of embodiment 34.

Embodiment 56. The method of embodiment 55, wherein said immune cells are T cells.

Embodiment 57. The method of embodiment 55 or embodiment 56, said method further comprising administering, to said mammal, a checkpoint inhibitor.

Embodiment 58. The method of any one of embodiments 55-57, wherein said compound is a compound set forth in Formula (A):

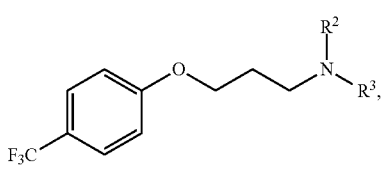

or a pharmaceutically acceptable salt thereof.

Embodiment 59. The method of any one of embodiments 55-58, wherein said compound is:

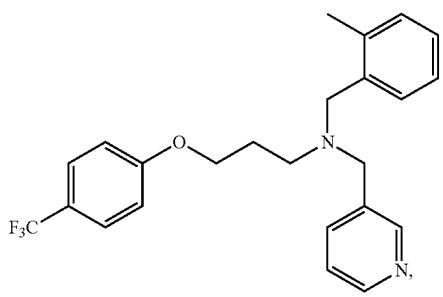 [SMILES: Cc1ccccc1CN(CCCOc1ccc(C(F)(F)F)cc1)Cc1cccnc1]

or a pharmaceutically acceptable salt thereof.

Embodiment 60. A method for expanding a population of immune cells, said method comprising obtaining a population of immune cells from a mammal and culturing said population of immune cells with a compound of any one of embodiments 1-33, or a pharmaceutically acceptable salt thereof, or a pharmaceutical composition of embodiment 34.

Embodiment 61. The method of embodiment 60, wherein said immune cells are T cells.

Embodiment 62. The method of embodiment 60 or embodiment 61, wherein said compound is a compound set forth in Formula (A):

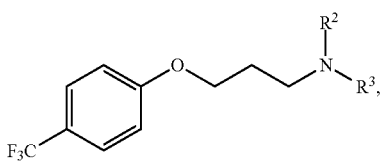

or a pharmaceutically acceptable salt thereof.

Embodiment 63. The method of any one of embodiments 60-62, wherein said compound is:

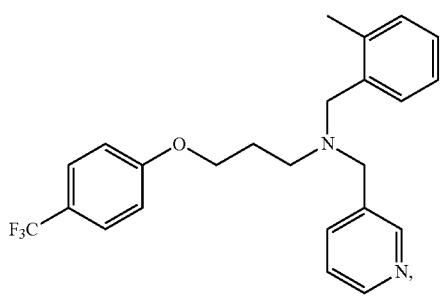 [SMILES: Cc1ccccc1CN(CCCOc1ccc(C(F)(F)F)cc1)Cc1cccnc1]

or a pharmaceutically acceptable salt thereof.

Embodiment 64. A method for treating an infection or reducing the risk of developing an infection in a mammal, said method comprising administering, to said mammal, a compound of any one of embodiments 1-33, or a pharmaceutically acceptable salt thereof, or a pharmaceutical composition of embodiment 34.

Embodiment 65. The method of embodiment 64, wherein said compound is a compound set forth in Formula (A):

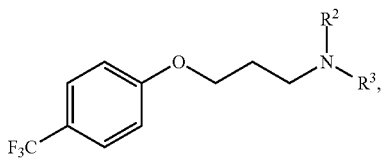

or a pharmaceutically acceptable salt thereof.

Embodiment 66. The method of embodiment 64 or embodiment 65, wherein said compound is:

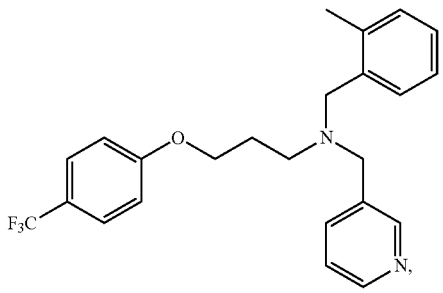 [SMILES: Cc1ccccc1CN(CCCOc1ccc(C(F)(F)F)cc1)Cc1cccnc1]

or a pharmaceutically acceptable salt thereof.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

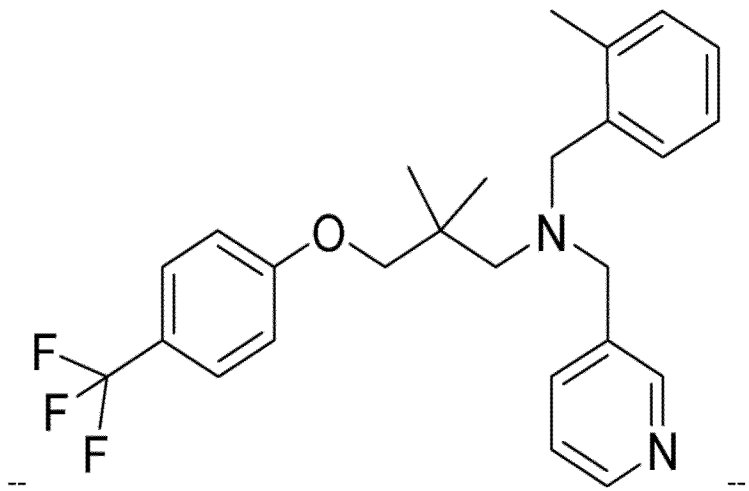

What is claimed is:

1. A compound of Formula (I):

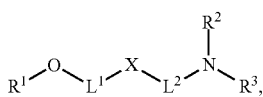

or a pharmaceutically acceptable salt thereof, wherein:
$R^1$ is a group of formula

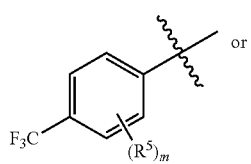

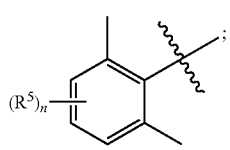

$L^1$ is $C_{1-4}$ alkylene optionally substituted with halo or $OR^4$;

$L^2$ is $C_{1-4}$ alkylene or $L^2$ is absent;

X is selected from $CR^7(OR^4)$ and C=O; or X is absent;

$R^7$ is selected from H, $C_{1-6}$ alkyl, $C_{1-6}$ haloalkyl, $C_{2-6}$ alkenyl, and $C_{2-6}$ alkynyl;

$R^2$ is —$CH_2$-phenyl, wherein said phenyl is optionally substituted with 1, 2, 3, 4, or 5 substituents independently selected from $R^{Cy1}$;

$R^3$ is —$CH_2$-(5-10 membered monocyclic or bicyclic heteroaryl), wherein said heteroaryl is optionally substituted with 1, 2, 3, 4, or 5 substituents independently selected from $R^{Cy1}$;

$R^4$ is selected from H, $C(O)R^{b1}$, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^g$;

m is 0, 1, 2, 3, or 4;

n is 0, 1, 2, or 3;

each $R^5$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, —SH, $C_{1-6}$ alkylthio, carboxy, amino, $C_{1-6}$ alkylamino, and di($C_{1-6}$ alkyl)amino;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^2$ is independently selected from $C_{6-10}$ aryl, $C_{3-10}$ cycloalkyl, 5-10 membered monocyclic or bicyclic heteroaryl, and 4-10 membered monocyclic or fused or spiro bicyclic heterocycloalkyl, each of which is optionally substituted with 1, 2, 3, 4, or 5 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered monocyclic or bicyclic heteroaryl, 4-10 membered monocyclic or fused or spiro bicyclic heterocycloalkyl, $C_{6-10}$ aryl-$C_{1-4}$ alkylene, $C_{3-10}$ cycloalkyl-$C_{1-4}$ alkylene, (5-10 membered monocyclic or bicyclic heteroaryl)-$C_{1-4}$ alkylene, and (4-10 membered monocyclic or fused or spiro bicyclic heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered monocyclic or bicyclic heteroaryl, 4-10 membered monocyclic or fused or spiro bicyclic heterocycloalkyl, $C_{6-10}$ aryl-$C_{1-4}$ alkylene, $C_{3-10}$ cycloalkyl-$C_{1-4}$ alkylene, (5-10 membered monocyclic or bicyclic heteroaryl)-$C_{1-4}$ alkylene, and (4-10 membered monocyclic or fused or spiro bicyclic heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered monocyclic heterocycloalkyl optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered monocyclic or bicyclic heteroaryl, 4-10 membered monocyclic or fused or spiro bicyclic heterocycloalkyl, $C_{6-10}$ aryl-$C_{1-4}$ alkylene, $C_{3-10}$ cycloalkyl-$C_{1-4}$ alkylene, (5-10 membered monocyclic or bicyclic heteroaryl)-$C_{1-4}$ alkylene, (4-10 membered monocyclic or fused or spiro bicyclic heterocycloalkyl)-$C_{1-4}$ alkylene, amino, $C_{1-6}$ alkylamino, di($C_{1-6}$ alkyl)amino, —SH, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; wherein each 5-10 membered monocyclic or bicyclic heteroaryl independently has 1, 2, 3, or 4 heteroatom ring members independently selected from nitrogen, sulfur, and oxygen; and each 4-10 membered monocyclic or fused or spiro bicyclic heterocycloalkyl and each 4-7 membered monocyclic heterocycloalkyl independently has 1, 2, 3, or 4 heteroatom ring members independently selected from nitrogen, oxygen, and sulfur and contains 0 to 3 double bonds.

2. The compound of claim 1, wherein the compound of Formula (I) is selected from the group consisting of:

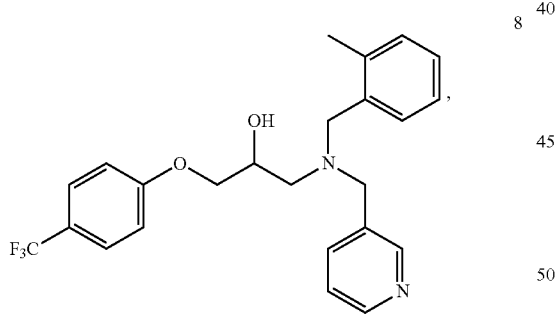

BC19806

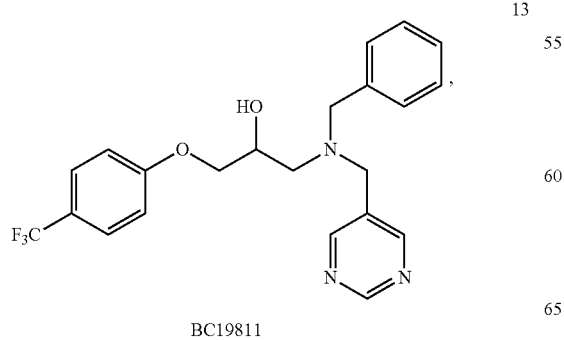

BC19811

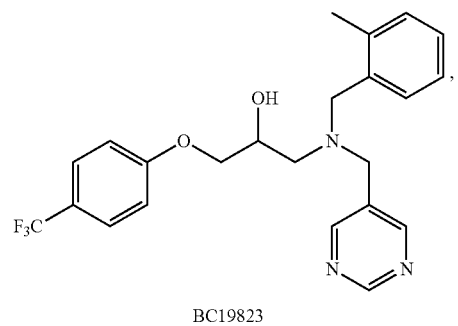

BC19823

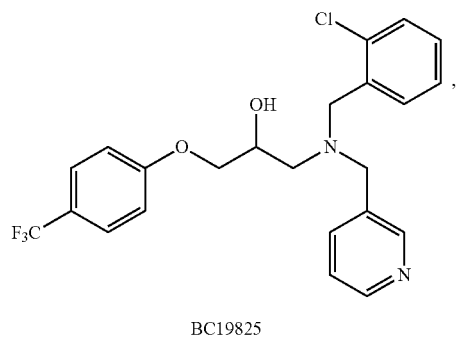

BC19825

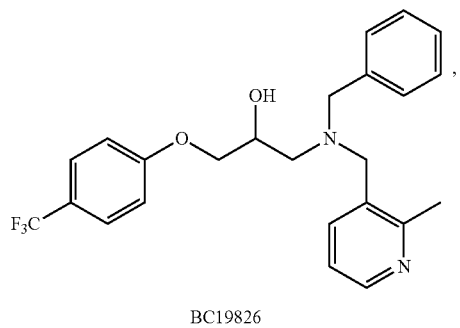

BC19826

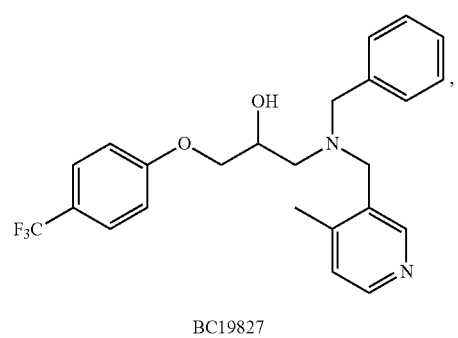

BC19827

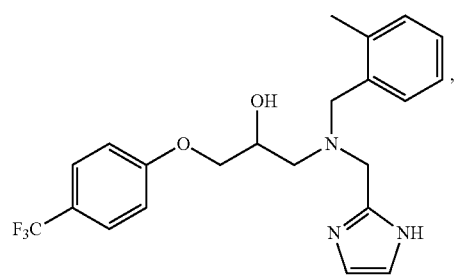
BC19836
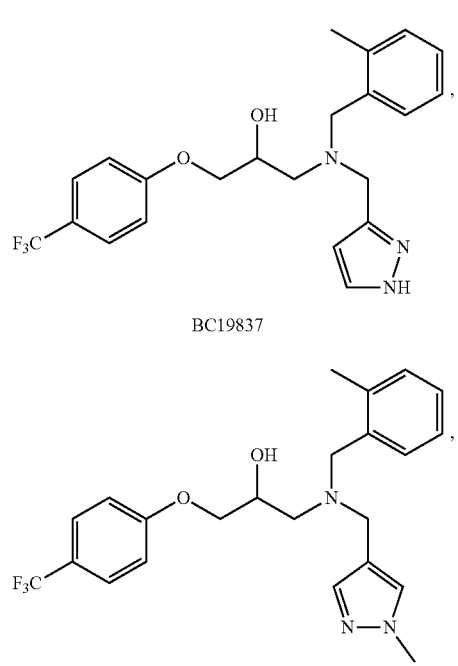
BC19837
BC19838
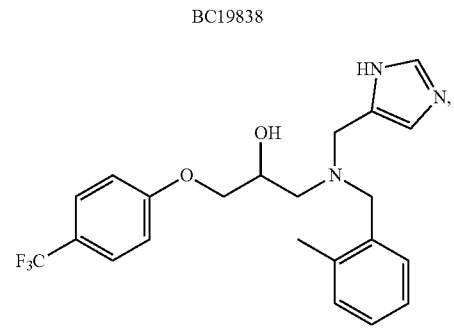
BC19839
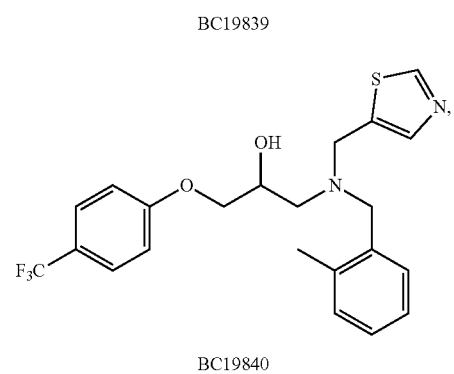
BC19840
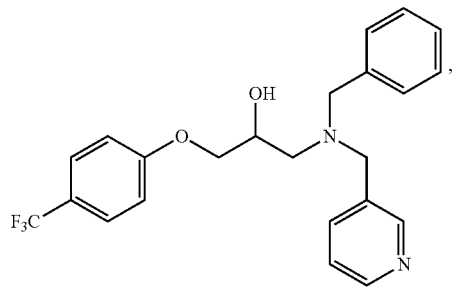
BC19843
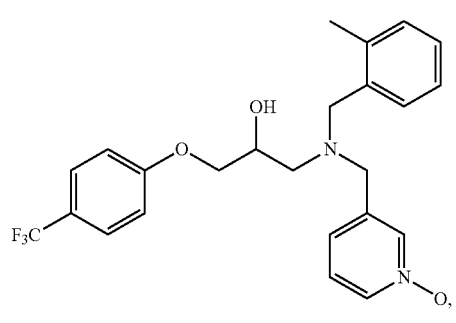
BC19851
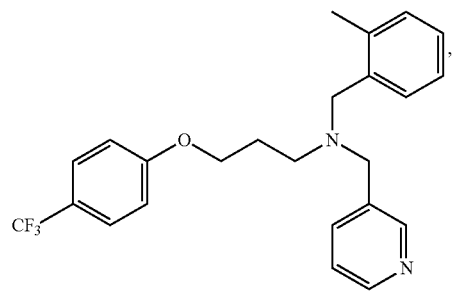
BC19863
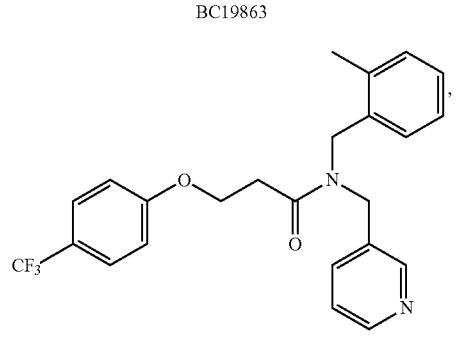
BC19864

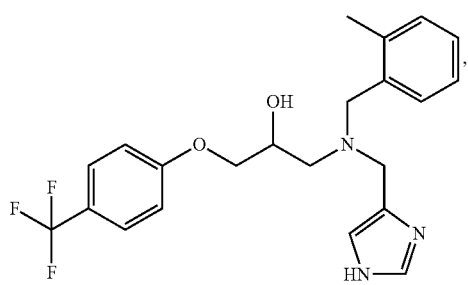
BC19869
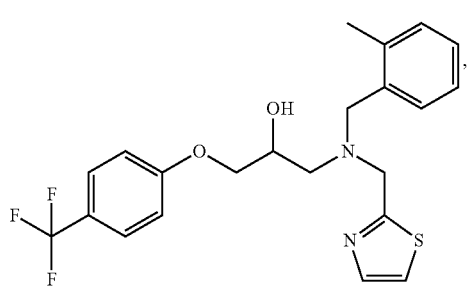
BC19870
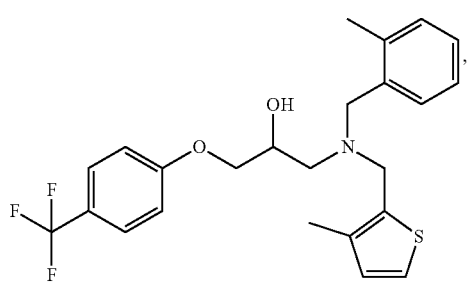
BC19871
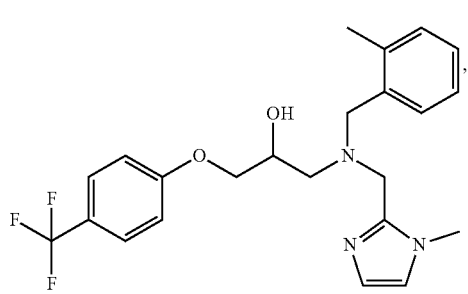
BC19872
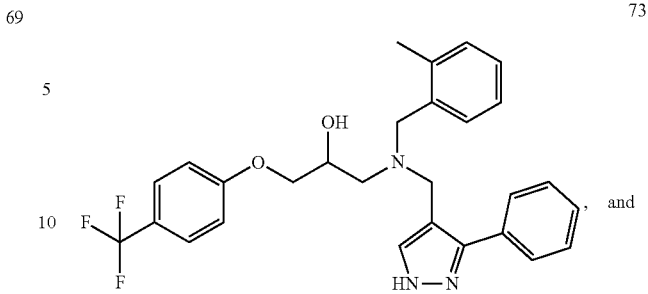
BC19873, and
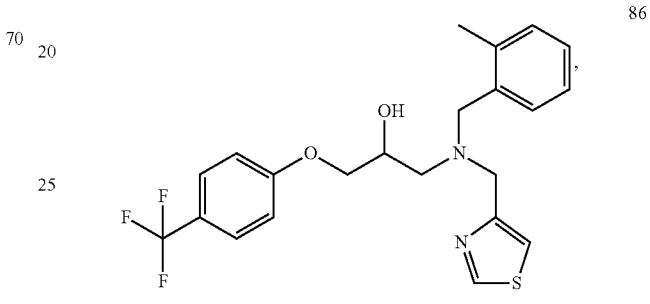
BC19886
or a pharmaceutically acceptable salt thereof.
3. The compound of claim 1, wherein the compound of Formula (I) is selected from the group consisting of:
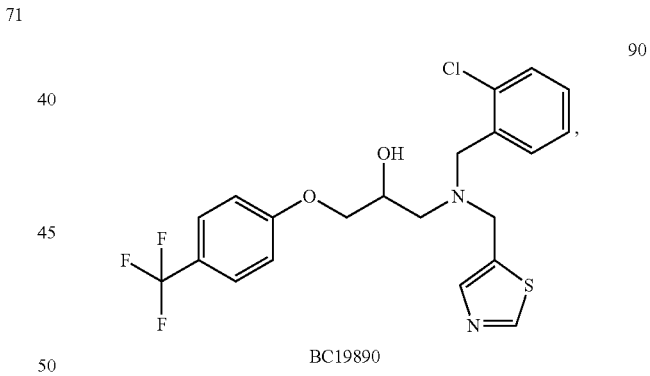
BC19890
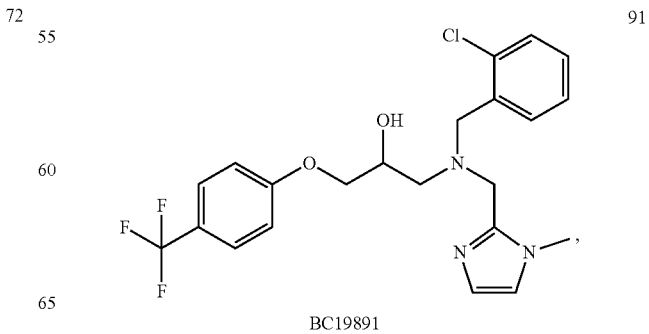
BC19891

| | |
|---|---|
| 97 BC19897 | 119 BC191014 |
| 104 BC191004 | 121 BC191016 |
| 105 BC191005 | 122 BC191017 |
| 106 BC191006 | |
| 117 BC191012 | 126 BC191021 |

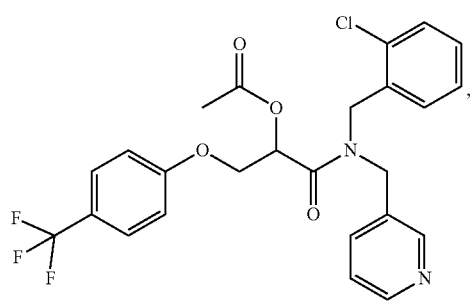
BC191022
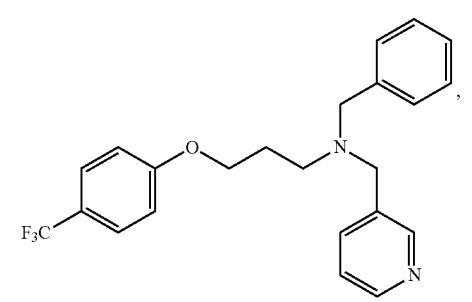
BC191025
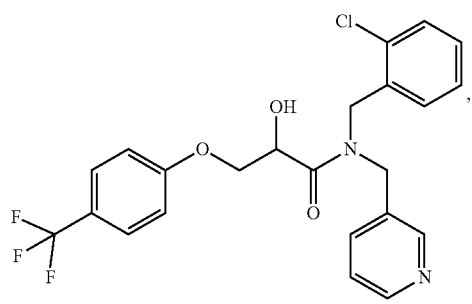
BC191026
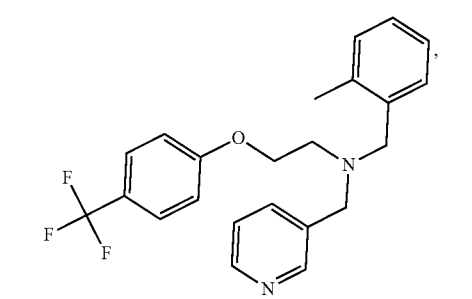
BC191039
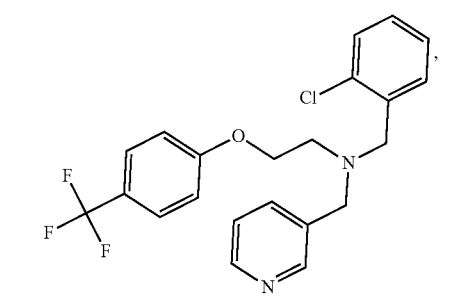
BC191040
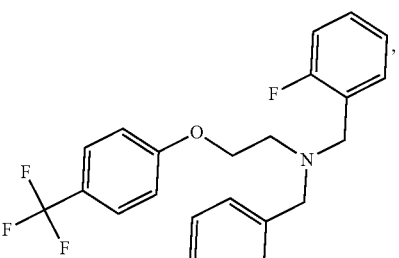
BC191041
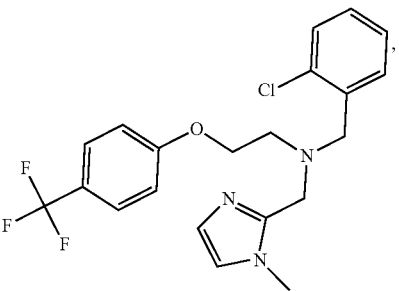
BC191042
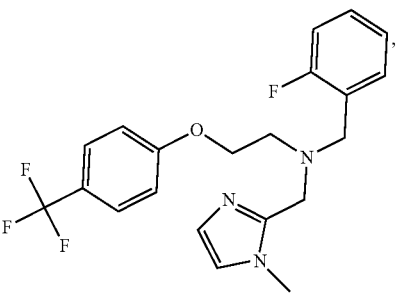
BC191043
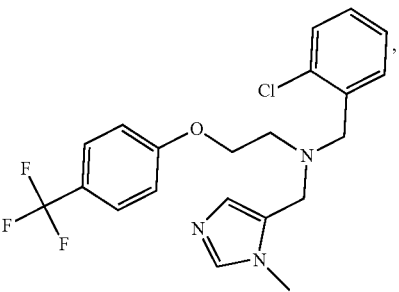
BC191044
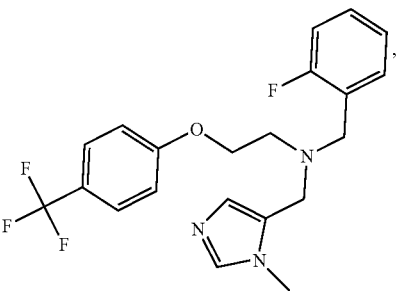
BC191045

| | |
|---|---|
| 164 BC191049 | 172 BC191057 |
| 165 BC191050 | 173 BC191058 |
| 170 BC191055 | 174 BC191059 |
| 171 BC191056 | 179 BC191064 |

269
-continued

180
BC191065

181
BC191066

182
BC191067

183
BC191068

270
-continued

185
BC191070

186
BC191071

191
BC191076

197
BC191082, and

200 BC191085

170 BC191055

171 BC191056

172 BC191057

173 BC191058

174 BC191059

179 BC191064

180 BC191065 or a pharmaceutically acceptable salt thereof.

4. A pharmaceutical composition comprising a compound of claim 1, or a pharmaceutically acceptable salt thereof, and a pharmaceutically acceptable carrier.

5. The compound of claim 1, wherein the compound is

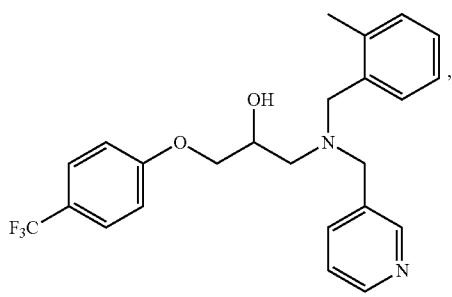 [SMILES: Cc1ccccc1CN(Cc1cccnc1)CC(O)COc1ccc(C(F)(F)F)cc1]

or a pharmaceutically acceptable salt thereof.

6. The compound of claim 1, wherein the compound is

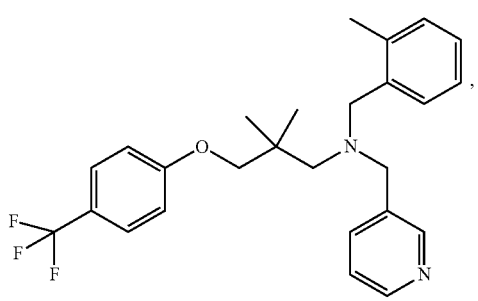 [SMILES: Cc1ccccc1CN(Cc1cccnc1)CC(C)(C)COc1ccc(C(F)(F)F)cc1]

or a pharmaceutically acceptable salt thereof.

7. The compound of claim 1, wherein the compound is

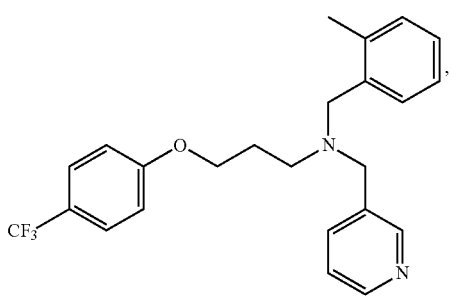

or a pharmaceutically acceptable salt thereof.

8. The compound of claim 1, wherein the compound is

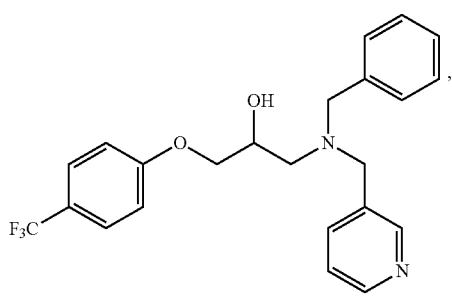 [SMILES: OC(COc1ccc(C(F)(F)F)cc1)CN(Cc1ccccc1)Cc1cccnc1]

or a pharmaceutically acceptable salt thereof.

9. The compound of claim 1, wherein the compound is

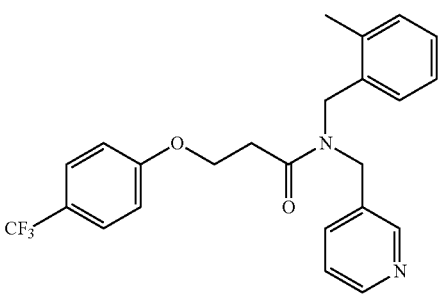

or a pharmaceutically acceptable salt thereof.

10. The compound of claim 1, wherein the compound is

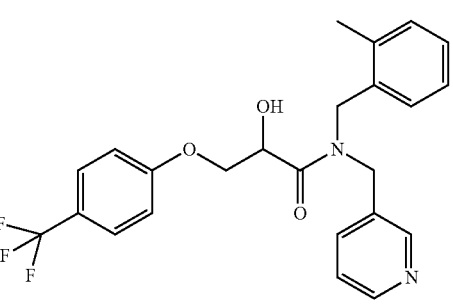

or a pharmaceutically acceptable salt thereof.

11. The compound of claim 1, wherein the compound is

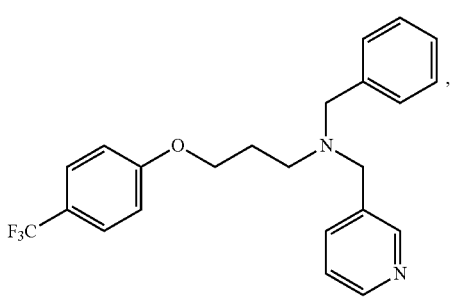 [SMILES: FC(F)(F)c1ccc(OCCCN(Cc2ccccc2)Cc2cccnc2)cc1]

or a pharmaceutically acceptable salt thereof.

12. The compound of claim 1, wherein the compound is

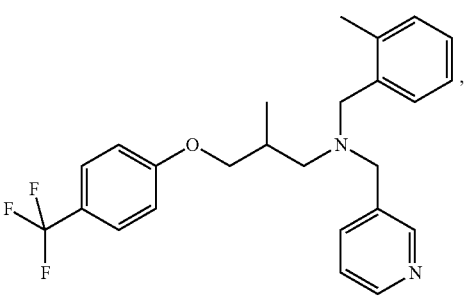 [SMILES: Cc1ccccc1CN(Cc1cccnc1)CC(C)COc1ccc(C(F)(F)F)cc1]

or a pharmaceutically acceptable salt thereof.

13. The compound of claim 1, wherein the compound is

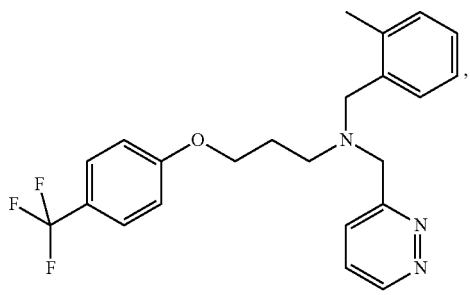 [SMILES: Cc1ccccc1CN(CCCOc1ccc(C(F)(F)F)cc1)Cc1cccnn1]

or a pharmaceutically acceptable salt thereof.

14. The compound of claim 1, wherein $R^3$ is —CH$_2$-(5- or 6-membered monocyclic heteroaryl), wherein said heteroaryl has 1 or 2 heteroatom ring members independently selected from nitrogen and sulfur and is optionally substituted with 1 or 2 substituents independently selected from $R^{Cy1}$.

15. The compound of claim 14, wherein said heteroaryl is selected from the group consisting of pyridinyl, pyrimidinyl, pyrazolyl, imidazolyl, thiazolyl, and pyridazinyl.

16. The compound of claim 15, wherein said heteroaryl is pyridinyl.

17. The compound of claim 1, wherein $R^{Cy1}$ is selected from the group consisting of halo, $C_{1-6}$ alkyl, and $C_{1-6}$ haloalkyl.

18. The compound of claim 1, wherein $R^1$ is a group of formula (i).

19. The compound of claim 18, wherein m is 0.

20. The compound of claim 1, wherein X is absent.

* * * * *

UNITED STATES PATENT AND TRADEMARK OFFICE
CERTIFICATE OF CORRECTION

Page 1 of 2

PATENT NO. : 12,428,378 B2
APPLICATION NO. : 17/641606
DATED : September 30, 2025
INVENTOR(S) : Beibei Chen, Toren Finkel and Yuan Liu It is certified that error appears in the above-identified patent and that said Letters Patent is hereby corrected as shown below:

In the Specification

Column 1, Line 6, after "This Application" please add -- is a National Stage application under 35 U.S.C. §371 of International Application No. PCT/US2018/056488, having an International Filing Date of October 18, 2018, which --

In the Claims

Column 264, Line 20, Claim 3 please delete:

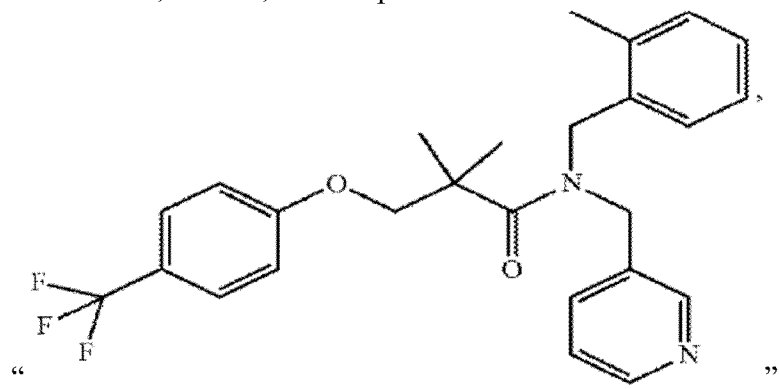

Signed and Sealed this
Ninth Day of December, 2025

John A. Squires
*Director of the United States Patent and Trademark Office*

CERTIFICATE OF CORRECTION (continued)
U.S. Pat. No. 12,428,378 B2

And insert therefor: